US010734117B2

(12) United States Patent
Gupta et al.

(10) Patent No.: US 10,734,117 B2
(45) Date of Patent: Aug. 4, 2020

(54) APPARATUSES AND METHODS FOR DETERMINING A PATIENT'S RESPONSE TO MULTIPLE CANCER DRUGS

(71) Applicant: Strand Life Sciences Private Limited, Bangalore (IN)

(72) Inventors: Vaijayanti Gupta, Bangalore (IN); Manimala Sen, Bangalore (IN); Satish Sankaran, Bangalore (IN); Kalyanasundaram Subramanian, Bangalore (IN); Ramesh Hariharan, Bangalore (IN); Vamsi Veeramachaneni, Bangalore (IN); Shanmukh Katragadda, Bangalore (IN); Rohit Gupta, Bangalore (IN); Radhakrishna Bettadapura, Bangalore (IN); Anand Janakiraman, Bangalore (IN); Arunabha Ghosh, Bangalore (IN); Smita Agrawal, Bangalore (IN); Sujaya Srinivasan, Bangalore (IN); Bhupender Singh, Bangalore (IN); Urvashi Bahadur, Bangalore (IN); Shuba Krishna, Bangalore (IN); Mahesh Nagarajan, Bangalore (IN); Nimisha Gupta, Bangalore (IN); Sudhir Borgonha, Bangalore (IN)

(73) Assignee: STRAND LIFE SCIENCES PRIVATE LIMITED, Bangalore (IN)

( * ) Notice: Subject to any disclaimer, the term of this patent is extended or adjusted under 35 U.S.C. 154(b) by 426 days.

(21) Appl. No.: 15/555,490

(22) PCT Filed: Mar. 2, 2016

(86) PCT No.: PCT/IB2016/000316
§ 371 (c)(1),
(2) Date: Sep. 1, 2017

(87) PCT Pub. No.: WO2016/139534
PCT Pub. Date: Sep. 9, 2016

(65) Prior Publication Data
US 2019/0006048 A1    Jan. 3, 2019

(30) Foreign Application Priority Data

Mar. 2, 2015   (IN) .......................... 1001/CHE/2015
Jan. 7, 2016   (IN) .............................. 201641000542

(51) Int. Cl.
*G16H 50/50*      (2018.01)
*G16H 50/20*      (2018.01)
(Continued)

(52) U.S. Cl.
CPC ......... *G16H 50/50* (2018.01); *G06F 19/3456* (2013.01); *G16H 10/40* (2018.01); *G16H 50/20* (2018.01)

(58) Field of Classification Search
CPC ........ G16H 50/20; G16H 10/40; G16H 50/70; G06F 19/00; G06F 19/325; G06Q 50/22
See application file for complete search history.

(56) References Cited

U.S. PATENT DOCUMENTS

2010/0118041 A1   5/2010   Chen et al.
2011/0104147 A1   5/2011   Sahin et al.
(Continued)

OTHER PUBLICATIONS

Banterle et al. "A Fast Implementation of the Octagon Abstract Domain on Graphics Hardware," Static Analysis, Aug. 22, 2007 (Aug. 22, 2007), vol. 4634, Lecture Notes in Computer Science, pp. 315-322.
(Continued)

*Primary Examiner* — Joseph D Burgess
(74) *Attorney, Agent, or Firm* — Kilpatrick Townsend & Stockton LLP

(57) ABSTRACT

Apparatuses (including devices and systems) and methods for determining if a patient will respond to a variety of cancer drugs.

20 Claims, 66 Drawing Sheets

(51) Int. Cl.
*G06F 19/00* (2018.01)
*G16H 10/40* (2018.01)

(56) References Cited

U.S. PATENT DOCUMENTS

| | | |
|---|---|---|
| 2012/0239706 A1 | 9/2012 | Steinfadt |
| 2013/0143747 A1* | 6/2013 | Gutin .................. C12Q 1/6886 506/7 |
| 2013/0268206 A1 | 10/2013 | Porreca et al. |
| 2014/0222443 A1* | 8/2014 | Danenberg ....... G01N 33/57407 705/2 |
| 2016/0068915 A1* | 3/2016 | Kennedy ................ G16B 25/00 506/2 |

OTHER PUBLICATIONS

Alachiotis et al. "Coupling SIMD and SIMT architectures to boost performance of a phylogeny-aware alignment kernel", BMC Bioinformatics, Aug. 9, 2012 (Aug. 9, 2012), vol. 13, pp. 1-12.
Luo et al. "SOAP3-dp: Fast, Accurate and Sensitive GPU-Based Short Read Aligner", PLoS ONE, May 31, 2013 (May 31, 2013), vol. 8, e65632, pp. 1-11.
International Search Report and Written Opinion from International application No. PCT/IB2016/000316, dated Aug. 26, 2016, 26 pages.

* cited by examiner

FIG. 12A

Irinotecan ✓✓✓ (Enhanced Response)

Markers

TOP1

Evidence Details

Clinical studies in colon cancer establish the predictive value of TOP1 IHC. A large clinical study with 1313 patients reported no improvement in PFS, upon irinotecan-based therapy in patients with low TOP1 (hazard ratio [HR], 0.98; 95% CI, 0.78 to 1.22), while patients with moderate/high TOP1 benefited from the drug (HR, 0.48; interaction p = 0.005). In addition, high TOP1 was associated with a major overall survival benefit with first-line combination chemotherapy (HR, 0.60; median benefit, 5.3 months) while patients with moderate or low TOP1 did not benefit (HR, 0.92 and 1.09, respectively; interaction p = 0.005). Preclinical studies in colon cancer have also suggested sensitivity to camptothecin in cells with elevated TOP1 levels. [1,2] [3]

Marker Details

TOP1   IHC Positive

Drug Description

A semisynthetic derivative of camptothecin, a cytotoxic, quinoline-based alkaloid extracted from the Asian tree Camptotheca acuminata. Irinotecan, a prodrug, is converted to a biologically active metabolite 7-ethyl-10-hydroxy-camptothecin (SN-38) by a carboxylesterase-converting enzyme. One thousand-fold more potent than its parent compound irinotecan, SN-38 inhibits topoisomerase I activity by stabilizing the cleavable complex between topoisomerase I and DNA, resulting in DNA breaks that inhibit DNA replication and trigger apoptotic cell death. Because ongoing DNA synthesis is necessary for irinotecan to exert its cytotoxic effects, it is classified as an S-phase-specific agent.
Source: The National Cancer Institute's Cancer Drug Information References 1. Braun MS et al. 2008. Predictive biomarkers of chemotherapy efficacy in colorectal cancer: results from the UK MRC FOCUS trial. J. Clin. Oncol. 26(16):2690-8 (PMID: 18509181).
2. Gilbert DC et al. 2012. Topoisomerase I inhibition in colorectal cancer: biomarkers and therapeutic targets. Br. J. Cancer 106(1):18-24 (PMID: 22108516).
3. Giovanella BC et al. 1989. DNA topoisomerase I-targeted chemotherapy of human colon cancer in xenografts. Science 246(4933):1046-8 (PMID: 2555920).

FIG. 12B

Panitumumab ✓✓✓ (Enhanced Response)

Markers

NRAS, KRAS, BRAF, PIK3CA

Evidence Details

Non-detection of activating mutations in genes such as KRAS, NRAS, BRAF and PIK3CA, may indicate a favourable response to cetuximab and panitumumab. [1-5]

Marker Details

NRAS
No significant oncogenic variant detected in NRAS

KRAS
No significant oncogenic variant detected in KRAS, indicating wild-type status

BRAF
No significant oncogenic variant detected in BRAF

PIK3CA
No significant oncogenic variant detected in PIK3CA

Drug Description

A human monoclonal antibody produced in transgenic mice that attaches to the transmembrane epidermal growth factor (EGF) receptor. Panitumumab may inhibit autocrine EGF stimulation of tumor cells that express the EGF receptor, thereby inhibiting tumor cell proliferation.
Source: The National Cancer Institute's Cancer Drug Information References 1. Bokemeyer C et al. 2012. Addition of cetuximab to chemotherapy as first-line treatment for KRAS wild-type metastatic colorectal cancer: pooled analysis of the CRYSTAL and OPUS randomised clinical trials. Eur. J. Cancer 48(10):1466-75 [PMID: 22446022].
2. Douillard JY et al. 2013. Panitumumab-FOLFOX4 treatment and RAS mutations in colorectal cancer. N. Engl. J. Med. 369(11):1023-34 [PMID: 24024839].
3. De Roock W et al. 2010. Effects of KRAS, BRAF, NRAS, and PIK3CA mutations on the efficacy of cetuximab plus chemotherapy in chemotherapy-refractory metastatic colorectal cancer: a retrospective consortium analysis. Lancet Oncol. 11(8):753-62 [PMID: 20619739].
4. Di Nicolantonio F et al. 2008. Wild-type BRAF is required for response to panitumumab or cetuximab in metastatic colorectal cancer. J. Clin. Oncol. 26(35):5705-12 [PMID: 19001320].
5. Pietrantonio F et al. 2015. Predictive role of BRAF mutations in patients with advanced colorectal cancer receiving cetuximab and panitumumab: a meta-analysis. Eur J Cancer 41(5):587-94 [PMID: 25673558].

FIG. 12C

Cetuximab   ✓ ✓ ✓ (Enhanced Response)

Markers

NRAS, KRAS, BRAF, PIK3CA

Evidence Details

Non-detection of activating mutations in genes such as KRAS, NRAS, BRAF and PIK3CA, may indicate a favourable response to cetuximab and panitumumab [1-5].

Marker Details

NRAS
No significant oncogenic variant detected in NRAS

KRAS
No significant oncogenic variant detected in KRAS, indicating wild-type status

BRAF
No significant oncogenic variant detected in BRAF

PIK3CA
No significant oncogenic variant detected in PIK3CA

Drug Description

A recombinant, chimeric monoclonal antibody directed against the epidermal growth factor (EGFR) with antineoplastic activity. Cetuximab binds to the extracellular domain of the EGFR, thereby preventing the activation and subsequent dimerization of the receptor; the decrease in receptor activation and dimerization may result in an inhibition in signal transduction and anti-proliferative effects. This agent may inhibit EGFR-dependent primary tumor growth and metastasis. EGFR is overexpressed on the cell surfaces of various solid tumors.
*Source: The National Cancer Institute's Cancer Drug Information*

References

1. Bokemeyer C et al. 2012. Addition of cetuximab to chemotherapy as first-line treatment for KRAS wild-type metastatic colorectal cancer: pooled analysis of the CRYSTAL and OPUS randomised clinical trials. Eur. J. Cancer 48(10):1466-75 [PMID: 22446022].
2. Douillard JY et al. 2013. Panitumumab-FOLFOX4 treatment and RAS mutations in colorectal cancer. N. Engl. J. Med. 369(11):1023-34 [PMID: 24024839].
3. De Roock W et al. 2010. Effects of KRAS, BRAF, NRAS, and PIK3CA mutations on the efficacy of cetuximab plus chemotherapy in chemotherapy-refractory metastatic colorectal cancer: a retrospective consortium analysis. Lancet Oncol. 11(8):753-62 [PMID: 20619739].
4. Di Nicolantonio F et al. 2008. Wild-type BRAF is required for response to panitumumab or cetuximab in metastatic colorectal cancer. J. Clin. Oncol. 26(35):5705-12 [PMID: 19001320].

FIG. 12D

5. Pietrantonio F et al. 2015. Predictive role of BRAF mutations in patients with advanced colorectal cancer receiving cetuximab and panitumumab: a meta-analysis. *Eur J Cancer* 41(5):587-94 [PMID: 25673558].

Drug Description

An antimetabolite fluoropyrimidine analog of the nucleoside pyrimidine with antineoplastic activity. Fluorouracil and its metabolites possess a number of different mechanisms of action. In vivo, fluoruracil is converted to the active metabolite 5-fluoxyuridine monophosphate (F-UMP); replacing uracil, F-UMP incorporates into RNA and inhibits RNA processing, thereby inhibiting cell growth. Another active metabolite, 5-5-fluoro-2'-deoxyuridine-5'-O-monophosphate (F-dUMP), inhibits thymidylate synthase, resulting in the depletion of thymidine triphosphate (TTP), one of the four nucleotide triphosphates used in the in vivo synthesis of DNA. Other fluorouracil metabolites incorporate into both RNA and DNA; incorporation into RNA results in major effects on both RNA processing and functions.
*Source: The National Cancer Institute's Cancer Drug Information*

References

1. Qiu LX et al. 2008. Predictive value of thymidylate synthase expression in advanced colorectal cancer patients receiving fluoropyrimidine-based chemotherapy: evidence from 24 studies. *Int. J. Cancer* 123(10):2384-9 [PMID: 18729195].
2. Popat S et al. 2004. Thymidylate synthase expression and prognosis in colorectal cancer: a systematic review and meta-analysis. *J. Clin. Oncol.* 22(3):529-36 [PMID: 14752078].
3. Panczyk M 2014. Pharmacogenetics research on chemotherapy resistance in colorectal cancer over the last 20 years. *World J. Gastroenterol.* 20(29):9775-827 [PMID: 25110414].
4. Benatti P et al. 2005. Microsatellite instability and colorectal cancer prognosis. *Clin. Cancer Res.* 11(23):8332-40 [PMID: 16322293].
5. Sinicrope FA 2010. DNA mismatch repair and adjuvant chemotherapy in sporadic colon cancer. *Nat Rev Clin Oncol* 7(3):174-7 [PMID: 20180798].
6. Kim JC et al 2009. Chemoresponsiveness associated with canonical molecular changes in colorectal adenocarcinomas. *Anticancer Res.* 29(8):3115-23 [PMID: 19661324].
7. Chen SP et al 2009. Prognostic significance of interaction between somatic APC mutations and 5-fluorouracil adjuvant chemotherapy in Taiwanese colorectal cancer subjects. *Am. J. Clin. Oncol.* 32(2):122-6 [PMID: 19307944].
8. Martino-Echarri E et al. 2014. Targeting the DNA replication checkpoint by pharmacologic inhibition of Chk1 kinase: a strategy to sensitize APC mutant colon cancer cells to 5-fluorouracil chemotherapy. *Oncotarget* 5(20):9889-900 [PMID: 25301728].
9. Fearnhead NS et al 2001. The ABC of APC. *Hum. Mol. Genet.* 10(7):721-33 [PMID: 11257105].
10. Azzopardi D et al 2008. Multiple rare nonsynonymous variants in the adenomatous polyposis coli gene predispose to colorectal adenomas. *Cancer Res.* 68(2):358-63 [PMID: 18199528].
11. Kohler EM et al 2009. Beta-catenin degradation mediated by the CID domain of APC provides a model for the selection of APC mutations in colorectal, desmoid and duodenal tumours. *Hum. Mol. Genet.* 18(2):213-26 [PMID: 18854358].
12. Kohler EM et al 2008. Functional definition of the mutation cluster region of adenomatous polyposis coli in colorectal tumours. *Hum. Mol. Genet.* 17(13):1978-87 [PMID: 18387958].

FIG. 12E

Oxaliplatin       ✗ (Poor Response)

Markers

ERCC1

Evidence Details

Clinical evidence from studies in colon and other cancers suggest that elevated levels of ERCC1 protein is associated with poor response to platinum-based chemotherapy regimens. A clinical study with a small subset of metastatic colon cancer patients evaluable for ERCC1 expression reported an association of shorter PFS (median 5.8 vs 9.2 months) and overall survival (median 11.5 vs 18.5 months) and a lower response rate (33.3% vs 39.1%) with high ERCC1 expression compared to low expression. In lung cancer, a meta-analysis of 11 small clinical studies concluded that NSCLC patients with high ERCC1 levels, treated with platinum based therapy have a significantly lower response (risk ratio [RR], 0.80) and significantly higher risk of death (hazard ratio [HR], 2.04) when compared to patients with low ERCC1 levels. [1], [2], [3,4]

Marker Details

ERCC1  IHC Positive

Drug Description

An organoplatinum complex in which the platinum atom is complexed with 1,2-diaminocyclohexane (DACH) and with an oxalate ligand as a 'leaving group.' A 'leaving group' is an atom or a group of atoms that is displaced as a stable species taking with it the bonding electrons. After displacement of the labile oxalate ligand leaving group, active oxaliplatin derivatives, such as monoaquo and diaquo DACH platinum, alkylate macromolecules, forming both inter- and intra-strand platinum-DNA crosslinks, which result in inhibition of DNA replication and transcription and cell-cycle nonspecific cytotoxicity. The DACH side chain appears to inhibit alkylating-agent resistance.
Source: The National Cancer Institute's Cancer Drug Information References 1. Li P et al. 2013. ERCC1, defective mismatch repair status as predictive biomarkers of survival for stage III colon cancer patients receiving oxaliplatin-based adjuvant chemotherapy. Br. J. Cancer 106(6):1230-44 [PMID: 23481188].
2. ASCO_Abstr 3537
3. Yang Y et al. 2014. The Prognostic Value of Excision Repair Cross-Complementation Group 1 (ERCC1) in Patients with Small Cell Lung Cancer (SCLC) Receiving Platinum-Based Chemotherapy: Evidence from Meta-Analysis. PLoS ONE 9(11):e111651 [PMID: 25375151].
4. Roth JA et al. 2011. Prognostic role of ERCC1 in advanced non-small-cell lung cancer: a systematic review and meta-analysis. Clin Lung Cancer 12(6):393-401 [PMID: 21733793].

FIG. 12F

Limitations of Gene Coverage

For each test gene, the percentage of the gene target regions and COSMIC mutations covered by less than 100 reads is provided below:

| Gene | COSMIC mutants not covered | % of gene under covered |
|---|---|---|
| BRAF | 2/371 | 5.28 |

Signatures

Supplementary Information

Malignant transformation of cells is driven largely by somatic DNA mutations. While current modes of treatment are successful in limiting the growth of a large number of tumors, there is considerable variability in the degree of effectiveness of conventional therapies. It is often difficult to predict the sensitivity of a given therapy for a particular patient. Identification of changes in the genome would enable personalized treatment. Increasing evidence links somatic mutations in key genes involved in cancer to overall outcome and / or responsiveness to particular types of therapy. It may thus be useful to determine which of these mutations is present in a given patient's tumor type. Additionally, variants in certain genes associated with drug metabolism and transport may provide added information on response to chemotherapy.

Test Description

StrandAdvantage Test is a Next Generation Sequencing based test which profiles a patient's tumor genotype in order to detect genetic alterations in key regions in a comprehensive panel of well curated 152 tumor genes. Some of the alterations detected may have bearing on prognosis and / or therapeutic options and may provide relevant information that allows a doctor and / or to consider various lines of targeted treatment for the patient.

SOC Test Description

The StrandAdvantage SOC test examines certain well studied markers that can impact response to approved therapy for a particular cancer type. These markers are tested by NGS or other methods such as immunohistochemistry.

Genes evaluated by NGS: 11 genes

*APC, BRAF, DPYD, EGFR, KRAS, MET, NRAS, PIK3CA, PTEN, SMAD4, UGT1A1*

External Lab Tests

| Gene | Test | Company |
|---|---|---|
| TS | IHC | ProPath |
| MSI | MSI | Provided with Sample |
| ERCC1 | IHC | ProPath |
| TOP1 | IHC | ProPath |

Methodology

Sample preparation: Genomic DNA isolated from FFPE or any other fresh tumor tissue source is used for preparation of the 'DNA sequencing-ready' library. The DNA is quantified using Qubit and 200 ng is taken for shearing and library preparation. The DNA is sheared by Covaris using appropriate settings for FFPE or intact DNA, to 150 bp. Library preparations using the Sure Select XT2 involves repairing the ends of the sheared DNA and ligating the adaptors and indices. A limited cycle PCR step is performed to generate adequate quantity sequencing libraries.

Target Enrichment: The tagged and amplified sample libraries are checked for quality and quantified before enrichment. Approximately 250ng of 6 individual libraries are pooled and combined into a single tube and set up for enrichment to generate targeted sequencing for each sample on a MiSeq sequencer. Target libraries are then amplified using limited PCR steps and about approximately 8pM pooled library is loaded for sequencing.

FIG. 12G

Sequencing Details: Sequencing is performed using a standard v3 kit on Illumina MiSeq with the expected data output of 6-9 GB. For this panel, the output size of 1.3-1.5 GB per sample results from an optimum cluster density of 900-1100 clusters per sqmm.

Analysis

The trimmed FASTQ files were generated using MiSeq Reporter from Illumina. The reads were aligned against the whole genome build hg19 using Strand® NGS v2.5.1. Five base pairs from the 3' end of the reads were trimmed, as were 3' end bases with quality below 10. Reads which had length less than 25 bp after trimming were not considered for alignment. A maximum of 5 matches of alignment score at least 90% were computed. The maximum allowed gap was 45% of the read length to identify medium sized InDels. The reads which had an alignment score below 95 or were unaligned are aligned using the split read aligner. Reads that failed vendor QC, reads with average quality less than 20, reads with ambiguous characters as well as duplicate reads were all filtered out. The Strand® NGS binomial variant caller was used to detect variants at locations in the target regions covered by a minimum of 10 reads with at least 2 variant reads. Variants with a decibel score of at least 30 were reported and annotated with dbSNP141. Variants with supporting reads <2%, tail distance bias -PV4 <0.00001, substitution variants with a StrandBias >90% and total reads >100 and InDel variants in homopolymer stretch >4 with supporting reads <10% were filtered out. Targeted copy number analysis is performed against a profile for 10 normal FFPE samples using GC-bias correction. Structural variants (gene fusions) are identified based on split reads with a minimum of 10 reads supporting the variant. A single merged VCF file was created including SNVs, CNVs and SVs and uploaded into StrandOmics v3.0 for further interpretation and reporting. Annotation and prioritization of variants was done by automated pipelines in StrandOmics. The StrandOmics user interface was then used for identifying variants of interest and for reporting these variants. All variants reported were verified to have good read quality using the Strand® NGS genome browser before final reporting.

Primary Tools

STRAND®NGS: Strand® NGS (http://www.strand-ngs.com) is an NGS analysis platform from Strand Life Sciences. It comprises algorithms for alignment, variant calling, copy number variation analysis, and structural variant calling. A built-in genome browser enables inspection of read level data. Several QC steps enable inspection of read quality. STRAND® NGS has been cited in over 50 publications.

Literature: Strand has developed its text mining technology which is integrated with Strand's proprietary data mining platform - Avadis®. Avadis Text Mining engine can extract key concepts, sentiments, and relationships from textual or "unstructured" data and convert them to a structured format that can be used to create predictive models. In the first pass, PubMed abstracts are processed using this tool to find mutations in key genes. All extracted information is then manually curated for validation.

StrandOmics: StrandOmics (https://clinical.strandomics.com) is a clinical genomics interpretation and reporting platform from Strand Life Sciences. The StrandOmics Variant Annotation engine includes algorithms to identify variant impact from both public content (HGMD, ClinVar, OMIM, HPO, dbSNP, 1000 Genomes, Exome Variant Server, COSMIC and bioinformatics prediction tools such as SIFT, LRT, PolyPhen HVAR/HDIV, Mutation Taster, FATHMM) and proprietary content on genes, diseases and therapeutic impact of somatic variants. The 'Interpretation interface' in StrandOmics allows quick filtering and evaluation of variants along with capture of justification for inclusion/exclusion. The 'Reporting interface' in StrandOmics enables identified variants to be carried into template-driven reports efficiently. StrandOmics has already been used for interpretation and reporting of approximately one thousand clinical cases.

Limitations and Disclaimer

Treatment Decisions based upon test results

This clinical report should be carefully assessed by the treating physician and further interpreted along with clinical, histopathological findings, contraindications and guidelines before deciding the course of therapy. Treatment decisions are the responsibility of the clinician. It is recommended that the most recent block is used for testing as the mutation profile may change in response to treatment and hence differ at different sampling points.

FIG. 12H

Interpretation of Variants

The therapeutic implications listed in the report are based on the interpretation derived as a result of analysis of up-to-date scientific literature from various sources. Interpretation of this report is based on the clinical diagnosis provided and certain other relevant clinical information provided. Some findings listed in this report may be based on pre-clinical studies or studies not in the given patient's tumor type. Not all mutations detected are listed in this report. Inclusion of mutations is dependent upon our assessment of their significance. A mutation is considered actionable or significant if it can be linked to potential response or resistance to a particular therapy, or prognosis or diagnosis or sub-typing of the disease. Variants identified are not confirmed somatic variants. Additional testing may be warranted in certain cases are suspected to be germline variants.

Genomic Alterations Detection Limitations

A negative result from StrandAdvantage test cannot rule out the possibility that the tested individual's tumor sample carries mutations not previously associated with cancer and hence not included in the panel. StrandAdvantage analyzes point mutations and indels >5% frequency in the tumor DNA sample. There is a possibility that the tumor sample carries mutations at a lower frequency. These low frequency mutations may not be detected by the test. The quality of sequencing and coverage varies between regions. If the mutations are in regions of low or no coverage, they may be missed. Many factors such as homopolymers, GC-rich regions etc. influence the quality of sequencing and coverage. This may result in an occasional error in sequence reads or lack of detection of a particular genetic lesion.

Sample Quality and Analytical Sensitivity

Improper formalin fixing of the tissue and storage of the formalin fixed paraffin embedded (FFPE) blocks leads to DNA cross linking and degradation and results in poor quality of DNA. The starting quality and quantity of DNA from the tumor specimens also have an impact on the analytical sensitivity of StrandAdvantage. Genes with low coverage are listed in every report and can vary from sample to sample.

Tumor Content and Analytical Sensitivity

The StrandAdvantage test requires tumor specimens with at least 30% tumor content. If a tumor specimen has less than 30% tumor content, we cannot guarantee that StrandAdvantage will be able to detect ANY somatic mutations. Furthermore, even in samples with >30% tumor content, the sensitivity of the test can vary from sample to sample due to tumor heterogeneity.

Prediction of Clinical Response

The StrandAdvantage test report does not guarantee that a suggested drug will be effective in the particular case. It also does not promise that a drug with potential lack of effect will indeed provide no clinical benefit.

Reimbursement

Strand Life Sciences does not guarantee that the cost of this test will be reimbursed by a healthcare provider, insurer or other third party payor.

Compliance Statement

StrandAdvantage is a laboratory developed test/procedure that was developed by Strand Genomics Inc., a subsidiary of Strand Life Sciences. It has not been cleared or approved by the US Food and Drug Administration. StrandAdvantage is intended to be used for clinical purposes and its performance characteristics have been determined by Strand Genomics Inc. Strand Genomics's clinical reference laboratory is certified under the CLIA (Clinical Laboratory Improvement Amendments of 1988), CLIA ID NUMBER – 05D2091182.

End of report

Drugs not Indicated

Ceritinib

Rationale

Ceritinib is approved for previously treated metastatic non-small cell lung cancers positive for ALK kinase. Hence, it is not relevant therapy for this mutation profile.

Osimertinib

Rationale

Osimertinib is approved only for non-small cell lung cancer tumors with EGFR Thr790Met mutation. Hence, this therapy is not relevant for this mutation profile.

Gefitinib

Rationale

Gefitinib is approved for metastatic non-small cell lung cancers positive for specific EGFR gene mutations. Non-detection of activating alterations in EGFR indicates poor response to anti-EGFR tyrosine kinase inhibitors such as erlotinib and gefitinib.

Alectinib

Rationale

Alectinib is approved for previously treated metastatic non-small cell lung cancers positive for ALK kinase. Hence, it is not relevant therapy for this mutation profile.

Crizotinib

Rationale

Crizotinib is approved for non-small cell lung cancers that are ALK positive or recommended for patients who are positive for MET amplifications or ROS1 translocations. Hence, it is not relevant therapy for this mutation profile.

Vemurafenib

Rationale

Vemurafenib is only approved for BRAF p.Val 600 mutated cancers. Hence, this therapy is not relevant for this mutation profile.

Cabozantinib

FIG. 13B

Rationale

Cabozantinib is only recommended for non-small cell lung cancer cases with activating alterations in RET. Hence, this therapy is not relevant for this mutation profile.

Erlotinib

Rationale

Erlotinib is approved for metastatic non-small cell lung cancers positive for specific EGFR gene mutations. Non-detection of activating alterations in EGFR indicates poor response to anti-EGFR tyrosine kinase inhibitors such as erlotinib and gefitinib.

Afatinib

Rationale

Afatinib is approved for metastatic non-small cell lung cancers positive for specific EGFR gene mutations. Non-detection of activating alterations in EGFR indicates poor response to anti-EGFR tyrosine kinase inhibitors such as afatinib.

Dabrafenib

Rationale

Dabrafenib is only approved for BRAF p.Val 600 mutated cancers. Hence, this therapy is not relevant for this mutation profile.

Trastuzumab

Rationale

Trastuzumab is only recommended for non-small cell lung cancer cases with alterations in ERBB2. Hence, this therapy is not relevant for this mutation profile.

FIG. 13C

Pembrolizumab ✓✓✓ (Enhanced Response)

Markers

PD-L1

Evidence Details

Pembrolizumab is approved for previously treated metastatic non-small cell lung cancers positive for PD-L1. Large clinical studies have shown marked benefit upon pembrolizumab therapy in patients with at least 50% of PD-L1 positive cells. Clinical evidence in previously treated, PD-L1-positive, advanced NSCLC patients demonstrated a longer overall survival (OS) and progression free survival (PFS) in the pembrolizumab arm when compared to the docetaxel arm (OS: 14.2 months vs 8.2 months, HR 0.54, p=0.0002 and PFS: median 5.0 months vs 4.1 months; HR 0.59, p=0.0001). Additionally, a small clinical study has observed a response rate of 44% (4 of 9 patients with partial response) among NSCLC patients with untreated brain metastases, upon pembrolizumab treatment. [1,2][3][4]

Marker Details

PD-L1 IHC Positive
Positive for Keytruda eligibility, greater than or equal to 50% positive cells

Drug Description

A humanized monoclonal IgG4 antibody directed against human cell surface receptor PD-1 (programmed death-1 or programmed cell death-1) with potential immunopotentiating activity. Upon administration, pembrolizumab binds to PD-1, an inhibitory signaling receptor expressed on the surface of activated T cells, and blocks the binding to and activation of PD-1 by its ligands, which results in the activation of T-cell-mediated immune responses against tumor cells. The ligands for PD-1 include PD-L1, which is expressed on antigen presenting cells (APCs) and overexpressed on certain cancer cells, and PD-L2, which is primarily expressed on APCs. Activated PD-1 negatively regulates T-cell activation through the suppression of the PI3K/Akt pathway.
*Source: The National Cancer Institute's Cancer Drug Information*

References

1. Carbognin L et al. 2015. Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. 10(6) [PMID: 26086854].
2. Garon EB et al. 2015. KEYNOTE-001 Investigators. Pembrolizumab for the treatment of non-small-cell lung cancer. N Engl J Med. 372(21):2018-28 [PMID: 25891174].
3. Lancet
4. ASCO Abstr_8035

FIG. 13D

Nivolumab ✓✓✓ (Enhanced Response)

Markers

PD-L1

Evidence Details

Evidence from clinical studies in lung and other cancers indicates that high expression of PD-L1 is associated with higher response to nivolumab-based therapy regimens. Preliminary evidence from an ongoing study in lung cancer patients, wherein of 15 evaluable tumor samples, 8 were positive for PD-L1 expression, PD-L1 status correlated with objective response rate (ORR) and progression-free survival (PFS). A recent study carried out a pooled analysis of 20 trials using anti-PD-L1 therapy (nivolumab/pembrolizumab/MPDL3280A) in cancers including NSCLC. They reported that the ORR in nivolumab treated PD-L1 positive patients was significantly higher than in PD-L1 negative patients [1], [2-6]

Marker Details

PD-L1 IHC Positive

Drug Description

A fully human monoclonal antibody directed against the negative immunoregulatory human cell surface receptor PD-1 (programmed death-1 or programmed cell death-1/PCD-1) with immunopotentiation activity. Nivolumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3k/Akt pathway activation.
Source: The National Cancer Institute's Cancer Drug Information

References

1. ASCO_Abstr 8024
2. Taube JM et al 2014. Association of PD-1, PD-1 Ligands, and Other Features of the Tumor Immune Microenvironment with Response to Anti-PD-1 Therapy. Clin. Cancer Res. 20(19):5064-74 [PMID: 24714771].
3. Rajan A et al 2014. Nivolumab (anti-PD-1, BMS-936558, ONO-4538) in patients with advanced non-small cell lung cancer. Transl Lung Cancer Res. 3(6):403-5 [PMID: 25806334].
4. Sundar R et al 2015. Nivolumab in NSCLC: latest evidence and clinical potential. Ther Adv Med Oncol. 7(2):85-96 [PMID: 25755681].
5. Weber JS et al 2015. Nivolumab versus chemotherapy in patients with advanced melanoma who progressed after anti-CTLA-4 treatment (CheckMate 037): a randomised, controlled, open-label, phase 3 trial. Lancet Oncol. 16(4):375-8 [PMID: 25795410].
6. Carbognin L et al 2015. Differential Activity of Nivolumab, Pembrolizumab and MPDL3280A according to the Tumor Expression of Programmed Death-Ligand-1 (PD-L1): Sensitivity Analysis of Trials in Melanoma, Lung and Genitourinary Cancers. PLoS One. 10(6) [PMID: 26086854].

FIG. 13E

Gemcitabine ✓✓✓ (Enhanced Response)

Markers

RRM1

Evidence Details

Evidence from clinical and preclinical studies in lung cancer associates low levels of RRM1 protein expression with higher response to gemcitabine-based chemotherapy regimens. A study in lung cancer demonstrated a marked benefit in a group of patients treated with personalized gemcitabine therapy based on the RRM1 levels compared to those treated with standard therapy, in terms of disease control rate (DCR) (82.9% vs 55.3%, p = 0.004), and PFS (median: 5.5 months vs 3.0 months, p = 0.005). [1-4] [5,6]

Marker Details

RRM1   IHC Negative

Drug Description

A broad-spectrum antimetabolite and deoxycytidine analogue with antineoplastic activity. Upon administration, gemcitabine is converted into the active metabolites difluorodeoxycytidine diphosphate (dFdCDP) and difluorodeoxycytidine triphosphate (dFdCTP) by deoxycytidine kinase. dFdCTP competes with deoxycytidine triphosphate (dCTP) and is incorporated into DNA. This locks DNA polymerase thereby resulting in "masked termination" during DNA replication. On the other hand, dFdCDP inhibits ribonucleotide reductase, thereby decreasing the deoxynucleotide pool available for DNA synthesis. The reduction in the intracellular concentration of dCTP potentiates the incorporation of dFdCTP into DNA.
Source: The National Cancer Institute's Cancer Drug Information References 1. Nie X et al. 2013. The tailored chemotherapy based on RRM1 immunohistochemical expression in patients with advanced non-small cell lung cancer. Cancer Biomark 13(6):433-40 [PMID: 24595080].
2. Dong K et al. 2014. Response to first-line chemotherapy in patients with non-small cell lung cancer according to RRM1 expression. PLoS ONE 9(3):e92320 [PMID: 24647522].
3. Gong W et al. 2012. RRM1 expression and clinical outcome of gemcitabine-containing chemotherapy for advanced non-small-cell lung cancer: a meta-analysis. Lung Cancer 75(3):374-80 [PMID: 21889227].
4. Zhao LP et al. 2012. Expression of RRM1 and its association with resistancy to gemcitabine-based chemotherapy in advanced nasopharyngeal carcinoma. Chin J Cancer 31(10):476-83 [PMID: 22892073].
5. Davidson JD et al. 2004. An increase in the expression of ribonucleotide reductase large subunit 1 is associated with gemcitabine resistance in non-small cell lung cancer cell lines. Cancer Res. 64(11):3761-6 [PMID: 15172981].
6. Bepler G et al. 2006. RRM1 modulated in vitro and in vivo efficacy of gemcitabine and platinum in non-small-cell lung cancer. J. Clin. Oncol. 24(29):4731-7 [PMID: 16966686].

FIG. 13F

Docetaxel            ✗ (Poor Response)

Markers

TLE3, PgP, TUBB3

Evidence Details

Evidence from clinical studies in lung cancer suggests benefit from taxane-based therapy in patients with low TUBB3 levels. A meta-analysis of 10 studies with 552 NSCLC patients undergoing taxane/vinorelbine-based chemotherapy reported a significantly prolonged median survival time (MS) in patients with low/negative TUBB3 expression, compared to patients with high/positive TUBB3 expression (median ratio/MR= 1.4, p<0.00001) [MR: mean MS for low TUBB3/mean MS for high TUBB3]. Additionally, preliminary clinical evidence in lung and other cancers has recently identified TLE3 overexpression as a biomarker for response to taxane-based therapy. A small retrospective analysis of TLE3 levels in taxane treated NSCLC patients reported statistically significant response in those with TLE3 staining (HR=0.42 p=0.0047). However, limited clinical evidence and preclinical studies in lung suggests elevated MDR1 levels may indicate poor response to taxanes. A small clinical study assessing the response to paclitaxel therapy in NSCLC patients reported 58% of the patients with elevated MDR1 levels responded poorly to the drug (p<0.05). Clinical evidence from breast also supports poor response to paclitaxel upon MDR1 overexpression. Thus, tumors with TUBB3, TLE3 and MDR1 overexpressed may show limited response to taxanes. [1-11], [12]

Marker Details

PgP   IHC Positive

TLE3   IHC Positive

TUBB3   IHC Positive

Drug Description

A semi-synthetic, second-generation taxane derived from a compound found in the European yew tree, Taxus baccata. Docetaxel displays potent and broad antineoplastic properties; it binds to and stabilizes tubulin, thereby inhibiting microtubule disassembly which results in cell- cycle arrest at the G2/M phase and cell death. This agent also inhibits pro-angiogenic factors such as vascular endothelial growth factor (VEGF) and displays immunomodulatory and pro-inflammatory properties by inducing various mediators of the inflammatory response. Docetaxel has been studied for use as a radiation-sensitizing agent.
Source: *The National Cancer Institute's Cancer Drug Information*

References

1. Yeh JJ *et al.* Predicting chemotherapy response to paclitaxel-based therapy in advanced non-small-cell lung cancer with P-glycoprotein expression. *Respiration* 70(1):32-5 [PMID: 12584398].
2. Kim B *et al.* 2013. Neoadjuvant chemotherapy induces expression levels of breast cancer resistance protein that predicts disease-free survival in breast cancer. *PLoS ONE* 8(5):e63776 [PMID: 23658773].

FIG. 13G

3. Zhang Z. et al. 2014. Evaluating the response of neoadjuvant chemotherapy for treatment of breast cancer: are tumor biomarkers and dynamic contrast enhanced MR images useful predictive tools? *J Thorac Dis* 6(6):786-94 [PMID: 24977004].
4. Litviakov NV et al. 2013. Changing the expression vector of multidrug resistance genes is related to neoadjuvant chemotherapy response. *Cancer Chemother Pharmacol* 71(1):153-63 [PMID: 23053273].
5. Samimi G et al. 2012. TLE3 expression is associated with sensitivity to taxane treatment in ovarian carcinoma. *Cancer Epidemiol Biomarkers Prev* 21(2):273-9 [PMID: 22194527].
6. Kulkarni SA et al. 2009. TLE3 as a candidate biomarker of response to taxane therapy. *Breast Cancer Res.* 11(2):R17 [PMID: 19320505].
7. Yang YL et al. 2014. The prognostic role of the class III β-tubulin in non-small cell lung cancer (NSCLC) patients receiving the taxane/vinorelbine-based chemotherapy: a meta-analysis. *PLoS ONE* 9(4):e93997 [PMID: 24705847].
8. Zhang HL et al. 2012. Association between class III β-tubulin expression and response to paclitaxel/vinorelbine-based chemotherapy for non-small cell lung cancer: a meta-analysis. *Lung Cancer* 77(1):9-15 [PMID: 22306125].
9. Vilmar A et al. 2012. RT-PCR versus immunohistochemistry for correlation and quantification of ERCC1, BRCA1, TUBB3 and RRM1 in NSCLC. *Lung Cancer* 75(3):306-12 [PMID: 21995987].
10. Vilmar AC et al. 2011. Class III β-tubulin in advanced NSCLC of adenocarcinoma subtype predicts superior outcome in a randomized trial. *Clin. Cancer Res.* 17(15):5205-14 [PMID: 21896672].
11. Azuma K et al. 2009. Expression of ERCC1 and class III beta-tubulin in non-small cell lung cancer patients treated with carboplatin and paclitaxel. *Lung Cancer* 64(3):326-33 [PMID: 18977553].
12. AACR_Abstr 3734

FIG. 13H

Paclitaxel ✗ (Poor Response)

Markers

TLE3, PgP, TUBB3

Evidence Details

Evidence from clinical studies in lung cancer suggests benefit from taxane-based therapy in patients with low TUBB3 levels. A meta-analysis of 10 studies with 552 NSCLC patients undergoing taxane/vinorelbine-based chemotherapy reported a significantly prolonged median survival time (MS) in patients with low/negative TUBB3 expression, compared to patients with high/positive TUBB3 expression (median ratioMR= 1.4, p<0.00001) [MR: mean MS for low TUBB3/mean MS for high TUBB3]. Additionally, preliminary clinical evidence in lung and other cancers has recently identified TLE3 overexpression as a biomarker for response to taxane-based therapy. A small retrospective analysis of TLE3 levels in taxane treated NSCLC patients reported statistically significant response in those with TLE3 staining (HR=0.42 p=0.0047). However, limited clinical evidence and preclinical studies in lung suggests elevated MDR1 levels may indicate poor response to taxanes. A small clinical study assessing the response to paclitaxel therapy in NSCLC patients reported 68% of the patients with elevated MDR1 levels responded poorly to the drug (p<0.05). Clinical evidence from breast also supports poor response to paclitaxel upon MDR1 overexpression. Thus, tumors with TUBB3, TLE3 and MDR1 overexpressed may show limited response to taxanes. [1-11], [12]

Marker Details

PgP   IHC Positive

TLE3   IHC Positive

TUBB3   IHC Positive

Drug Description

A compound extracted from the Pacific yew tree Taxus brevifolia with antineoplastic activity. Paclitaxel binds to tubulin and inhibits the disassembly of microtubules, thereby resulting in the inhibition of cell division. This agent also induces apoptosis by binding to and blocking the function of the apoptosis inhibitor protein Bcl-2 (B-cell Leukemia 2).
Source: The National Cancer Institute's Cancer Drug Information References 1. Yeh JJ et al. Predicting chemotherapy response to paclitaxel-based therapy in advanced non-small-cell lung cancer with P-glycoprotein expression. Respiration 70(1):32-5 (PMID: 12584388).
2. Kim B et al. 2013. Neoadjuvant chemotherapy induces expression levels of breast cancer resistance protein that predict disease-free survival in breast cancer. PLoS ONE 8(5):e62766 (PMID: 23638771).
3. Zhang Z et al. 2014. Evaluating the response of neoadjuvant chemotherapy for treatment of breast cancer: are tumor biomarkers and dynamic contrast enhanced MR images useful predictive tools? J Thorac Dis 6(6):785-94 (PMID: 24977004).
4. Litviakov NV et al. 2013. Changing the expression vector of multidrug resistance genes is related to neoadjuvant chemotherapy response. Cancer Chemother Pharmacol. 71(1):153-63 (PMID: 23053373).

FIG. 13I

5. Samimi G et al. 2012. TLE3 expression is associated with sensitivity to taxane treatment in ovarian carcinoma. *Cancer Epidemiol. Biomarkers Prev.* 21(2):273-9 [PMID: 22194527].
6. Kulkarni SA et al. 2009. TLE3 as a candidate biomarker of response to taxane therapy. *Breast Cancer Res.* 11(C):R17 [PMID: 19320508].
7. Yang YL et al. 2014. The prognostic role of the class III β-tubulin in non-small cell lung cancer (NSCLC) patients receiving the taxane/vinorebine-based chemotherapy: a meta-analysis. *PLoS ONE* 9(4):e93997 [PMID: 24705847].
8. Zhang HL et al. 2012. Association between class III β-tubulin expression and response to paclitaxel/vinorebine-based chemotherapy for non-small cell lung cancer: a meta-analysis. *Lung Cancer* 77(1):9-15 [PMID: 22336125].
9. Vilmar A et al. 2012. RT-PCR versus immunohistochemistry for correlation and quantification of ERCC1, BRCA1, TUBB3 and RRM1 in NSCLC. *Lung Cancer* 75(3):306-12 [PMID: 21899867].
10. Vilmar AC et al. 2011. Class III β-tubulin in advanced NSCLC of adenocarcinoma subtype predicts superior outcome in a randomized trial. *Clin. Cancer Res.* 17(15):5205-14 [PMID: 21690572].
11. Azuma K et al. 2009. Expression of ERCC1 and class III beta-tubulin in non-small cell lung cancer patients treated with carboplatin and paclitaxel. *Lung Cancer* 64(3):326-33 [PMID: 18977053].
12. AACR_Abstr 3734

FIG. 13J

Vinorelbine ✗ (Poor Response)

Markers

TUBB3

Evidence Details

Evidence from clinical studies in lung cancer suggests poor response to vinorelbine-based therapy in patients with high TUBB3 levels. A meta-analysis of 26 studies with 2401 NSCLC patients undergoing taxane/vinorelbine-based chemotherapy reported positive TUBB3 levels to be associated with a poorer overall survival rate (ORR) (OR = 0.24, p<0.001), an unfavorable overall survival (OS) (HR = 1.52, p<0.001), and a worse event free survival (EFS) (HR = 1.47, p<0.001) when compared to negative or low TUBB3 levels. [1-4]

Marker Details

TUBB3  IHC Positive

Drug Description

A semisynthetic vinca alkaloid. Vinorelbine binds to tubulin and prevents formation of the mitotic spindle, resulting in the arrest of tumor cell growth in metaphase. This agent may also interfere with amino acid, cyclic AMP, and glutathione metabolism; calmodulin-dependent Ca++ transport ATPase activity; cellular respiration; and nucleic acid and lipid biosynthesis.
*Source: The National Cancer Institute's Cancer Drug Information*

References

1. Yang YL. et al. 2014. The prognostic role of the class III β-tubulin in non-small cell lung cancer (NSCLC) patients receiving the taxane/vinorelbine-based chemotherapy: a meta-analysis. PLoS ONE 9(4):e93997 (PMID: 24705847).
2. Zhang HL. et al. 2012. Association between class III β-tubulin expression and response to paclitaxel/vinorelbine-based chemotherapy for non-small cell lung cancer: a meta-analysis. Lung Cancer 77(1):9-15 (PMID: 22306125).
3. Vilmar A. et al. 2012. RT-PCR versus immunohistochemistry for correlation and quantification of ERCC1, BRCA1, TUBB3 and RRM1 in NSCLC. Lung Cancer 75(3):306-12 (PMID: 21865087).
4. Vilmar AC. et al. 2011. Class III β-tubulin in advanced NSCLC of adenocarcinoma subtype predicts superior outcome in a randomized trial. Clin. Cancer Res. 17(15):5205-14 (PMID: 21880572).

FIG. 13K

Carboplatin  ✗ (Poor Response)

Markers

ERCC1

Evidence Details

Evidence from clinical studies in lung cancer associates high ERCC1 expression with poor response to platinum-based therapy. A meta-analysis of 11 small clinical studies concluded that NSCLC patients with high ERCC1 levels, treated with platinum-based therapy have a significantly lower response (risk ratio (RR) = 0.80) and significantly higher risk of death (hazard ratio (HR) = 2.04) when compared to patients with low ERCC1 levels. [1-4]

Marker Details

ERCC1  IHC Positive

Drug Description

A second-generation platinum compound with a broad spectrum of antineoplastic properties. Carboplatin contains a platinum atom complexed with two ammonia groups and a cyclobutane-dicarboxyl residue. This agent is activated intracellularly to form reactive platinum complexes that bind to nucleophilic groups such as GC-rich sites in DNA, thereby inducing intrastrand and interstrand DNA cross-links, as well as DNA-protein cross-links. These carboplatin-induced DNA and protein effects result in apoptosis and cell growth inhibition. This agent possesses tumoricidal activity similar to that of its parent compound, cisplatin, but is more stable and less toxic.
*Source: The National Cancer Institute's Cancer Drug Information*

References

1. Zhang Q et al. 2014. A prospective study of biomarker-guided chemotherapy in patients with non-small cell lung cancer. Cancer Chemother. Pharmacol. 74(4):839-46 (PMID: 25118181).
2. Roth JA et al. 2011. Prognostic role of ERCC1 in advanced non-small-cell lung cancer: a systematic review and meta-analysis. Clin Lung Cancer 12(6):393-401 (PMID: 21729796).
3. Olaussen KA et al. 2006. DNA repair by ERCC1 in non-small-cell lung cancer and cisplatin-based adjuvant chemotherapy. N. Engl. J. Med. 355(10):983-91 (PMID: 16957145).
4. Lord RV et al. 2002. Low ERCC1 expression correlates with prolonged survival after cisplatin plus gemcitabine chemotherapy in non-small cell lung cancer. Clin. Cancer Res. 8(7):2286-91 (PMID: 12114432).

FIG. 13L

Cisplatin    ✗ (Poor Response)

Markers

ERCC1

Evidence Details

Evidence from clinical studies in lung cancer associates high ERCC1 expression with poor response to platinum-based therapy. A meta-analysis of 11 small clinical studies concluded that NSCLC patients with high ERCC1 levels, treated with platinum-based therapy have a significantly lower response (risk ratio (RR) = 0.80) and significantly higher risk of death (hazard ratio (HR) = 2.04) when compared to patients with low ERCC1 levels. [1-4]

Marker Details

ERCC1  IHC Positive

Drug Description

An alkylating-like inorganic platinum agent (cis-diamminedichloroplatinum) with antineoplastic activity. Cisplatin forms highly reactive, charged, platinum complexes which bind to nucleophilic groups such as GC-rich sites in DNA inducing intrastrand and interstrand DNA cross-links, as well as DNA-protein cross-links. These cross-links result in apoptosis and cell growth inhibition.
*Source: The National Cancer Institute's Cancer Drug Information*

References

1. Zhang Q et al. 2014. A prospective study of biomarker-guided chemotherapy in patients with non-small cell lung cancer. *Cancer Chemother. Pharmacol.* 74(4):839-46 [PMID: 25119181].
2. Roth JA et al. 2011. Prognostic role of ERCC1 in advanced non-small-cell lung cancer: a systematic review and meta-analysis. *Clin Lung Cancer* 12(6):393-401 [PMID: 21723790].
3. Olaussen KA et al. 2006. DNA repair by ERCC1 in non-small-cell lung cancer and cisplatin-based adjuvant chemotherapy. *N. Engl. J. Med.* 355(10):983-91 [PMID: 16957145].
4. Lord RV et al. 2002. Low ERCC1 expression correlates with prolonged survival after cisplatin plus gemcitabine chemotherapy in non-small cell lung cancer. *Clin. Cancer Res.* 8(7):2286-91 [PMID: 12114433].

FIG. 13M

Limitations of Gene Coverage

For each test gene, the percentage of the gene target regions and COSMIC mutations covered by less than 100 reads is provided below:

| Gene | COSMIC variants not covered | % of gene under covered | Gene | COSMIC variants not covered | % of gene under covered |
|---|---|---|---|---|---|
| ALK | 3/392 | 1.35 | BRAF | 3/371 | 5.60 |
| EGFR | 1/364 | 0.28 | ERBB2 | 1/227 | 3.94 |
| MET | 44/342 | 10.85 | VHL | 315/732 | 35.99 |

Signatures

FIG. 13N

Supplementary Information

Malignant transformation of cells is driven largely by somatic DNA mutations. While current modes of treatment are successful in limiting the growth of a large number of tumors, there is considerable variability in the degree of effectiveness of conventional therapies. It is often difficult to predict the sensitivity of a given therapy for a particular patient. Identification of changes in the genome would enable personalized treatment. Increasing evidence links somatic mutations in key genes involved in cancer to overall outcome and / or responsiveness to particular types of therapy. It may thus be useful to determine which of these mutations is present in a given patient's tumor type. Additionally, variants in certain genes associated with drug metabolism and transport may provide added information on response to chemotherapy.

Test Description

StrandAdvantage Test is a Next Generation Sequencing based test which profiles a patient's tumor genotype in order to detect genetic alterations in key regions in a comprehensive panel of well curated 152 tumor genes. Some of the alterations detected may have bearing on prognosis and / or therapeutic options and may provide relevant information that allows a doctor and / or to consider various lines of targeted treatment for the patient.

SOC Test Description

The StrandAdvantage SOC test examines certain well studied markers that can impact response to approved therapy for a particular cancer type. These markers are tested by NGS or other methods such as immunohistochemistry.

Genes evaluated by NGS: 10 genes

*ALK, BRAF, EGFR, ERBB2, KRAS, MET, PIK3CA, RET, ROS1, VHL.*

External Lab Tests

| Gene  | Test | Company |
|-------|------|---------|
| TS    | IHC  | ProPath |
| TUBB3 | IHC  | ProPath |
| TLE3  | IHC  | ProPath |
| ERCC1 | IHC  | ProPath |
| PD-L1 | IHC  | ProPath |
| RRM1  | IHC  | ProPath |
| PgP   | IHC  | ProPath |

Methodology

Sample preparation: Genomic DNA isolated from FFPE or any other fresh tumor tissue source is used for preparation of the 'DNA sequencing-ready' library. The DNA is quantified using Qubit and 200 ng is taken for shearing and library preparation. The DNA is sheared by Covaris using appropriate settings for FFPE or intact DNA, to 150 bp. Library preparations using the Sure Select KT2 involves repairing the ends of the sheared DNA and ligating the adaptors and indices. A limited cycle PCR step is performed to generate adequate quantity sequencing libraries.

FIG. 13O

Target Enrichment: The tagged and amplified sample libraries are checked for quality and quantified before enrichment. Approximately 250ng of 6 individual libraries are pooled and combined into a single tube and set up for enrichment to generate targeted sequencing for each sample on a MiSeq sequencer. Target libraries are then amplified using limited PCR steps and about approximately 6pM pooled library is loaded for sequencing.

Sequencing Details: Sequencing is performed using a standard v3 kit on Illumina MiSeq with the expected data output of 8-9 GB. For this panel, the output size of 1.3-1.5 GB per sample results from an optimum cluster density of 900-1100 clusters per sqmm.

Analysis

The trimmed FASTQ files were generated using MiSeq Reporter from Illumina. The reads were aligned against the whole genome build hg19 using Strand® NGS v2.6.1. Five base pairs from the 3' end of the reads were trimmed, as were 3' end bases with quality below 10. Reads which had length less than 25 bp after trimming were not considered for alignment. A maximum of 5 matches of alignment score at least 85% were computed. The maximum allowed gap was 45% of the read length to identify medium sized InDels. The reads which had an alignment score below 95 or were unaligned are aligned using the split read aligner. Reads that failed vendor QC, reads with average quality less than 20, reads with ambiguous characters as well as duplicate reads were all filtered out. The Strand® NGS binomial variant caller was used to detect variants at locations in the target regions covered by a minimum of 10 reads with at least 2 variant reads. Variants with a decibel score of at least 50 were reported and annotated with dbSNP141. Variants with supporting reads <2%, tail distance bias -PV4 <0.00001, substitution variants with a StrandBias >90% and total reads >100 and InDel variants in homopolymer stretch >4 with supporting reads <10% were filtered out. Targeted copy number analysis is performed against a profile for 10 normal FFPE samples using GC-bias correction. Structural variants (gene fusions) are identified based on split reads with a minimum of 10 reads supporting the variant. A single merged VCF file was created including SNVs, CNVs and SVs and uploaded into StrandOmics v3.0 for further interpretation and reporting. Annotation and prioritization of variants was done by automated pipelines in StrandOmics. The StrandOmics user interface was then used for identifying variants of interest and for reporting these variants. All variants reported were verified to have good read quality using the Strand® NGS genome browser before final reporting.

Primary Tools

STRANDNGS: Strand® NGS (http://www.strand-ngs.com) is an NGS analysis platform from Strand Life Sciences. It comprises algorithms for alignment, variant calling, copy number variation analysis, and structural variant calling. A built-in genome browser enables inspection of read level data. Several QC steps enable inspection of read quality. STRAND® NGS has been cited in over 50 publications.

Literature: Strand has developed its text mining technology which is integrated with Strand's proprietary data mining platform - Avadis®. Avadis Text Mining engine can extract key concepts, sentiments, and relationships from textual or "unstructured" data and convert them to a structured format that can be used to create predictive models. In the first pass, PubMed abstracts are processed using this tool to find mutations in key genes. All extracted information is then manually curated for validation.

StrandOmics: StrandOmics (https://clinical.strandomics.com) is a clinical genomics interpretation and reporting platform from Strand Life Sciences. The StrandOmics Variant Annotation engine includes algorithms to identify variant impact from both public content (HGMD, ClinVar, OMIM, HPO, dbSNP, 1000 Genomes, Exome Variant Server, COSMIC and bioinformatics prediction tools such as SIFT, LRT, PolyPhen HVAR/HDIV, Mutation Taster, FATHMM) and proprietary content on genes, diseases and therapeutic impact of somatic variants. The 'Interpretation interface' in StrandOmics allows quick filtering and evaluation of variants along with capture of justification for inclusion/exclusion. The 'Reporting interface' in StrandOmics enables identified variants to be carried into template-driven reports efficiently. StrandOmics has already been used for interpretation and reporting of approximately one thousand clinical cases.

Limitations and Disclaimer

Treatment Decisions based upon test results

FIG. 13P

This clinical report should be carefully assessed by the treating physician and further interpreted along with clinical, histopathological findings, contraindications and guidelines before deciding the course of therapy. Treatment decisions are the responsibility of the clinician. It is recommended that the most recent block is used for testing as the mutation profile may change in response to treatment and hence differ at different sampling points.

Interpretation of Variants

The therapeutic implications listed in the report are based on the interpretation derived as a result of analysis of up-to-date scientific literature from various sources. Interpretation of this report is based on the clinical diagnosis provided and certain other relevant clinical information provided. Some findings listed in this report may be based on pre-clinical studies or studies not in the given patient's tumor type. Not all mutations detected are listed in this report. Inclusion of mutations is dependent upon our assessment of their significance. A mutation is considered actionable or significant if it can be linked to potential response or resistance to a particular therapy, or prognosis or diagnosis or sub-typing of the disease. Variants identified are not confirmed somatic variants. Additional testing may be warranted in certain cases are suspected to be germline variants.

Genomic Alterations Detection Limitations

A negative result from StrandAdvantage test cannot rule out the possibility that the tested individual's tumor sample carries mutations not previously associated with cancer and hence not included in the panel. StrandAdvantage analyzes point mutations and indels >5% frequency in the tumor DNA sample. There is a possibility that the tumor sample carries mutations at a lower frequency. These low frequency mutations may not be detected by the test. The quality of sequencing and coverage varies between regions. If the mutations are in regions of low or no coverage, they may be missed. Many factors such as homopolymers, GC-rich regions etc. influence the quality of sequencing and coverage. This may result in an occasional error in sequence reads or lack of detection of a particular genetic lesion.

Sample Quality and Analytical Sensitivity

Improper formalin fixing of the tissue and storage of the formalin fixed paraffin embedded (FFPE) blocks leads to DNA cross linking and degradation and results in poor quality of DNA. The starting quality and quantity of DNA from the tumor specimens also have an impact on the analytical sensitivity of StrandAdvantage. Genes with low coverage are listed in every report and can vary from sample to sample.

Tumor Content and Analytical Sensitivity

The StrandAdvantage test requires tumor specimens with at least 30% tumor content. If a tumor specimen has less than 30% tumor content, we cannot guarantee that StrandAdvantage will be able to detect ANY somatic mutations. Furthermore, even in samples with >30% tumor content, the sensitivity of the test can vary from sample to sample due to tumor heterogeneity.

Prediction of Clinical Response

The StrandAdvantage test report does not guarantee that a suggested drug will be effective in the particular case. It also does not promise that a drug with potential lack of effect will indeed provide no clinical benefit.

Reimbursement

Strand Life Sciences does not guarantee that the cost of this test will be reimbursed by a healthcare provider, insurer or other third party payor.

Compliance Statement

StrandAdvantage is a laboratory developed test/procedure that was developed by Strand Genomics Inc., a subsidiary of Strand Life Sciences. It has not been cleared or approved by the US Food and Drug Administration. StrandAdvantage is intended to be used for clinical purposes and its performance characteristics have been determined by Strand Genomics Inc. Strand Genomics's clinical reference laboratory is certified under the CLIA (Clinical Laboratory Improvement Amendments of 1988); CLIA ID NUMBER – 05D2081162.

End of report

FIG. 13Q

Empowering Personalized Cancer Care    Email: client.services@strandis.com

| | | |
|---|---|---|
| Patient xxx | TRF ID xxx | Clinician xxx |
| Gender Female | Block ID xxx | Hospital xxx |
| Age Not Available | Specimen Type FFPE Curls and H&E Slide | Test StrandAdvantage Test |
| MRN * | Specimen Site Bone | Type Full Report |
| | Date Collected 2015-08-14 | Date Generated 2015-09-03 |
| | Date Received 2015-07-29 | Report Version v1 |

| Clinical Indications | Breast carcinoma (ER/PR -ve, HER2 -ve) |
|---|---|

Summary for Standard Drugs

| Therapy | Identified Marker | Tested Markers | Recommendation |
|---|---|---|---|
| Epirubicin | -- | TOP2A | ✓ |
| Bevacizumab | -- | VHL | ✓ |
| Doxorubicin | -- | TOP2A | ✓ |
| Cisplatin | -- | BRCA2, BRCA1 | ✓ |
| Tamoxifen | -- | EGFR, HER2, ER, ERBB2 | ✗ |
| Everolimus | -- | HER2, ER, PIK3CA, PTEN | ✗ |
| Lapatinib | -- | HER2, ERBB2, PIK3CA | ✗ |
| Palbociclib | -- | CDKN2A, HER2, ER | ✗ |
| Pertuzumab | -- | EGFR, HER2, ERBB2, PIK3CA | ✗ |
| Fluorouracil | SMAD4 | SMAD4, DPYD | ✗ |
| Trastuzumab | -- | EGFR, HER2, ERBB2, PIK3CA | ✗ |

Markers for Exemestane, Toremifene, Carboplatin, Goseretin, Fulvestrant, Paclitaxel, Docetaxel, Letrozel, Anastrozole, Capecitabine, Ixabepilone, Cyclophosphamide, Megestrol, Methotrexate, Gemcitabine, Thiotepa, Vinblastine, Eribulin are not part of the StrandAdvantage SOC Report ✓✓✓ Enhanced Response – Better than standard population response due to the presence or absence of specific markers.

✓✓ Enhanced but Limited Response – better than standard population response mitigated by the presence of conflicting markers.

✓ Standard Response – Expected response similar to the typical population response for the specific therapy.

✗ Poor response – Likely poorer response or increased toxicity than the standard population response due to the presence of specific markers.

Summary for Investigational Drugs

| Therapy | Identified Marker | Approved Indications | Trials |
|---|---|---|---|
| Sorafenib | JAK3 | Hepatocellular carcinoma, Kidney Cancer, Thyroid Cancer | NCT01640665 |

*FIG. 14A*

| Therapy | Identified Marker | Approved Indications | Trials |
|---|---|---|---|
| Bevacizumab | SMAD4 | Non-small Cell Lung Cancer (NSCLC), Ovarian Epithelial Cancer, Kidney Cancer, Glioblastoma, Colorectal Cancer | NCT00733408, NCT02101385 |
| Everolimus | PIK3CA | Pancreatic Neuroendocrine Tumor, Kidney Cancer, Astrocytoma, Hormone receptor-positive HER2-negative Breast Cancer | NCT02101385, NCT02120469 |
| PI3K Inhibitor BYL719 | PIK3CA | -- | NCT01623349 |
| Buparlisib | PIK3CA | -- | NCT01623349, NCT02000882 |
| WEE1 Inhibitor MK-1775 | TP53 | -- | NCT01748825, NCT01827384 |
| Dinaciclib | MYC | -- | NCT01624441, NCT01676753 |
| MDM2/MDMX inhibitor ALRN-6924 | MDM2 | -- | NCT02264613 |
| MDM2 Inhibitor AMG-232 | MDM2 | -- | NCT01723020 |

Prognosis

| Clinical Impact | Identified Marker | Description |
|---|---|---|
| Poor | TP53 | Associated with an aggressive phenotype and poor prognosis |

| Patient | ▓▓▓ | Test ID | SOMATIC-81 | Clinician | ▓▓▓ |
|---|---|---|---|---|---|
| Cancer | ▓▓▓ | Block ID | ▓▓▓ | Hospital | ▓▓▓ |
| Age | Not Available | Specimen Type | FFPE Curls and H&E Slide | Test | StrandAdvantage Test |
| MRN | - | Specimen Site | Colon | Type | Full Report |
| | | Date Collected | 2015-07-23 | Date Generated | 2015-09-03 |
| | | Date Received | 2015-07-28 | Report Version | v1 |

Clinical Indications — Colon Adenocarcinoma

Summary for Standard Drugs

| Therapy | Identified Markers | Tested Markers | Recommendation |
|---|---|---|---|
| Fluorouracil | SMAD4 | MSI, DPYD, UGT1A1, TS, MTHFR | ✓✓✓ |
| Irinotecan | TOP1 | TOP1, UGT1A1 | ✓✓✓ |
| Capecitabine | -- | DPYD | ✓ |
| Bevacizumab | -- | KRAS | ✓ |
| Oxaliplatin | -- | KRAS, ERCC1 | ✓ |
| Panitumumab | BRAF | EGFR, NRAS, KRAS, BRAF, MET, PIK3CA, PTEN | ✗ |
| Cetuximab | BRAF | EGFR, NRAS, KRAS, BRAF, MET, PIK3CA, PTEN | ✗ |

Markers for Zv-Aflibercept, Leucovorin, Regorafenib are not part of the StrandAdvantage SOC Report.

✓✓✓ Enhanced Response - Better than standard population response due to the presence or absence of specific markers.
✓✓ Enhanced but Limited Response - Better than standard population response mitigated by the presence of conflicting markers.
✓ Standard Response - Expected response similar to the typical population response for the specific therapy
✗ Poor response - Likely poorer response or increased toxicity than the standard population response due to the presence of specific markers.

Summary for Investigational Drugs

| Therapy | Identified Marker | Approved Indications | Trials |
|---|---|---|---|
| Dabrafenib | BRAF | Melanoma | NCT01760918, NCT01902173 |
| Vemurafenib | BRAF | Melanoma | NCT01787500, NCT02104916 |
| Regorafenib | BRAF | Gastrointestinal Stromal Tumor (GIST), Colorectal Cancer | -- |
| Trametinib | BRAF | Melanoma | NCT01760918, NCT02079740 |

FIG. 15A

Fluorouracil  ✓✓✓ (Enhanced Response)

Markers

MSI, SMAD4, TS

Evidence Details

Although loss of SMAD4 is associated with poor response to 5-fluorouracil, MSS (MSI stable) and TS IHC negative are strong markers for response to 5-fluorouracil. Large clinical studies suggest that patients with MSS tumors in stage II CRC, respond better to 5-FU therapy than those with MSI-H tumors. Clinical studies strongly suggest an association of therapy benefit with 5-FU in tumors with low TS levels. A meta-analysis of 24 studies associated a relative ratio 1.63 for overall response rate in TS low patients. [1,2] [3-5] [6,7] [8,9]

Marker Details

MSI   Genetic Testing Negative

SMAD4   Deletion
Loss of function variant results in loss of SMAD4 protein function, promoting oncogenesis [10,11]

TS   IHC Negative

Drug Description

An antimetabolite fluoropyrimidine analog of the nucleoside pyrimidine with antineoplastic activity. Fluorouracil and its metabolites possess a number of different mechanisms of action. In vivo, fluorouracil is converted to the active metabolite 5-fluoroxyuridine monophosphate (F-UMP); replacing uracil, F-UMP incorporates into RNA and inhibits RNA processing, thereby inhibiting cell growth. Another active metabolite, 5-5-fluoro-2'-deoxyuridine-5'-O-monophosphate (F-dUMP), inhibits thymidylate synthase, resulting in the depletion of thymidine triphosphate (TTP), one of the four nucleotide triphosphates used in the in vivo synthesis of DNA. Other fluorouracil metabolites incorporate into both RNA and DNA; incorporation into RNA results in major effects on both RNA processing and functions.
Source: The National Cancer Institute's Cancer Drug Information References 1. Alhopuro P et al. 2005. SMAD4 levels and response to 5-fluorouracil in colorectal cancer. Clin. Cancer Res. 11(17):6311-6 [PMID: 16144935].
2. Boulay JL et al. 2002. SMAD4 is a predictive marker for 5-fluorouracil-based chemotherapy in patients with colorectal cancer. Br. J. Cancer 87(6):630-4 [PMID: 12237773].
3. Qiu LX et al. 2008. Predictive value of thymidylate synthase expression in advanced colorectal cancer patients receiving fluoropyrimidine-based chemotherapy: evidence from 24 studies. Int. J. Cancer 123(10):2384-9 [PMID: 18729195].
4. Popat S et al. 2004. Thymidylate synthase expression and prognosis in colorectal cancer: a systematic review and meta-analysis. J. Clin. Oncol. 22(3):529-36 [PMID: 14752078].
5. Panczyk M 2014. Pharmacogenetics research on chemotherapy resistance in colorectal cancer over the last 20 years. World J. Gastroenterol. 20(29):9775-827 [PMID: 25110414].

FIG. 15B

6. Sinicrope FA 2010. DNA mismatch repair and adjuvant chemotherapy in sporadic colon cancer. *Nat Rev Clin Oncol* 7(3):174-7 [PMID: 20180798].
7. Benatti P et al. 2005. Microsatellite instability and colorectal cancer prognosis. *Clin. Cancer Res.* 11(23):8332-40 [PMID: 16322293].
8. Zhang B et al. 2014. Loss of Smad4 in colorectal cancer induces resistance to 5-fluorouracil through activating Akt pathway. *Br. J. Cancer* 110(4):946-57 [PMID: 24384683].
9. Papageorgis P et al. 2011. Smad4 inactivation promotes malignancy and drug resistance of colon cancer. *Cancer Res.* 71(3):998-1008 [PMID: 21245094].
10. Ma Y 2014. Deletion and down-regulation of SMAD4 gene in colorectal cancers in a Chinese population *Chin J Cancer Res.* 26(5):525-31 [PMID: 25400417].
11. Miyaki M et al. 2003. Role of Smad4 (DPC4) inactivation in human cancer. *Biochem. Biophys. Res. Commun.* 306(4):799-804 [PMID: 13821112].

Summary for Investigational Drugs

| Therapy | Identified Marker | Approved Indications | Trials |
|---|---|---|---|
| Palbociclib | CCND1 | Hormone receptor-positive HER2-negative Breast Cancer | NCT03022382, NCT02389842 |
| Temsirolimus | STK11 | Kidney Cancer | NCT02423954 |
| CDK4/6 Inhibitor LEE011 | CCND1 | --- | NCT02187783 |
| mTOR Kinase Inhibitor AZD2014 | STK11 | --- | NCT02193633 |

Summary for Investigational Drugs

| Therapy | Matched Marker | Approved Indications | Trials |
|---|---|---|---|
| Palbociclib | CCND1 | Hormone receptor-positive HER2-negative Breast Cancer | NCT02022982, NCT02338642 |
| Temsirolimus | STK11 | Kidney Cancer | NCT02423954 |
| CDK4/6 inhibitor LEE 011 | CCND1 | -- | NCT02187783 |
| mTOR Kinase inhibitor AZD2014 | STK11 | -- | NCT02193633 |

With the utilization of Next Generation Sequencing (NGS) technology the 152-gene pan-cancer panel provides a complete view of genomic changes in solid tumors matched to relevant treatment options and clinical trials.

The StrandAdvantage test results are released in two stages, Standard of Care (SOC) Test and the full 152 gene panel. The Standard of Care (SOC) Test results in 8-10 days* and provides NCCN-recommended gene tests for Breast Cancer, Colorectal Cancer, and Lung Cancer with IHC markers. The full 152-gene panel is delivered 2 weeks* later with the complete StrandAdvantage test results.

*The above TAT does not apply to samples that do not meet the sample acceptance criteria. See StrandAdvantage Specimen Preparation Instructions for detailed sample criteria.

STANDARD OF CARE TEST

| | BREAST | | | COLON | | | LUNG | | |
|---|---|---|---|---|---|---|---|---|---|
| NGS: | BRCA1 BRCA2 CDKN2A DPYD | ERBB2 EGFR PIK3CA PTEN | SMAD4 TOP2A VHL | APC BRAF DPYD EGFR | KRAS MET NRAS PIK3CA | PTEN SMAD4 UGT1A1 | ALK BRAF EGFR ERBB2 | KRAS MET PIK3CA | RET ROS VHL |
| IHC/PCR*: | ER PR MDR1 | PTEN TOP2A TS | TUBB3 ERBB2/HER2 | TS TOPO1 | ERCC1 | MSI* | MDR1 TLE3 TS | TUBB3 ERCC1 | RRM1 PD-L1 |

152-GENE COMPREHENSIVE PANEL

| | | | | | | | |
|---|---|---|---|---|---|---|---|
| ALK | AR | AXL | CDK4 | EGFR | ERBB2 | ERBB3 | ERBB4 |
| ESR1 | FGFR1 | FGFR2 | FGFR3 | FLT1 | FLT3 | FLT4 | HGF |
| JAK1 | JAK2 | JAK3 | KDR | KIT | MET | PDGFRA | PDGFRB |
| RET | SMO | SYK | AKT1 | AKT2 | AKT3 | ATM | BRAF |
| BRCA1 | BRCA2 | C11orf30 | CBL | CCND1 | CCND2 | CCNE1 | CDKN1A |
| CDKN1B | CDKN2A | DDR2 | EP300 | FANCA | FANCC | FANCD2 | FBXW7 |
| GSK3B | HRAS | KRAS | MAP2K1 | MAP2K2 | MAP3K1 | NF1F | MRE11A |
| MTOR | MYCN | MYD88 | NRAS | PIK3CA | PIK3R1 | PIK3R2 | PTEN |
| RAD51C | RAF1 | ROS1 | RPTOR | SRC | STK11 | STK11IP | TSC1 |
| TSC2 | VHL | AURKA | AURKB | BCL2 | BCL2L1 | CSF1R | EPHA3 |
| EZH2 | FGFR4 | IGF1R | MDM2 | MDM4 | NTRK1 | STAT3 | TGFBR2 |
| GNA11 | GNAQ | HNF1E | MED12 | MYC | NF2 | NOTCH1 | NOTCH2 |
| PLK1 | PTPN11 | TET2 | TP53 | CDK8 | CTNNB1 | TNFAIP3 | CHEK1 |
| PARP1 | TOP1 | APC | ATM | ATRX | CHEK2 | DAXX | ERCC1 |
| ERCC2 | ERCC5 | GATA3 | GNAS | GSTP1 | JUN | KEAP1 | MLH1 |
| NFE2L2 | PRKD1 | RAD50 | RAD51 | RB1 | RRM1 | SMAD4 | SPARC |
| TOP2A | TOP2B | XPA | XPC | XRCC1 | ABCB1 | ABCC1 | CYP2B6 |
| CYP2C8 | CYP2C9 | CYP2D6 | DHFR | DPYD | MTHFR | SLC19A1 | SLCO1B1 |
| SULT1A1 | TPMT | TYMP | UGT1A1 | IDH1 | IDH2 | MAP2K4 | PRRX1 |

| TEST RESULT CONSULTATION | COMMENTS/SPECIAL INSTRUCTIONS |
|---|---|
| Strand provides test result consultation to the ordering physician at no charge. ☐ I would like to participate in this service. Please contact me to schedule a consultation for the above patient's completed test results. | |

FIG. 19B $$M(i,j) = \max(M(i-1,j-1)+S(R_1[i], R_2[j]), E(i,j), F(i,j), 0) \qquad (1)$$

$$E(i,j) = \max(E(i-1,j) - g_e, M(i-1,j) - (g_o + g_e)) \qquad (2)$$

$$F(i,j) = \max(F(i,j-1) - g_e, M(i,j-1) - (g_o + g_e)) \qquad (3)$$

$$S(a,b) = \begin{cases} 1, & \text{if } a = b, \\ g_m, & \text{otherwise.} \end{cases} \qquad (4)$$

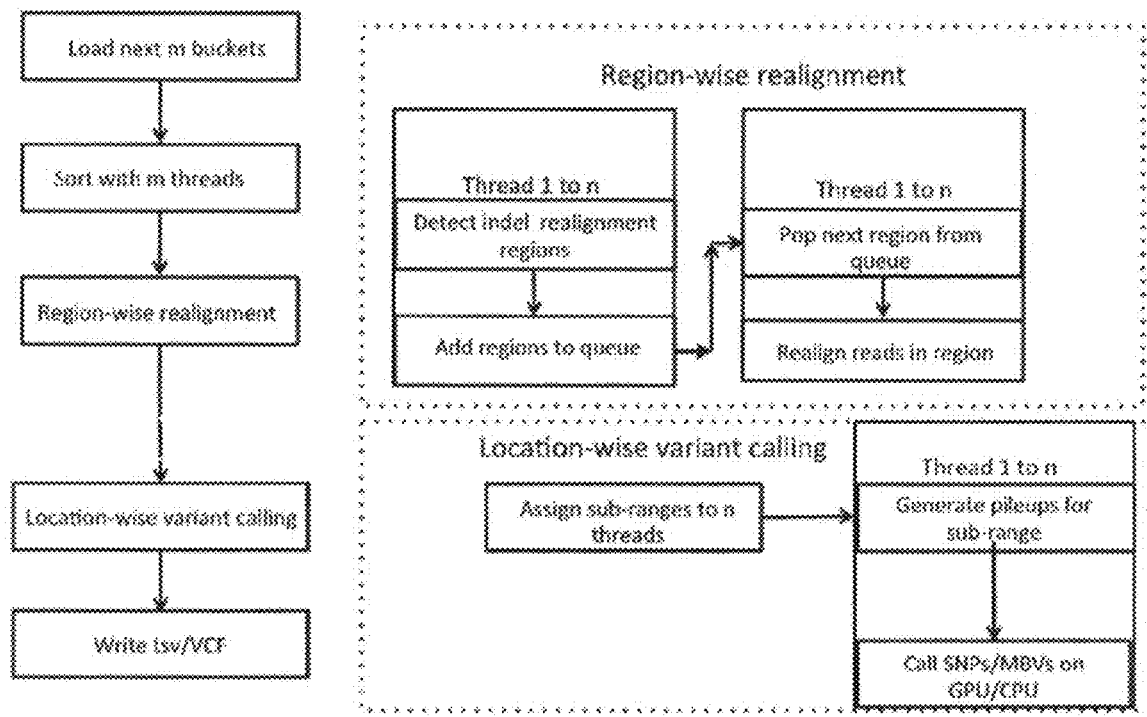
FIG. 24
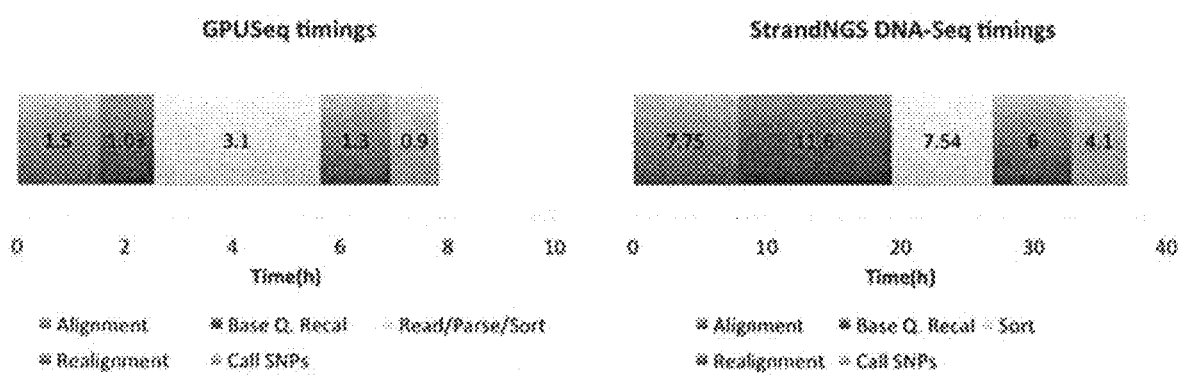
FIG. 25A
FIG. 25B

Type A: Simple split
- Deletion
- Translocation
- Inverted translocation
Type B: Both segment flip (segment swap)
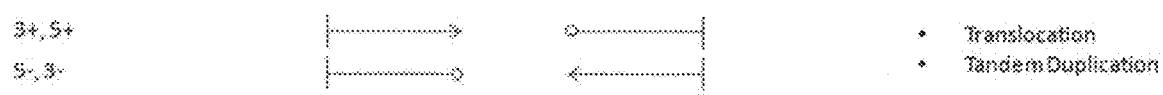
- Translocation
- Tandem Duplication
Type C: One segment flip
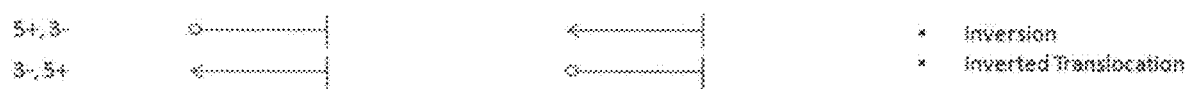
- Inversion
- Inverted Translocation
Type D: One segment flip
- Inversion
- Inverted Translocation
Type E: Partial alignment
- Insertion
FIG. 36

APPARATUSES AND METHODS FOR DETERMINING A PATIENT'S RESPONSE TO MULTIPLE CANCER DRUGS

CROSS REFERENCE TO RELATED APPLICATIONS

This patent application claims priority to Indian Patent applications numbers 1001/CHE/2015, filed Mar. 2, 2015, and 201641000542, filed Jan. 7, 2016. Each of these patent applications are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are apparatuses (including devices and systems) and methods for determining if a patient will respond to a variety of cancer drugs.

BACKGROUND

Although there are a number of cancer therapies known and in development to treat various forms of cancer, it is difficult or impossible to predict which cancer therapies (including cancer drugs) will be effective in treating a particular cancer type of a particular patient. In the last decade there has been a rapid increase in evidence showing the effects of one or a few markers for the treatment of various cancers. Unfortunately, this information has been exceedingly difficult to generalize between patients, particularly to patients not possessing the specific value for the markers examined.

Further, there is a confusing, and sometimes conflicting, variety of markers and marker values relevant to patient drug response. Many markers are DNA based. Deoxyribonucleic acids (DNA) are the building blocks of the genome. Human genome has about 3 billion base pairs organized into 22 pairs of autosomes (1 through 22) and a pair of sex determining chromosomes X and Y. There are 4 DNA bases Adenine, Guanine, Thymine, Cytosine. A series of DNA organized in a specific fashion form a gene. Each gene is associated with one or more traits of the organism such as color of eye, height, etc. Only about 2% of the human genome encodes for around 23000 genes. Rest of the 98% of the genome is not well understood and is currently considered as "junk DNA". The variation in the genome sequence between any two individuals is expected to be less than 0.01%. This small variation at various positions across the human genome is believed to account for all the visible differences among individuals as well as plays a role in health, disease and aging. Some genes are more critical to the normal functioning of the human than others. Currently about 4800 genes are known to have clinical relevance. Some DNA base positions are so critical that even a single DNA base modification or substitution (called a single nucleotide variation or SNV) can cause disease with one or more manifestations. For e.g., CFTR gene is well established to be associated with Cystic Fibrosis with many known mutations. Many mutations are also well established in BRCA1 and BRCA2 genes to be associated with breast cancer, etc. Such SNVs are called Mutations. Variations can also span more than one base position such as multi-base insertions or deletions (indels) and translocations of large regions of the genome. Such changes are called structural variations. These also include copy number variations or CNVs which occur when the number of copies of a region of the human genome deviates from its normal number 2 (for diploid). Any of these variations occurring in clinically sensitive regions of the genome can cause diseases of varying severity depending on the function of the genes involved.

Genetic markers, whose values may be identified by sequencing, such as next-generation sequencing, have been proposed as helping identify therapy response in cancer patients. Next-Generation Sequencing (NGS) refers to the recent advances in sequencing the deoxyribonucleic acids (DNA) in a massively parallel manner faster and cheaper without loss of accuracy compared to earlier methods such as Sanger sequencing. While the cost of sequencing the first complete human genome took as 13 years and cost about 3 billion USD at a rate of $1 per base in 2000, many laboratories around the world can now apply NGS to sequence human genomes routinely for about $1000 (or $0.000003 per base sequenced) per genome. NGS technology is agnostic of the origin of the DNA (i.e., source organism). There are a number of vendors of NGS technology with Illumina leading the market with several variant products including X10, HiSeq, Miseq and NextSeq. Life technologies Ion torrent platform is the second largest player. Various smaller players are attempting to break into this market.

Since the genome of every individual in this world is unique, there is no such thing called "normal genome" or "standard genome". However, in order to serve as a reference, free and open reference genome databases are made available to the scientific research community (academic and commercial) by National Institutes of Health in USA. The human genome assembly builds (the stable hg19 build and the latest hg20 build) and annotations are constantly upgraded and also enhanced by external groups marking their own annotations to the genome builds released by NIH.

What is needed are rapid and accurate methods and apparatuses for determining which therapies may be effective (and/or ineffective) in treating a particular patient.

Described herein are methods apparatuses that may provide a caregiver (e.g. physician, nurse, etc.) to treat a cancer patient by predicting which drugs may be effective in treating that patient. As will be described in greater detail below, these methods and apparatuses may improve traditional clinical genomics, and may combine them with other marker information and provide powerful and accurate predictions for patient therapy.

Clinical genomics is the application of NGS and other genomic technologies for clinical utility such as diagnosis of a disease at the molecular (DNA, RNA, or Protein) level. Most currently published clinical genomics methods involve one or more of the following steps: identifying genes or regions of the genome of interest to a particular disease or group of diseases. (Target regions selection); designing a method to capture only the target DNA regions of interest. (Target capture); amplification of the target DNA capture by polymerase chain reaction (PCR); prepare libraries for NGS; NGS and generation of millions of short reads of same length (around 75 to 150 bases each); aligning the short reads coming out of NGS to the human reference genome hg19 allowing for a reasonable number of mismatches to account for SNVs and small indels. Many open source or commercial algorithms and tools are available to perform this step of the analysis. From the aligned regions of the genome, calling all SNVs, indels and CNVs by comparing against the reference genome databases. Many algorithms and tools are available to perform this step of the analysis. Annotation and interpretation of the variations called in the previous step may also be performed. This integrates information from literature curated databases of variant-disease associations for previously published variants. For discovery of novel (previously unknown) clinically relevant variants, various tools are used to predict the possible functional/clinical impact of variants. From these steps, it would be beneficial to generate clear, concise and precise clinical reports that are readily interpretable by physicians to make clinical decisions. An example of a workflow for clinical genomics based diagnostics are illustrated in FIGS. 1A-1B. Additional descriptions and examples are provided below.

SUMMARY OF THE DISCLOSURE

The methods and apparatuses described herein may determine the response of patient having cancer to one or more cancer drugs and/or therapies. In general, these methods and apparatuses may assist a physician in treating a patient. For example, described herein are marker processing apparatuses that can receive a wide variety of patient-specific marker values, including marker values that do not match to know maker values (e.g., variants, polymorphisms, etc.), and can determine how equivalent such patient-specific marker values to known markers. The apparatus (e.g., device, system, etc.) may then apply this equivalence determination to estimate a patient's response to a variety of different drugs. Methods of operating the maker processing apparatuses are also described. The marker processing apparatuses described herein are capable of receiving and transforming a number of different types of markers, including genetic sequence information (polynucleotide sequences), immunohistochemical information, fluorescent in-situ hybridization information, etc. Each of these markers may have multiple possible values, only some of which are known. Examples of values may include, for polynucleotide markers: polymorphisms, mutations, truncations, reading frame shift, deletions, repetitions, etc., or any other status of a gene or portion of a gene. Examples of values for florescence markers may include: florescence patterns, florescence intensities, combinations of immunohistochemical markers, tissue-specificity, etc. The known values for the marker(s) may be linked to clinical or literature information regarding the efficacy of one or more drugs or therapies.

In addition, described herein are apparatuses that may assist in interpreting marker information received from a patient, which may be separate from or integrated into the maker processing apparatuses. In particular, graphical processing units for graphically processing marker information.

Also described herein are methods and kits for determining if a patient has one or more makers, including genetic screens/panels and methods of performing them. Also described are immunohistochemical methods and markers.

The methods and apparatuses described herein may generally be used to concurrently examine a large number of cancer drugs and therapies. In some variations the user (physician, technician, etc.) may input into the marker processing apparatus the type of cancer or type of tissue being examined by the markers. In general, the marker processing apparatus may operate to analyze a sub-set of cancer therapies (e.g., drugs, treatments, dosing regimes, clinical trials, etc.) quickly in an initial, streamlined phase, before analyzing a larger set of cancer therapies. The methods or apparatus may be adapted to provide a rapid response on this sub-set of cancer therapies by first receiving the patient-specific marker values (including receiving all patient-specific marker values for the larger set of markers), and determining a level of equivalence compared to a sub-set of markers predetermined to have an effect on the sub-set of cancer therapies (such as a set of "standard of care" drugs specific to a type of cancer). The level of equivalence may be quantitative (e.g., between 0 and 100%) or qualitative, e.g., high equivalence (which may include perfect matching), medium equivalence, low equivalence, and no equivalence, etc.

For example, these apparatuses and methods may determine a response of a cancer patient with a specific type of cancer to a plurality of cancer drugs specific to the cancer type of the patient, referred to as the standard of care drugs (for that cancer type, a class of cancer types, or all cancers) and may be limited to this collection of drugs. In some variation this "standard of care" output, indicating a predicted response from the standard of care drugs, may be rapidly determined using the marker processing apparatus, e.g., within 1-14 days of receiving a patient sample, and/or the patient-specific marker values, despite testing for all of the patient-specific marker values in the superset, before continuing to determine responses or predicted responses from other therapies outside of the standard of care.

Any of the methods described herein may optionally include testing a sample from the patient for a plurality of markers to identify patient specific marker values. The marker values tested may include, but are not limited to, genomic events such as single nucleotide variants (SNVs), Insertions and Deletions (InDels), and copy number variants (CNVs). They may also include specific structural variants (SVs) such as translocations, micro satellite instability (MSI) and protein expression levels. The markers may be measured using appropriate technologies including Next Generation Sequencing (NGS), Immunohistochemistry (IHC), Polymerase Chain Reaction (PCR) and fluorescent in-situ hybridizations (FISH). In one example, in reference to colon cancer, the markers tested to determine the response to a set of standard of care drugs for colon cancer comprising makers for at least 14 genes including APC, BRAF, DPYD, EGFR, MET, KRAS, NRAS, PIK3CA, PTEN, SMAD4, UGT1A1, TS, TOP1 and ERCC1 and micro satellite instability (MSI). In this exemplary embodiment, 11 genes (each gene may covered by one or more makers) may be examined to determine patient-specific marker values for markers spanning these genes using an NGS panel (APC, BRAF, DPYD, EGFR, MET, KRAS, NRAS, PIK3CA, PTEN, SMAD4, UGT1A1), and markers for protein expression levels for TS, TOP1 and ERCC1 may be measured via IHC, and MSI may be measured via PCR. Thus, in this example the markers may have known reference values, which may be part of a larger library of reference maker values that are linked (in the library) to a predetermined therapeutic effect. As described herein, the methods may be used to determine from the entire set of patient-specific marker values, a level of equivalence to these reference marker values patient-specific marker values for these markers. A marker processing apparatus may be used to determine a level of equivalence for patient-specific marker values for the standard of care markers and the level(s) of equivalence to reference maker values may be used to significantly more accurately weigh possible effects (e.g., predicted outcomes) of one or more of these standard of care drugs to that specific patient. In general, the methods and apparatuses described herein provide for much more than matching of patient-specific marker values (patient values) to known reference values for one or more makers; instead, they provide a nuanced level of equivalence (e.g., high, medium, low, none) that improves their predictive ability well beyond what is currently available.

In another example, an NGS panel may be designed to include genomic regions from a set of 152 genes that modulate the response to chemotherapies and targeted therapies, or modulate the metabolism of some of these drugs, or impact prognosis and disease progression. Further, in this exemplary embodiment, the regions included in the panel may be optimized to cover all genic regions for tumor suppressor genes, all regions that cover variants from one version of the Catalogue Of Somatic Mutations In Cancer (COSMIC) database for oncogenes, regions that rover known translocations, regions that optimize copy number detection and regions that contain germ line mutations known to impact disease metabolism or prognosis. For each marker tested using IHC, the antibody may be designed and the protocol standardized to optimize the detection of protein expression from the patient sample.

Any appropriate patient sample may be used. For example, a sample drawn from the patient may be fresh tissue extracted from the area of the cancer via a biopsy, and/or stored in the form of Formalin-fixed, paraffin-embedded (FFPE) tissue. On one hand, FFPE tissues render themselves to long term storage of the sample. On the other hand, the quality of DNA in FFPE tissues is highly variable and poses significant challenges to various aspects of the methods of the invention. In particular, the steps of the lab protocol of the NGS panel are standardized to handle FFPE tissues with a wide range of quality. In one exemplary embodiment, the protocol includes pulldown in-solution using SureSelect XT2 RNA baits and sequencing using Illumina's sequencing instrument such as MiSeq, NextSeq or HiSeq. As described herein, the lab protocol may be optimized to handle samples that contain at least 20% of tumor content and at least 200 ng of input tumor DNA.

The raw data generated from the lab for the NGS panel may be in the form of sequence reads, 2×151 bp in length in one exemplary embodiment, and are transformed to patient-specific marker values by performing alignment, SNP detection, copy number calling, translocation detection, and Quality Checks (QC), which may be executed as part of a patient-specific marker value generation procedure. In one exemplary embodiment, these algorithms are executed by a computer processor. In another embodiment, these steps may be executed by a computer processor in tandem with a graphics processor resulting in overall speed improvements of up to 10×.

The patient-specific marker value generation methods may include pre-alignment filtering steps and steps such as trimming low quality bases and using contaminant databases to filter out noise. An alignment algorithm may use a Burrows-Wheeler Transform (BWT) based index search followed by a Dynamic Programming (DP) method to find an optimal match for each read. It may include steps for seeding matches from the read, aggregating matches to identify candidate regions, performing a banded DP, mate rescue, split read alignment, and local realignment. The SNV detection may use an iterative binomial caller and include a framework to specify complex Boolean filters based on properties of reads near the location of the SNP being called. The copy number calling method (steps) may involve creating GC-corrected normalized coverages for the normal profile, in one embodiment by computing iterative average for each region. Copy number calls made at the exon level may be summarized to the gene level. The translocation detection may use split read alignment to identify known translocation. The patient-specific marker value generation steps may also include QC checks to determine sample contamination, sample degradation and sample mixup using the SNV calls. The patient-specific marker value generation steps may also include checks on number of novel SNP calls, the number of copy number calls to QC the algorithm execution, etc., The QC results may be used to pass or reject the patient-specific marker values generated by the pipeline for the patient sample.

For markers measured by IHC, the scoring criteria and cut-offs used may be standardized separately for each IHC marker based on published literature and vendor provided catalogues.

Any of the methods described herein may include entering the patient specific marker values into the marker processing apparatus. The marker processing apparatus typically includes a processor (e.g., computer processor), one or more inputs (control, e.g., keyboards, dials, buttons, touch-screens, etc.) and one or more outputs (e.g., screens, connections to screens, etc.). The marker processing apparatus may be software, hardware or firmware. The marker processing apparatus typically includes or is able to read from a database of reference markers, including reference marker values that are linked to functional therapeutic outcome. For example, the marker processing apparatus may include a manually curated database of reference markers and their functional significance. Each reference marker may be annotated, e.g., using peer reviewed journal literature, as having a Loss of Function, a Gain of Function or an Unknown Functional impact on the gene that it falls in.

A marker processing apparatus may also include standard of care logic or rules, called the SOC rules, that may relate collections of reference markers to the expected response of the SOC drugs for a specific tissue. The SOC rules may be manually curated using information from disparate peer reviewed literature. Each rule may be recorded as an expression that quantifies the response of a specific drug in the presence of a marker M in the patient's sample: Response (drug D|marker M causing functional significance F)=R based on literature evidence L.

The marker can be as specific as a single variant, for example, the V600E variant in BRAF gene, or as general as any Loss of Function variant in a gene (e.g., any variant in SMAD4 gene that causes a LOF) or with some intermediate level of generality (e.g., any variant in exons 23, 24 or 25 of ALK gene that causes a GOF). In addition, it can also be the negative of a variant or variant class (e.g., any variant in EGFR gene that does NOT cause a GOF) or a Boolean combination of a plurality of variant classes for the same gene or different genes with specific or generic exceptions (e.g., any variant in EGFR gene except T790M that causes a GOF or any variant in XXX gene that is NOT an in-frame insertion in exon 20 and causes a GOF). The drug reference in the SOC rule may include specific drugs (for e.g., Everolimus) or a class of drugs (e.g., mTOR inhibitors). The functional significance may include loss of function (LOF), gain of function (GOF) or unknown function. The response value for a drug could be sensitive or resistance.

As mentioned, after entering the patient specific marker values into the marker processing apparatus, the marker processing apparatus may be used to determine an equivalence level for the subset of patient specific marker values relative to the reference SOC marker values based on equivalence rules. For each patient-specific marker measured with a specific value, the marker processing apparatus may evaluate its equivalence with any of the reference SOC marker values and may output an equivalence level, such as with high, medium or low confidence. The apparatus may determine how to apply the equivalence rules, dependent on the type of the patient-specific marker value and may annotate the functional significance of the patient specific marker value based on the functional significance of the reference marker value. In one exemplary embodiment of an equivalence rule, a patient specific marker value that indicates a premature truncation in a Tumor Suppressor gene is equivalent to a reference marker with high confidence if it is an exact match or if the reference marker is a premature stop, or a frameshift variant or an Exonic Splicing Silencer (ESS) resulting in a premature stop downstream of the patient specific marker value, and is annotated with a LOF functional significance if such a reference marker is found.

In this aspect of the invention, the marker processing apparatus may then execute the SOC rules based on the functional significance of the patient-specific marker values derived using equivalence to the reference marker values. The marker processing apparatus may execute only the most specific rule for each drug, and may execute all possible rules based on the patient-specific marker values. Once all the rules have been fired, the apparatus may provide an overall recommendation for each drug. Where the response predicted by individual SOC rules for a drug are all consistent, the overall recommendation for the drug may be the same as the individual response prediction. Where the different SOC rules predict contradicting responses, the apparatus may resolve the apparent conflict. In some variations, the apparatus prepares the conflict (e.g., the marker, the relevant patient-specific marker values and/or their levels of equivalence to reference marker values) and present the conflict for manual intervention to resolve the conflict based on the literature evidence associated with each individual SOC rule. Alternatively or additionally, the apparatus may resolve the conflict automatically by applying the weights from the levels of equivalence and/or by applying a SOC rule. The resolved outcome may be recorded in the system as a new specific SOC rule. If the conflict cannot be resolved, the drug response may be called Inconclusive.

The marker processing apparatus may thus be used to predict the estimated drug response given the unique patient-specific marker values for the standard of care set of drugs for a patient sample. The estimated drug response for each drug may vary between Enhanced Response for drugs that are found sensitive and Poor Response for drugs that are found resistant. Conflicting SOC rules may be resolved to predict the response of the drug as either Limited Response or Inconclusive. The SOC drugs for which none of the SOC rules were fired may have a Standard Response for the patient, and may be reported thus. The marker processing apparatus may further be used to generate the patient's report automatically with minimal manual intervention, needed only when a conflict arises. The report may include the estimated response of each of the standard of care drugs for the patient sample, along with the details of the patient-specific marker values that were measured and used to estimate the responses.

In some variations, the response of a cancer patient with a specific type of cancer to a plurality of cancer drugs not specific to the cancer type of the patient, referred to as off-label drugs, and to a plurality of clinical trials for the specific type of cancer is determined using the marker processing apparatus with the object of determining additional therapies that may be applicable to the patient.

For example, the marker processing apparatus may further comprise a collection of cancer pathways that provide for each gene in the panel above, a list of targetable upstream or downstream genes from the pathways. The apparatus may also comprise a plurality of cancer drugs from different tissues and clinical trials annotated with the target gene and additional conditions of applicability.

The marker processing apparatus may perform an equivalence of the patient-specific marker values with the reference marker values to predict the functional significance of the patient-specific marker values as causing Loss of Function or Gain of Function. The patient-specific marker values that are not found equivalent to the curated markers with known functional significance, may be further categorized using bioinformatics predictions, and database lookup.

One step may involve using the marker processing apparatus to prioritize the rest of the variants and shortlist patient-specific marker values that are expected to have a damaging functional significance on targetable genes in cancer pathways. This step may involve using the tools provided by the marker processing apparatus including, but not limited to a tool that enables quick assessment of the cleanliness of the alignment in the neighborhood of the variant location; a tool that displays the copynumber distribution to in superimposing the copynumber calls of the sample against the distribution of calls from each of the panel's regions over the samples in the system; and a tool to present all the relevant information about the marker in a concise visualization.

Another step may involve using an automatically created list of drugs approved in other tissues and clinical trials for the specific tissue to identify additional therapies that may be applicable to the patient, given the patient-specific marker values. Literature evidence to support the applicability of the drug or trial to the patient may be recorded in the marker processing apparatus for reuse in subsequent patient samples.

The marker processing apparatus may further generate the patient's report automatically. In addition to the Standard of Care drugs, the report may include additional off-label drugs and clinical trials applicable to the patient sample, along with the details of the patient-specific marker values that were measured and used to estimate the responses.

For example, described herein are methods of estimating a patient's response to a plurality of cancer drugs using a marker processing apparatus, the method comprising: entering a plurality of patient-specific marker values into the marker processing apparatus, wherein the plurality of patient-specific maker values were identified by testing a patient sample for a plurality of markers to identify the patient-specific marker values; using the marker processing apparatus to determine an equivalence level for at least some of the patient-specific marker values relative to reference marker values in a library of reference marker values for markers associated with the plurality of cancer drugs, wherein the equivalence level includes: high equivalence, low equivalence or no equivalence; and outputting, from the marker processing apparatus, an estimated drug response a plurality of cancer drugs based on the determined equivalence level for the at least some of the patient-specific marker values.

In any of these methods, the method may further comprise using the marker processing apparatus to compare at least some of the patient-specific marker values to the library of reference marker values for markers associated with the plurality of cancer drugs.

Any of these methods may include using the maker processing apparatus to determine the estimated drug response to each of the cancer drugs in the plurality of cancer drugs by, for a marker associated with each drug in the marker processing apparatus, scaling an a reference drug response associated with a reference marker value by the equivalence level for the patient-specific marker values associated with that marker.

The marker processing apparatus may be used to determine an equivalence level for at least some of the patient-specific marker values relative to reference marker values comprises using the marker processing apparatus to compare a subset of the patient-specific marker values to the library of reference marker values for markers associated with the plurality of cancer drugs.

For example, using the marker processing apparatus to determine an equivalence level for at least some of the patient-specific marker values relative to reference marker values may comprise using the marker processing apparatus to compare a subset of the patient-specific marker values for markers correlated to a type of cancer.

Any of these methods may also include testing a sample from the patient for the plurality of markers to identify the patient-specific marker values. As described above, any appropriate testing (NGS, immunohistochemistry, FISH, etc.) may be used. For example, the plurality of markers may include makers for one or more of: next generation sequencing (NGS) markers, immunohistochemical (IHC) markers, or florescent in-situ hybridization (FISH) markers. The methods and apparatuses may also be configured to include selecting, in the marker processing apparatus, a standard of care set of drugs based on a cancer type, and wherein using the marker processing apparatus to compare the patient-specific marker values to the library of reference marker values comprises comparing the patient-specific marker values to the library of reference marker values associated with the selected standard of care set of drugs in the marker processing apparatus.

Any of these methods may also include selecting, in the marker processing apparatus, a standard of care set of drugs based on a cancer type, and wherein using the marker processing apparatus to compare the patient-specific marker values to the library of reference marker values comprises comparing the patient-specific marker values to the library of reference marker values associated with the selected standard of care set of drugs in the marker processing apparatus, and further wherein using the marker processing apparatus to determine the equivalence level for the patient-specific markers relative to reference markers in the library of reference marker values comprises determining the equivalence level for the patient-specific markers relative to the reference markers based on a set of equivalence rules for the selected standard of care set of drugs in the marker processing apparatus.

In general, using the marker processing apparatus to determine an equivalence level may comprise applying a set of equivalence rules when comparing the the patient-specific markers against the reference markers in the library of reference markers values to set the equivalence level to a level selected from the set of: high equivalence, medium equivalence, low equivalence, or no equivalence.

Outputting may include presenting the output of the marker processing apparatus to a user. For example, outputting the estimated drug responses comprises indicating, for each cancer drug in the plurality of cancer drugs, one or more of: enhanced response, standard response, and poor response.

As mentioned above, any of the method described herein may include manually curating the reference marker values and the rules from published literature sources.

A method of predicting a patient's response to a plurality of cancer drugs using a marker processing apparatus may include: testing a sample from the patient for a plurality of markers to identify patient-specific marker values; entering the patient-specific marker values into the marker processing apparatus; selecting, in the marker processing apparatus, a standard of care set of drugs based on a cancer type; using the marker processing apparatus to compare a subset of the patient-specific marker values to a library of reference marker values for markers associated with the selected standard of care set of drugs, and determine an equivalence level for the subset of patient-specific marker values relative to reference marker values based on a set of equivalence rules; and outputting from the marker processing apparatus, an estimated drug response for the standard of care set of drugs based on the determined equivalence level.

Any of these methods may generally include, after quickly performing a standard-of-care check for a subset of standard-of-care drugs as described, a full screen of all of the markers (in some variations excluding the standard of care markers already examined) may be performed against the rest of the reference library marker values to determine which, if any, therapies may be used to treat the patient based on the patient-specific marker values.

For example, any of these methods may include, after outputting the estimated drug response: using the marker processing apparatus to compare all of the rest of the patient-specific marker values that were not part of the subset of patient-specific marker values to the library of reference marker values and determine an equivalence level for all of the rest of the patient-specific marker values relative to reference marker values in the library of reference marker values; and outputting an estimated drug response for a second plurality of drugs based on the determined equivalence level for all of the rest of the patient-specific marker values.

The full analysis may be performed after the standard of care analysis. For example, the standard of care screen may be performed within 1-14 days (e.g., within less than 14 days, less than 13 days, less than 12 days, less than 11 days, less than 10 days, less than 9 days, less than 8 days, less than 7 days, less than 6 days, less than 5 days, less than 4 days, less than 3 days, etc.) from either receiving the patient sample (and therefore determining the patient-specific maker values) or from receiving the patient-specific marker values. Following this, the method may include looking at the remaining markers as described above, and providing output within another three weeks (e.g., within less than 3 weeks, less than 2.5 weeks, less than two weeks, less than 13 days, less than 12 days, less than 11 days, less than 10 days, less than 9 days, less than 8 days, less than 7 days, less than 6 days, less than 5 days, less than 4 days, less than 3 days, etc.) following the SOC results/output. For example, the methods may include the estimated drug response based on the determined equivalence level for the standard of care set of drugs is performed within a first time period; and wherein outputting the estimated drug response for the second plurality of drugs is performed within a second time period following the first time period by at least 4 days.

In general, the methods described herein may include selecting the standard of care set of drugs based on the cancer type comprises selecting a standard of care set of drugs for one of: breast cancer, lung cancer, colon cancer, and melanoma. Outputting the estimated drug response may comprise indicating one or more of: enhanced response, standard response, and poor response.

As mentioned, any of these methods may include resolving conflicts between two or more patient-specific marker values associated one or more markers for a same drug in the standard of care set of drugs. The step of using the marker processing apparatus to determine an equivalence level may include applying the set of equivalence rules to determine if the patient-specific marker value is identical to the reference marker value, functionally similar to the reference marker value, or structurally similar to the reference marker value.

In general, any of these methods may include modifying the equivalence rules (e.g., learning). For example, any of these methods may include modifying the set of equivalence rules based on a determined equivalence level.

The methods may include using the maker processing apparatus to determine the estimated drug response to each of the standard of care cancer drugs in the standard of care set of cancer drugs by scaling a reference drug response associated with a reference marker value by the equivalence level determined for a patient-specific marker value related to that reference marker value.

The method of claim 14, wherein the plurality of markers include one or more of: next generation sequencing (NGS) markers, immunohistochemical (IHC) markers, or florescent in-situ hybridization (FISH) markers.

As mentioned, in any of the maker processing apparatuses described herein may include a database of reference markers, SOC rules (e.g., encoded based on literature values), definitions of equivalence rules. In general, these apparatuses are configured to estimate equivalence (determine equivalence levels) to predict the function of patient-specific marker values.

As mentioned, the plurality of markers may include next generation sequencing (NGS) markers, immunohistochemical (IHC) markers, or florescent in-situ hybridization (FISH) markers, or any other marker.

In any of these methods, using the marker processing apparatus to determine an equivalence level may include applying a set of equivalence rules when comparing the the patient-specific markers against the reference markers in the library of reference markers values to set the equivalence level to a level selected from the set of: high equivalence, medium equivalence, low equivalence, or no equivalence.

Any of the methods described herein may be configured to examine all and/or a subset of reference marker values against patient-specific markers. For example, a method of estimating a patient's response to a plurality of cancer drugs or therapies using a marker processing apparatus may include: entering a plurality of patient-specific marker values into the marker processing apparatus, wherein the plurality of patient-specific maker values were identified by testing a patient sample for a plurality of markers to identify the patient-specific marker values; using the marker processing apparatus to determine an equivalence level for at least some of the patient-specific marker values relative to reference marker values in a library of reference marker values, wherein the equivalence level includes: high equivalence, low equivalence or no equivalence; using the marker processing apparatus to determine patient-specific marker values that are likely benign from those having no equivalence to a reference marker value; using the marker processing apparatus to automatically prioritize patient-specific marker values; identifying drugs or therapies related to markers corresponding to patient-specific marker values having equivalence to a reference marker value; and outputting an estimated response to the identified drug or therapy based on the determined equivalence level patient-specific marker values.

Using the marker processing apparatus to determine an equivalence level may comprise comparing the at least some of the patient-specific marker values to the reference marker values in the library and applying equivalence rules to determine the equivalence levels.

Any of these methods may include associating patient-specific marker values that are equivalent to a reference marker value with high equivalence or low equivalence with a marker characteristic from the reference marker value.

Any of these methods may include associating patient-specific marker values that are equivalent to a reference marker value with high equivalence or low equivalence with a marker characteristic from the reference marker value and comprising one of: gain of function or loss of function.

These methods may include associating patient-specific marker values that are equivalent to a reference marker value with high equivalence or low equivalence with a drug or therapy effect that is already associated with the reference marker value.

These methods may include, after using the marker processing apparatus to determine an equivalence level for at least some of the patient-specific marker values relative to reference marker values in a library of reference marker values, using the marker processing apparatus to find a match from a Catalogue Of Somatic Mutations In Cancer (COSMIC) database of variants for patient-specific marker values having no equivalence to a reference marker value. The methods may further include associating patient-specific marker values having no equivalence to a reference marker value but with a match to the COSMIC database to the matched COSMIC variant. After using the marker processing apparatus to determine an equivalence level for at least some of the patient-specific marker values relative to reference marker values in a library of reference marker values and after using the marker processing apparatus to find matches from the COSMIC database of variants, the method may use the marker processing apparatus to apply a structural rule to patient-specific marker values having no equivalence to a reference marker value and no match to the COSMIC database of variants, to identify a structural defect in a marker referenced by the patient specific marker value.

Any of these methods may also include, after using the marker processing apparatus to determine an equivalence level for at least some of the patient-specific marker values relative to reference marker values in a library of reference marker values, using the marker processing apparatus apply a structural rule to patient-specific marker values having no equivalence to a reference marker value to identify a structural defect in a marker referenced by the patient specific marker value.

For example, any of these methods may also include, after using the marker processing apparatus to determine an equivalence level for at least some of the patient-specific marker values relative to reference marker values in a library of reference marker values, using the marker processing apparatus apply structural rules to patient-specific marker values having no equivalence to a reference marker value to identify a structural defect in a marker referenced by the patient specific marker value, wherein the structural defect comprises one of: low minimum allele frequency, protein shortening, and modification of highly conserved region. The methods may also include associating patient-specific marker values having no equivalence to a reference marker value but with a structural defect, with the structural defect.

Also described herein are methods including using the marker processing apparatus to determine patient-specific marker values that are likely benign from those having no equivalence to a reference marker value comprises identifying patient-specific marker values as likely benign where the patient-specific marker values have no equivalence to a reference marker value, and do not have a match with a Catalogue Of Somatic Mutations In Cancer (COSMIC) database of variants, and for which a set of structural rules does not indicate a structural defect.

Any of these methods may include using the marker processing apparatus to automatically prioritize patient-specific marker values comprises prioritizing based on prioritizing patient-specific marker values having equivalence to a reference marker value before patient-specific marker values that have a match from a Catalogue Of Somatic Mutations In Cancer (COSMIC) database of variants, and before patient-specific markers having a structural defect.

The step of identifying drugs or therapies related to markers corresponding to patient-specific marker values having equivalence to the reference marker values may include identifying drugs or therapies when a marker corresponding to one of the patient-specific marker values is a gene, and identifying a drug or therapy associated with that gene or a gene downstream of the gene.

Any of these methods may include identifying drugs or therapies including identifying drugs or therapies related to markers corresponding to the patient-specific marker values that match to the COSMIC database or have a structural defect in the marker.

In general, any of these methods may perform a pathway analysis to identify targetable genes based on markers corresponding to patient-specific marker values having equivalence to the reference marker values.

For example, described herein are methods of estimating a patient's response to a plurality of cancer drugs or therapies using a marker processing apparatus, the method comprising: entering a plurality of patient-specific marker values into the marker processing apparatus, wherein the plurality of patient-specific maker values were identified by testing a patient sample for a plurality of markers to identify the patient-specific marker values; using the marker processing apparatus to determine an equivalence level for at least some of the patient-specific marker values relative to reference marker values in a library of reference marker values, wherein the equivalence level includes: high equivalence, low equivalence or no equivalence by comparing the patient-specific marker values to the library of reference marker values and applying equivalence rules to determine equivalence level; using the maker processing apparatus to find a match from a Catalogue Of Somatic Mutations In Cancer (COSMIC) database of variants for patient-specific marker values having no equivalence to a reference marker value; using the marker processing apparatus to apply structural rules to patient-specific marker values having no equivalence to a reference marker value and no match with the COSMIC database of variants, to identify a structural defect in the marker; using the marker processing apparatus to determine patient-specific marker values that are likely benign because they have no equivalence to the reference marker, do not match with variants in the COSMIC database of makers, and do not have a structural defect in the marker; using the marker processing apparatus to automatically prioritize patient-specific marker values based first on patient-specific marker values having equivalence to a reference marker value, then on patient-specific marker values that match with the COSMIC database of variants, then based on any structural defect in the maker; and identify drugs or therapies related to the markers corresponding to patient-specific marker values; and outputting an estimated response to the identified drug or therapy.

Also described herein are methods for estimating a patient's response to a plurality of cancer drugs using a marker processing apparatus, the method comprising: (optionally) testing a patient sample for a plurality of markers to determine a plurality of patient-specific marker values; entering the patient-specific marker values into the marker processing apparatus; using the marker processing apparatus to determine an equivalence level for at least some of the patient-specific marker values relative to reference marker values in a library of reference marker values; outputting, from the marker processing apparatus, an estimated drug response for the plurality of cancer drugs based on the determined equivalence level for the at least some of the patient specific marker values (which may optionally be in the form of a report); and modifying the marker processing apparatus based on the equivalence level of the patient-specific marker values.

As mentioned above, any of the method described herein may include using the marker processing apparatus to determine an equivalence level by using the marker processing apparatus to perform one or more (or all) of: applying a set of equivalence rules when comparing the patient-specific markers against the reference markers in the library of reference markers values; setting the equivalence level to a level selected from the set of: high equivalence, medium equivalence, low equivalence, or no equivalence; and estimating the functional significance of the patient-specific marker value based on the functional significance of its equivalent reference marker value.

Any of these methods may include selecting, in the marker processing apparatus, a first plurality of drugs based on cancer type, and using the marker processing apparatus to estimate the patient's response to the selected first plurality of cancer drugs based on the equivalence level of the at least some of the patient specific marker values to the set of reference marker values with a known association to the response of the selected first plurality of cancer drugs.

In general, the method may include using the marker processing apparatus to determine an equivalence level all of the patient-specific marker values relative to reference marker values in the library of reference marker values and determining, using the marker processing apparatus, a second plurality of cancer drugs estimated to have a favorable patient response based on the determined equivalence level for the patient specific marker values.

The method may also include selecting the first plurality of drugs from amongst a set of approved drugs for the cancer type of the patient and recommended drugs for early stage treatment of the cancer type of the patient.

A method of estimating a patient's response to a plurality of cancer drugs may also include selecting the first plurality of drugs based on the cancer type comprises selecting the first plurality of drugs for one of: breast cancer, non-small cell lung cancer, colon cancer, melanoma, ovarian cancer and brain cancer.

In general, the marker processing apparatus may comprise a library of reference marker values, the library comprising an indicator of a functional significance of the reference marker values and an association of the reference marker values to a response of one or more cancer drugs of the selected first plurality of cancer drugs. For example, the library may include a matrix, listing, or any other appropriate data structure including reference marker values and each reference marker value (note that individual markers may have multiple reference marker values in the database) may be linked to a cancer drug and cancer drug response based associated with the reference marker value. The associated cancer drug and response to that cancer drug (and multiple cancer drugs and responses may be linked to the same reference marker value) may be based on clinical data (including published results). The links between drugs, drug response and reference marker values may be two-way, meaning that a drugs and/or drug responses may connect to particular reference marker values.

Thus, any of these methods may include using the library of reference marker values in the marker processing apparatus to estimate a response for each of the selected first plurality of cancer drugs based on the equivalence values of patent-specific reference values that are equivalent to reference marker values which refer to a drug from the first plurality of cancer drugs.

As mentioned, any of these methods and apparatuses may be configured to resolve conflicts when patient-specific marker values have an equivalence level (non-zero or high, medium, low equivalence) for multiple reference marker values. Either the patient-specific reference marker may match with multiple reference marker values (less likely) or different patient-specific maker values may match to multiple reference maker values. These conflicts may be resolve automatically or may be manually resolved with automatic assistance. Conflicts may be resolved using the equivalence level (e.g., weighting potential drug outcomes more heavily where there are higher equivalence values). The apparatus may 'learn' the outcome of the resolved conflicts (particularly when manually or partially manually resolved) and may therefore automatically resolve these conflicts based on the learned resolution. Learning (e.g., progressively enhancing the components of the marker processing apparatus by modifying the marker processing apparatus) may include forming a new rule that the apparatus applies.

For example, any of these methods may include using the library of reference marker values in the marker processing apparatus to estimate a response comprises using the library of reference marker values to estimate a single response for each of the selected first plurality of cancer drugs, by resolving conflicts in estimated responses based on the patent-specific reference values that are equivalent to reference marker values which refer to the same drug from the first plurality of cancer drugs.

As mentioned, in general, the estimated response for each of the drugs (e.g., each of the first plurality of cancer drugs) may comprise one of: enhanced response, poor response or an intermediate response.

In general, the step of outputting from the marker processing apparatus the resport on the first plurality of cancer drugs (e.g., the first set or the standard-of-care set) may be done quickly, e.g., outputting the report within 4 hours or less. A more full report may follow within a few days or weeks, where the full report may predict a response from a larger set of potential therapies (e.g., drugs). For example, any of these methods may include determining the second plurality of cancer drugs estimated to have a favorable response from amongst a second set of drugs. The second set of drugs may include off-label drugs approved or recommended for cancer types other than the cancer type of the patient, and drugs in clinical trials. Any of these methods may also include using the marker processing apparatus to prioritize the patient-specific marker values and identify those that may be targetable by drugs with a favorable response for the patient's cancer and to identify targetable genes from cancer pathways based on those identified as targetable. For example, the second plurality of cancer drugs may be chosen from a database of clinical and pre-clinical studies published in peer reviewed literature.

Any of these methods may include prioritizing the patient specific marker values. The step of using the marker processing apparatus to prioritize the patient-specific marker values may generally include automatically prioritizing by giving a higher priority to patent-specific marker values having a functional significance, giving a moderate significance to patient-specific marker values that have a match from known public database of somatic variants, and giving a lower priority to patient-specific marker values having a damaging prediction based on a standard criteria selected from the group of: protein shortening criteria, conservation criteria, and allele frequency criteria.

As mentioned, any appropriate marker (and marker values) may be used. The plurality of markers may include markers for genomic events including nucleotide variants (SNVs), Insertions and Deletions (InDels), copy number variants (CNVs), structural variants (SVs) including translocations, micro satellite instability (MSI) and protein expression levels.

In any of these methods a patient sample may be tested. Testing the patient sample may include testing a sample from fresh tissue or from formalin-fixed paraffin-embedded (FFPE) blocks, using: Next Generation Sequencing (NGS), Immunohistochemistry (IHC), Polymerase Chain Reaction (PCR) and fluorescent in-situ hybridizations (FISH) to determine the plurality of marker values. Testing a patient sample for a plurality of markers to determine a plurality of patient-specific marker values may include using an automated patient-specific marker value generation pipeline.

The patient-specific marker value generation pipeline may include: aligning, SNP detection, copy number calling, translocation detection, and Quality Checks (QC). For example, the method patient-specific marker value generation pipeline may include: aligning, SNP detection, copy number calling, translocation detection, and Quality Checks (QC), using a Central Processing Unit (CPU) and a Graphical Processing Unit (GPU) to augment the execution on the CPU.

As mentioned, any of these methods may include modifying the marker processing apparatus (e.g., learning) by, e.g., progressively enhancing the components of the marker processing apparatus. Modifying the marker processing apparatus may include enriching the library of reference marker values by patient-specific marker values found equivalent to reference marker values. Modifying the marker processing apparatus may include enriching the association of the library of reference marker values to the response of drugs when conflicts are encountered between patient-specific marker values to a same marker. Modifying the marker processing apparatus may include recording the patient-specific marker values and drug responses reported from the marker processing apparatus for future reference.

In general, a marker processing apparatus may be configured to perform any of the methods described herein. For example, also described herein are marker processing apparatuses to estimate a patient's response to a plurality of cancer drugs, the apparatus comprising: an input to receive patient-specific marker values; a control to allow a user to select a standard of care set of drugs based on a cancer type; one or more computer readable media storing one or more sets of computer readable instructions; a processor in communication with the one or more computer readable media and configured to execute the computer readable instructions to to: compare at least some of the patient-specific marker values to a library of reference marker values associated with a selected standard of care set of drugs and determine an equivalence level for the at least some of the patient-specific markers relative to reference markers in the library of reference marker values based on a set of equivalence rules for the selected standard of care set of drugs in the marker processing apparatus; and output a predicted drug response based on the determined equivalence level.

The processor may be further configured to: compare a remainder of the patient-specific marker values, which were not part of the at least some of the patient-specific marker values already compared to the library of reference markers, to the library of reference marker values and determine an equivalence level for all of the rest of the patient-specific marker values relative to reference marker values in the library of reference marker values.

In any of these apparatuses, the processor may be configured to output an estimated drug response for a second plurality of drugs based on the determined equivalence level for all of the rest of the patient-specific marker values.

The processor may be configured to output the estimated drug response based on the determined equivalence level for the standard of care set of drugs within a first time period and to output the estimated drug response for the second plurality of drugs within a second time period following the first time period by at least 4 days.

In any of these apparatuses, the control may be configured to allow the user to select the standard of care set of drugs based on the cancer type by selecting from one of: breast cancer, lung cancer, colon cancer, and melanoma.

The output may be configured to indicate one or more of; enhanced response, standard response, and poor response (e.g., for each therapy, e.g., drug, presented). The processor may be further configured to resolve conflicts between two or more patient-specific marker values associated with a same drug in the standard of care set of drugs.

In general, the processor may be configured to determine the equivalence level by applying the set of equivalence rules to determine if the patient-specific marker value is identical to the reference marker value, functionally similar to the reference marker value, or structurally similar to the reference marker value. The processor may be configured to modify the set of equivalence rules based on a determined equivalence level. The processor may be configured to determine the estimated drug response to each of the standard of care cancer drugs in the standard of care set of cancer drugs by scaling a reference drug response associated with a reference marker value by the equivalence level determined for a patient-specific marker value related to that reference marker value.

In any of these apparatuses, the processor may be configured to apply the set of equivalence rules when comparing the the patient-specific markers against the reference markers in the library of reference markers values to set the equivalence level to a level selected from the set of: high equivalence, medium equivalence, low equivalence, or no equivalence.

Also described herein are non-transitory computer-readable storage medium storing a set of instructions capable of being executed by a computer processor, that when executed by the computer processor causes the computer to: receive a plurality of patient-specific marker values; receive a user selection of a standard of care set of drugs specific to a cancer type; compare the patient-specific marker values to a library of reference marker values associated with the selected standard of care set of drugs; determine an equivalence level for the patient-specific markers relative to reference markers in the library of reference marker values based on a set of equivalence rules for the selected standard of care set of drugs in the marker processing apparatus; and output an estimated drug response based on the determined equivalence level.

The set of instructions, when executed by the computer processor, may further cause the computer to: compare a remainder of the patient-specific marker values, which were not part of the at least some of the patient-specific marker values already compared to the library of reference markers, to the library of reference marker values and determine an equivalence level for all of the rest of the patient-specific marker values relative to reference marker values in the library of reference marker values.

The set of instructions, when executed by the computer processor, may further cause the computer to: output an estimated drug response for a second plurality of drugs based on the determined equivalence level for all of the rest of the patient-specific marker values. The set of instructions, when executed by the computer processor, may further cause the computer to: output the estimated drug response based on the determined equivalence level for the standard of care set of drugs within a first time period and to output the estimated drug response for the second plurality of drugs within a second time period following the first time period by at least 4 days.

The set of instructions, when executed by the computer processor, may further cause the computer to: allow the user to select the standard of care set of drugs based on the cancer type by selecting from one of: breast cancer, lung cancer, colon cancer, and melanoma.

The set of instructions, when executed by the computer processor, may further cause the computer to: output the estimated drug response based on the determined equivalence level by indicating one or more of; enhanced response to the drug, standard response to the drug, and poor response to the drug.

The set of instructions, when executed by the computer processor, may further cause the computer to: resolve conflicts between two or more patient-specific marker values associated with a same drug in the standard of care set of drugs.

The set of instructions, when executed by the computer processor, may further cause the computer to: determine the equivalence level by applying the set of equivalence rules to determine if the patient-specific marker value is identical to the reference marker value, functionally similar to the reference marker value, or structurally similar to the reference marker value. The set of instructions, when executed by the computer processor, may further cause the computer to: modify the set of equivalence rules based on a determined equivalence level.

The set of instructions, when executed by the computer processor, may further cause the computer to: determine the estimated drug response to each of the standard of care cancer drugs in the standard of care set of cancer drugs by scaling a reference drug response associated with a reference marker value by the equivalence level determined for a patient-specific marker value related to that reference marker value.

The set of instructions, when executed by the computer processor, may further cause the computer to: apply the set of equivalence rules when comparing the the patient-specific markers against the reference markers in the library of reference markers values to set the equivalence level to a level selected from the set of: high equivalence, medium equivalence, low equivalence, or no equivalence.

In general, also described herein are methods and apparatuses (e.g., tools) for assisting in analyzing patient-specific markers, including analyzing patient-specific markers relative to a library of reference maker values. For example, described herein are methods of aligning a number of reads from a DNA sample to a reference genome. Such methods may include: (a) using a computing processing unit (CPU) to precompute a Burrows-Wheeler search index from the reference genome; (b) using the CPU to use the index to find all locations in the sample containing a match where a read approximately or exactly matches the reference genome; (c) using a graphics processing unit (GPU) to refine each match by introducing a limited number of gaps on the read to generate an alignment; and (d) using the CPU to rank all alignments for the read to find a best alignment which is written to output.

A method of aligning a number of reads from a DNA sample to a reference genome may include repeating steps b, c, and d for each read.

In general, a Smith-Waterman dynamic programming algorithm may be used to return a best alignment between a pair of input strings. A single backtracking matrix may be stored in local memory. The GPU-based constant memory may be used to store static variables that do not change during execution of the algorithm. The memory operations may be expressed as primitive mathematical operations. If-else statements may be re-expressed as primitive bitwise operations. The input sequences may be sorted in increasing order of length before executing the algorithm.

As described in detail herein, the algorithm may have a processing speed of about 22 GCUPs. The GPU and CPU may comprise independent sets of instructions. The throughput may be 0.0025 Gbps/pt or greater.

For example, a system for aligning a number of reads from a DNA sample to a reference genome may include: a computing processing unit (CPU) configured to execute instructions for precomputing a Burrows-Wheeler search index from the reference genome and using the Burrows-Wheeler search index to find all reads that approximately or exactly matches a portion of the reference genome; a graphics processing unit (GPU) configured to execute instructions for refining at least some reads by introducing a limited number of gaps on the at least some reads to generate an alignment, wherein the CPU is further configured to execute instructions for ranking all alignments for the at least some reads to find a best alignment which is written to output.

The CPU and GPU may generally include instructions for repeating the using, refining, and ranking for each read. The GPU may be configured to execute instructions for using a Smith-Waterman dynamic programming algorithm to eturn a best alignment between a pair of input strings. The GPU may be configured to execute instructions for storing a single backtracking matrix in local memory.

In some variations, the GPU-based constant memory may be used to store static variables that do not change during execution of the algorithm. The GPU may be configured to execute instructions for expressing memory operations as primitive mathematical operations. The GPU may be configured to execute instructions for re-expressing if-else statements as primitive bitwise operations. As mentioned, the GPU and CPU may comprise independent sets of instructions.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 12A-12I illustrate an example of a SoC Report for a patient with a clinical indication of colorectal carcinoma.

FIGS. 13A-13Q illustrate another example of a SoC Report for a patient with a clinical indication of lung adenocarcinoma.

FIGS. 14A-14C show an example of a portion of a report for a patient with a clinical indication of breast carcinoma.

FIGS. 15A-15C depict another example of a portion of a report for a patient with a clinical indication of colorectal carcinoma.

FIGS. 16A-16B illustrate another example of a portion of a report for a patient with a clinical indication of lung adenocarcinoma.

FIG. 17 show another example of a portion of a report for a patient with a clinical indication of colorectal carcinoma.

Figure 18A:
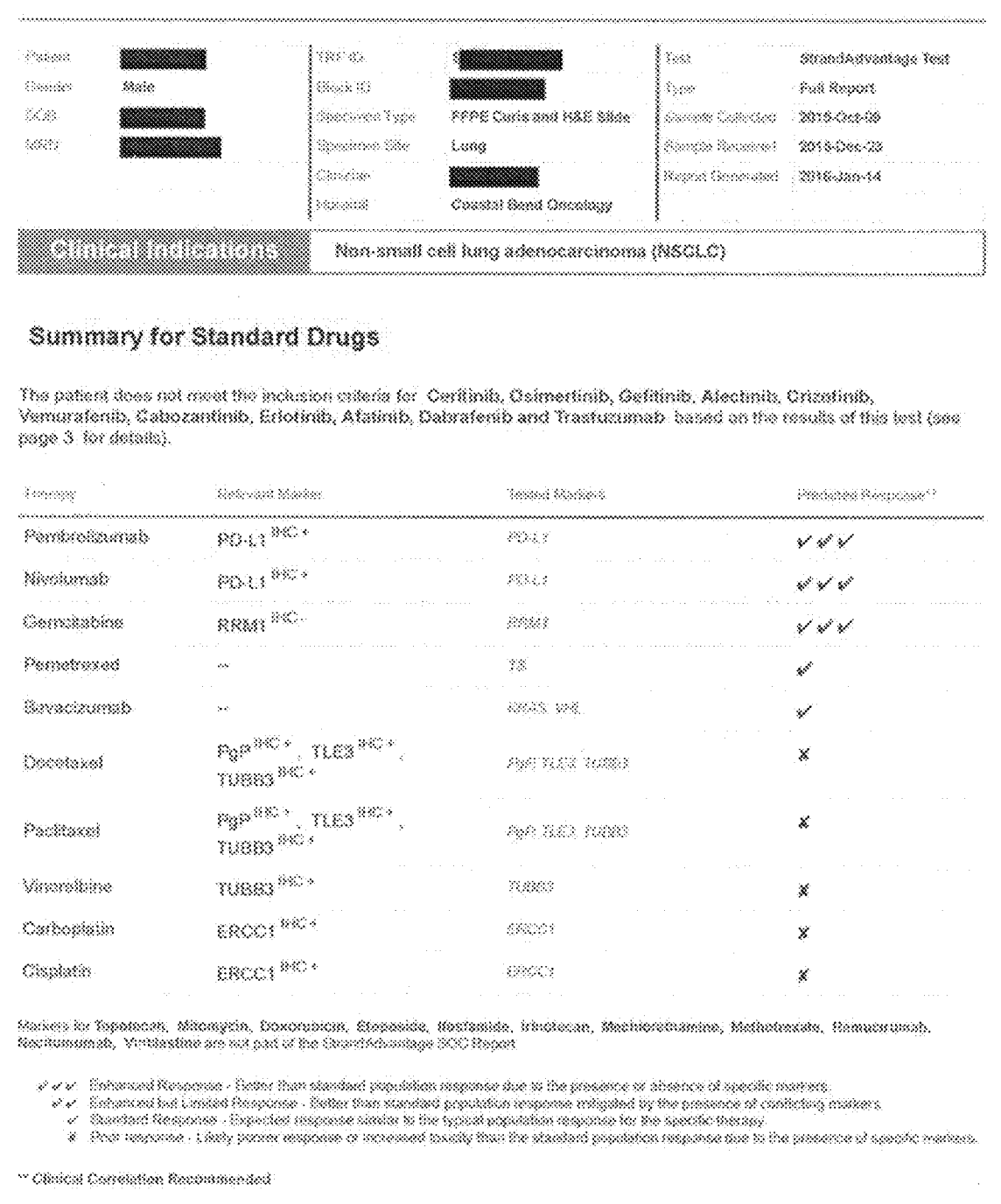

FIGS. 18A-18B show another example of a portion of a report for a patient with a clinical indication of lung adenocarcinoma.

FIGS. 19A-19B illustrate an example of a test requisition form.

FIG. 24 depicts an example of a VariantCaller workflow.

FIGS. 25A and 25B show an example of a performance comparison of GPUSeq and StrandNGS DNA-Seq.

FIG. 36 illustrates different types of split alignments and the possible underlying SVs.

DETAILED DESCRIPTION

Figure 1A:
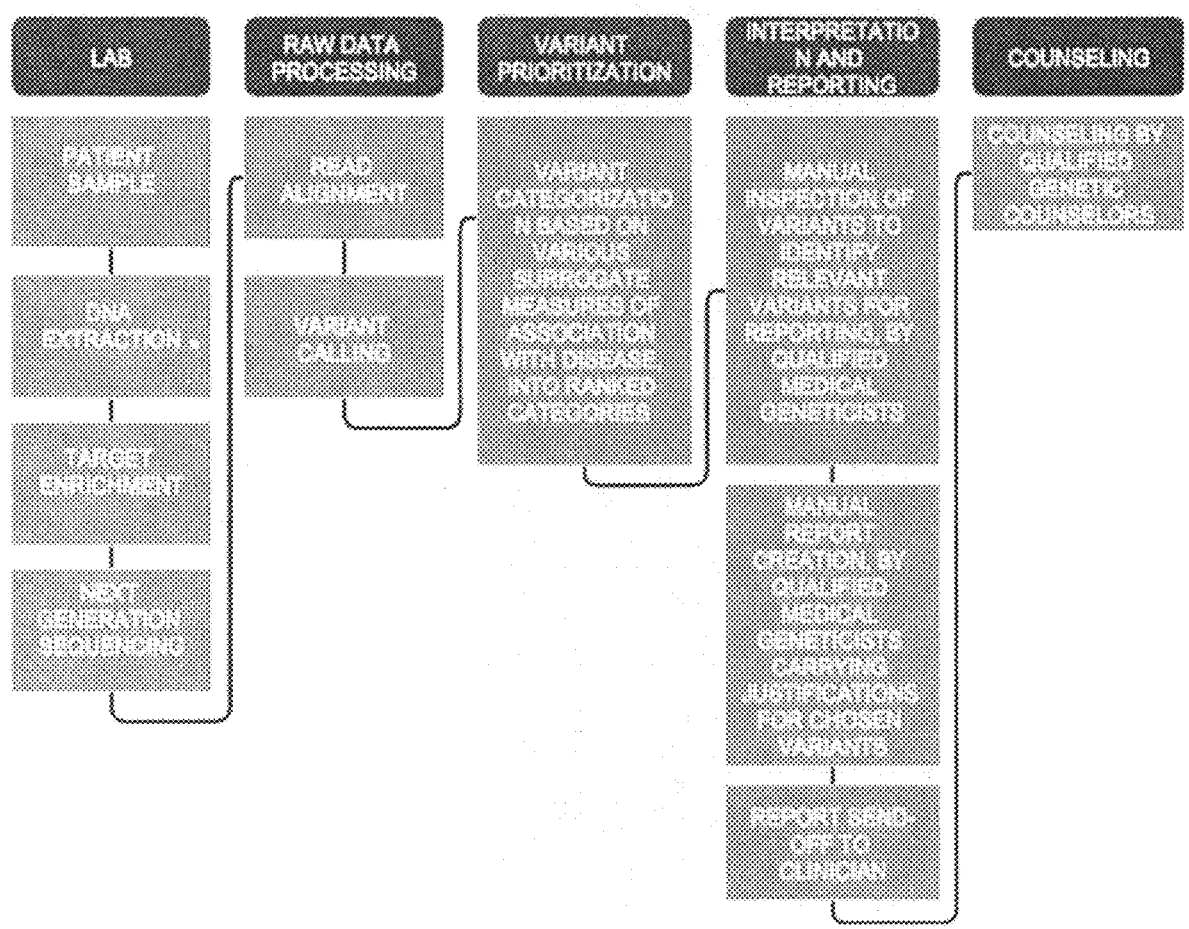
FIG. 1A is an example of a workflow for clinical genomics.
Figure 1B:
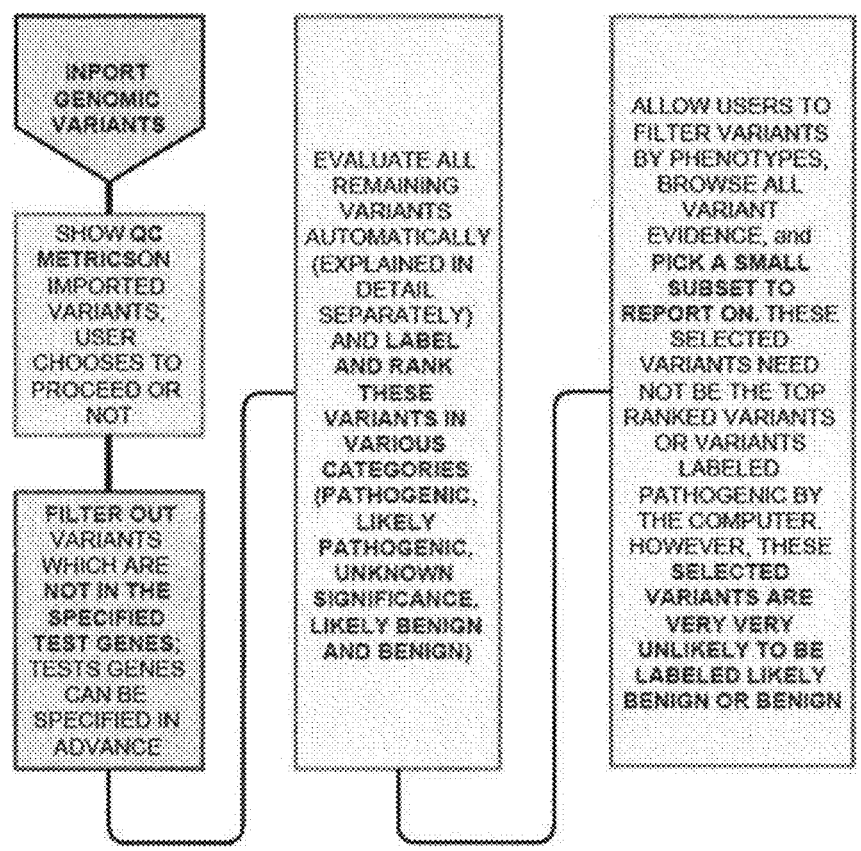
FIG. 1B is another example of a workflow ("Strandomics workflow").

Described herein in general are methods, systems and treatments including (or related to) patient risk assessment, diagnosis, therapy recommendation, and clinical trials. For example, described herein are workflows including workflows for generic clinical genomics as described above, in reference to FIG. 1. There are minor variations to this workflow for each of the following 3 applications areas: (1) Germline Cancer; (2) Somatic Cancer; and (3) Inherited diseases.

Also described herein are systems and methods that may be used as part of a biopharma or government sponsored clinical trial. For example, described herein are clinical exome panels (including whole exome sequencing approaches) followed by a pipeline (described herein) for NGS data analysis and interpretation that may help discover novel biomarkers to aide in new drug clinical trials process. Once biomarkers are established for a particular drug to stratify patients into groups such as responders, non-responders, responders with adverse side effects, and non-responders with adverse side effects, companion diagnostic panel(s) can then be designed using the process described herein ("Panel Design") The current invention provides methods and apparatus with the object of determining the response of a cancer patient with a specific type of cancer to a plurality of cancer drugs using a marker processing apparatus.

Part I: Clinical Applications

In one aspect of this invention, the response of a cancer patient with a specific type of cancer to a plurality of cancer drugs specific to the cancer type of the patient, referred to as the standard of care drugs and limited to this collection of drugs, is determined using the marker processing apparatus.

The methods in this aspect of the invention comprises the step of testing a sample from the patient for a plurality of markers to identify patient specific marker values. The nature of marker values tested may include, but is not limited to, genomic events such as single nucleotide variants (SNVs), Insertions and Deletions (InDels), and copy number variants (CNVs). It may also include specific structural variants (SVs) such as translocations, micro satellite instability (MSI) and protein expression levels. Each of the markers may be measured using technologies including Next Generation Sequencing (NGS), Immunohistochemistry (IHC), Polymerase Chain Reaction (PCR) and fluorescent in-situ hybridizations (FISH). In one example, limited to colon cancer, the markers tested to determine the response to the standard of care drugs comprise those from at least 14 genes including APC, BRAF, DPYD, EGFR, MET, KRAS, NRAS, PIK3CA, PTEN, SMAD4, UGT1A1, TS, TOP1 and ERCC1 and micro satellite instability (MSI). In this exemplary embodiment, 11 genes may be measured using an NGS panel (APC, BRAF, DPYD, EGFR, MET, KRAS, NRAS, PIK3CA, PTEN, SMAD4, UGT1A1), protein expression levels for TS, TOP1 and ERCC1 may be measured via IHC, and MSI may be measured via PCR.

In one exemplary embodiment of this aspect of the invention, the NGS panel may be designed to include genomic regions from a set of genes (e.g., 152) that modulate the response to chemotherapies and targeted therapies, or modulate the metabolism of some of these drugs, or impact prognosis and disease progression. Further, in this exemplary embodiment, the regions included in the panel may be optimized to cover all genic regions for tumor suppressor genes, all regions that cover variants from one version of the COSMIC database for oncogenes, regions that cover known translocations, regions that optimize copy number detection and regions that contain germline mutations known to impact disease metabolism or prognosis. For each marker tested using IHC, the antibody may be designed and the protocol standardized to optimize the detection of protein expression from the patient sample.

The sample drawn from the patient may include in one form fresh tissue extracted from the area of the cancer via a biopsy, and in another form, sample that has been stored in the form of Formalin-fixed, paraffin-embedded (FFPE) tissue. On one hand, FFPE tissues render themselves to long term storage of the sample. On the other hand, the quality of DNA in FFPE tissues is highly variable and poses significant challenges to various aspects of the methods of the invention. In particular, the steps of the lab protocol of the NGS panel are standardized to handle FFPE tissues with a wide range of quality. In one exemplary embodiment, the protocol includes pull-down in-solution using SureSelect XT2 RNA baits and sequencing using Illumina's sequencing instrument such as MiSeq, NextSeq or HiSeq. In this exemplary embodiment, the lab protocol is optimized to handle samples that contain at least 20% of tumor content and at least 200 ng of input tumor DNA.

The raw data generated from the lab for the NGS panel is in the form of sequence reads, 2×151 bp in length in one exemplary embodiment, and are transformed to patient-specific marker values using algorithms including but not limited to alignment, SNP detection, copy number calling, translocation detection, and Quality Checks (QC) executed as part of a patient-specific marker value generation pipeline. In one exemplary embodiment, these algorithms are executed by a computer processor. In another embodiment, these algorithms are executed by a computer processor in tandem with a graphics processor resulting in overall speed improvements of up to 10×.

The patient-specific marker value generation pipeline includes pre-alignment filtering steps and steps such as trimming low quality bases and using contaminant databases to filter out noise. The alignment algorithm may use a Burrows-Wheeler Transform (BWT) based index search followed by a Dynamic Programming (DP) algorithm to find an optimal match for each read. It may include steps for seeding matches from the read, aggregating matches to identify candidate regions, performing a banded DP, mate rescue, split read alignment, and local realignment. The SNV detection algorithm may use an iterative binomial caller and include a framework to specify complex Boolean filters based on properties of reads near the location of the SNP being called. The copy number calling algorithm involves creating GC-corrected normalized coverages for the normal profile, in one embodiment by computing iterative average for each region. Copy number calls made at the exon level may be summarized to the gene level. The translocation detection may use split read alignment to identify known translocations. The patient-specific marker value generation pipeline may also include QC checks to determine sample contamination, sample degradation and sample mix-up using the SNV calls. It may also include checks on number of novel SNP calls, the number of copy number calls to QC the algorithm execution. The QC results may be used to pass or reject the patient-specific marker values generated by the pipeline for the patient sample.

For markers measured by IHC, the scoring criteria and cut-offs used may be standardized separately for each IHC marker based on published literature and vendor provided catalogues.

In this aspect of the invention, the method next comprises entering the patient specific marker values into the marker processing apparatus. The marker processing apparatus comprises a manually curated database of reference markers and their functional significance. Each reference marker may be annotated using peer reviewed journal literature as having a Loss of Function, a Gain of Function or an Unknown Functional impact on the gene that it falls in.

The marker processing apparatus further comprises rules, called the SOC rules, that relate collections of reference markers to the expected response of the SOC drugs for a specific tissue. The SOC rules are manually curated using information from disparate peer reviewed literature. Each rule may be recorded as an expression that quantifies the response of a specific drug in the presence of a marker M in the patient's sample: Response (drug D|marker M causing functional significance F)=R based on literature evidence L.

The marker can be as specific as a single variant—say the V600E variant in BRAF gene for example, or more general, for example, any Loss of Function (LOF) variant in a gene (e.g., any variant in SMAD4 gene that causes a LOF) or with some intermediate level of generality (e.g. any variant in exons 23, 24 or 25 of ALK gene that causes a GOF). In addition, it can also be the negative of a variant or variant class (e.g., any variant in EGFR gene that does NOT cause a GOF) or a Boolean combination of a plurality of variant classes for the same gene or different genes with specific or generic exceptions (e.g., any variant in EGFR gene except T790M that causes a GOF or any variant in XXX gene that is NOT an in-frame insertion in exon 20 and causes a GOF). The drug reference in the SOC rule may include specific drugs (for e.g., Everolimus) or a class of drugs (for e.g., mTOR inhibitors). The functional significance may include loss of function (LOF), gain of function (GOF) or unknown function. The response value for a drug could be sensitive or resistance.

Upon entering the patient specific marker values into the marker processing apparatus, the marker processing apparatus may be used to determine an equivalence level for the subset of patient specific marker values relative to the reference SOC marker values based on a set of equivalence rules. For each patient specific marker measured with a specific value, the marker processing apparatus may evaluate its equivalence with any of the reference SOC marker values and may output an equivalence level with high, medium or low confidence. The equivalence rules may be dependent on the type of the patient specific marker value and may be used to annotate the functional significance of the patient specific marker value based on the functional significance of the reference marker value. In one exemplary embodiment of an equivalence rule, a patient specific marker value that indicates a premature truncation in a Tumor Suppressor gene is equivalent to a reference marker with high confidence if it is an exact match or if the reference marker is a premature stop, or a frameshift variant or an Exonic Splicing Silencer (ESS) resulting in a premature stop downstream of the patient specific marker value, and is annotated with a LOF functional significance if such a reference marker is found.

In this aspect of the invention, the marker processing apparatus may then execute the SOC rules based on the functional significance of the patient-specific marker values derived using equivalence to the reference marker values. The marker processing apparatus may execute only the most specific rule for each drug, and may execute all possible rules based on the patient-specific marker values. Once all the rules have been fired, the apparatus may provide an overall recommendation for each drug. Where the response predicted by individual SOC rules for a drug are all consistent, the overall recommendation for the drug may be the same as the individual response prediction. Where the different SOC rules predict contradicting responses, the apparatus may allow manual intervention to resolve the conflict based on the literature evidence associated with each individual SOC rule. The resolved outcome may be recorded in the system as a new specific SOC rule. If the conflict cannot be resolved, the drug response may be called Inconclusive.

In this aspect of the invention, the marker processing apparatus may thus be used to predict the estimated drug response given the unique patient-specific marker values for the standard of care set of drugs for a patient sample. The estimated drug response for each drug may vary between Enhanced Response for drugs that are found sensitive and Poor Response for drugs that are found resistant. Conflicting SOC rules may be resolved to predict the response of the drug as either Limited Response or Inconclusive. The SOC drugs for which none of the SOC rules were fired may have a Standard Response for the patient, and may be reported thus. The marker processing apparatus may further be used to generate the patient's report automatically with minimal manual intervention, needed only when a conflict arises. The report may include the estimated response of each of the standard of care drugs for the patient sample, along with the details of the patient-specific marker values that were measured and used to estimate the responses.

In another aspect of this invention, the response of a cancer patient with a specific type of cancer to a plurality of cancer drugs not specific to the cancer type of the patient, referred to as off-label drugs, and to a plurality of clinical trials for the specific type of cancer is determined using the marker processing apparatus with the object of determining additional therapies that may be applicable to the patient.

In this aspect of the invention, the marker processing apparatus may further comprise a collection of cancer pathways that provide for each gene in the panel above, a list of targetable upstream or downstream genes from the pathways. The apparatus may also comprise a plurality of cancer drugs from different tissues and clinical trials annotated with the target gene and additional conditions of applicability.

In this aspect of the invention, the marker processing apparatus performs an equivalence of the patient-specific marker values with the reference marker values to predict the functional significance of the patient-specific marker values as causing Loss of Function or Gain of Function. The patient-specific marker values that are not found equivalent to the curated markers with known functional significance may be further categorized using bioinformatics predictions, and database lookup.

In this aspect of the invention, one step involves using the marker processing apparatus to prioritize the rest of the variants and shortlist patient-specific marker values that are expected to have a damaging functional significance on targetable genes in cancer pathways. This step may involve using the tools provided by the marker processing apparatus including, but not limited to a tool that enables quick assessment of the cleanliness of the alignment in the neighborhood of the variant location; a tool that displays the copy number distribution to in superimposing the copy number calls of the sample against the distribution of calls from each of the panel's regions over the samples in the system; and a tool to present all the relevant information about the marker in a concise visualization.

In this aspect of the invention, another step may involve using an automatically created list of drugs approved in other tissues and clinical trials for the specific tissue to identify additional therapies that may be applicable to the patient, given the patient-specific marker values. Literature evidence to support the applicability of the drug or trial to the patient may be recorded in the marker processing apparatus for reuse in subsequent patient samples.

The marker processing apparatus may further generate the patient's report automatically. In addition to the Standard of Care drugs, the report may include additional off-label drugs and clinical trials applicable to the patient sample, along with the details of the patient-specific marker values that were measured and used to estimate the responses.

In some embodiments, the marker processing apparatus comprises a processor configured to run marker processing algorithms as described herein. For example, the marker processing apparatus can comprise a general purpose computer configure to run marker processing software.

Panel Design

In general, described herein are multi-gene panels. One variation of a multi-gene panel (referred to herein as "StrandAdvantage") covers (a) all oncogenes and tumor suppressor genes, (b) genes that can help guide the choice of therapy options, (c) predictors of response or resistance to targeted and chemotherapy drugs (d) markers for prognosis and (e) those involved in drug metabolism.

Multi-gene testing can provide many advantages as compared to single gene testing approaches. For example, multi-gene testing can allow short turnaround time to start therapy, including first-line options; testing of many genes concurrently (simultaneous identification of a driver mutation, as well as a secondary mutation in the gene); identification of resistance to targeted therapy for the driver gene, thus helping predict the contraindications of a targeted drug; targeting tumors of different origins with the same drive mutations, using a single drug; testing a tumor for mutations and genes other than the ones typically associated with that tumor for more information; determining with very high sensitivity extremely subtle mutations that are unique to the tumor; and capturing tumor heterogeneity with high sensitivity, often missed with other molecular testing approaches.

Sequencing the entire genic content of these (e.g., 161) genes would result in a very large amount of sequencing and increase the cost of the test. The StrandAdvantage test selectively sequences just 0.5 MB of the target genes to keep sequencing costs and long term data storage costs to a minimum. It may be, however, difficult to determine which sub-regions to sequence, and how to guide analysis of these regions. The regions have been broadly chosen as follows:

All important COSMIC mutations involved in solid tumors are covered by the target regions. Briefly, all Refseq, UCSC and Ensembl transcripts were combined for each gene. All transcripts were merged to construct a "super transcript" for each gene. The DNA coordinates for all known transcripts were merged to construct "super transcript DNA coordinate" for each gene. All known COSMIC mutations (SNV, INDELs up to 35 hp) that overlap with the super transcript coordinates were considered as targets.

In addition to COSMIC, coding germline mutations from ClinVar and HGMD were included for the genes involved in drug metabolism.

For genes whose copy number status is important, the design ensures that the target regions are spread across the gene to maximize detection accuracy of whole gene copy number alteration events. Briefly, probes were equally interspaced along the entire length of the gene, covering all exons, wherever possible. If the distance between two adjacent exons was too large (>xkb), an intronic probe was introduced to ensure adequate representation.

For genes involved in translocations, the most common breakpoints (based on frequency of occurrence as per COSMIC) have been identified and these breakpoint regions have been densely covered with probes to enable high-resolution breakpoint detection.

To optimize the panel size and number of probes. Overlapping and adjacent targets within 120 bp were merged.

Probe design was set to balance specificity and coverage and set to 1× tiling.

The bioinformatics pipelines that support the test may ensure that the above objectives are achievable.

Design Confirmations: (1) Hapmap and cell line DNA from 20 samples were used to analyze coverage of all intended target regions. No target base was found to be covered less than 1×. This proves that all probes in the panel are functional and that all intended target regions are covered. (2) We confirmed that all off-target regions with significant coverage had high similarity (were pseudogenes or members of the gene family originally targeted).

Analytical validation: The panel is being confirmed on Cell lines hosting various types of DNA alterations. For INDELS, copy number changes and translocations, cell lines have been identified and validation is ongoing. Limit of detection for each type of event is being evaluated. For copy number changes, higher fold changes in more pure tumor samples are easier to identify. So we have designed a series of experiments testing a range of amplifications from 2-15 or more copies and over a range of tumor content.

Clinical validation: multiple clinical studies involving over hundred samples have been designed with a number of hospitals in India, US and expanding globally.

Table 1, below lists all of the genes analyzed by one example of a panel, referred to as the "Strand-48" panel. These genes include:

TABLE 1

| Strand-48 Panel |
| --- |
| ABL1 |
| AKT1 |
| ALK |
| APC |
| ATM |
| BRAF |
| CDH1 |
| CDKN2A |
| CSF1R |
| CTNNB1 |
| EGFR |
| ERBB2 |
| ERBB4 |
| FBXW7 |
| FGFR1 |
| FGFR2 |
| FGFR3 |
| FLT3 |
| GNA11 |
| GNAQ |
| GNAS |
| HNF1A |
| HRAS |
| IDH1 |
| JAK2 |
| JAK3 |
| KDR |
| KIT |
| KRAS |
| MET |
| MLH1 |
| MPL |
| NOTCH1 |
| NPM1 |
| NRAS |
| PDGFRA |
| PIK3CA |
| PTEN |
| PTPN11 |
| RB1 |
| RET |
| SMAD4 |
| SMARCB1 |
| SMO |
| SRC |
| STK11 |
| TP53 |
| VHL |

Note that the gene names listed are accepted in the art as their abbreviated alias. For example, "ABL1" may also be referred to as "C-Abl Oncogene 1, Non-Receptor Tyrosine Kinase" (as well as other aliases referred to in the literature).

Table 2, below is another example of the list of genes analyzed by a second panel. ("Strand-161" also referred to herein as "StrandAdvantage"). These genes include:

TABLE 2

| StrandAdvantage Panel | | | | | | |
| --- | --- | --- | --- | --- | --- | --- |
| ABCB1 | C11orf30 | DDR2 | FGFR3 | JAK3 | MYC | PTPN11 |
| ABCC1 | CBL | DHFR | FGFR4 | JUN | MYCN | RAD50 |
| ABL1 | CCND1 | DPYD | FLT1 | KDR | MYD88 | RAD51 |
| AKT1 | CCND3 | EGFR | FLT3 | KEAP1 | NF1 | RAD51C |
| AKT2 | CCNE1 | EP300 | FLT4 | KIT | NFE2L2 | RAF1 |
| AKT3 | CDH1 | EPHA3 | GATA1 | KRAS | NOTCH1 | RB1 |
| ALK | CDK4 | ERBB2 | GNA11 | MAP2K1 | NOTCH2 | RET |
| APC | CDK8 | BRBB3 | GNAQ | MAP2K2 | NPM1 | ROS1 |
| AR | CDKN1A | ERBB4 | GNAS | MAP2K4 | NRAS | RPTOR |
| ATM | CDKN1B | ERCC1 | GSK3B | MAP3K1 | NTRK1 | RRM1 |
| ATR | CDKN2A | ERCC2 | GSTP1 | MDM2 | PARP1 | SLC29A1 |
| ATRX | CHEK1 | ERCC5 | HGF | MDM4 | PBRM1 | SLCO1B1 |
| AURKA | CHEK2 | ESR1 | HNF1A | MED12 | PDGFRA | SMAD4 |
| AURKB | CSF1R | EZH2 | HRAS | MET | PDGFRB | SMARCB1 |
| AXL | CTNNB1 | FANCA | IDH1 | MITF | PIK3CA | SMO |
| BCL2 | CYP2B6 | FANCC | IDH2 | MLH1 | PIK3R1 | SPARC |
| BCL2L2 | CYP2C19 | FANCD2 | IGF1R | MPL | PIK3R2 | SRC |
| BRAF | CYP2C8 | FBXW7 | IKBKE | MRE11A | PLK1 | STAT3 |
| BRCA1 | CYP2D6 | FGFR1 | JAK1 | MTHFR | PRKCD | STK11 |
| BRCA2 | DAXX | FGFR2 | JAK2 | MTOR | PTEN | STK11IP |
| SULT1A1 | SYK | TET2 | TGFBR2 | TNFAIP3 | TOP1 | TOP2A |
| TOP2B | TP53 | TPMT | TSC1 | TSC2 | TYMP | UGT1A1 |
| VHL | XPA | XPC | XRCC1 | | | |

A more complete description of the genes for this panel is given in Table 3, below.

TABLE 3

| Description of StrandAdvantage Gene Panel | | | | | |
| --- | --- | --- | --- | --- | --- |
| Gene | Note(s) | Total bp covered in panel | Total Ref coding ST bp | Ref coding ST covered in panel | % RefCoding covered in panel |
| ROS1 | Translocation | 5209 | 7044 | 501 | 7.11 |
| SLC29A1 | HGMD + SNPedia | 320 | 1371 | 115 | 8.39 |
| SULT1A1 | HGMD + SNPedia | 640 | 1026 | 319 | 31.09 |
| DHFR | HGMD + SNPedia | 640 | 564 | 222 | 39.36 |
| CYP2C8 | HGMD + SNPedia | 1600 | 1498 | 772 | 51.54 |

TABLE 3-continued

Description of StrandAdvantage Gene Panel

| Gene | Note(s) | Total bp covered in panel | Total Ref coding ST bp | Ref coding ST covered in panel | % RefCoding covered in panel |
|---|---|---|---|---|---|
| DPYD | HGMD + SNPedia | 5797 | 3117 | 2418 | 77.57 |
| GSTP1 | All COSMIC loci; COSMIC only small variations | 1358 | 633 | 492 | 77.73 |
| CYP2C19 | HGMD + SNPedia | 2605 | 1473 | 1189 | 80.72 |
| HRAS | COSMIC only small variations | 1149 | 633 | 513 | 81.04 |
| PIK3R2 | All COSMIC loci; COSMIC only small variations | 3914 | 2187 | 1789 | 81.80 |
| STAT3 | All COSMIC loci; COSMIC only small variations | 5680 | 2313 | 1914 | 82.75 |
| MAP2K1 | COSMIC only small variations | 2800 | 1182 | 1004 | 84.94 |
| FANCC | All exons | 4560 | 1827 | 1564 | 85.60 |
| AKT1 | COSMIC only small variations | 3384 | 1443 | 1246 | 86.35 |
| TOP2A | COSMIC only small variations | 9166 | 4596 | 3999 | 87.01 |
| GNA11 | COSMIC only small variations | 2031 | 1080 | 944 | 87.41 |
| SLCO1B1 | HGMD + SNPedia | 3840 | 2076 | 1820 | 87.67 |
| MAP2K4 | All COSMIC loci; COSMIC only small variations | 3680 | 1233 | 1085 | 88.00 |
| MAP3K1 | All COSMIC loci; COSMIC only small variations | 8258 | 4539 | 4057 | 89.38 |
| RAD51 | All exons | 3504 | 1141 | 1020 | 89.40 |
| CYP2B6 | HGMD + SNPedia | 2648 | 1476 | 1330 | 90.11 |
| STK11IP | All exons | 8031 | 3300 | 2982 | 90.36 |
| RAF1 | COSMIC only small variations | 4685 | 1947 | 1765 | 90.65 |
| CHEK1 | All exons | 3634 | 1431 | 1299 | 90.78 |
| MAP2K2 | COSMIC only small variations | 3099 | 1203 | 1095 | 91.02 |
| TOP1 | COSMIC only small variations | 6120 | 2298 | 2095 | 91.17 |
| IDH2 | COSMIC only small variations | 3039 | 1359 | 1244 | 91.54 |
| PARP1 | All COSMIC loci; COSMIC only small variations | 6960 | 3045 | 2796 | 91.82 |
| NFE2L2 | All COSMIC loci; COSMIC only small variations | 2346 | 1818 | 1680 | 92.41 |
| CHEK2 | All exons | 5480 | 1761 | 1632 | 92.67 |
| IDH1 | COSMIC only small variations | 2840 | 1245 | 1154 | 92.69 |
| ERCC1 | All exons | 2800 | 1023 | 951 | 92.96 |
| TOP2B | COSMIC only small variations | 10729 | 4866 | 4535 | 93.20 |
| FANCD2 | All exons | 13770 | 4491 | 4195 | 93.41 |
| TSC2 | All exons | 14406 | 5424 | 5090 | 93.84 |
| TGFBR2 | All COSMIC loci; COSMIC only small variations | 3241 | 1779 | 1685 | 94.72 |
| GSK3B | All COSMIC loci; COSMIC only small variations | 3760 | 1302 | 1234 | 94.78 |
| PRKCD | All COSMIC loci; COSMIC only small variations | 5001 | 2031 | 1936 | 95.32 |
| AURKB | COSMIC only small variations | 2228 | 1038 | 990 | 95.38 |
| DDR2 | COSMIC only small variations | 5640 | 2568 | 2473 | 96.30 |
| IKBKE | All COSMIC loci; COSMIC only small variations | 6010 | 2151 | 2074 | 96.42 |
| FLT1 | COSMIC only small variations | 10609 | 4273 | 4123 | 96.49 |

TABLE 3-continued

Description of StrandAdvantage Gene Panel

| Gene | Note(s) | Total bp covered in panel | Total Ref coding ST bp | Ref coding ST covered in panel | % RefCoding covered in panel |
|---|---|---|---|---|---|
| GNAS | COSMIC only small variations | 6439 | 3994 | 3855 | 96.52 |
| IGF1R | COSMIC only small variations | 8052 | 4104 | 3964 | 96.59 |
| MDM2 | All COSMIC loci; COSMIC only small variations; For CNV | 3639 | 1494 | 1444 | 96.65 |
| MED12 | All COSMIC loci; COSMIC only small variations | 14513 | 6534 | 6318 | 96.69 |
| SPARC | All COSMIC loci; COSMIC only small variations | 2680 | 912 | 883 | 96.82 |
| FANCA | All exons | 13808 | 4373 | 4237 | 96.89 |
| FGFR1 | COSMIC only small variations; For CNV | 6439 | 2635 | 2557 | 97.04 |
| AXL | All COSMIC loci; COSMIC only small variations | 6719 | 2685 | 2607 | 97.09 |
| FLT4 | COSMIC only small variations | 9722 | 4096 | 3980 | 97.17 |
| NOTCH2 | All COSMIC loci; COSMIC only small variations | 14441 | 7469 | 7266 | 97.28 |
| MITF | COSMIC only small variations; For CNV | 4479 | 1786 | 1738 | 97.31 |
| ABCC1 | HGMD + SNPedia + COSMIC; COSMIC only small variations | 10480 | 4596 | 4486 | 97.61 |
| DAXX | All exons | 3429 | 2276 | 2223 | 97.67 |
| NTRK1 | COSMIC only small variations | 6303 | 2513 | 2455 | 97.69 |
| ATR | All exons | 19481 | 7935 | 7759 | 97.78 |
| ERBB3 | COSMIC only small variations | 9094 | 4160 | 4069 | 97.81 |
| RET | Translocation; For CNV; COSMIC only small variations | 9655 | 3377 | 3304 | 97.84 |
| HGF | COSMIC only small variations | 6141 | 2203 | 2156 | 97.87 |
| CCNE1 | COSMIC only small variations; For CNV | 2956 | 1233 | 1210 | 98.13 |
| ATRX | All exons | 16167 | 7479 | 7347 | 98.24 |
| BRAF | COSMIC only small variations | 6280 | 2301 | 2264 | 98.39 |
| EP300 | COSMIC only small variations | 13586 | 7245 | 7135 | 98.48 |
| JAK3 | COSMIC only small variations | 7574 | 3375 | 3337 | 98.87 |
| BRCA2 | All exons | 16736 | 10257 | 10148 | 98.94 |
| MTOR | COSMIC only small variations | 19051 | 7650 | 7572 | 98.98 |
| ALK | Translocation; For CNV; COSMIC only small variations | 12904 | 4863 | 4817 | 99.05 |
| NOTCH1 | All COSMIC loci; COSMIC only small variations | 14164 | 7668 | 7596 | 99.06 |
| AR | All COSMIC loci; COSMIC only small variations; For CNV | 4852 | 2783 | 2763 | 99.28 |
| CBL | All COSMIC loci; COSMIC only small variations | 6063 | 2721 | 2704 | 99.38 |
| FGFR2 | COSMIC only small variations; For CNV | 6907 | 2710 | 2704 | 99.78 |

TABLE 3-continued

Description of StrandAdvantage Gene Panel

| Gene | Note(s) | Total bp covered in panel | Total Ref coding ST bp | Ref coding ST covered in panel | % RefCoding covered in panel |
|---|---|---|---|---|---|
| EGFR | COSMIC only small variations; For CNV | 10211 | 3889 | 3882 | 99.82 |
| JAK1 | COSMIC only small variations | 8228 | 3465 | 3459 | 99.83 |
| ERCC2 | All exons | 7196 | 2336 | 2334 | 99.91 |
| MRE11A | All exons | 7840 | 2127 | 2126 | 99.95 |
| GATA1 | COSMIC only small variations | 2220 | 1242 | 1242 | 100.00 |
| ABCB1 | HGMD + SNPedia + COSMIC; COSMIC only small variations; For CNV | 9897 | 3843 | 3843 | 100.00 |
| AKT2 | COSMIC only small variations; For CNV | 4239 | 1446 | 1446 | 100.00 |
| AKT3 | COSMIC only small variations; For CNV | 4720 | 1484 | 1484 | 100.00 |
| APC | All exons | 13120 | 8697 | 8697 | 100.00 |
| ATM | All exons | 25680 | 9171 | 9171 | 100.00 |
| AURKA | COSMIC only small variations; For CNV | 2723 | 1212 | 1212 | 100.00 |
| BCL2 | COSMIC only small variations | 1240 | 753 | 753 | 100.00 |
| BCL2L2 | COSMIC only small variations | 1016 | 582 | 582 | 100.00 |
| BRCA1 | All exons | 12440 | 5658 | 5658 | 100.00 |
| C11orf30 | COSMIC only small variations; For CNV | 8455 | 3969 | 3969 | 100.00 |
| CCND1 | COSMIC only small variations; For CNV | 2597 | 888 | 888 | 100.00 |
| CCND3 | COSMIC only small variations; For CNV | 2800 | 879 | 879 | 100.00 |
| CDK4 | COSMIC only small variations; For CNV | 2205 | 912 | 912 | 100.00 |
| CDK8 | COSMIC only small variations | 4197 | 1395 | 1395 | 100.00 |
| CDKN1A | All exons | 1000 | 495 | 495 | 100.00 |
| CDKN1B | All exons | 1120 | 597 | 597 | 100.00 |
| CDKN2A | All exons | 2760 | 912 | 912 | 100.00 |
| CSF1R | COSMIC only small variations | 6946 | 2919 | 2919 | 100.00 |
| CTNNB1 | COSMIC only small variations | 5089 | 2346 | 2346 | 100.00 |
| CYP2D6 | HGMD + SNPedia | 3014 | 1494 | 1494 | 100.00 |
| EPHA3 | All exons | 7600 | 2978 | 2978 | 100.00 |
| ERBB2 | COSMIC only small variations; For CNV | 8949 | 3768 | 3768 | 100.00 |
| ERBB4 | COSMIC only small variations | 11146 | 3927 | 3927 | 100.00 |
| ERCC5 | All exons | 8297 | 3561 | 3561 | 100.00 |
| ESR1 | All COSMIC loci; COSMIC only small variations | 3520 | 1788 | 1788 | 100.00 |
| EZH2 | COSMIC only small variations | 6357 | 2256 | 2256 | 100.00 |
| FBXW7 | All exons | 6633 | 2562 | 2562 | 100.00 |
| FGFR3 | COSMIC only small variations | 5392 | 2572 | 2572 | 100.00 |
| FGFR4 | COSMIC only small variations; For CNV | 5094 | 2483 | 2483 | 100.00 |
| FLT3 | COSMIC only small variations | 7745 | 2982 | 2982 | 100.00 |
| GNAQ | COSMIC only small variations | 2480 | 1080 | 1080 | 100.00 |

TABLE 3-continued

Description of StrandAdvantage Gene Panel

| Gene | Note(s) | Total bp covered in panel | Total Ref coding ST bp | Ref coding ST covered in panel | % RefCoding covered in panel |
|---|---|---|---|---|---|
| JAK2 | COSMIC only small variations | 8193 | 3399 | 3399 | 100.00 |
| JUN | COSMIC only small variations; For CNV | 1876 | 996 | 996 | 100.00 |
| KDR | COSMIC only small variations; For CNV | 10800 | 4071 | 4071 | 100.00 |
| KEAP1 | All COSMIC loci; COSMIC only small variations | 2920 | 1875 | 1875 | 100.00 |
| KIT | COSMIC only small variations; For CNV | 7050 | 2931 | 2931 | 100.00 |
| KRAS | COSMIC only small variations; For CNV | 2800 | 687 | 687 | 100.00 |
| MDM4 | All COSMIC loci; COSMIC only small variations; For CNV | 3935 | 1473 | 1473 | 100.00 |
| MET | COSMIC only small variations; For CNV | 8482 | 4227 | 4227 | 100.00 |
| MLH1 | All exons | 7734 | 2271 | 2271 | 100.00 |
| MTHFR | HGMD + SNPedia | 4230 | 1971 | 1971 | 100.00 |
| MYC | All COSMIC loci; COSMIC only small variations; For CNV | 2160 | 1365 | 1365 | 100.00 |
| MYCN | All COSMIC loci; COSMIC only small variations; For CNV | 1738 | 1395 | 1395 | 100.00 |
| MYD88 | All COSMIC loci; COSMIC only small variations | 1770 | 954 | 954 | 100.00 |
| NF1 | All exons | 26265 | 8581 | 8581 | 100.00 |
| NRAS | COSMIC only small variations | 1520 | 570 | 570 | 100.00 |
| PBRM1 | COSMIC only small variations | 11919 | 4749 | 4749 | 100.00 |
| PDGFRA | COSMIC only small variations | 8195 | 3270 | 3270 | 100.00 |
| PDGFRB | COSMIC only small variations | 8175 | 3321 | 3321 | 100.00 |
| PIK3CA | COSMIC only small variations; For CNV | 7592 | 3207 | 3207 | 100.00 |
| PIK3R1 | All COSMIC loci; COSMIC only small variations | 5691 | 2297 | 2297 | 100.00 |
| PLK1 | All COSMIC loci; COSMIC only small variations | 3770 | 1812 | 1812 | 100.00 |
| PTEN | All exons | 3600 | 1212 | 1212 | 100.00 |
| PTPN11 | All exons | 5978 | 1786 | 1786 | 100.00 |
| RAD50 | All exons | 10956 | 3939 | 3939 | 100.00 |
| RAD51C | All exons | 4160 | 1135 | 1135 | 100.00 |
| RB1 | All exons | 10215 | 2787 | 2787 | 100.00 |
| RPTOR | COSMIC only small variations | 11482 | 4008 | 4008 | 100.00 |
| RRM1 | All exons | 7508 | 2379 | 2379 | 100.00 |
| SMO | COSMIC only small variations | 5071 | 2364 | 2364 | 100.00 |
| SRC | COSMIC only small variations | 4019 | 1611 | 1611 | 100.00 |
| STK11 | All exons | 4400 | 1302 | 1302 | 100.00 |
| SYK | All COSMIC loci; COSMIC only small variations | 4880 | 1908 | 1908 | 100.00 |
| TET2 | All exons | 8882 | 6098 | 6098 | 100.00 |

TABLE 3-continued

Description of StrandAdvantage Gene Panel

| Gene | Note(s) | Total bp covered in panel | Total Ref coding ST bp | Ref coding ST covered in panel | % RefCoding covered in panel |
| --- | --- | --- | --- | --- | --- |
| TNFAIP3 | All COSMIC loci; COSMIC only small variations | 4116 | 2373 | 2373 | 100.00 |
| TP53 | All exons | 4319 | 1263 | 1263 | 100.00 |
| TPMT | HGMD + SNPedia | 3238 | 738 | 738 | 100.00 |
| TSC1 | All exons | 8902 | 3495 | 3495 | 100.00 |
| TYMP | HGMD + SNPedia | 2874 | 1464 | 1464 | 100.00 |
| UGT1A1 | HGMD + SNPedia | 2733 | 1602 | 1602 | 100.00 |
| VHL | All exons | 1560 | 642 | 642 | 100.00 |
| XPA | All exons | 3080 | 822 | 822 | 100.00 |
| XPC | All exons | 6960 | 2823 | 2823 | 100.00 |
| XRCC1 | All exons | 6021 | 1902 | 1902 | 100.00 |

These panel tests described herein may generally be performed by: (1) a clinician provides patient tumor specimen in collection kit; (2) the tissue is tested by a lab (as described herein), which sequence the DNA from, e.g., a formalin fixed, paraffin embedded tumor sample, by sequencing numerous sub-regions of the genes of interest, as described herein; (3) data is analyzed as described herein, including use of the an apparatus (e.g., "StrandOmics") including analytic software; (4) consultation with clinicians and Ph.Ds by telephone consult.

These assays, such as the Strand-48 and Strand-161 gene panels described above, may not necessarily be used as diagnostic tests; instead, they may be performed after the clinical and pathology diagnosis is performed. The clinical utility of these panels may be to stratify patients (such as in the case for Strand-161, solid tumor cancer patients) in a meaningful way, e.g., according to their tumor mutation profiles and, and inform their physician about relevant treatments to guide rational treatments, including informing them about possible drug interactions and counter indications. For example, the Strand-161 assay may be used to inform the patient's oncologist about clinically valid cancer therapies that are available in the market or in clinical trials. The methods and apparatuses described herein enable the practice of personalized medicine, e.g., by an oncologist, by providing them with clinical decision support.\

In any of these methods and apparatuses, the process may advantageously be structured as a stratified assay, in which, a quick result looking at a sub-set of the genes (and/or specific polymorphism of these genes) is first provided to the physician, followed by a more detailed report a few days thereafter. Thus, although many (e.g., hundreds) of genes including thousands of polymorphisms (including duplications, breaks, deletions, etc.) may be identified and analyzed, the assay may be configured to quickly (e.g., within a day, a few days, etc.) give initial results on a sub-set of relevant genes, followed up within a short time by the complete (or another sub-set) of results for the panel.

For example, clinicians may receive (e.g., within 5 days, within 6 days, within 7 days, within 8 days, within 9 days, within 10 days) a case report on their patient's subset of NCCN "standard of care" genes tested. The subset may consist of 8 standard of care genes (or 9, 10, 11, 12, 13, 14, 15, 16, 17, 18, 19, 20, 21, 22, 23, 24, 25, 26, 27, 28, 29, 30, 31, 32, etc. standard of care genes). The number and identity of the genes forming the standard of care subset may be determined based on those genes identified by scientific/medical consensus, e.g., from the published literature. In 15 days or less (e.g., combining the StrandOmics described herein with our expert interpreters) the full case report may be provided to clinicians. In practice, the methods and apparatuses described herein provide more than 40% faster than current competitors and at a much lower cost. The 8 standard-of-care genes may include: KRAS, BRAF, NRAS, PIK3CA, EGFR, AKT1, KIT, and PDGFRA.

The assays described herein may be next generation sequencing ("NGS") based tests, and may detect any SNV, indels that overlap with the panel region. Thus, the number on the number of SNVs and indels may vary, although there may be minimum number (e.g., "X" SNVs and indels); novel variants detected may be analyzed bioinformatically.

All the oncogenes and tumor suppressors in the panels may be analyzed for CNVs. Oncogene amplifications and tumor suppressor losses may be measured, and reported (e.g., on a gene sheet providing an idea of the number of oncogenes and tumor suppressors). Translocations that cause fusion proteins may also be detected and analyzed. The most common fusion proteins involve ALK, ROS and RET. The panels described herein may be designed such that a fusion involving these and any other gene will be detected with high confidence (e.g., by placing probes in the entire introns of ALK/ROS/RET where the breakpoint could occur). For example, there are 10 well-known translocations involving these 3 partners and the assay should be able to capture them with high confidence. Any other translocation involving these 3 genes also has a good chance of being captured.

Lab Protocols

One example of a lab protocol is based upon Agilent technologies' SureSelect XT2 Enrichment protocol. It has been optimized to handle hybridization based selection of targets from FFPE tumor samples. Although the method and systems described herein for producing the library and sequences described herein may be particularly useful for the downstream processes and apparatuses also described, any appropriate methods and apparatuses, including currently known systems and methods, may be used for much of the downstream methods and apparatuses (including alignment, analysis, treatment recommendations, and the like). For example, alternative technologies being optimized for this include library preparation kits from New England Biotechnologies and Roche Nimblegen, along with Lockdown DNA probes from IDT. In addition, library preparation kits from new vendors may be useful if cost effective and of equivalent performance. The choice of platform and the protocol standardization steps are designed towards automation compatibility.

Described herein is a method of sequencing that is optimized as described herein, which has numerous advantages over prior art methods and apparatuses. Briefly the protocol is as follows:

1. DNA is extracted using a standard FFPE DNA extraction kit.
2. Since FFPE DNA is highly fragmented and of inferior quality compared to fresh tissue, it is assessed using a real time PCR assay.
3. 200 ng of qubit (Life technologies) quantified d.s. DNA is sheared using a Covaris for 260-280 seconds to ensure >70% of the original DNA lies between 150 and 200 bp peak.*
4. All standard steps in the preparation of sample library are followed except that no size selection is performed. PCR for 8 and 14 cycles are performed for fresh tissue/cell line and FFPE DNA respectively to get adequate DNA library from individual samples
5. The pre-capture library for each sample is individually assessed using a tape station (Agilent technologies). If greater than 10% of the total library is made up of 120 bp fragments which could arise from adaptor dimers as well, a mild size selection using 1.4:1 ampure beads to DNA is used to remove these smaller fragments*.
6. 6 to 8 individual libraries* are quantified and pooled in equal concentration to make up a total amount of 1500 ng DNA and hybridized to probes, for 24 hours.
7. The hybridization protocol is followed as per SS-XT2 standard protocol, except for avoiding any size selection after hybridization. Following cleanup, 12 (FFPE) PCR cycles* are performed to get the final pooled library.
8. The final library is cleaned using 1.5:1 ampure beads to DNA*.
9. As previously described, the library is checked on Tape station and if the 120 bp fragment is greater than 10% of the pooled library, it is cleaned up again using Ampure beads.
10. 8 pM library is loaded on a v3 sequencing kit (2×150 PE sequencing)* to obtain 8-9 GB total output, ~1200 cluster density and >90% Q30 reads. This allows for ~1-1.2 GB (more than five million reads) sequencing output per sample.

(*Steps indicate may be particularly important steps)

Analysis consists of multiple steps: alignment, filtering, somatic SNP detection, copy number variation detection, and detection of translocations. All these steps may be carried out using Strand NGS and are described in greater detail below.

Described herein is a method of sequencing that is optimized for starting with 50-100 ng of input DNA as described herein, which has numerous advantages over prior art methods and apparatuses. Briefly the protocol is as follows:

(1) DNA is extracted using a standard FFPE DNA extraction kit.
(2) Since FFPE DNA is highly fragmented and of inferior quality compared to fresh tissue, it is assessed using a real time PCR assay.
(3) 50-100 ng of qubit (Life technologies) quantified d.s. DNA is sheared using a Covaris for 350-500 seconds. A mild size selection is performed to remove the smaller fragments that adversely affect the size of library preparation.*
(4) All subsequent standard steps in the preparation of library are followed except that no size selection is performed. Optimized adaptors concentration for library generation is 6 X10^4 pM (lower than recommended protocol). Adaptor ligation efficiency is enhanced by the use of 3% PEG in ligation reaction for FFPE sample.
(5) PCR for 10-11 cycles are performed for fresh tissue/cell line and control FFPE DNA for generating adequate pre-cap libraries. For clinical FFPE DNA 13 cycle PCR is performed to get adequate DNA library from individual samples.
(6) The pre-capture library for each sample is individually assessed using a tape station (Agilent technologies). If greater than 10% of the total library is made up of 120 bp fragments which could arise from adaptor dimers as well, a mild size selection using 1:1.8 ampure beads to DNA is used to remove these smaller fragments*. The library is eluted in 50 ul of buffer.
(7) 1-4 individual libraries* are quantified and pooled in equal concentration to make up a total amount of 1500 ng DNA and hybridized to probes, for 24 hours
(8) The hybridization protocol is followed as per SS-XT2 standard protocol. For individual capture (single sample), the probes used are SS-XT. Following cleanup, 11-12 (FFPE) PCR cycles* are performed to get the final pooled library. The final library is cleaned using 1:1.8 ampure beads to DNA*. Optimized elution volume for library: 50 ul post ligation and final.
(9) As previously described, the library is checked on Tape station and if the 120 bp fragment is greater than 10% of the pooled library, it is cleaned up again using Ampure beads. Optimized sequencing plexing: single or pooled capture is 1-4 libraries.
(10) 13 pM library is loaded on a v3 sequencing kit (2×151 PE sequencing)* to obtain 8-9 GBtotal output, ~1200 cluster density and >90% Q30 reads. This allows for ~1-1.2 GB (more than five million reads) sequencing output per sample.

*Steps indicate may be particularly important/critical steps

Alignment

Reads generated by the sequencer are mapped to the reference genome using a combination of a fast exact-match lookup algorithm, BWT, to narrow the potential match locations and an accurate dynamic programming for the final alignment. The following parameters may be used during alignment. Bases with poor quality (<Q10) at the 3' end of the read are clipped before alignment. Reads whose length is less than 35 bp (possibly because of the 3' clipping) are ignored. Reads that match the genome more than 5 times with alignment score >90% are ignored. Reads are screened against a contaminant database before alignment. The alignment is set up to allow incorporation of indels whose length is up to 40% of the read length.

Reads which differ substantially from the reference genome pose special problems and are handled as follows: reads with medium indels (10-50 bp): the Strand NGS aligner uses a special score function that does not penalize the largest indel in a read. This allows reads with a single medium indel to be aligned accurately without any loss in specificity; reads spanning breakpoints caused by large indels, copy number changes or structural variants (SVs): the Strand NGS aligner has a split-read alignment module. Reads which do not align in the first phase are passed through the split-read aligner—this helps align reads which have at least 30 bp on either side of the breakpoint. The breakpoints discovered in this manner are used to improve the alignments of reads near the breakpoint, and also to rescue some unaligned reads. This comprehensive approach allows for high-resolution detection of large indels and SVs; reads spanning small near-tandem duplications: an innovative duplication detection algorithm, detects duplicates within reads, and checks whether the alignment for the read can be improved after the duplicated stretch is removed. The duplicated stretch is replaced in the match record as a putative insertion.

Example: Benchmark Study of a DNA Read Aligner

Background: Next generation sequencing technology has led to the generation of millions of short reads at an affordable cost. Aligning these short reads to a reference genome is a crucial task for many downstream applications. However due to the large size of such data, the process of alignment is computationally challenging and requires sophisticated algorithms which are both, fast and accurate. In this work, we will briefly discuss the Strand NGS (formerly Avadis NGS) alignment algorithm but more importantly present the benchmarking results on several simulated data sets and a real whole-genome data to compare it with other standard state-of-the-art algorithms.

Results: Multiple aligners like Strand NGS, BWA, BWA-Mem, Bowtie2 and Novoalign3 are compared for accuracy and computational efficiency using 4 simulated data sets from the GCAT website and a real Illumina HiSeq 2500 whole-genome paired-end data of 1000 genomes CEU female sample, NA12878. Strand NGS and Novoalign3 showed comparable accuracy in terms of both, % correctly mapped reads and receiver operating curves (ROC). They also seem to outperform other algorithms especially on data sets with longer InDels. For reads potentially originating from complex genomic locations like repeat regions (and therefore assigned low mapping quality), Strand NGS aligner, with careful and intelligent filtering of false positives based on mapping qualities, produces a higher true positive rate compared to Novoalign3. As for the performance comparison based on computational efficiency, other than minor differences, practically all the included algorithms showed comparable performance.

Conclusions: Alignment of millions of short reads to a large reference genome with many complex regions is still a hard problem and almost all current algorithms adopt some form of strategy to trade-off accuracy and computational efficiency. The benchmarking results presented in this study suggest that Strand NGS is a powerful approach for short read alignment and either compares well or even outperforms other state-of-the-art algorithms.

Introduction: There has been an unprecedented growth in sequencing data due to the rapid advancements in the next-generation sequencing (NGS) technology. For a whole-genome sample, the number of reads can vary from few million long reads (>=400 bp) generated by instruments like PacBio and 454, to 2-3 billion short reads (>=75 bp) generated by instruments like Illumina/Solexa and SOLID. Further, there has been a significant cost reduction in DNA sequencing, attracting more and more researchers to use NGS technology in their own labs. However, unless we have proper bioinformatics tools to process and analyze this large amount of sequencing data, data by itself is not of much use.

Problem Statement and Challenges: One of the first steps in the analysis of NGS data, other than of course checking the quality and filtering out bad quality reads, is alignment or mapping of the generated sequencing reads to the respective reference genome. An accurate and efficient alignment of reads to a reference genome is crucial for many downstream applications, for example variant calling, structural variant detection including copy number changes, detecting protein-DNA binding sites using ChIP Sequencing, comparing expression of genes/transcripts across different biological conditions, understanding methylation patterns in DNA, determining species composition using metagenomics workflow, etc. However, alignment is a challenging problem due to the following reasons:

a) A reference genome is typically long (~billions) and has complex regions like repetitive elements etc.

b) Reads are short in length (typically, 50-150 bp), presenting issues with accuracy, and large in number, presenting issues with efficiency.

c) Reads have sequencing errors and must be mapped to unique positions in the reference genome.

d) The subject genome (for example tumor sample) may inherently be different from the reference genome because of acquired alterations over time, making the alignment difficult.

In order to address the above challenges, numerous approaches (MAQ, BWA, BWA-Mem, BWA-SW, Bowtie, Bowtie2, SOAP2, Novoalign, Novoalign3, mrFAST, mrsFAST, SHRIMP, etc.) have been developed in the past. There have also been some benchmarking studies discussing and comparing results from different subsets of these approaches.

Evaluation Approach: Since the alignment task can very quickly become a bottleneck in the analysis pipeline due to the ever-increasing volume of the sequencing data, most of the above approaches adopt a trade-off between accuracy and speed. The choice of number of mismatches or gaps allowed, neglecting quality of data and known SNP information during alignment are some of the ways to trade-off accuracy in favor of the speed or efficiency. Due to this trade-off, it is important to assess the performance of different algorithms on both metrics, i.e., accuracy of read alignment, and computational efficiency. However since accuracy of the alignment process directly impacts the results of many downstream applications, accuracy is a more important metric than efficiency as long as the algorithm runs in a reasonable amount of time given the computational resources at hand.

To measure performance in terms of accuracy, we use simulated data sets for benchmarking and use the following four evaluation criteria:

Fraction (or %) of correctly, incorrectly and unmapped reads when alignment was done for: (a) All reads; (b) Only reads with SNPs; (c) Only reads with InDels; (d) Only reads with both SNPs and InDels; (e) Trade-off between True Positive Rate (TPR) and False Positive Rate (FPR). In this case, TPR and FPR correspond to correctly mapped and incorrectly mapped reads respectively; (f) Mapping quality distribution of incorrectly mapped reads; (g) Fraction (or %) of correctly, incorrectly and unmapped reads for special case of reads that are assigned low mapping qualities (representing ambiguous reads possibly originating from repeat regions in the genome).

To measure performance in terms of computational efficiency, we use a real data set (a whole-genome sequencing run for a widely used sample NA12878) and the total run-time of the chosen algorithms is used as an evaluation criterion. The total time taken for alignment includes the following times: a) Time taken for Burrows Wheeler Transform (BWT) search to find the initial exact seeds. b) Time taken for Dynamic Programming (DP) around the seeds found. c) Time taken for post-processing to produce final alignment results.

Also, it is important to note that the total time reported should not include the time taken in the following tasks: a) Time taken to build the BWT index on the reference genome (since this is a one-time task). b) Time taken to import the sample and collect/calculate QC metrics.

Algorithms Compared for Benchmarking: To make the alignment process more efficient, most alignment algorithms start by building an index on the reference genome. This index is then used to find the genomic locations for each read. There are some algorithms that build index on the reads but most of the popular recent algorithms build index on the reference genome. This is because the same index once built on a reference genome can be used repeatedly for aligning different read sets. There are two main techniques used for building the index on reference genome: hash tables and Burrows-Wheeler transform (BWT). In this study, we only consider the following algorithms that build an index (either BWT- or hash table-based) on the reference genome:

Strand NGS: It is BWT-based aligner, which in the first step, uses the Ferrazina and Manzini algorithm to find the seeds of each read quickly in the reference. Then for every seed match found for the read, a Smith-Waterman type dynamic programming (DP) algorithm is applied to determine if the read matches around the area anchored by the seed. This match must satisfy the specified mismatches and gaps threshold.

Data Sets Used: The GCAT (Genome Comparison and Analytic Testing) platform which is developed by Arpeggi Inc. and hosted on the bioplanet website, is heavily used in this study. GCAT provides a solid testing platform for comparing the performance of multiple genomic analysis tools across a standard set of metrics. For alignment tests, the GCAT website hosts different simulated data sets covering read lengths of 100, 150, 250, and 400; single-end and paired-end library protocols; and both short and long InDels. Assuming a typical use-case scenario where Illumina paired-end data is used, we selected four data sets from GCAT in this study for benchmarking purposes. The details of these data sets are shown in Table 4. The base quality for each base in all the four simulated data sets is 17, producing an average read quality of 17.

For computational performance benchmarking, we used the data from whole-genome sequencing of the sample, NA12878 on Illumina HiSeq 2500 using paired-end library. This data is ~103 GB and comprises of 1,165,216,818 (~1.16 billion) paired-end reads of length 150 bp.

TABLE 4

Description of GCAT data sets

| Data set | Read Length | Library Protocol | Indel | Total # of reads | # of reads with SNPs | # or reads with InDels | # of reads with both SNPs and InDels |
|---|---|---|---|---|---|---|---|
| D1 | 100bp | PE | Short | 11,945,250 | 1,202,587 | 313,753 | 31,731 |
| D2 | 100bp | PE | Long | 11,945,250 | 1,195,002 | 308,029 | 31,135 |
| D3 | 150bp | PE | Short | 7,963,500 | 1,158,693 | 304,788 | 44,449 |
| D4 | 150bp | PE | Long | 7,960,500 | 1,164,160 | 310,750 | 45,782 |

BWA: It is a BWT-based aligner, which uses the Ferrazina and Manzini matching algorithm to find seeds. Then a backtracking algorithm is used that searches for matches between a substring of the reference genome and the query within a certain defined distance.

BWA-Mem: It is conceptually based on BWA but reported to handle long reads and considered to be more accurate and faster.

Bowtie2: It is a BWT-based aligner but just like BWA, uses the Ferrazina and Manzini matching algorithm to find seeds. Bowtie2 is designed to handle long reads and supports additional features that are not supported by Bowtie.

Novoalign3: It is a hash table based tool, which first builds the index on the reference using hash tables and then uses the Neddleman-Wunsch algorithm with affine gap penalties to find the optimal alignment.

Other than Novoalign3, which uses the hash table based index, others used BWT based index. Despite the conceptual similarities among the BWT index-based algorithms, there are still differences in their seeding strategies and optimizations. For example, Bowtie2 search for the seeds of length 16 with a gap of 10 then prioritize the seed locations and perform DP around them. BWA on the other hand, does the inexact matching in the BWT index itself. In Strand NGS, we keep extending the seed till the seed is present in the reference. Then we jump by one/third of the seed and start searching for the next seed. In the end, we take the 4 longest seeds and find the seed locations in the reference. After removing the duplicate seed locations, DP is performed at each seed location.

There are some limitations of using simulated data sets for accuracy benchmarking. First, it is difficult to mimic the error patterns in the generated reads that matches the true error model of the sequencer; and second it is not guaranteed that the true genomic location of the generated read with simulated sequencing errors is the one where the read is generated from. The read with simulated sequencing errors and/or SNPs/InDels can very well align at a different location with better accuracy. However barring few instances like these, still the ease of defining the truth, makes this approach viable and useful for benchmarking studies. Therefore despite some shortcomings, most of the high-level comparisons that can be derived about different algorithms using simulated data sets still hold, thereby providing a useful resource to the users to understand the pros and cons of multiple alignment algorithms.

Accuracy Benchmarking Results: In an effort to keep this article short, we only provide detailed results and discussion on one of the GCAT data sets for accuracy benchmarking. Since reads with large InDels pose greater challenge in alignment, we'll only cover the benchmarking results on data set D4 in more detail. For comparison of alignment algorithms on other data sets (D1, D2, and D3), we have reviewed our results. Most of the conclusions made in this study using the results on data set D4 hold good for other data sets, however the differences in the algorithms for data sets with short InDels (D1 and D3) are less pronounced.

Alignment Accuracy on Data Set D4: As per the evaluation criteria mentioned above, Table 5 shows the fraction of correctly, incorrectly and unmapped reads for four different algorithms in various scenarios. All the algorithms were run on default parameters.

TABLE 5

Alignment Accuracy of Strand NGS, BWA, Bowtie2, and Novoalign3 on simulated data set 'D4'.

| | | All Reads [7,963,500] | Reads with SNPs [1,164,160] | Reads with InDels [310,750] | Reads with SNPs and InDels [45,782] |
|---|---|---|---|---|---|
| Strand NGS | Correctly Mapped | 99.22 | 99.11 | 96.58 | 95.88 |
| | Incorrectly Mapped | 0.5868 | 0.6452 | 2.550 | 2.728 |
| | Unmapped | 0.1938 | 0.2468 | 0.8692 | 1.396 |
| BWA | Correctly Mapped | 98.54 | 97.96 | 90.48 | 89.86 |
| | Incorrectly Mapped | 0.6914 | 0.6948 | 3.868 | 3.862 |
| | Unmapped | 0.7673 | 1.346 | 5.648 | 6.275 |
| Bowtie2 | Correctly Mapped | 96.87 | 96.29 | 93.46 | 93.02 |
| | Incorrectly Mapped | 2.696 | 3.035 | 5.405 | 5.515 |
| | Unmapped | 0.4294 | 0.6718 | 1.139 | 1.468 |
| Novoalign3 | Correctly Mapped | 98.99 | 98.94 | 95.80 | 95.72 |
| | Incorrectly Mapped | 0.1411 | 0.1441 | 3.34 | 3.355 |
| | Unmapped | 0.8672 | 0.9187 | 0.8608 | 0.9218 |

Since the reads with SNPs or InDels, which typically makes the read alignment difficult, constitute a small percentage of the data, all the algorithms particularly Strand NGS, BWA, and Novoalign3 have comparable alignment accuracy when all reads are used. Bowtie2 has a slightly worse alignment accuracy compared to others on both metrics i.e. % correctly mapped and % incorrectly mapped. However for all practical purposes, alignment accuracy for all the four algorithms can be considered in the same ballpark when results are summarized across all reads.

On the other hand, if we focus on the alignment accuracy considering only reads with SNPs, only reads with InDels, or only reads with both SNPs and InDels, there are more clear differences in the accuracy of different algorithms. For example, comparing the accuracy of different algorithms on 45,782 reads that have both SNPs and InDels, Strand NGS and Novoalign3 seem to be performing equally well but relatively better than BWA and Bowtie2 in terms of both metrics, producing higher % of correctly mapped reads (high TPR) and lower % of incorrectly mapped reads (low FPR).

Relationship between True Positive and False Positive Rate: Typically, there is a tradeoff between TPR and FPR and the relationship between them is an important and commonly used metric to compare different algorithms. To assess the relationship between TPR and FPR, we restrict the analysis to the reads with both SNPs and InDels (45,782 reads in this case), since these reads are most difficult to align and therefore represent a good set to compare the pros and cons of different algorithms. As per the description on the GCAT website, to generate the plot showing relationship between true positive and false positive rate, first reads are sorted based on their normalized mapping qualities from high to low, and then correct and incorrect percentages are calculated. Incorrect read % is plotted in log-scale on the y-axis and correct read % is plotted on the x-axis.

The further the line goes to the right before turning upwards, the better the accuracy. This is because typically the percentage of incorrectly mapped reads is low for reads with high mapping quality, with this percentage increasing with the decrease in the mapping quality.

Figure 2:
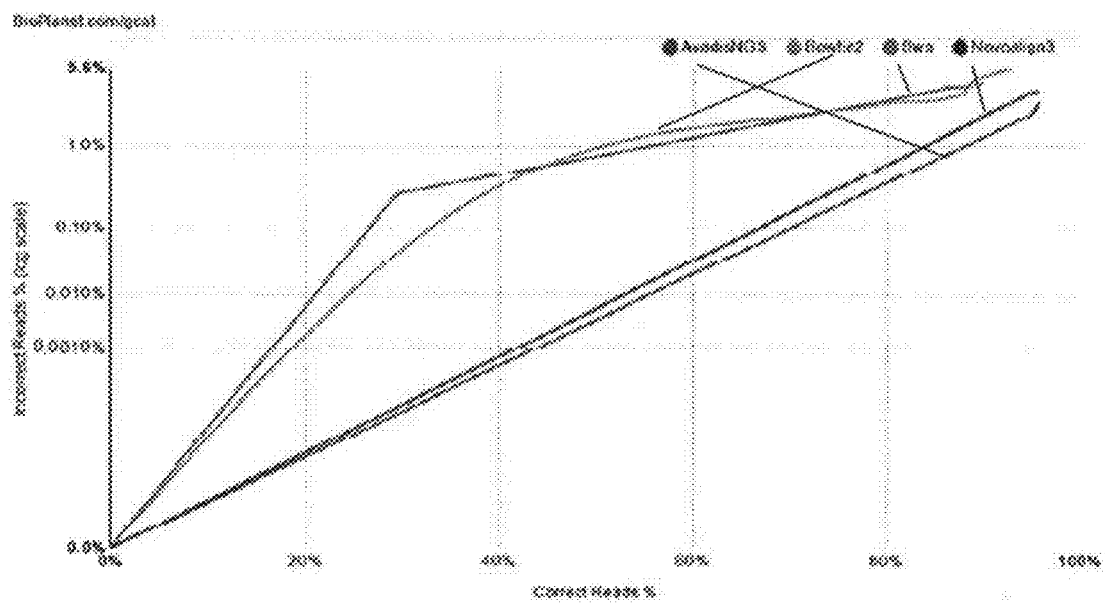
FIG. 2 shows an example of a relationship between true positive and false positive rate for various aligners.

FIG. 2 shows the relationship between true positive and false positive rate when only reads with both SNPs and InDels are considered. As can be seen from FIG. 2, BWA and Bowtie2 show a steep curve upwards compared to Strand NGS and Novoalign3, indicating larger percentage of incorrectly mapping reads even for reads that are assigned higher mapping quality by the respective algorithms. On the other hand, this curve for Strand NGS and Novoalign3 goes up more gradually indicating only a mild increase in FPR as TPR increases.

Distribution of Mapping Quality of Incorrectly Mapped Reads: Regardless of the choice of the alignment algorithm, due to short length of the reads, sequencing errors and complex genomic locations including repeat regions, there will be some percentage of incorrectly mapped reads. These incorrectly mapped reads are likely to produce false positives in downstream analysis like variant calling. However since most variant calling algorithms take into account the read/base quality as well as mapping quality assigned by the alignment algorithm, it is possible to avoid some false positives if low mapping qualities are assigned to the incorrectly mapped reads. Therefore, one of the important criterions to compare alignment algorithms is to assess the distribution of mapping qualities assigned by them to incorrectly mapped reads. As mentioned, if an algorithm incorrectly maps the read but assign a low mapping quality to it, the read can be filtered out in the variant calling step avoiding false positive calls originating from it. On the other hand, if incorrectly mapped reads are assigned high mapping quality, there is no way to filter these out leading to more false positives.

Figure 3A:
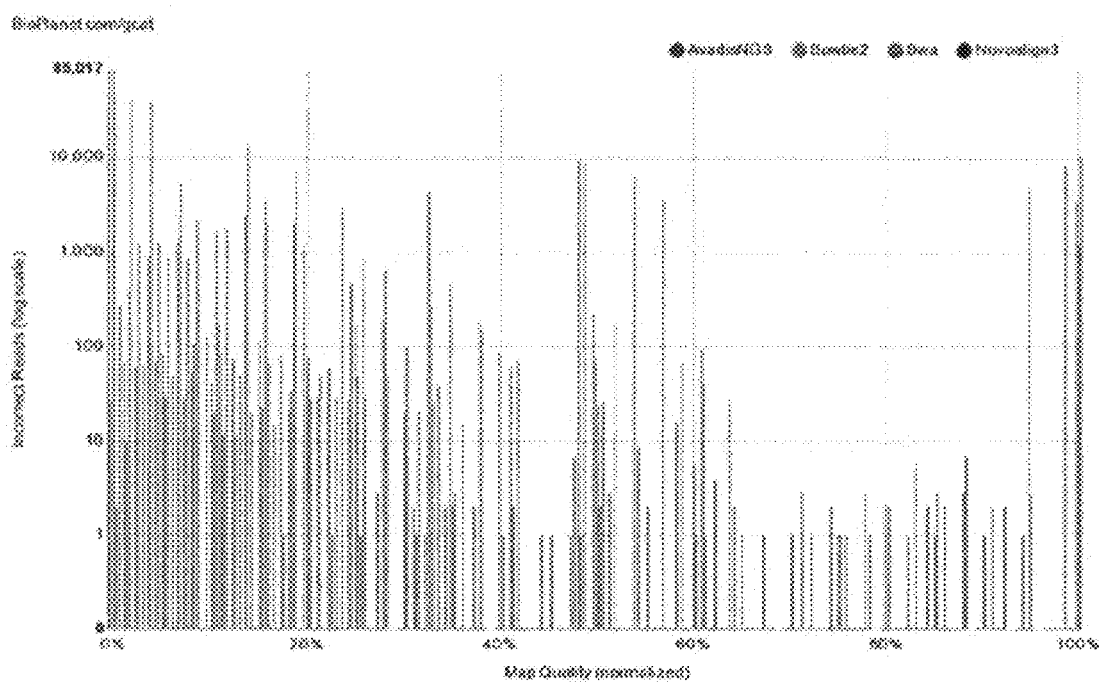
FIGS. 3A and 3B show an example of distributions of mapping qualities assigned to incorrectly mapped reads.
Figure 3B:
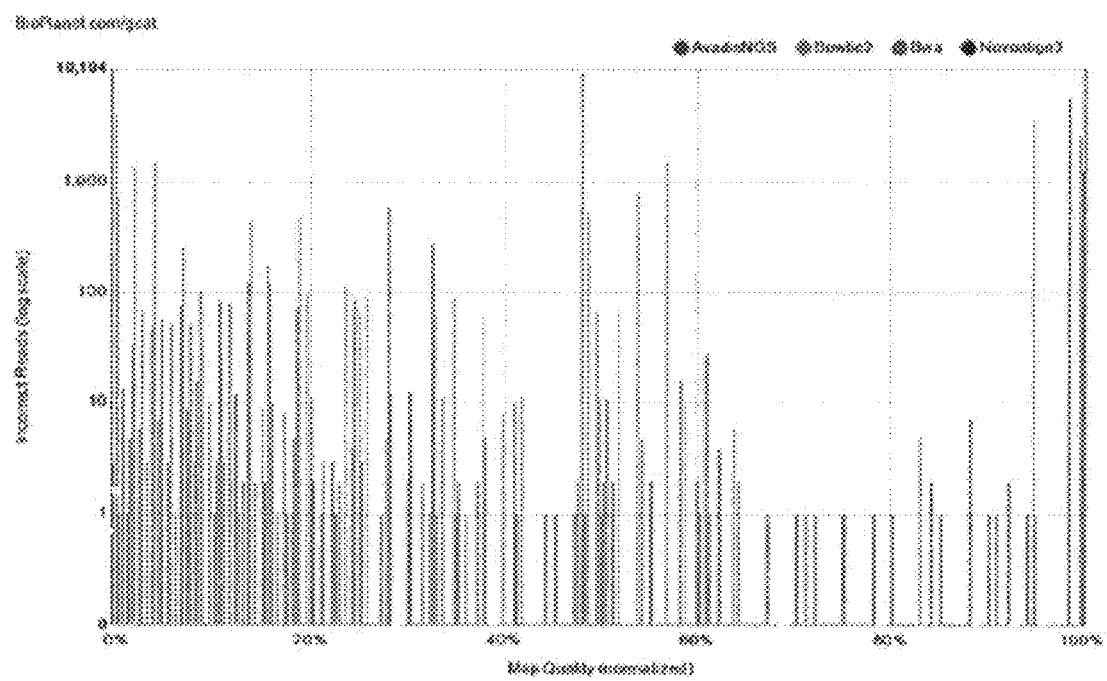
Figure 4A:
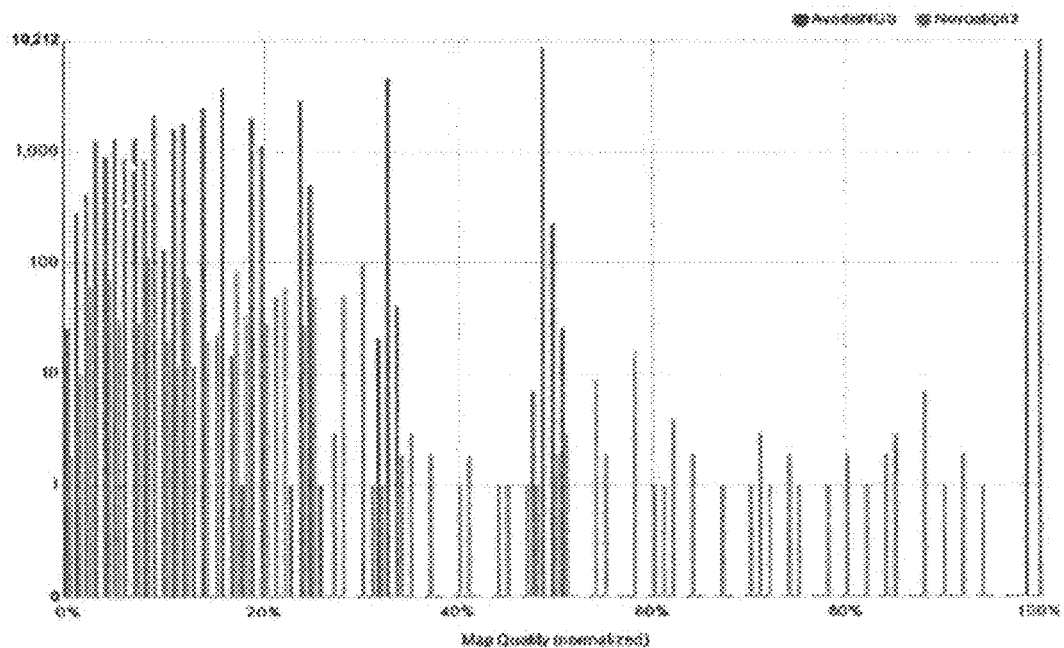
FIGS. 4A and 4B also show an example of distributions of mapping qualities assigned to incorrectly mapped reads.
Figure 4B:
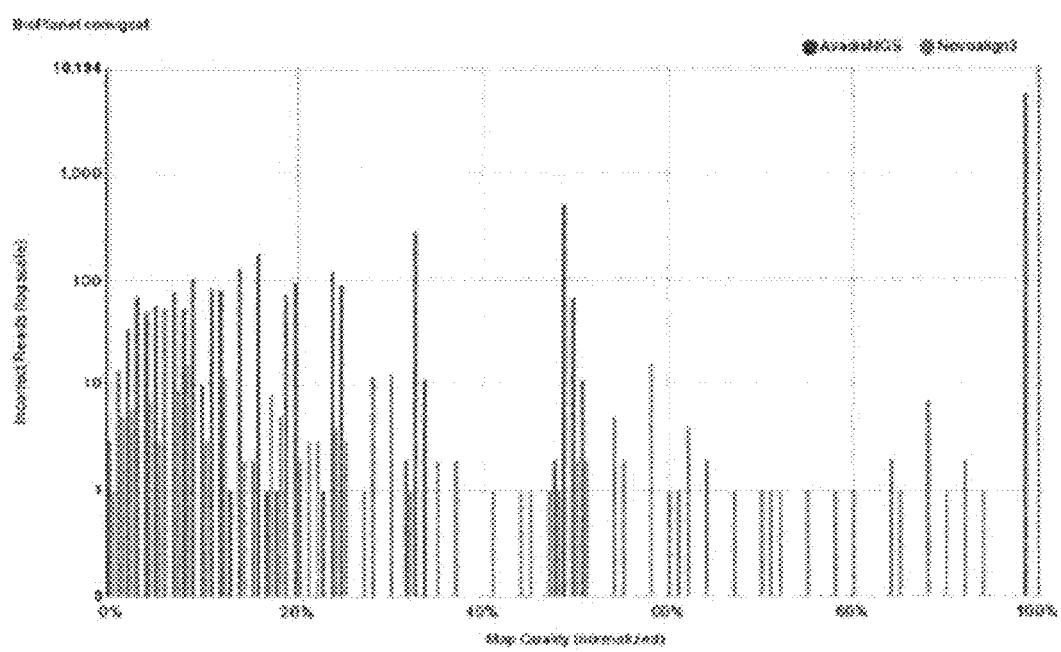

To assess what mapping qualities are assigned to incorrectly mapped reads by different algorithms, GCAT provides a plot showing the mapping quality distribution for incorrectly mapped reads. FIG. 3A shows this distribution for all reads, and FIG. 3B shows the same distribution for only reads with InDels. For better visualization, we also show in FIGS. 4A and 4B the similar distributions, however comparing only Strand NGS and Novoalign3 since both of these algorithms are found to have comparable but higher alignment accuracy as compared to BWA and Bowtie2 (refer to table 5).

There are two important points to observe from FIGS. 3A and 3B, which apply to all the algorithms. First, every algorithm aligns a fraction of reads incorrectly with mapping quality as 100. There is most likely no ambiguity in aligning these reads due to multiple locations being equally likely, but still the reads are mapped incorrectly due to other issues. Second, a higher fraction of incorrectly mapped reads are towards the left side of the plot indicating an assignment of lower mapping quality to them. This is good because later these incorrectly mapped reads can be filtered out using an appropriate mapping quality threshold before proceeding with the variant calling step. If we ignore the incorrectly mapped reads with mapping quality 100, and focus on the rest which are likely incorrectly aligned due to ambiguous locations, we observe that particularly Strand NGS assigns lower mapping quality to these reads compared to the other three algorithms. The maximum mapping quality assigned by Strand NGS to incorrectly mapped reads (ignoring reads with mapping quality 100) is around 50, whereas rest of the algorithms, including Novoalign3 assigns much higher mapping quality to these reads, thereby making it difficult to filter out these reads in the variant calling step. This is more clearly visualized in FIGS. 4A and B, where only Strand NGS and Novoalign3 are compared.

Alignment Accuracy for Reads with Low Mapping Quality: The reads that originate from complex genomic locations like repeat regions for example are difficult to align. Typically these reads are classified as ambiguous by most algorithms as multiple locations in the genome are found to be equally likely for alignment of these reads. Depending on the algorithm or the choice of parameter settings, either all the genomic locations are reported or one random location is chosen and reported for these ambiguous reads. In either case, most of the algorithms reduce the mapping quality of these reads to reflect the ambiguity in their alignment. In this section, to assess the performance of algorithms in terms of accuracy on these ambiguous reads, we'll only compare Strand NGS and Novoalign3 because of the following reasons: 1) In terms of % correctly and % incorrectly mapped reads (which is used as the primary metric of accuracy), Strand NGS and Novoalign3 have similar accuracy, and both are found to be better than BWA and Bowtie2. Therefore, we believe that this additional analysis is valuable for comparing Strand NGS and Novoalign3 only. 2) Each algorithm has its own way of assigning mapping qualities. In addition, the mapping qualities assigned by different algorithms are in various ranges. This is the reason GCAT normalizes the mapping qualities between 0 and 100. Despite normalization, number of reads falling in different normalized mapping quality bins as per different algorithms, could be very different. Comparing algorithms on largely different number of reads may not be very useful. Strand NGS and Novoalign3 have similar number of reads that are assigned normalized mapping quality between 0 and 20, hence making the comparison more meaningful. On the other hand, Bowtie2 particularly has much higher number of reads with normalized mapping quality between 0 and 20. In this analysis, we have also included another algorithm, BWA-Mem which is a higher version of BWA and have assigned a normalized mapping quality between 0-20 to a comparable number of reads as Strand NGS and Novoalign.

Out of the total 7,963,500 reads in data set D4, Strand NGS, Novoalign3 and BWA-Mem assigns a normalized mapping quality of 0-20 to 164,071, 158,498 and 158,083 reads respectively. Table 6 shows the alignment accuracy of the three algorithms on these reads.

TABLE 6

Alignment Accuracy of Strang NGS, Novoalign3 and BWA-Mem on reads with low mapping quality

|  | Strand NGS 164,071 Reads | Novoalign3 158,498 Reads | BWA-Mem 158,083 Reads |
| --- | --- | --- | --- |
| Correctly Mapped | 126,906 (77.35%) | 88,834 (56.05%) | 113,817 (72%) |
| Incorrectly Mapped | 21,731 (13.24%) | 603 (0.3804%) | 44,266 (28%) |
| Unmapped | 15,434 (9.407%) | 69,061 (43.57%) | 0 (0%) |

It is clear from table 6 that Strand NGS has a higher percentage of correctly mapped reads (high TPR) compared to both Novoalign3 and BWA-Mem. On the other hand, percentage of incorrectly mapped reads (FPR rate) of Strand NGS is lower than BWA-Mem, thereby making it better than BWA-Mem on both metrics, but higher than Novoalign3 making the comparison between Strand NGS and Novoalign3 non-trivial. However, if we refer to the previous section and particularly FIGS. 4A and 4B where distributions of mapping qualities assigned by these two algorithms to incorrectly mapped reads are examined, we also know that Strand NGS assigned relatively low mapping quality to incorrectly mapped reads. Therefore it is easy to filter out many incorrectly mapped reads by Strand NGS before the variant calling step, which is one of the most common downstream analysis steps. For example, a mapping quality threshold of 50% would filter out a large fraction of the incorrectly mapped reads, thereby reducing FPR to a large extent without sacrificing high TPR obtained using Strand NGS. Further, it is also important to note that incorrectly mapped reads by BWA-Mem cannot be filtered out using a threshold on normalized mapping quality because similar to Novoalign3, normalized mapping qualities assigned by BWA-Mem are more or less spread uniformly in the range 0-100 (data not shown here but accessible on the GCAT report, link to which is provided above).

Computational Performance Benchmarking Results: For computational performance benchmarking, we performed the alignment of real whole-genome sample NA12878 (details above), using the algorithms Strand NGS, BWA-Mem, and Bowtie2; on a machine with 64 GB RAM and 15 cores. BWA-Mem is used instead of BWA because BWA-Mem is reported to be faster than BWA. Further, we did not include Novoalign3 in computational performance benchmarking because it is a proprietary algorithm and the academic version doesn't support multi-threading, making it harder to compare the run-time of Novoalign3 with the rest of the algorithms.

As per the evaluation criteria defined above, Table 7 shows the total time taken by different algorithms in aligning ~1.16 billion paired-end reads generated from the sample NA12878 against hg19 human genome reference.

TABLE 7

Computational performance of algorithms on whole-genome sequence data for sample NA12878.

| Algorithm | Total Time Taken |
| --- | --- |
| Strand NGS | 9 hours 32 minutes |
| BWA-Mem | 12 hours 09 minutes |
| Bowtie2 | 11 hours 0 minutes |

It is clear from table 7 that Strand NGS, in addition to offering higher alignment accuracy as demonstrated in the previous section, is computationally fast compared to other standard alignment algorithms.

Conclusions: In this work, we presented a benchmarking study to compare the performance, in terms of accuracy and computational run-time, of multiple alignment algorithms: Strand NGS, BWA, BWA-Mem, Bowtie2, and Novoalign3. In terms of accuracy measured as the fraction of correctly and incorrectly mapped reads, Strand NGS and Novoalign3 seem to be comparable to each other but superior to other algorithms considered in this study. Further for both Strand NGS and Novoalign3, FPR rate increases mildly with the increase in TPR rate, as opposed to steeper increase in case of BWA and Bowtie2. However when we focused closely on the assigned mapping qualities by Strand NGS and Novoalign3 to incorrectly mapped reads, we noticed that Strand NGS assigns lower mapping quality to them compared to Novoalign3, thereby providing a way to remove them before the downstream analysis.

In addition, we also focused on a subset of the reads, which are assigned very low mapping quality by both Strand NGS and Novoalign3. We found that Strand NGS has a higher true positive rate, albeit at the cost of higher false positive rate. However, we argue that since Strand NGS assigns low mapping quality to incorrectly mapped reads, false positive rate can be significantly reduced by choosing a lower cut-off on mapping quality without affecting the true positive rate.

Overall, based on the results presented in this study, we strongly believe that Strand NGS offers a solid approach for DNA read alignment and either performs comparably well or outperforms most of the state-of-the-art algorithms, including Novoalign3 in one or more aspects. Further since Strand NGS offers a GUI-based solution with a visually appealing and convenient way to change parameters, we believe it is one of the easiest tools to use by researchers with limited or even no knowledge of algorithms or bioinformatics.

Variant Calling

The somatic variant caller in Strand NGS is an adaptation of the standard binomial SNP calling method to take the base qualities into account. The SNP calling method considers the base taken by each read covering the location, as well as its associated base quality, denoted collectively by D, and decides whether there is a variant at that location. This is done by computing the probability, P of observing a data D' with the same total number of bases and at least as many variant bases as D has, with the assumption that the location has the reference genotype, and that the variants are due to sequencing error only. Only the variant allele with the highest frequency of occurrence is considered for the computation of the probability P and the other variant alleles are ignored. This probability is then converted into a score as Score=$-10 \log_{10} P$. If this score is greater than 50, then the location is reported as a variant location.

The standard binomial test for calling SNPs requires one overall error rate and cannot use the qualities of all the individual bases. One way to arrive at the overall error rate from the base qualities in D is to compute the error rate corresponding to the lowest base quality from D. But this may make the results very sensitive to any noisy outlier bases with very low quality which may lead to false negatives. In order to avoid this problem, we ignore all the bases with qualities less than a threshold $Q_t$, and run the binomial test with the error rate corresponding to the lowest quality from the remaining bases. To make the test more robust, this process is repeated for multiple values of $Q_t$ and a variant is reported if it is called for any of the thresholds $Q_t$. Typically $Q_t$ is varied from 20 to 30 and if a variant is called in any of these tests, the method reports the variant and the lowest Q at which the variant is called. In case different variants are called at the same locus in these multiple tests, only the one with the highest score is reported.

Somatic copy number detection: Somatic copy number is typically detected using a depth-of-coverage (DOC) approach which computes for each genomic region, the ratio of the number of reads in the tumor and matched normal samples. Since sequencing two biological samples—normal and tumor—for each patient is expensive, StrandAdvantage uses a precomputed normal profile derived from a collection of normal samples. To improve accuracy, the allele fraction of known heterozygous loci in the regions is also used; this ratio is ~50% in copy-neutral regions and the divergence from the 50% is an estimate of the copy number variation. A Bayesian approach uses the GC-corrected DOC ratios, the tumor content estimate from the pathology report, and the allele fraction of heterozygous loci to compute for each gene the copy number value and its likelihood. A second method for detecting copy number variation is the allele fraction of known heterozygous loci in the affected region; this ratio is ~50% in copy-neutral regions and the divergence from the 50% is an estimate of the copy number variation. Two approaches are under investigation: (1) an empirical method that is largely based on the DOC method and the tumor content estimate from the pathology report but which uses the B-allele frequencies to validate the detected CNVs; (2) a Bayesian approach that uses the GC-corrected DOC ratios, the tumor content estimate from the pathology report, and the allele fraction of heterozygous loci to compute for each gene the copy number value and its likelihood.

The accuracy of copy number detection is a function of the extent of copy number change, the number of probes in the region undergoing copy number change, and the tumor purity. Simulations will be carried out for each combination to assess the limits of detection for each copy number event. These limits will be further refined by experimenting with cell lines harboring known copy number events and various mixtures of the same.

Results of a study comparing the Strand NGS variant calling and variant calls from a GATK UnifiedGenotyper are provided below.

Background: To realize the potential and promise of Next Generation Sequencing (NGS) technology towards research and clinical applications, computational approaches are essential to call variants and translate them into actionable knowledge. Many algorithms are developed for variant calling, however they differ on multiple variant call predictions. In this paper, we'll present Strand NGS (formerly Avadis NGS) variant calling approach and benchmarking results on a whole-genome sample NA12878 and compare our variant calls with those from GATK UnifiedGenotyper.

Results: Strand NGS and GATK identified a total of U.S. Pat. Nos. 6,393,054 and 6,105,466 variants respectively with very similar Het/Hom and Ti/Tv ratios. We observed a high overlap (93%) in these variant calls with overlap in fact increasing to ~98% after filtering based on quality metrics, making Strand NGS and GATK very similar. Assessment of different quality metrics like supporting reads %, variant score, coverage, strand bias and other PV4 biases, for overlapping versus uniquely identified variants, provides a useful way to filter the likely false positives.

Conclusions: Due to several issues with the raw sequencing data, variant calling is still a challenging problem. Although numerous open-source and proprietary algorithms are available, assessing how well these algorithms perform on different data sets is not trivial. The benchmarking results presented in this paper suggest that Strand NGS variant caller is a powerful and flexible approach to call variants and provides a visually appealing way to assess their quality using a variety of metrics. The results compare very well with GATK, which is one of the widely used variant callers.

Introduction: Most organisms within a particular species differ very little in their genomic structure. A single nucleotide variation between two complementary DNA sequences corresponding to a specific locus is referred to as a SNP or Single Nucleotide Polymorphism and is the most common variation observed within a species. This variation could be due to insertion, deletion or substitution of a nucleotide. The variations are referred to as allele changes at the specific chromosomal loci.

Typically, SNPs commonly observed in a population exhibit two alleles—a major allele, which is more prevalent, and a relatively rarely occurring minor allele. Such variations, if they occur in genic regions, can result in changed phenotypes and may even cause disease. Sometimes, SNPs occur together. A set of adjacent SNPs is termed a Multiple Nucleotide Polymorphism or MNP. Thus MNP alleles have multiple nucleotides. Microarrays for SNP detection use probes with specific targets when searching for SNPs. Next-generation sequencing (NGS) allows SNP identification without prior target information. The high coverage possible in NGS also facilitates discovery of rare alleles within population studies.

SNP or generally speaking variant detection algorithms compare the nucleotides present on aligned reads against the reference, at each position. Based on the distribution of As, Ts, Gs, and Cs at that position, and the likelihood of error, a judgment is made as to the existence of a variant. Some issues that must be handled by variant detection algorithms are mentioned below:

Quality of base-calls: A sequencer outputs a sequence of nucleotides corresponding to each read. It also assigns a quality value based on the confidence with which a particular base is called. Clearly, variant detection algorithms must put greater weight on bases called with higher confidence.

Mapping quality of reads: Most alignment algorithms assign quality scores to a read based on how well the read aligned with the reference. These scores are relevant in variant detection because they measure the likelihood of a read originating from the suggested position on the reference. Even if the individual bases on a read are called with high quality values, the read may align imperfectly with the reference. The mapping quality score takes into account the insertions, deletions, and substitutions necessary for alignment at a particular position.

Depth of coverage: The number of reads covering a position also determines how confidently a variant can be called. Obviously greater sequencing depths lead to higher variant calling accuracy.

Homopolymer: A homopolymer is a repetitive sequence of a single nucleotide, e.g., AAAAAA. Sequencers often exhibit inaccurate representations of homopolymers and their immediate neighbors due to limitations in the next-generation sequencing technology. Such regions need to be handled carefully by variant detection algorithms.

Ploidy: Ploidy is the number of sets of chromosomes in a cell. Haploid organisms have one set of chromosomes per cell, while diploid organisms like humans have two. Polyploidy, the state where all cells have multiple (but more than two) sets of chromosomes is chiefly observed in plants. SNP detection must take into account the ploidy while calling SNPs. For example, in a haploid organism, each position can correspond to only one nucleotide. Reads must ideally agree at each position, and any deviation is easily detected as a sequencing error. Diploid organisms inherit one set of chromosomes from each parent and so reads can show two nucleotides at each position, one from each set. Currently, variant analysis in Strand NGS assumes that the ploidy is two. In this case a SNP can be called under two circumstances: (i) Homozygous SNP: One when the consensus reached from the sample reads shows a single nucleotide at the location and this consensus differs from the reference nucleotide. (ii) Heterozygous SNP: Alternatively, the sample reads may show considerable presence of two different nucleotides; typically one of the two agrees with the reference nucleotide. The two alleles should ideally show close to 50% presence each.

In the following section, we'll describe our variant calling approach briefly and then discuss the variants detected on the whole genome sample NA12878 comprising of ~1.16 billion paired-end reads obtained from Illumina HiSeq 2500 sequencer. These resultant variants obtained from Strand NGS will also be benchmarked with those obtained from GATK UnifiedGenotyper tool.

Our Variant Calling Approach: The variant calling algorithm in Strand NGS is capable of detecting three types of variants, namely substitution (or mutation), deletion and insertion. While reporting, these variants are categorized into four events namely substitution, insertion, deletion and complex. Substitution consists of one or more substitutions occurring in consecutive locations; similarly deletions and insertions comprise of events where one or more deletions or insertions, as the case may be, occur together. A deletion event is modeled as a mutation from a nucleotide value {A, T, G, C} to "gap". Complex events are reported when there is a mixture of multiple types of variants occurring together in consecutive locations.

The variant detection algorithm works on a per-sample basis. For each sample, data for each chromosome is analyzed, with a capability for parallel computation per chromosome. The computation is optimized for memory usage by segregating the data into windows based on maximum read size.

Note: Strand NGS provides two different variant callers, one for calling germline variants and the other for calling somatic variants. A brief description of the somatic variant caller is given below, whereas all the other sections below refer to the germline caller.

Selection of Potential Variant Sites: Variant detection is only performed at sites determined by pre-processing to be likely variant locations. Locations are only considered potential variant sites if they satisfy all the following requirements: (a) Read coverage threshold: The number of reads covering the location must exceed a user-defined threshold; (b) Variant coverage threshold: The number of reads covering the location and differing from the reference at the location must also exceed a user-defined threshold.

Bayesian Algorithm for Variant Calling: At every location that is declared significant in the previous step, the Bayesian variant calling algorithm is applied to identify the most likely genotype, and to report the variant if detected. The algorithm considers the nucleotide or the base taken by each read covering the location, as well as its associated base quality and finds the consensus genotype. The consensus genotype is the one most likely to have caused the observed data and is computed using Bayes principle.

Calculation of Posterior Probability: If the observed data is collectively denoted by D, then the task is to infer the consensus genotype from D. Variants are then detected by comparison to the reference sequence. The algorithm selects the genotype G that maximizes the posterior probability, P(G|D), defined by the probability of a genotype G given the observed data. This is easily computed under Bayes principle as:

$$P(G|D) = \frac{P(D|G).P(G)}{P(D)}$$

Where P(G) is the prior probability of genotype G and P(D) is the likelihood of data, calculated over all possible genotypes, $$P(D) = \Sigma_{\forall G_i} P(D|G_i) \cdot P(G_i)$$

The conditional probability P(D|G) represents the probability of observing the data D under the given genotype G.

Strand NGS specifies a score to represent the confidence with which a variant is called at a locus. This score is a function of the posterior probability of the locus being the reference genotype RR given the observed data and is defined as $$\text{Score} = -\log_{10} P(G=RR|D)$$

If the consensus genotype is not the reference genotype, and if the above score is greater than the user-specified cut-off, then the location is reported as a variant location and the alleles corresponding to the consensus genotype, which are different from the reference are reported as the variant alleles.

Calculation of the Prior Probabilities P(G): We may calculate the prior probabilities of different genotypes at a given location by taking into account the following parameters.

(a) The reference base at the location.

(b) Heterozygosity Rate: This is representative of the prior expectation of a position being heterozygous in the organism. The default value is set to 0.001, which correlates with the population SNP rate for the human genome.

(c) Homozygous to heterozygous ratio: This is the prior expectation of the ratio of the number of homozygous mutations to the number of heterozygous mutations. It has been observed that heterozygous variants are twice as frequent as homozygous variants in any diploid or human genome. Hence the default value is set to 0.5.

(d) InDel to substitution ratio: This is the prior expectation of the ratio of the number of indels to the number of substitutions. Based on the information from the literature, the default value is set to 0.125.

(e) Ti/Tv ratio: This is the prior expectation of the ratio of the number of transitions to the number of transversions. A transition is a point mutation that changes a purine nucleotide (A or G) to another purine, or a pyrimidine nucleotide (T or C) to another pyrimidine, whereas a transversion refers to the substitution of a purine for a pyrimidine or vice versa. Although there are twice as many possible transversions, because of the molecular mechanisms by which they are generated, transition mutations are generated at higher frequency than transversions. Expected value of this ratio for genome wide variations is in the range 2.0-2.1, whereas it is in the range 3.0-3.3 for the exonic variations. The default value for this parameter is set to 2.6 to make it suitable for both whole genome and exome data analysis.

Calculation of the Conditional Probabilities P(D|G): The computation of P(D|G) takes into account the probability of errors observed in the data under each genotype G. It is assumed that the error in the observation of any base is independent of observation error in any other base. In most cases, error rates are derived from the associated base qualities as follows:

$$\epsilon = 10^{-(\text{base quality})/10}$$

The error rates may be adjusted by taking the mapping quality into consideration. A mis-aligned read creates unreliable results irrespective of the base-qualities. Therefore, Strand NGS has an option to take into account the mapping qualities whenever provided by the aligner and uses the minimum of the read mapping quality and individual base quality in place of base quality for its computations.

In the absence of error rates, hard-coded error rates (that are technology-specific) are used. If error rates for a particular technology are not present in Strand NGS, it assumes a quality score of 30 for the base, which is interpreted as an error rate of 0.001.

Results—Benchmarking against GATK: We ran both Strand NGS and GATK variant caller on NA12878 whole-genome data using their default parameters. Strand NGS identified a total of 6,544,450 variants on the raw read set and a total of 6,335,487 variants on the processed read set which is obtained after performing steps like local realignment, base quality score recalibration and duplicate read removal. Since the focus of this article is to compare the results of Strand NGS variant caller with GATK caller, we want to remove differences that could be introduced by these pre-processing steps. Therefore, we used the GATK processed (after local realignment and base quality score recalibration) BAM file as an input in the Strand NGS variant calling algorithm as well. With this read set as an input, a summary of the variants detected by Strand NGS and GATK UnifiedGenotyper along with their characteristics is shown in table 8.

TABLE 8

Number of Variants detected by Strand NGS and GATK

|  | Strand NGS | GATK |
| --- | --- | --- |
| Number of total variants | 6,393,054 | 6,105,466 |
| Number of substitutions | 5,199,005 | 5,085,477 |
| Number of insertions | 467,267 | 468,203 |
| Number of deletions | 549,043 | 503,689 |
| Number of complex variants | 177,739 | 48,097 |
| Het/Hom ratio | 2.55 | 2.08 |
| Ti/Tv ratio | 1.92 | 1.93 |

Of the 6,393,054 variants identified by Strand NGS, 5,948,107 variants (5,005,771 substitutions and 942,336 InDels and complex) are identified by GATK also, producing an overlap of ~93%. If we only focus on substitutions, there is an overlap of ~96% between Strand NGS and GATK, confirming that for most practical purposes, variant calling results from these two algorithms are very similar.

There are a total of 444,947 variants (193,234 substitutions, 251,713 InDels and complex) identified by Strand NGS but not by GATK; and a total of 157,359 (79,706 substitutions, 77,653 InDels and complex) variants identified by GATK but not by Strand NGS.

Figures 5A, 5B:
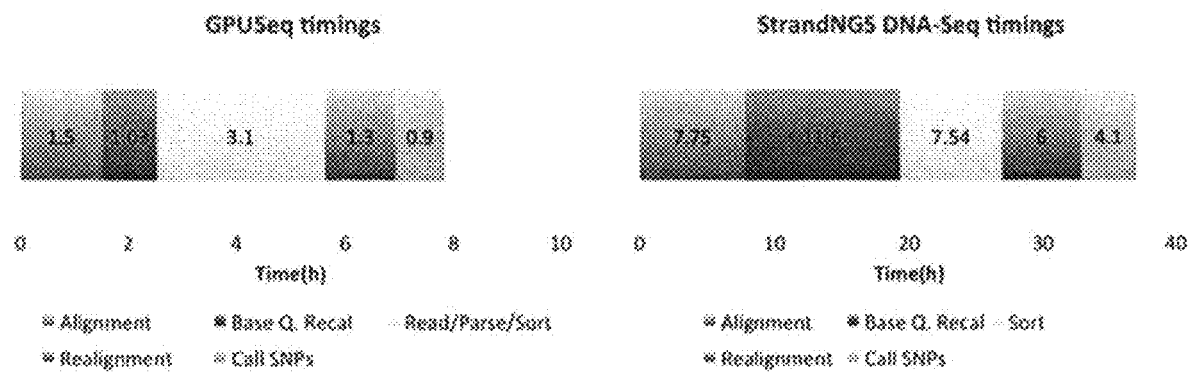
FIGS. 5A and 5B show an example of a histogram of supporting reads for substitutions and InDels and complex variants.

Characteristics of Variants Identified by both Strand NGS and GATK: The hypothesis is that variants that are identified by both Strand NGS and GATK are generally of good quality. To assess this, we examined variety of characteristics of these variants. Strand NGS provides a very intuitive way to quickly assess the quality of the variants across various quality metrics like presence/absence of the variant in dbSNP database, supporting reads %, variant score, PV4 biases etc. FIGS. 5A and 5B show the histogram of supporting reads % for substitutions (FIG. 5A) and 'InDels+ Complex' variants (FIG. 5B). First, if we focus on substitutions, we can clearly observe a set of variants with 100% supporting reads, representing homozygous variants. For the rest, there is a peak at 50%, which is ideally expected for heterozygous variants, however there is a spread around the peak indicating the fact that heterozygous variants are not always detected at 50% supporting reads, possibly due to sequencing errors, total coverage issues, non-uniform allele sampling etc. Substitutions are colored by dbSNP match category with red, blue and brown color indicating known, novel, and overlapping variants according to dbSNP138 database. In addition, it can be observed from FIG. 1 that most of the novel substitutions appear at the lower side of supporting read %, making them likely false positives. The distribution of supporting reads % for 'InDels+complex' has a wider spread compared to substitutions, however majority have a supporting read % below 50%.

Figures 6A, 6B:
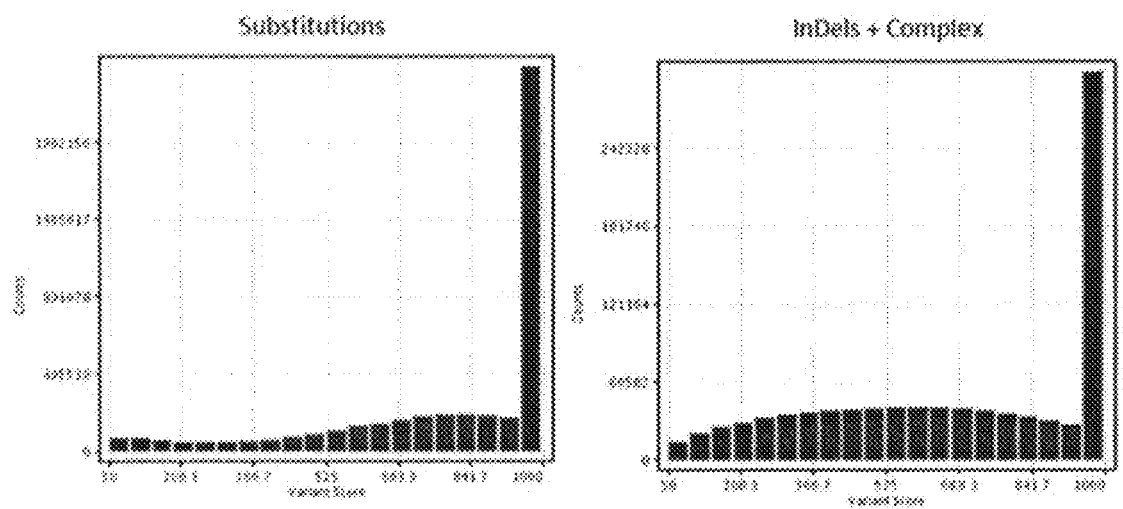
FIGS. 6A and 6B show examples of distributions of scores assigned to overlapping variants.

FIGS. 6A and 6B show the distribution of variant score that was assigned by Strand NGS to the overlapping variants (identified by both Strand NGS and GATK). Most of the variants are assigned high scores. Again, blue indicates novel; red indicates known; and brown indicates overlap. Additionally, there is a higher fraction of novel variants than known variants on the lower side of the score, further indicating that these are likely false positives. Regardless, given the fact that larger percentage of variants are assigned a higher score, it can be concluded that most of the overlapping variants are indeed of good quality.

Figure 7A:
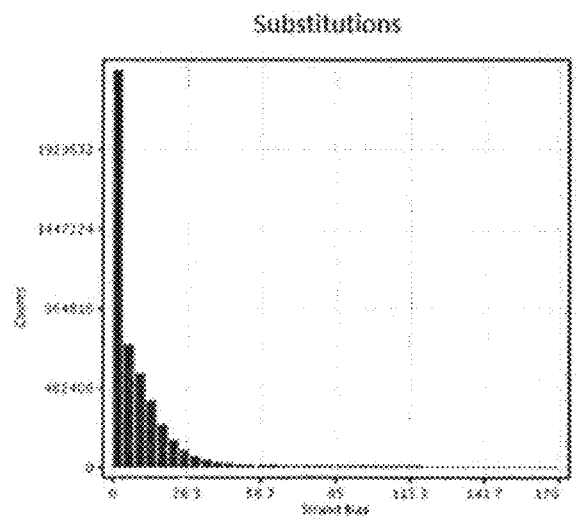
FIGS. 7A and 7B show examples distributions of strand bias.
Figure 7B:
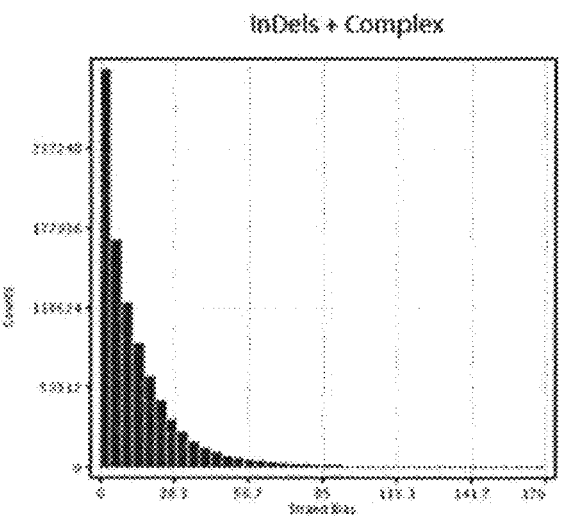

FIGS. 7A and 7B show the distribution of strand bias for the same set of overlapping variants. Again, blue indicates novel; red indicates known; and brown indicates overlap. Strand bias varies from 0-200, with smaller numbers indicating low strand bias. As can be seen from the figure, most of the variants have low strand bias and novel variants for all practical purposes are more or less uniformly distributed, again indicating overall high quality of overlapping variants.

Characteristics of Variants Uniquely Identified by Strand NGS: As mentioned, there are a total of 444,947 variants (~7%) that are identified by Strand NGS but not by GATK. Out of these, 193,234 are substitutions and 251,713 are 'InDels+complex' variants. One of the important points to note is that compared to the overlapping variants, a larger fraction of the variants in this category is novel according to dbSNP138 database.

Figure 8A:
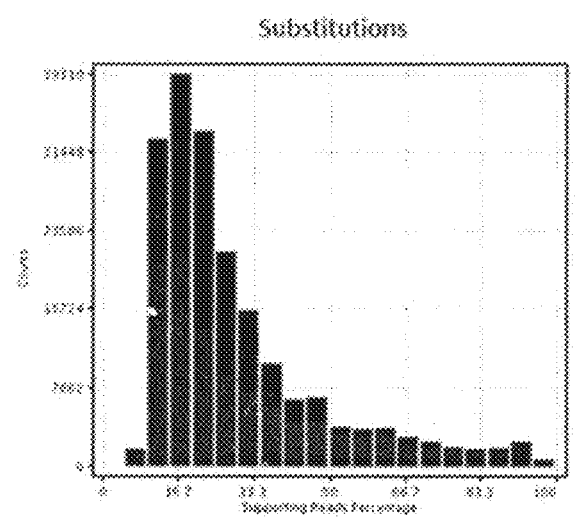
FIGS. 8A and 8B show example distributions of supporting read percentage for variants.
Figure 8B:
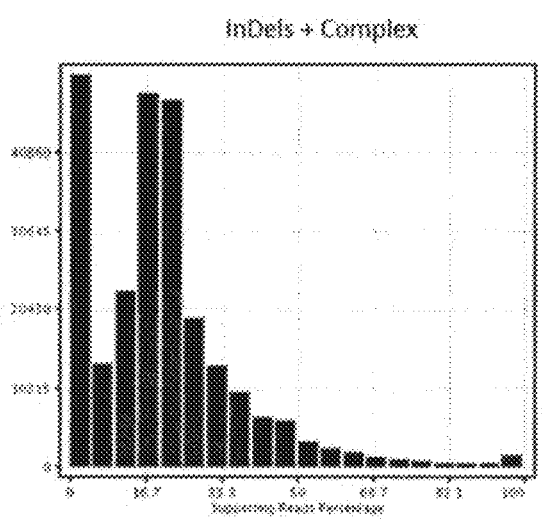
Figure 9A:
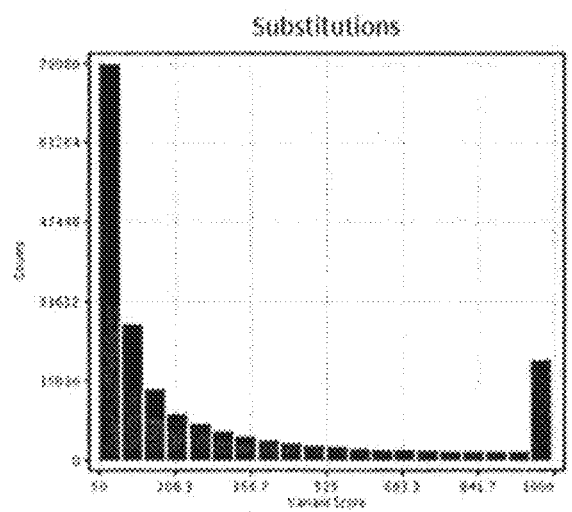
FIGS. 9A and 9B show example distributions of variant scores for variants.
Figure 9B:
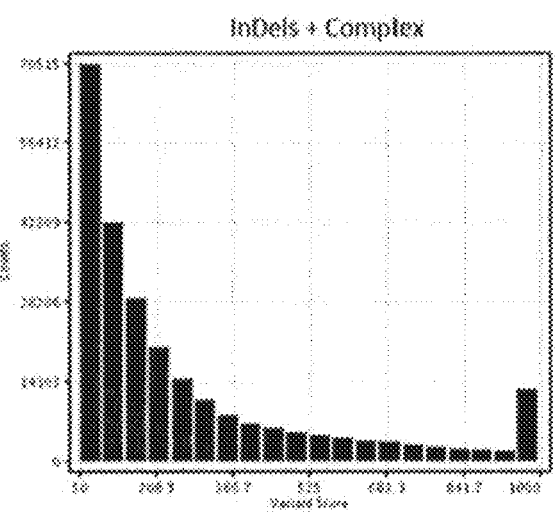
Figure 10A:
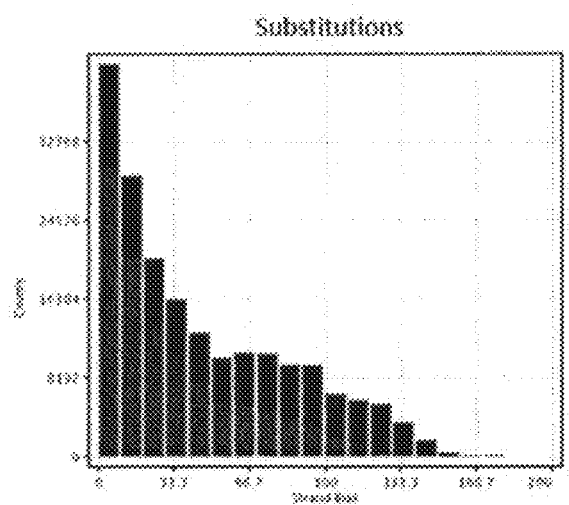
FIGS. 10A and 10B show example distributions of strand bias.
Figure 10B:
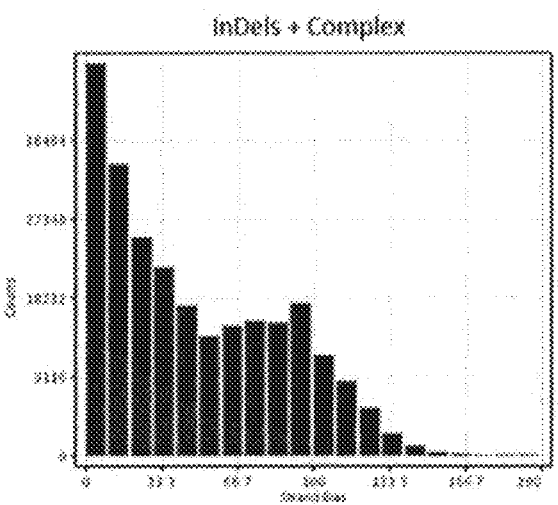

FIGS. 8A (substitutions) and B (InDels+Complex) show distributions of supporting read percentage for variants identified by Strand NGS alone. FIGS. 9A (substitutions) and 9B (InDels+Complex) show distributions of variant scores for variants identified by Strand NGS alone. Further, if we observe the distributions of the same metrics (as last section) for these variants, we observe that unlike the data in FIGS. 5A-6B, supporting read % and variant score is skewed towards the left, as shown in FIGS. 8A-9B respectively, indicating heterozygosity of these variants with low supporting read % and low score. This also makes them likely false positives. Also strand bias as shown in FIGS. 10A (substitutions) and 10B (InDels+Complex) for these variants shows a substantial fraction of variants with strand bias more than 50, unlike what was observed with overlapping variants as shown in FIGS. 7A and B. As earlier, variants are colored by their presence or absence in dbSNP database (red: known; blue: novel; brown: overlap). These metrics therefore provide a useful as well as intuitive way to filter out the bad quality variants.

Further, in addition to these metrics, Strand NGS also calculates base quality bias, mapping quality bias, tail distance bias and neighborhood quality measures. These metrics can also be used in addition to the ones used above to further filter out the bad quality variants. While Strand NGS provides a visually appealing way to examine each of these metrics individually and then filter the variants based on thresholds set on individual metrics, GATK uses a variant quality score recalibration step, which is based on a machine learning approach. The objective of this step is to use the training data and build a model describing which variant characteristics or combinations thereof makes it a bad versus good quality variant, and then recalibrate the variant scores using the model. These recalibrated scores can then be used to discard the bad quality variants. One of the downside of such a machine learning approach is the difficulty for the end-user to easily narrow down and understand a set of variables, which are actually responsible for the change in the variant quality and hence filtering. Another issue with this approach is the requirement of sufficient and good training data to build the model. One has to carefully select the training data and make sure it has the same underlying properties as the test data under consideration and further adopt ways to avoid model over-training.

As an example to show the effectiveness of the simple but visually intuitive approach of Strand NGS to filter variants using individual variables, if we set the supporting read % '>30%', variant score '>60', and strand bias '<50', we are only left with 145,324 variants in this category, making the overlap between Strand NGS and GATK as ~98%. This comparison makes more sense since the variant call set from GATK includes the variant quality score recalibration step.

Characteristics of Variants Uniquely Identified by GATK: There are a total of 157,359 (~2.5%) variants identified by GATK but not by Strand NGS. Of these, 79,706 are substitutions and 77,653 are 'InDels and complex'. Out of 157,359 variants in this category, ~21% are novel according to dbSNP138, again indicating these may be likely false positives. Additional evidence in favor of these variants being likely false positives may be low coverage locations (GATK's default is 2, much lower than Strand NGS default of 10), low supporting read %, high strand bias, low variant score, presence of other PV4 biases etc. For instance, ~53% of 79,706 substitutions identified by GATK have a total coverage below 10, the default cut-off for Strand NGS.

Figures 11A, 11B:
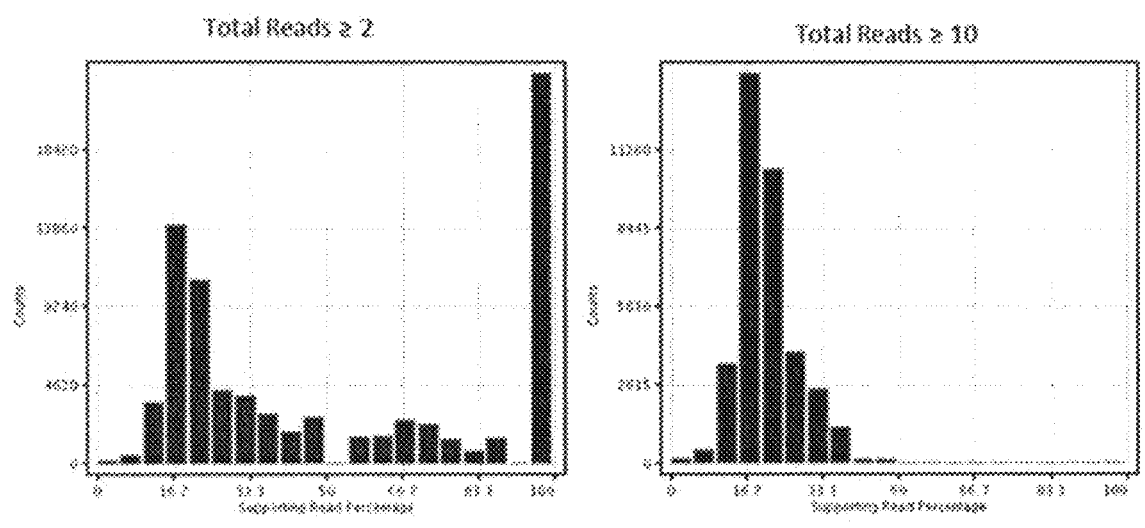
FIGS. 11A and 11B show example distributions of supporting read percentages

Further, distribution of supporting read % is shown in FIGS. 11A and 11B for variants with coverage more than or equal to 2 (FIG. 11A) and with coverage more than or equal to 10 (FIG. 11B). This figure clearly shows that variants with higher supporting reads % have low coverage and hence did not meet the total reads threshold of 10. Since Strand NGS uses a default of 10 reads, these variant locations are not even considered for variant calling. If we set the coverage threshold as 10, then the supporting reads % for the remaining variants is skewed towards the left, indicating many of them could be false positives and hence can be filtered out. Therefore majority of the variants uniquely identified by GATK are either not considered by Strand NGS because of low coverage or can be filtered out due to relatively bad quality.

Conclusions: In this study, we discussed the variant calling approach adopted in our software Strand NGS and presented the benchmarking results on whole-genome sample NA12878. We compared the variants identified by Strand NGS to those identified by GATK UnifiedGenotyper.

We demonstrated a high overlap (98%) in the filtered variant calls by Strand NGS and GATK. The high overlap makes Strand NGS and GATK very similar for most practical purposes. The unique variants identified by each of these algorithms first of all constitutes a very small percentage of the total variants identified and additionally many of these variants can be filtered out using quality metrics like presence/absence in dbSNP, supporting reads %, variant score, total read coverage, strand bias and other PV4 biases.

Overall, using the benchmarking results presented in this paper, we demonstrated that Strand NGS variant caller offers a solid approach for calling variants. The software also provides visually intuitive ways to intelligently filter the variant calls in order to improve specificity without affecting sensitivity. We also found the results of Strand NGS very similar to GATK, which is one of the most commonly used variant callers.

A Brief Note on Somatic Variant Caller: The somatic variant caller in Strand NGS is an adaptation of the standard binomial SNP calling method to take the base qualities into account. Here we briefly describe the approach.

The SNP calling method considers the base taken by each read covering the location, as well as its associated base quality, denoted collectively by D, and decides whether there is a variant at that location. This is done by computing the probability, P of observing a data D' with the same total number of bases and at least as many variant bases as D has, with the assumption that the location has the reference genotype, and that the variants are due to sequencing error only. Only the variant allele with the highest frequency of occurrence is considered for the computation of the probability P and the other variant alleles are ignored. This probability is then converted into a score as Score=10 $\log_{10} P$. If this score is greater than 50, then the location is reported as a variant location.

The standard binomial test for calling SNPs requires one overall error rate and cannot use the qualities of all the individual bases. One way to arrive at the overall error rate from the base qualities in D is to compute the error rate corresponding to the lowest base quality from D. But this may make the results very sensitive to any noisy outlier bases with very low quality which may lead to false negatives. In order to avoid this problem, we ignore all the bases with qualities less than a threshold $Q_t$ and run the binomial test with the error rate corresponding to the lowest quality from the remaining bases. To make the test more robust, this process is repeated for multiple values of $Q_t$ and a variant is reported if it is called for any of the thresholds $Q_t$. Typically $Q_t$ is varied from 20 to 30 and if a variant is called in any of these tests, the method reports the variant and the lowest Q at which the variant is called. In case different variants are called at the same locus in these multiple tests, only the one with the highest score is reported.

Translocation detection: The SV detection algorithm in Strand NGS helps discover all SVs (including translocations) from aberrant paired-end reads and the split reads generated by the aligner. However, in the cancer context, discovery can be difficult because only a small fraction of cells that were sequenced may harbor the translocation. A special test has been implemented which considers a list of well-known translocations and identifies reads that support the translocation event. The Elastic Genome Browser™ in Strand NGS can then show a genome browser view which simulates the translocation and aids in visual verification.

Interpretation

During interpretation, the variants generated by Strand NGS are considered and those that can explain the cancer phenotype or are relevant to treatment are identified. See, e.g., FIG. 1A. StrandOmics presents data from ~30 different sources, including those listed in Table 9, below (though note that the methods and apparatuses described herein allow the addition of other data sources that are available or might become available in the future) in an intuitive manner and helps experts create a clinical report that describes the variants, their implications, and the rationale for the recommended therapy.

TABLE 9

External data sources that have been integrated in Strandomics for automated interpretation and reporting

| Data Source | Description | Germline | Somatic |
| --- | --- | --- | --- |
| hg19 Human reference genome from NCBI | Human reference genome assembly sequence | Yes | Yes |
| NCBI Gene (www.ncbi.nlm.nih.gov/gene) | Refseq genedescriptions | Yes | Yes |
| UCSC (http://genome.ucsc.edu/) | List of genes and transcripts mapped to hg19 reference assembly; Conservation Scores; chromosomal coordinates for cytobands | Yes | Yes |
| Swissprot/Uniprot (http://www.uniprot.org/) | Protein information and description, gene-protein association, protein sequences, Diseaseassociated variants. | Yes | Yes |
| NCBI dbSNP (http://www.ncbi.nlm.nih.gov/SNP/) | Single nucleotide polymorphisms that occur frequently in the human population. | Yes | Yes |
| 1000 Genomes (http://www.1000genomes.org/) | Genetic variants that occur frequently in the human population. | Yes | Yes |
| Exome Variant server (http://evs.gs.washington.edu/EVS/) | Genetic variants database with variant frequencies from the NHLBI GO Exome sequencing project | Yes | Yes |
| NCBI BioSystems (http://www.ncbi.nlm.nih.gov/biosystems/) | NCBI database containing pathways from Kegg, Reactome, Biocyc, Wiki Pathways, Pathway Interaction Database, and gene-pathways associations. | Yes | Yes |
| Gene ontology (http://geneontology.org/) | GO process annotations. | Yes | Yes |
| NCBI Gene2go (ftp.ncbi.nlm.nih.gov/gene/DATA/gene2go.gz) | Gene to GO process association. | Yes | Yes |
| Human Phenotype Ontology (http://www.humanphenotypeontology.org/) | Human Phenotype ontology, Genephenotype and OMIM diseasephenotype information. | Yes | |
| Clinical Genome Database (http://research.nhgri.nih.gov/CGD/) | Association of genes to Clinical manifestations | Yes | |
| OMIM ® (http://www.omim.org) | List of Mendelian diseases, genedisease associations, descriptions, inheritance modes. | Yes | |

TABLE 9-continued

External data sources that have been integrated in Strandomics for automated interpretation and reporting

| Data Source | Description | Germline | Somatic |
|---|---|---|---|
| Orphanet (http://www.orpha.net) | Mendelian and rare diseases descriptions, prevalence frequency and age of onset | Yes | |
| Medgen (http://www.ncbi.nlm.nih.gov/medgen) | Disease descriptions | Yes | |
| HGMD ® Professional from Biobase (http://www.biobaseinternational.com/product/hgmd) | Licensed source containing information on variants associated with diseases | Yes | |
| ClinVar (http://www.ncbi.nlm.nih.gov/clinvar/) | Public database with relationships Between variants and phenotypes and Diseases | Yes | |
| dbNSFP (https://sites.google.com/site/jpopgen/dbNSFP) | Functional predictions for nonsynonymous single Nucleotide variants in the human genome from SIFT, Polyphen2 HVAR, Polyphen2 HDIV, MutationTaster, LRT) | Yes | |
| Mouse Genome Informatics - MGI (http://www.informatics.jax.org/) | Mouse phenotypes | Yes | |
| TIS Miner (http://dnafsminer.bic.nus.edu.sg/) | Prediction of alternate Translation Initiation sites | Yes | |
| Pubmed (http://www.ncbi.nlm.nih.gov/pubmed) | Literature references. | Yes | Yes |
| National Cancer Institute (http://www.cancer.gov/) | Cancer descriptions, | | Yes |
| NCI Thesaurus (http://ncit.nci.nih.gov/) | Cancer drugs, synonyms, drug classes, Drug descriptions. | | Yes |
| NCI PDQ (http://www.cancer.gov/cancertopics/pdq/cancerdatabase) | Cancer clinical trials in the US, cancer drug dictionary. | | Yes |
| Clinical trials database (http://www.clinicaltrials.gov/) | Clinical trials in the US. | | Yes |
| FDA (http://www.fda.gov/) | FDA approved cancer drugs and indications for use | | Yes |
| COSMIC (http://cancer.sanger.ac.uk/cancergenome/projects/cosmic/) | Catalogue of Somatic Mutations in Cancer - Gene mutation frequency in Different cancers, classification of cancers, list of somatic variants. | | Yes |

A comprehensive database of genomic variants links to FDA-approved chemotherapy, targeted cancer therapies, and clinical trials. This allows development of a fully personalized treatment regimen for a patient using a single biopsy sample, a feat that is not possible using single gene tests of hot spot gene mutation tests.

Sequencing large panels can result in thousands of variants and StrandOmics uses the following strategies to quickly guide interpreters to the most useful variants.

Variants with poor quality: a variant detected by Strand NGS is associated with several numerical attributes like total reads, supporting reads, variants reads, variant call score, average base/mapping/quality, average alignment score, tail/base/mapping bias etc. These attributes are used to color-code the variants into 3 different quality buckets. Variants with poor quality can usually be disregarded.

Variants with moderate quality: occasionally it is hard to determine the correctness of a variant call purely from the numerical attributes. In these cases, the interpreter can consult the Variant Support View (VSV) images associated with the variant. The VSV—a Strand innovation—is a condensed representation of the neighborhood of a variant and graphically depicts all the haplotypes and the number of reads supporting each haplotype. It allows a quick visual verification of strand, quality and positional biases and helps in the elimination of false positives.

Variants with high quality which are polymorphisms, result of reference errors or systematic sequencing errors: a Pooled Patient DataBase (PPDB) is maintained by StrandOmics and it registers all variants observed across all cases. Variants which occur with high frequency in the PPDB, or have a high minor-allele frequency in sources such as dbSNP/Exome-Variant-Server are likely to be harmless since disease causing mutations are expected to be rare. These variants are de-prioritized.

Novel variants with high quality which are harmless: StrandOmics automatically computes the effect of a variant on the overlapping gene/transcript. Variants which are not associated with any information in Strand's curated variant knowledgebase, which do not have any matches with public databases, and which are likely to have no effect on the gene's function are de-prioritized.

Other novel missense variants with high quality: the effect of the missense variant can be hard to predict. StrandOmics annotates the variant with pathogenicity predictions from 7 different algorithms, the conservation status of the loci and depicts the neighborhood of the loci with information from multiple variant sources. Novel missense variants which are rated as harmless by most pathogenicity predictors, or occur in non-conserved regions, or in regions with no known deleterious mutations are likely to be harmless and are de-prioritized by the software.

Variants previously reported upon: StrandOmics allows interpreters to comment on a variant and indicate whether the variant is relevant or not. These comments are stored and displayed when the variant is encountered in other cases. They may also be chosen for inclusion in the final clinical report.

The above steps help interpreters quickly identify the subset of variants they would like to include in the final report. Most tools simply annotate the variants with some of the attributes mentioned above and leave the task of prioritization to the user. By applying recommended guidelines automatically and presenting the most likely candidate variants in a visual setting where all the relevant attributes (and past notes) are readily visible, StrandOmics considerably reduces the variant filtering and prioritization time.

Driver somatic mutations in cancer typically cause a signaling cascade to become active even in the absence of external signals. The end point of these signaling cascades is usually some tumerigenic endpoint like cell proliferation, immortality etc. Targeted therapy is based to a large extent on accurately identifying the problematic signaling cascades that have been activated and recommending the drugs which by activating on proteins in the cascade prevent the signal from reaching the endpoint. For making the right recommendations it is essential to consult an accurate and comprehensive collection of cascades (or signaling pathways). The Strand curation team creates this collection by first consulting well-known pathway sources such as KEGG, Reactome, and WikiPathways. These pathways are then augmented to include protein-protein interactions extracted from Medline abstracts by Strand's NLP technology. The pathway extensions are meant to increase the explanatory power of the pathways. For instance, whenever the Strand curation team comes across an article that mentions that "drugX which targets proteinY has been shown be effective in tumors which have mutations in geneZ", they consult the curated pathway collection to check if any pathway can explain the reason for the drug's effectiveness. If no satisfactory explanation can be found, a literature search and an exploration of Strand's NLP derived interactions is carried out to see if the pathways need to be augmented.

StrandOmics maintains a curated collection of signaling pathways that are relevant to cancer. The effect of the selected somatic variants on the pathways is computed and the minimal set of therapies that can counter the effect of the somatic variants is shown. Therapy recommendations are prioritized based on the tissue and the status of the drug (FDA approved, clinical trial phase etc.).

When an interpreter changes to the reporting mode, a template is used to pre-fill the preliminary template with information about the variants, the genes affected by the variant, and the therapy implications. Any standard treatments are contraindicated because of the presence of somatic mutations conferring resistance are also mentioned. To distinguish mutations which are truly absent from those that are undetected because of low coverage, StrandOmics analyzes the coverage for all regions in the panel and especially the resistance-associated loci. Any undercovered regions may be automatically reported in the Appendix and their presence is indicated in the report.

Knowledge about actionable variants increases at a fairly slow rate. StrandOmics will index each case with the following attributes: (1) phenotype of the patient—histopathology status, IHC status; (2) actionable variants detected in the analyzed sample; When a new case is analyzed, the similarity of the case with all cases that have been analyzed previously is computed. A case which is substantially similar (or identical) with respect to the abovementioned attributes to a prior case can be reported upon very quickly especially of the prior case was not too distant in the past.

"Alchemy"

The interpretation of variants is done using a large collection of heterogeneous bioinformatics resources. However, data sources can be contradictory, may even be erroneous, and are frequently updated. Most data sources are external but Strand's curation team is a source of variants and domains as well.

The sources may be used to create a wide variety of biological objects such as genes, transcripts, proteins, domains, variants, pathways, diseases, tissues, phenotypes, drug/therapies, clinical trials etc. Frequently multiple data sources are used for creation of a single object—genes are created using NCBI Gene, Ensembl and Uniprot resources. Ensuring that the data used for interpretation is "correct" at all times is a challenging task which the framework described herein (referred to as "Alchemy") addresses in the following manner.

Visual data inspection and editing: Alchemy is based on the Eclipse Modeling Framework (EMF) and allows bioinformaticians to specify the model for each object using a visual interface. Constraints can be placed on: different fields of an individual model: e.g. "A gene must have exactly one Entrez ID and the description cannot be empty"; relationships between models: a gene can have several transcripts, but each transcript must be associated with a single gene.

The formal specification of the models reduces the chance of creating incorrect (or partially filled objects). For each type of object, the framework automatically provides a custom web interface form for manual creation or editing.

Data provenance and versioning: While the framework allows objects to be created manually, the objects are usually created programmatically from multiple external data sources. For instance, a gene object can be based on an Entrez Gene, but may be associated with transcripts from Ensembl and RefSeq, and its description may be derived from a UniProt protein associated with the gene. To make the origin of each element of the gene object transparent, we adopt the following approach: each external data sources is modeled independently: Thus, Entrez Gene, RefSeq transcripts, Ensembl transcripts, UniProt proteins are all modeled separately in a manner that is faithful to their original representation; the association between the Strand object and the external objects is specified: e.g. a Strand Gene is first linked to an Entrez Gene, from which it is linked to an Ensembl gene, and from there on to Ensembl transcripts. The policy for filling each attribute is defined: e.g. the GO terms for a Strand Gene object are taken from the associated Entrez Gene; the description is taken from Entrez Gene but if it is empty it is to be taken from the associated UniProt protein etc.

When an external source such as Ensembl changes the following events take place: the Alchemy framework checks for each Ensembl object whether it has truly changed or not—most updates in reality only change a few genes/transcripts. If the object has indeed changed a new version of the Ensembl object is created in the system and the revision history is updated; the framework checks if any other object in the system is dependent on the newly updated object. If so it identifies the object and executes the defined policies to update the object if necessary. Note that there may be a cascade of updates.

Data correctness and consistency: the framework allows several named tests to be associated with models. Test suites are run at regular intervals and test reports indicate the number of objects which failed each test. For each test that an object fails, a ticket (or issue) is created on a ticketing system with details of the failure. Bioinformaticians use the web-based ticketing system to view the object which failed the test and resolve the issue by either fixing the cause of the error or overriding the test report.

To make this more concrete, consider a "CodonStartTest", which specifies that "The start codon for each transcript must be AUG". When this test is executed a ticket will be created for each transcript with a seemingly incorrect start codon. A transcript could have failed due to two reasons: an error in the specification of the coding region: the bioinformatician handling the ticket will manually edit the coding region co-ordinates using the web-interface. The Alchemy framework is intelligent enough not to override these manual changes during the next cycle of updates. The transcript has a non-canonical start codon: here the data cannot be fixed, the bioinformatician overrides the test report and comments on why this is being done. The testing framework recognizes the override and does not apply the "CodonStartTest" to this transcript in the next round of testing.

Tests can also check for consistency across different models. E.g. a "TranscriptSequenceCheck" test creates a ticket if the protein sequence implied by the transcript object and the human genome reference does not match the amino acid sequence in the corresponding RefSeq protein.

The robust testing framework, the system of overrides, and the complete audit trail helps minimize the manual effort involved in maintaining a correct and consistent set of annotations.

Utilities are provided to export the objects which have passed the test criteria into StrandOmics for use in the automated interpretation.

The whole process described above (and variations thereof) is innovative and may allow advantages not previously realizable. For example, all or parts of the processes and apparatuses described above may allow integration of tests with direct links to the failed entities, the ability to see a difference, seamless correction of errors, and update the data source back. These methods and apparatuses may also allow tracking changes made to the data from different sources—manual curation, automatic upload and manual review after a test.

"Elixir"

Also described herein are methods and systems for personalized medicine, which may be referred to herein as "Elixir". The process of tracking a sample from the time an order is placed to when the report is generated and delivered to the doctor is tracked by the Elixir system. Elixir provides the ability for the members in each of the roles in the workflow to track the tasks that they need to work upon, the ability to monitor the process of a specific case in the workflow and the ability to have a dashboard of all cases that have been processed by the system. Elixir is built as a Personalized Medicine Laboratory process modeling for processing lab developed tests. In Elixir, process definition is separated out into data files rather than embedded in the code. Elixir includes the ability to model a variety of tasks in the process, apply decisions upon execution of each task, model loops of tasks, and raise alerts in the case of task timeouts. Each task can be configured separately and assigned to a specific user or a group. The interface for each task is automatically built based on the configuration of the fields and actions associated with the task. Each task can also have attachments and comments associated with it. Finally, each task can also be associated with object definitions (done in Alchemy) that it can read from or update. The entire process is displayed in a diagrammatic manner.

Execution of a process triggers a new instance of that process. Upon completion of a task in the process, the next task in the process gets assigned to the appropriate user or is available to all users of the group for taking up. Notifications are sent to the appropriate user/group emails when a task is ready for being taken up. The status of multiple process executions can be visualized in a tabular form. The workflow diagram for the process instance also shows a superimposition of the current state of that process—including which tasks have been executed, what path was followed in the execution of the process, which tasks have not yet been started, and which one is currently available for taking up.

Elixir also provides access controls at multiple levels—process level, on who can create process definitions, initiate process executions, whom each task is allocated to, as well as access controls to the different parts of the data model associated with the process. It is possible to configure the process such that the patient information is accessible only to the physician and the client services roles and not accessible to the lab personnel.

Elixir also provides the ability to create customizable business reports on the overall execution of tasks and all the objects associated with the tasks. This helps in tracking parameters such as the overall sales volumes, lab throughput, identify trends in samples, and generate graphic reports.

Elixir also provides the ability to integrate various other systems—whether internal or 3rd party—used in the process, by using the webservice APIs exposed by each of these systems. Thus, when the data analysis is completed by the Avadis NGS system, Elixir automatically integrates the outputs into Strand Omics for interpretation and reporting. Likewise, Elixir integrates with ordering and billing systems using web service APIs in a seamless manner.

The key innovation is to have a single end to end system that manages and keeps track of the entire process that each diagnostic test goes through. This provides the ability to monitor the case as it goes through the entire system, and also the ability to perform overall trending analysis on the mine of data collected over a large number of cases.

As mentioned above, the methods and apparatuses described herein may include reporting. For example, described herein are reports (e.g., soft copies) that may be made available to the physician. Also described are interactive (and/or interactable) reports, e.g., "StrandOmics" reports.

StrandOmics helps generate PDF reports for the cases, once case variants have been interpreted and actionable genes found. StrandOmics packages in a canned manner the clinical significance for each gene in the panel for a large number of tissues. Thus when a variant is identified in a gene with a specific function, StrandOmics provides the reporter with the clinical significance of the mutated gene instantly. This significantly reduces the time taken to generate the report.

The PDF report generated after interpretation is available to be sent to the physician via post, email or on a portal, depending on the physician's choice. Further, physicians can login to StrandOmics to access interactable reports for their cases. This provides the physician with the ability to interact with each variant and gene implicated for the case, go over the rationale for the same, and get a deeper understanding of the genetic basis for diagnosis and therapy. An embodiment of a StrandAdvantage report is provided as follows. The aim of an NGS clinical test that profiles tumors is to identify therapies that might be effective or those that would not be of benefit, based on the mutation profile of the tumor. The therapies may be well-known, standard therapies that oncologists usually recommend based for that cancer type, or they may be investigational therapies that are still in the clinical trials phase.

The StrandAdvantage report covers pre-defined variants and classes of variants that can be measured and has known therapeutic responses on drugs that are considered most relevant for a particular cancer type. The drugs can be either chemotherapy or targeted therapy drugs, and are typically FDA approved and/or recommended by the National Comprehensive Cancer Network (NCCN) for a cancer type. Each cancer type will have a different set of genes and variants that will be markers for the therapy recommendations. The markers may be detected either by NGS (point mutation, copy number, translocation or other structural variation), ImmunoHistoChemistry (protein expression), or any other molecular testing method The StrandAdvantage test can be a single (e.g., somatic) tumor test that covers all approved targeted therapy indications along with contra indications. Such a test can eliminate the need for sequential testing of a subset of genes/mutations at a time. Such a consolidated test can also prevent depleting of previous patient biopsy samples across multiple tests.

The SoC variants and genes could be defined only for a certain subset of cancer types. Since the SoC variants, genes, proteins and drugs as well as the rules are pre-defined, the software can automatically generate the SoC report.

Definition of SoC Genes, Variants and Variant Classes and Compound Markers

Individual Variants or Variant Classes

The SoC tests have a number of drugs for a cancer type. For each drug, the SoC test for a certain cancer type consists of the following: Marker-Specific variant/class of variants/Expression level; Functional effect of variant—Text for exact hit, equivalent variant; PMID references for function; Measured by—method by which the marker is measured (IHC, NGS, etc.); Novel/Found in COSMIC (COSMIC ID)—System generated; Supporting read percentage (% Frequency)—System generated; Recommendation (Enhanced response, Enhanced but limited response, Standard response, Likely poorer response); Clinical evidence in same cancer type—PMIDs; Clinical evidence in other cancer type—PMIDs; Preclinical evidence in other cancer type—PMIDs; Summary—Text that summarizes the evidence for the recommendation; Level of evidence—1A/1B/1C/2A/2B/2C.

Marker definition: A marker (#3 above) can have a complex condition that includes a variant or class of variants, and excludes variants or a class of variants. It can have complex Boolean expressions such as (Variant1 OR Variant2) AND (NOT(V3)).

All variants in a case are matched against each marker condition, and the marker is either TRUE or FALSE, based on a single case variant or multiple case variants.

Compound Markers

Drugs can have multiple markers that modulate response, for example, presence of marker M1 could induce sensitivity to drug D1, whereas presence of marker M2 could induce resistance to the same drug D1. If both M1 and M2 are present in the case, then the conflict can be resolved through a compound marker. A compound marker is defined by the following: Compound marker condition (Boolean expression consisting of individual markers or rules); Recommendation—Overall recommendation for a drug taking all markers in the compound marker into consideration; Expected effect; Summary.

As noted above, in some embodiments, a clinician can request a Standard-of-Care (SoC) report with the results regarding a subset of markers indicating or contra-indicating a subset of the clinically valid therapies known as SoC therapies. The SoC therapies can comprise those therapies that a clinician is most likely to consider for treatment. Because the SoC report only includes a subset of the genes or markers tested for in the Strand Advantage testing, the SoC report can have a shorter turn-around time, for example, within about 8 days (e.g., or within about 5, 6, 7, 8, 9, or 10 days). Providing relevant results in such a short time can empower a physician to provide accurate, personalized medicine in a short amount of time.

The SoC test and report can include a pre-defined subset of variants specific to patient diagnosis. As described above, the subset of variants can indicate whether or not the patient would likely respond to a particular treatment.

The tables below show examples of variants included in an SoC report/test for 6 types of cancer. As shown below, the variants can be indication variants, indicating likely response to a therapy or contra indication variants, indicating unlikely response to a therapy. The tables also display where the evidence for the indication of contra indication is found.

TABLE 10

Contra Indication Variants for Colorectal Cancer Therapies
Colorectal Cancer
Cetuximab, Panitumumab

| Contra Indication Variants | Evidence |
|---|---|
| KRAS: mutation in codons 12, 13, 14 | FDA |
| BRAF: mutation in codon 600 | NCCN |
| NRAS: mutation in codons 12, 13, or 61 | NCCN |
| PIK3CA (some cases): mutation E542K, E545K, H1047R or H10471 | De Roock et al., 2010; Prenen H et al. 2009; Sartore-Bianchi A et al. 2009. |

TABLE 11

Indication and Contra Indication Variants for Lung Cancer Therapies
Lung Cancer
Gefitinib, Erlotinib

| | Evidence |
|---|---|
| Indication Variants | |
| EGFR: deletion in exon 19 | FDA |
| EGFR: mutation in codon 719, L861Q or L858R | FDA |
| Contra Indication Variants | |
| KRAS: mutation in codons 12, 13, or 61 | FDA |
| BRAF: mutation in codon 600 | NCCN |
| NRAS: mutation in codons 12, 13, or 61 | NCCN |
| PIK3CA (some cases): mutation E542K, E545K, H1047R or H10471 | Gandhi et al., 2009; Pratilas et al., 2008 |

TABLE 12

Indication and Contra Indication Variants for GIST Therapies
GIST

| Imatinib | |
|---|---|
| | Evidence |
| Indication Variants | |
| KIT: alteration in exon 11 | NCCN |
| KIT: alteration in exon 9 | NCCN |
| Contra Indication Variants | |
| KIT: mutation D816V | NCCN |
| PDGFRA: mutation D842V | NCCN |
| BRAF: mutation in codon 600 | NCCN |

| Sunitinib | |
|---|---|
| Indication Variants | Evidence |
| KIT: alteration in exon 9 | NCCN |

TABLE 13

Indication and Contra Indication Variants for Melanoma Therapies
Melanoma

Trametinib, Dabrafenib, Vemurafenib

| Indication Variants | Evidence |
|---|---|
| BRAF: mutation in codon 600 | FDA |

Imatinib

| | Evidence |
|---|---|
| Indication Variants | |
| KIT: alteration in exon 11 | NCCN |
| Contra Indication Variants | |
| KIT: alteration in exon 9 | NCCN |
| KIT: mutation D816V | NCCN |

MEK162

| Indication Variants | Evidence |
|---|---|
| NRAS: activating mutations | Rusch et al., 2013 |

TABLE 14

Indication and Contra Indication Variants for Thyroid Cancer Therapies
Thyroid Cancer Radioactive Iodine

| Contra Indication Variants | Evidence |
|---|---|
| BRAF: mutation in codon 600 | NCCN |

Sorafenib

| Indication Variants | Evidence |
|---|---|
| BRAF: mutation in codon 600 | NCCN |

Differential Diagnosis

| Indication Variants | Evidence |
|---|---|
| KRAS: mutation in codons 12, 13, or 61 | NCCN |
| NRAS: mutation in codons 12, 13, or 61 | NCCN |

TABLE 15

Indication and Contra Indication Variants for Breast Cancer Therapies
Breast Cancer Trastuzumab, Lapatinib

| Contra Indication Variants | Evidence |
|---|---|
| PI3KCA: mutations E542K, E545K, H1047R, H10471 | Berns et al., 2007, Cizkova et al., 2013, Loibi et al., 2014, Wang et al. 2011 |

Everolimus

| | Evidence |
|---|---|
| Indication Variants | |
| PI3KCA: mutations E542K, E545K, H1047R, H10471 | Chavez-MacGregor and Gonzalez Angulo, 2012; Janku et al., 2013; Loi et al., 2013 |
| Contra Indication Variants | |
| AKT1: mutation E17K | Parikh et al. 2012; Lauring et al., 2013 |

Examples of SoC panels for non-small lung carcinoma (NSCLC), breast carcinoma, and colorectal carcinoma are provided below. The panels can comprehensively match actionable mutations in the tumor and match them to appropriate FDA approved/NCCN recommended therapy regimens. The panels can detect low-frequency sequence variations with high sensitivity and specificity from a single biopsy sample. A (*) indicates an IHC marker. Table 16 below summarizes an example panel for NSCLC.

TABLE 16

FDA Approved and NCCN Recommended Therapies Impacted by Genetic Markers
FDA Approved and NCCN Recommended Therapies Impacted by Genetic Markers

| | |
|---|---|
| Erlotinib, Gefitinib | EGFR, ERBB2, KRAS, MET |
| Afatinib | EGFR, ERBB2, KRAS, MET |
| Crizotinib | ALK, ROS1, MET |
| Ceritinib | ALK |
| Cabozantinib | RET |
| Gemcitabine | RRM1* |
| Pemetrexed | TS* |
| Paclitaxel, Docetaxel | TUBB3*, TLE3*, Pgp* |
| Vinorelbine | TUBB3* |
| Cisplatin, Carboplatin | ERCC1* |
| Bevacizumab | KRAS, VHL |
| Nivolumab | PD-L1* |
| Vemurafenib | BRAF |
| Dabrafenib | BRAF |
| Trastuzumab | EGFR, ERBB2, MET, PIK3CA |

Erlotinib, Gefitinib, Afatinib: Most EGFR alterations indicate response to erlotinib, gefitinib and afatinib, while some mutations indicate resistance to them. Alterations in MET or KRAS may indicate poor response to erlotinib, gefitinib and afatinib. Alterations in ERBB2 may indicate poor response to erlotinib and gefitinib but possible response to afatinib.

Trastuzumab: Alterations in ERBB2 are associated with response to trastuzumab while mutations in EGFR, MET or PIK3CA are associated with poor response.

Bevacizumab: Mutations in KRAS may indicate limited response to bevacizumab while alterations in VHL may indicate possible response.

Crizotinib, Ceritinib: ALK rearrangement indicates response to crizotinib and ceritinib. Alterations in MET and ROW1 rearrangement may indicate response to crizotinib.

Vemurafenib, Dabrafenib: Mutations in BRAF indicate possible response to vemurafenib and dabrafenib.

Nivolumab: High levels of PD-L1 are associated with enhanced response to nivolumab.

Cisplatin, Carboplatin: High levels of ERCC1 indicate poor response to platin-based therapy.

Cabozantinib: RET rearrangement indicates possible response to cabozantinib.

Paclitaxel, Docetaxel, Vinorelbine: High levels of TUBB3 indicate porr response to paclitaxel and docetaxel, whereas high levels of Pgp indicate poor response.

Pemetrexed: Low levels of TS indicate response to pemetrexed.

Gemcitabine: Low levels of RRM1 indicate response to gemcitabine.

Table 17 below summarizes an example panel for breast carcinoma.

TABLE 17

FDA Approved and NCCN Recommended Therapies Impacted by Genetic Markers
FDA Approved and NCCN Recommended Therapies Impacted by Genetic Markers

| | |
|---|---|
| Everolimus | ER*, HER2*, PIK3CA, PTEN* |
| Doxorubicin, Epirubicin | Pgp*, TOP2A* |
| 5-fluorouracil | DPYD, DMAD4, TS* |
| Bevacizumab | VHL |
| Lapatinib | ERBB2/HER2*, PIK3CA |
| Trastuzumab | EGFR, ERBB2/HER2*, PIK3CA, PTEN |
| Pertuzumab | EGFR, ERBB2/HER2*, PIK3CA, PTEN |
| Palbociclib | CDKN2A |
| Cisplatin | BRCA1, BRCA2 |
| Paclitaxel, Docetaxel | Pgp*, TUBB3* |
| Tamoxifen | ER*, ERBB2/HER2*, EGFR |

Cisplatin: Loss of BRCA2 and BRCA1 are associated with favorable response to cisplatin.

Bevacizumab: Loss of VHL may indicate high response to bevacizumab.

5-fluororacil: Loss of SMAD4 and high levels of TS indicate poor response to 5-fluororacil-based therapy, whereas low levels of TX indicate response. Certain variants in DPYD indicate toxicity to 5-fluororacil-based therapy.

Palbociclib: Loss of CDKN2A indicates possible response to CDK inhibitor, palbociclib.

Paclitaxel, Docetaxel: High levels of Pgp and TUBB3 indicate poor response to paclitaxel and docetaxel.

Doxorubicin, Epirubicin: Gain of TOP2A (gene amplification or protein expression) indicates response to doxorubicin and epirubicin. High levels of Pgp indicate poor response to doxorubicin and epirubicin.

Trastuzumab, Pertuzumab, Lapatinib: Alterations in ERBB2 indicate response to anti-HER2 therapy such as trastuzumab, pertuzumab and lapatinib. In HER2 positive breast cancers, mutation in PIK3CA, alterations in EGFR or low levels of PTEN indicate poor response to trastuzumab and pertuzumab.

Everolimus: In ER positive, HER2 negative breast cancer, mutations in PIK3CA or loss of PTEN expression or function may indicate enhanced response to everolimus.

Tamoxifen: In ER positive breast cancer, alterations in EGFR and ERBB2 and high levels of HER2 may indicate poor response to tamoxifen.

Table 18, below, shows FDA approved and NCCN recommended therapies impacted by various genetic markers.

TABLE 18

FDA Approved and NCCN Recommended Therapies Impacted by Genetic Markers

| Therapy | Genetic Marker |
|---|---|
| 5-fluorouracil | APC, DPYD, TS*, SMAD4, MSI* |
| Capecitabine | DPYD |
| Cetuximab | BRAF, EGFR, KRAS, MET, NRAS, PIK3CA, PTEN |
| Panitumumab | BRAF, EGFR, KRAS, MET, NRAS, PIK3CA, PTEN |
| Oxaliplatin | KRAS, ERCC1* |
| Bevacizumab | KRAS |
| Irinotecan | TIIO1*, UGT1A1 |

Cetuximab, Panitumumab: Mutations in KRAS or NRAS indicate poor response to cetuximab and panitumumab while wild type status of these genes indicates favorable response. Additionally, alterations in MET, PTEN, or PIK3CA may indicate poor response. Alterations in EGFR may indicate favorable response to cetuximab and panitumumab in the absence of alterations in the above genes.

Bevacizumab: Mutations in KRAS may indicate limited response to bevacizumab.

5-fluorouracil: Loss of APC and SMAD4 may indicate poor response to 5-fluororacil. Certain variants in DPYD may indicate toxicity to 5-fluororacil-based therapy. MSI positive and high levels of TS indicate poor response to 5-fluororacil.

Oxaliplatin: mUtations in KRAS indicate possible response to oxaliplatin. Elevated levels of ERCC1 protein indicate poor response to oxaliplatin.

Capecitabin: Certain variants in DPYD may indicate toxicity to capecitabine-based therapy.

Irinotecan: High levels of TOP1 are associated with response to irinotecan-based therapy. Certain variants in UGT1A1 may indicate toxicity to irinotecan-based therapy.

Figure 12A:
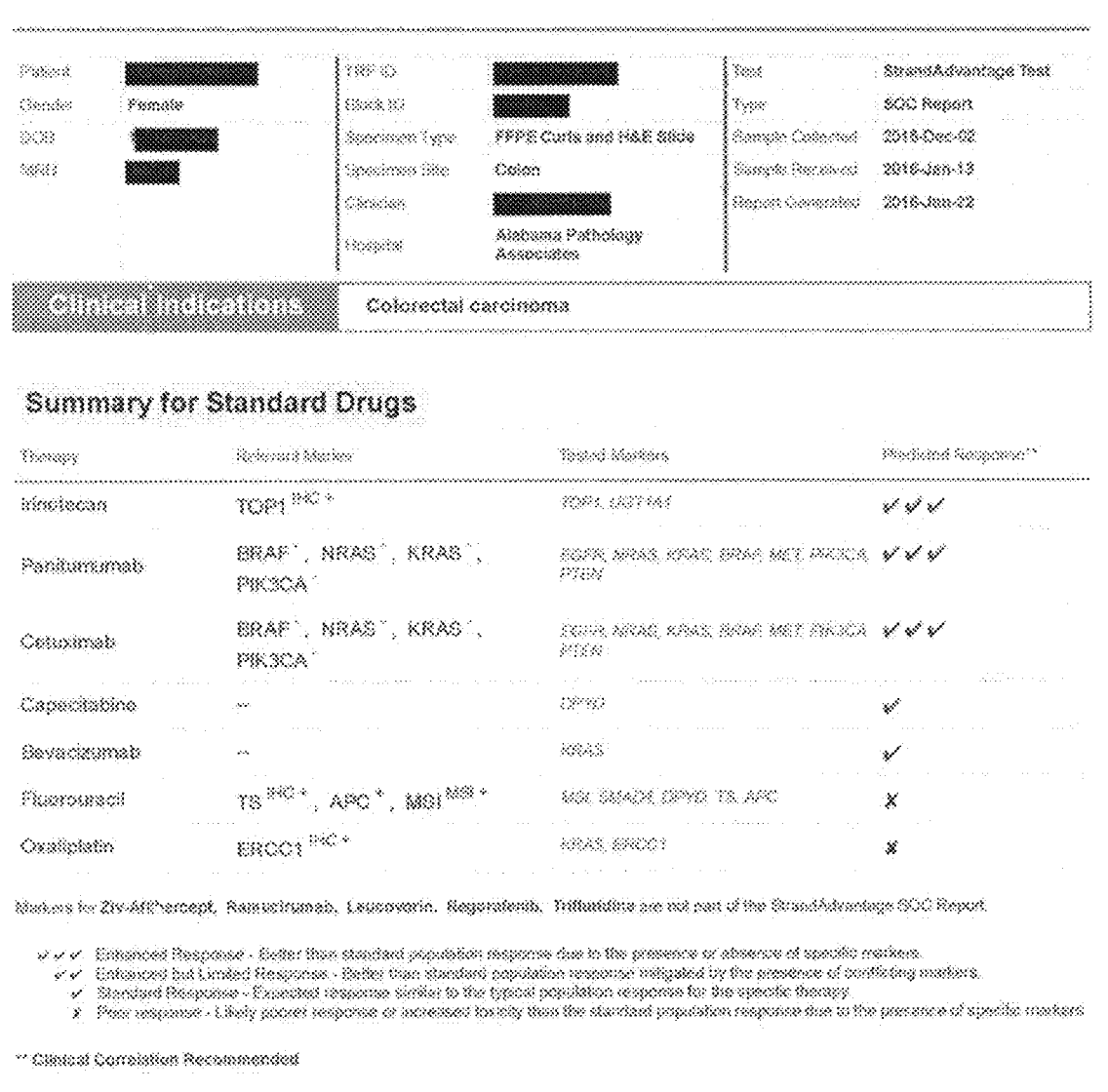
Figure 13A:
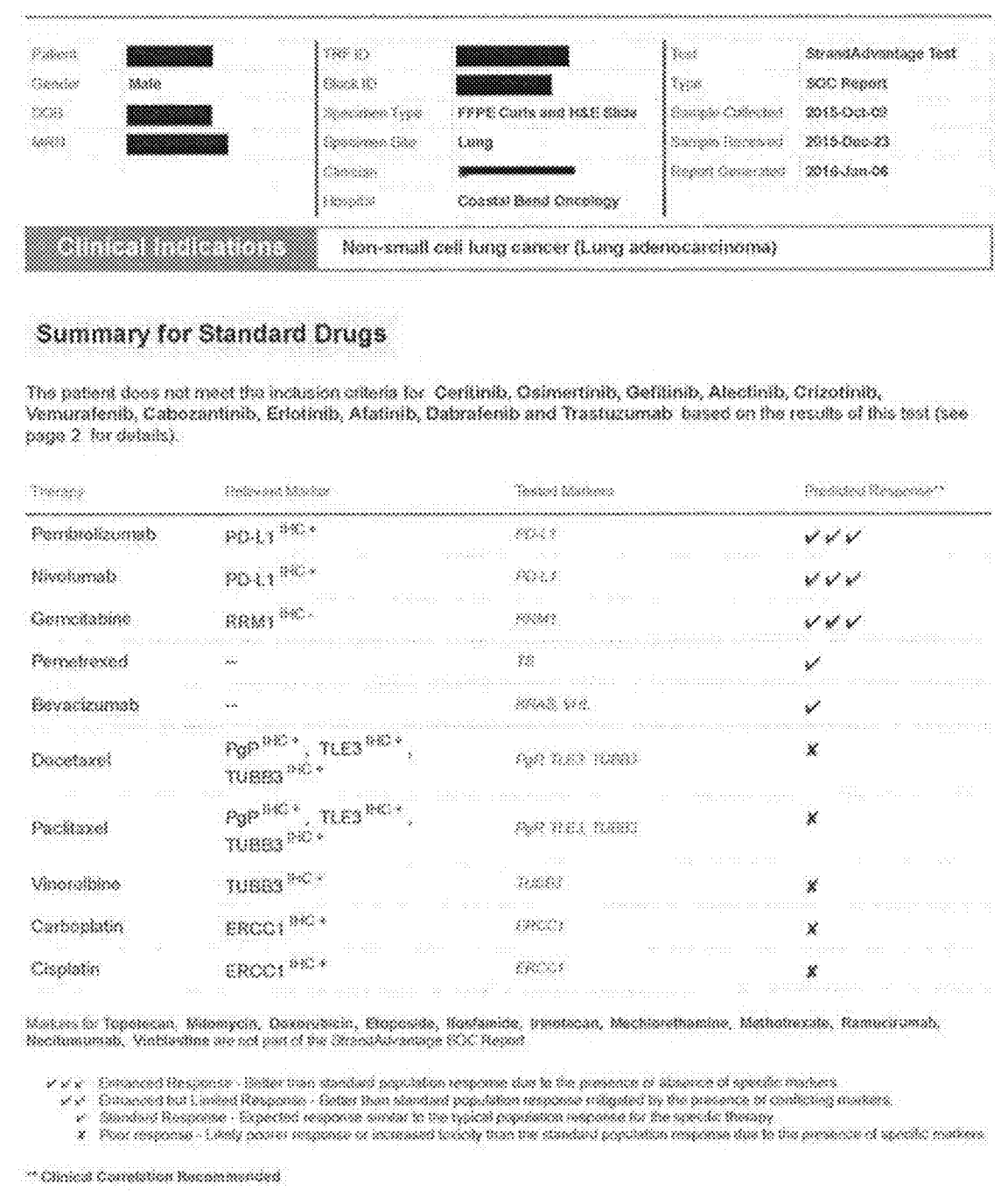

FIGS. 12A-12I illustrate an example of a SoC Report for a patient with a clinical indication of colorectal carcinoma. FIGS. 13A-13Q illustrate an example of a SoC Report for a patient with a clinical indication of lung adenocarcinoma. As shown in FIGS. 12A and 13A, the reports comprise identifying information at the top of the front page, as well as the clinical indication.

Automation of Report

In some embodiments, if a case has been created for an SoC cancer type, and SoC report has been chosen, the variants and markers that are part of the definition of the SoC test are automatically chosen to go into the report, with the pre-populated text. No other variants other than the SoC variants can be chosen to create a report. However, an interpreter may choose to negate a variant, based on the technical quality of the variant. It will be appreciated that in non-automated reports, the variants and markers can be specifically chosen to appear in the report. In some embodiments, automated reports can use a subset of variants and markers. In some embodiments, the reports can have customized text. These features can be included in the SoC report and the full report.

The individual rules are first applied and markers are turned on (or off). Then combinations are checked. If there is a hit on a combination, the recommendation, expected effect and summary is taken from the compound marker. The PMIDs from the individual markers are concatenated, and the variant text is taken for each individual variant. If the combination is not defined, then multiple rows are shown for the same drug (one for each marker). The interpreter can choose to resolve this by defining another compound marker that considers the combination of markers.

Figure 16A:
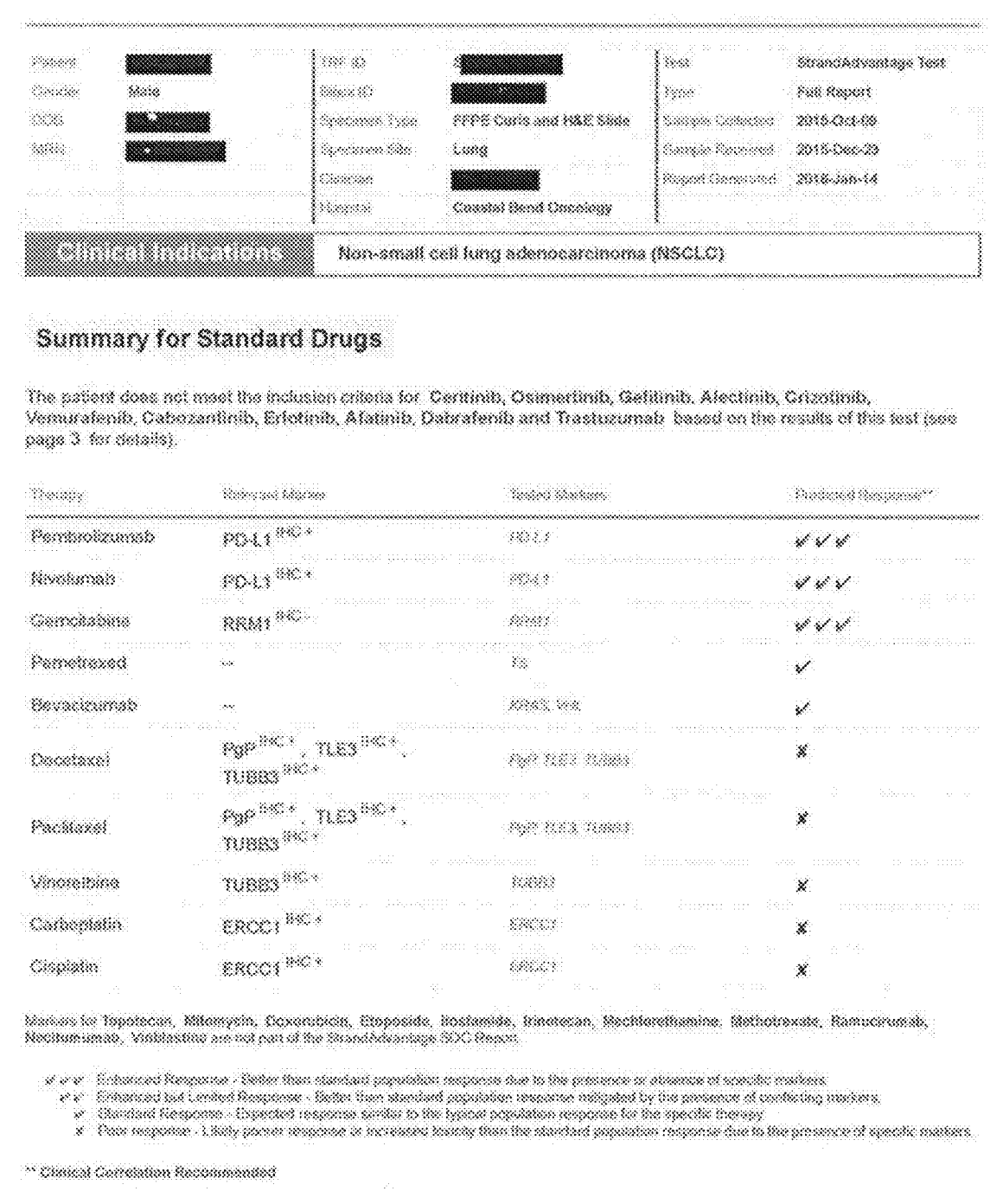

FIGS. 14A-16B provides examples of a full report generated by performance of an NGS clinical test (e.g., StrandAdvantage) for samples with clinical indications of breast carcinoma (FIGS. 14A-14C), colorectal carcinoma (FIGS. 15A-15C), and lung carcinoma (FIGS. 16A-16B). Further examples are shown for a sample with a clinical indication of colorectal carcinoma in FIG. 17 and lung adenocarcinoma in FIGS. 18A-18B. The report with a clinical indication of breast carcinoma, which comprises general information at the top of the report, as shown in FIGS. 14A, 15A, 16A, 17, and 18A. This section provides patient information (e.g., name, gender, age, MRN), sample information (e.g., TRF ID, block ID, specimen type, specimen site, date collected, date received) clinician, hospital, test, report type, date generated, and report version. Below that section is provided a 'Summary for Standard Drugs' at FIG. 14A (also shown at FIGS. 15A, 16A, 17, and 18A). The information is presented as a table and includes the following information: Therapy (e.g., drug), identified marker, tested markers, and recommendation. 'Tested markers' refers to the markers that the clinical test tests for. 'Identified markers' refers to any markers actually found within the sample. As shown in the example report and as described above, the recommendation can indicate a likely response to each therapy. The possible responses include 'Enhanced Response', 'Enhanced but Limited Response', 'Standard Response', and 'Poor Response'.

The report further comprises a Summary for Investigational Drugs at FIGS. 14A-14B (also shown at FIGS. 15A-15B, 16A, 17, and 18B). The information provided there comprises the following information: Therapy (e.g., drug), identified marker, approved indications, and trials. The identified marker refers to a marker found in the sample that is associated with the indicated therapy. 'Trials' refers to known clinical trials that can be identified using, for example, a clinical trial registry number.

Figure 17:
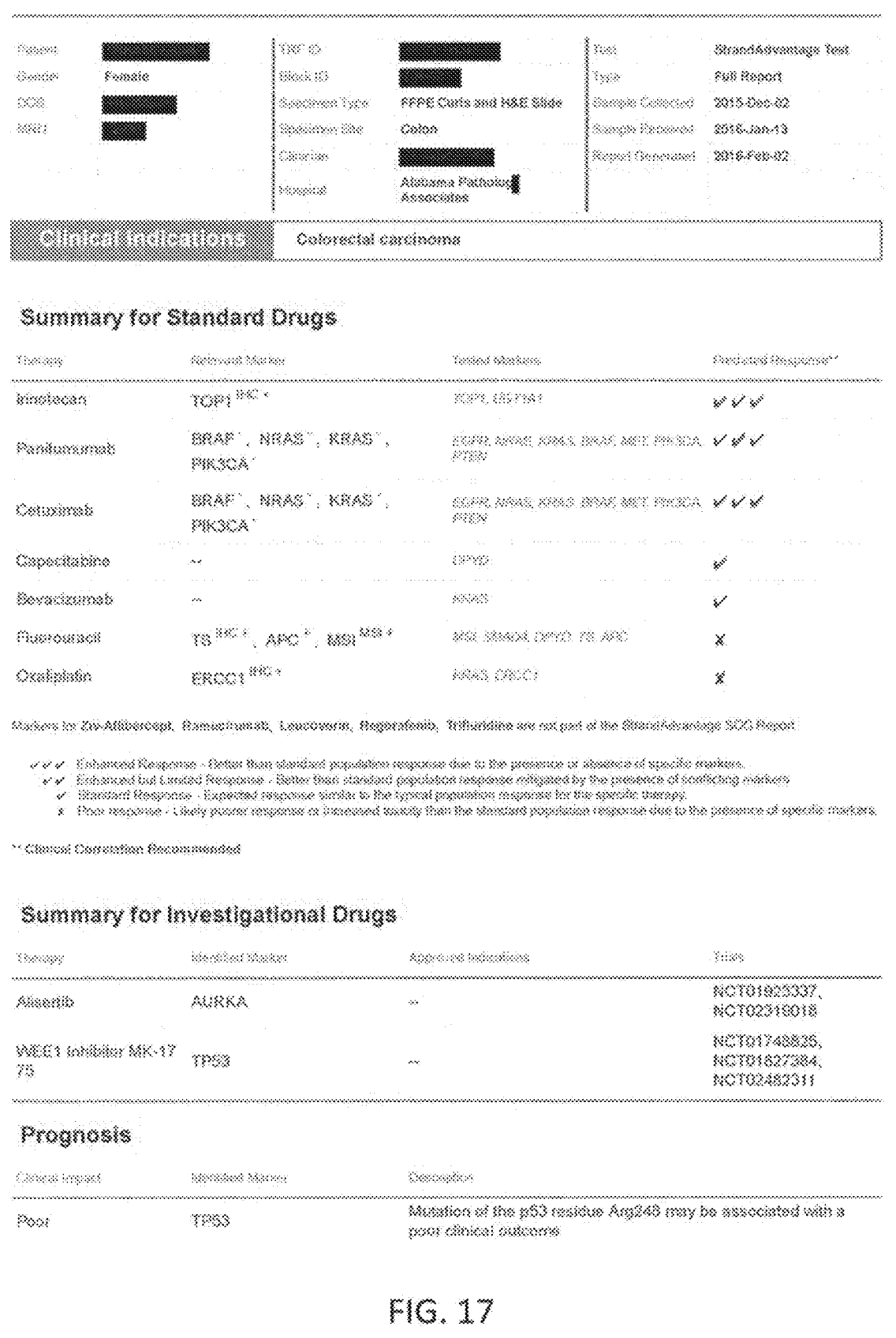

At the bottom of FIGS. 14B and 17, the report further comprises a Prognosis section that provides the following information: 'Clinical Impact', 'Identified Marker', and Description. This section can provide an overall prognosis based on any identified markers found within the sample. The 'Clinical impact' can refer to the overall impact of an identified marker. As shown in the example report, the 'Description' can provide information elaborating upon the identified marker's clinical impact.

In some embodiments, the report comprises a section showing ineligible drugs. Any of these reports may also include a section with drugs not indicated.

The example report further comprises a section, providing therapy or drug specific information (also shown in FIG. 15C). The report can provide the drug (e.g., Tamoxifen) and provide an overall recommendation (e.g., 'Enhanced Response', 'Enhanced but Limited Response', 'Standard Response', and 'Poor Response'). The report can further comprise additional details as described above. The additional details include the marker identified, evidence details relating to the identified marker, further details relating to the marker, drug description, and provide any relevant references (e.g., citing information, PMID number). Evidence details can include indications for the drug at issue and a determination as to whether the therapy is relevant for the mutation profile.

The report further includes a 'Limitations of Gene Coverage' section. In this section, the percentage of the gene target regions and COSMIC mutations covered by less than 100 reads is provided. The report also includes a Targeted Drugs section, that provides a drug name, PMID reference numbers, the gene, and variants. The report further comprises a 'Variants of Unknown Significance' section, which provides gene and variant information. The report concludes with a 'Supplementary Information' section, that provides information about the testing process (e.g., test description, genes evaluated, external lab tests, methodology, analysis, and primary tools used. Similar reports are provided for samples with colorectal carcinoma, and lung carcinoma clinical indications.

The report can include recommendation of off-label drugs and clinical trials.

Figure 19A:
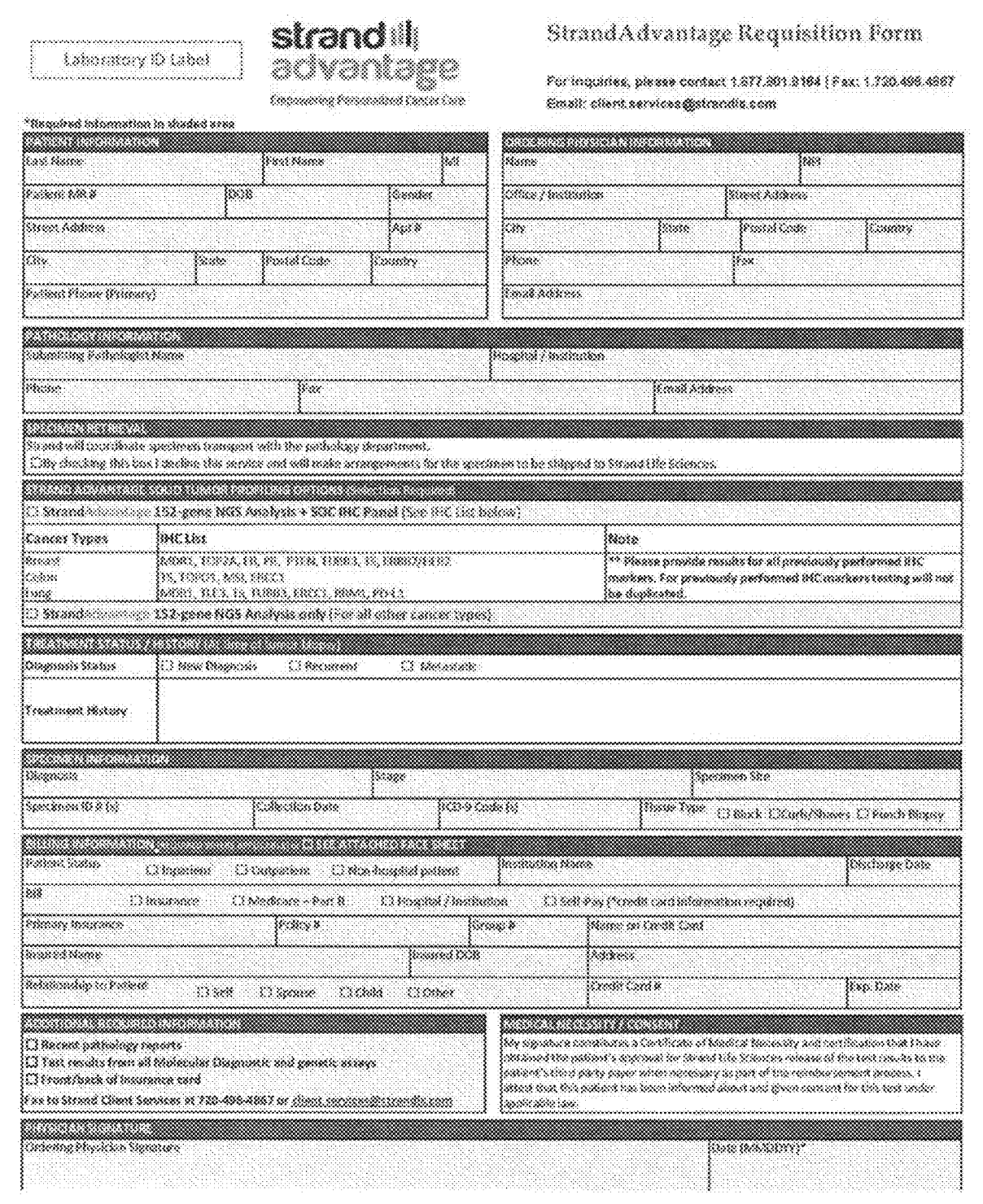

FIGS. 19A and 19B illustrate an example of a requisition form that physicians or clinicians can use to order a StrandAdvantage report. As shown in FIG. 19A, the form can request information regarding patient information, ordering physician information, pathology information specimen retrieval information, tumor profiling options, treatment status/history, specimen information, billing information, additional information, medical consent, and physician signature. The profiling options can, for example, include just the full StrandAdvantage test or both the full test and the SoC test. As shown in FIG. 19B, the form can include information about the SoC and full test. The form can also allow request for test result consultation.

These methods and apparatuses may provide a much-needed innovation in personalized genomic medicine makes cutting edge science accessible and comprehensible to the physicians community. Personalized or precision medicine can refer to delivery or personalized treatment based on the characteristics of an individual's tumor genetics, using targeted therapies that efficiently kill tumor cells. As advances in cancer research and drug development provide multiple treatment options, oncologists are faced with the challenging task of deciding which therapy works best for their patients. Delivering highly targeted, actionable treatment options based on the patients genetic profile, the reports, methods, and processes described herein enables optimized decision making. The genomic profiling, processing, and reporting described herein can eliminate the need for multiple tests and can provide a comprehensive view of therapy-relevant genomic and proteomic changes in an easy-to-read report.

While examples of reports and information provided by the reports are described herein, it will be appreciated that the present disclosure contemplates variations and combinations of elements of these reports. Additionally, it will be appreciated that the information can be visually represented in numerous different ways and still be within the scope of the present disclosure.

The methods and apparatuses described herein may also allow improvement of Turn-Around-Time (TAT, e.g., TAT Optimization). For example, the approaches described herein may permit TAT reduction from days (e.g., x FTE-days) to hours (e.g., y FTE-hours). For example, in some embodiments, the TAT can be about 7 working days. In some embodiments, the TAT can be dependent upon the tumor specimen passing a QC threshold.

Automated Recurring Report generation capabilities are enabled based on a trigger that is generated when new knowledge becomes available within the Alchemy and Elixir environments. For e.g., when a previously benign variant becomes designated as a pathogenic variant, or vice versa, or when new functional impacts of a known or novel variant becomes published in literature and gets into StrandOmics curated knowledgebases, or any new information relevant to any of the use cases of StrandAdvantage test (or any other Strand tests) becomes available that can alter the clinical decisions on a patient, a new report is automatically generated by the system and alerts the impacted physicians and patients with this life changing information.

The methods and apparatuses described herein may also improve the Standard-of-Care (SOC) workflow for clinicians and other healthcare providers. For example, standard-of-care workflow may be an automated pipeline for creating a report suggesting standard of care treatment for selected cancers based on analysis of variants in one or more subsets (e.g., of the most clinically relevant genes, e.g., in a somatic 161 gene panel), with turn-around-times comparable to single gene tests. The method and apparatuses described herein may offer improvements in one or more of:

Selection of variants: This test takes into account NCCN guidelines for genetic testing in various tumors. Known variants in select genes with strong implications on response to standard of care therapy are selected. Various genes relevant to a particular cancer type are tested for at one time. The therapeutic implication of the presence or absence of these variants is written up in a clear concise statement.

Sample QC: Coverage on the standard of care loci and regions is considered to qualify or reject a sample.

Variant Lookup: Somatic Variant Detection is performed on the sample to lookup variants of interest.

Report Creation: A cancer issue specific report is created in-silico using the presence or absence of statements generated previously.

Thus, these workflows may provide the TAT benefits of single-gene-tests yet retaining fair bit of comprehensiveness of using a multi-gene panel. It may eliminate the need for multiple tests and hence saves precious sample, cost of sequencing and time. Physician may have faster turnaround on the most relevant genes before deciding on a therapy without this information.

Also described herein are graphics processing unit (GPU) acceleration methods and apparatuses. For example, aligning NGS short reads to reference genome is one of the more time consuming automated steps. The Strand-NGS described herein has a built-in in aligner and an automated pipeline manager that performs better than many major aligners available in the market, and there is opportunity to further reduce the TAT of StrandAdvantage and other tests through GPU acceleration.

GPUSeq Alignment

Genome sequencers produce "short reads", fragments of the sequenced genome between 100 and 300 base-pairs long. In sequence alignment, these reads are mapped to a reference genome, ascribing them to a hopefully unique genetic locus. Sequence alignment is the first step in sequence analysis, a computational workflow whose goal is to discover biologically relevant variants at all possible genetic loci.

Because the sequenced reads are short relative to the length of the genome, many of them—roughly 30 per locus—are required to attain a reasonable sequencing accuracy. The average number of reads generated by a whole genome sequencing process is thus between a few hundred million and a billion, making sequence alignment a highly computationally intensive task, and one that takes tens to hundreds of CPU hours. However, since the alignment of each read to the reference is independent of all other alignments, sequence alignment is also inherently parallelisable, and speedups on multi-core CPUs are straightforwardly obtained. All popular alignment tools today have the ability to perform computations on multiple threads, deriving performance increases that are usually proportional to the number of cores used.

Any parallel program can be rewritten for, and thus benefit from, the Graphics Processing Unit (GPU). Apart from its parallel hardware paradigm, the GPU performs computations that are asynchronous of its host CPU; this asynchronicity means that programs can execute simultaneously on both the CPU and the GPU, obtaining a liveness, and thus a speedup, that is impossible in either one of them taken singly. For sequence alignment, a few notable GPU-based implementations have been developed, all for the CUDA/Nvidia platform. However, these implementations have either demonstrated a very modest improvement over their CPU-based counterparts, or have been confined to solving a single sub problem in the sequence analysis workflow. In particular, a multithreaded hybrid CPU/GPU program for sequence alignment, one that leverages both the asynchronicity and parallelism inherent to the GPU-CPU hybrid has not, to our knowledge, been discussed.

The GPUSeq Aligner is such a program. The development of the Aligner was motivated by two questions. 1) Where, and to what extent, can GPUs assist in the sequence analysis workflow? and 2) How do the bottlenecks influence the need for increased performance? In answering these questions, we show that the Aligner is: a fast, multithreaded, CPU-GPU hybrid program for short-read alignment. The Aligner can align both single- and paired-end reads, and is capable of a throughput of 31 megabases per second (MB/s). As an example, we show that reads from the 1.16 billion read NA12878 sample can be aligned in 90 minutes on a 32-core, 2-GPU machine. The Aligner is also an accurate program with user-options specifically tailored to DNA sequencing. The Aligner is extremely accurate, capable of mapping nearly 96% of reads from the NA12878 dataset with an alignment score of 90 or above. It is also equipped with several options, such as base quality recalibration and split-read alignment, that are unique to and necessary for users that seek to perform sequence analysis. The Aligner is also a scalable program. The time taken by the Aligner scales gracefully with increase in the average read length as well as the number of reads. It also scales gracefully with the size of the desired alignment gap.

We outline our overall approach to sequence alignment below, following which we discuss our GPU-based Smith Waterman program. We then discuss results and a comparison with other aligners.

Overall approach: The GPUSeq Aligner proceeds in four stages. 1. Search index pre-computation. In the first, and only offline, stage, a Burrows-Wheeler search index is precomputed from the reference. 2. Search. In the second stage, the index is used to find all locations at which a read approximately or exactly matches the reference; due to the index, this occurs in time proportional to the length of the read rather than, as in the naïve situation, the length of the reference. 3. Local alignment. In the third stage, each approximate match is refined by introducing a limited number of gaps, i.e. insertions, deletions and mismatches on the read, generating an alignment. 4. Postprocessing. In the fourth stage, all alignments for the read are ranked to find the best alignment, which is written to output. By convention, the output is bucket-based: the reference is subdivided into a number of user-specifiable buckets, and reads aligning to a particular range of locations on a chromosome are written to a particular bucket. Bucket-wise output makes it convenient to sort aligned reads after alignment.

Stages two, three and four, respectively, search, local alignment, and postprocessing, are repeated for each read.

The workflow above is similar to that of several popular alignment tools. In SOAP2 (Ruiqiang Li, Chang Yu, Yingrui Li, Tak-Wah Lam, Siu-Ming Yiu, Karsten Kristiansen, and Jun Wang. Soap2: an improved ultrafast tool for short read alignment. Bioinformatics, 25(15):1966-1967, 2009.), BWA (H Li and R Durbin. Fast and accurate short read alignment with burrows-wheeler transform. Bioinformatics, 25(14): 1755-1760, 2009.) and Bowtie2 (B. Langmead, C. Trapnell, M. Pop, and S. L. Salzberg. Ultrafast and memory-efficient alignment of short dna sequences to the human genome. Genome biology, 10(3), 2009.), the third stage is omitted, and instead the second stage is used to find reads with exact matches and a limited number of mismatches; these approaches cannot be efficiently used to detect alignments with gaps. BarraCUDA (Petr Klus, Simon Lam, Dag Lyberg, Ming Sin Cheung, Graham Pullan, Ian McFarlane, Giles SH Yeo, and Brian YH Lam. Barracuda—a fast short read sequence aligner using graphics processing units. BMC Research Notes, 5(27), 2012.) reimplements BWA (H Li and R Durbin. Fast and accurate short read alignment with burrows-wheeler transform. Bioinformatics, 25(14):1755-1760, 2009.) on the GPU, while SOAP3 (CM Liu, T Wong, E Wu, R Luo, S M Yiu, Y Li, B Wang, C Yu, X Chu, K Zhao, R Li, and T W Lam. Soap3: ultra-fast gpu-based parallel alignment tool for short reads. Bioinformatics, 28(6):878-789, 2011.), a successor of SOAP2, and CUSHAW2-GPU (Yongchao Liu and Bertil Schmidt. Cushaw2-gpu: Empowering faster gapped short-read alignment using gpu computing. Design and Test, IEEE, 31(1):31-39, October 2013.) uses the GPU for the search and the local alignment stages.

The GPUSeq Aligner implementation: Written in Java, C++ and CUDA, the GPUSeq Aligner implements a multi-threaded, SSD-output based sequence alignment scheme that works optimally on high-memory machines with multiple cores. The schematic is in FIG. 20. Let the number of threads with which the program is instantiated be n+2. The zeroth, execution, thread loads the precomputed BWT index into CPU memory, collects information from the input fastq file, and prepares for writing a number of chromosomal buckets. Threads 1 to n then execute stages two, three and four in parallel, obtaining a chunk of reads from the input, and aligning them in turn. In particular, stage three, which is implemented on the GPU, is batch-wise: each thread accumulates DPs for a number of reads before sending them to the GPU; due to the asynchronous nature of the GPU-based Smith-Waterman (See above), the thread does not have to wait for the results of these DPs, and can instead continue to process more reads until it runs out of a preallocated memory limit. At this stage, DPs on all pending reads are aggregated and post-processed, before writing them in chunks to a blocking queue. Finally, thread n+1 periodically flushes the blocking queue and writes the alignments to the respective buckets.

The post-processing stage includes a computation of the mapping quality and GPU-based mate rescue for paired-end reads. It also includes collection of statistics for base quality recalibration and split-read alignment, in which reads with large gaps are aligned to the reference.

The GPUSeq Aligner Smith-Waterman kernel: The Smith-Waterman dynamic programming algorithm returns the best alignment between a pair of input strings. We describe it briefly below.

Figures 20, 21:
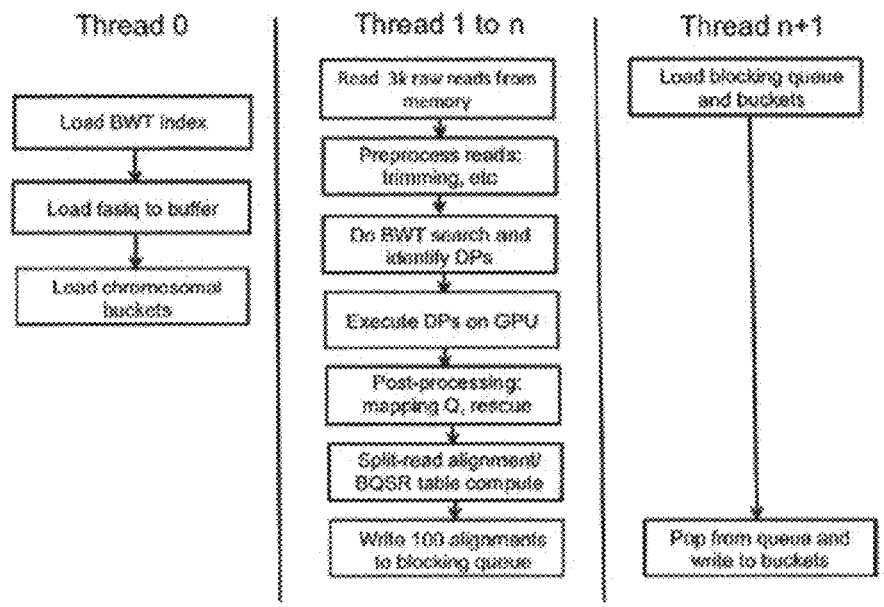
FIG. 20 shows an example of a GPUSeq Aligner workflow.
FIG. 21 illustrates an example of a matrix construction used in the GPUSeq Aligner.

Given a string R from the alphabet A={A, G, C, T, N}, let R[i, j] denote the substring that begins at position i and ends at position j, and let R[i] denote the ith character. Let the input to the algorithm be a pair of strings R1 and R2, respectively belonging to the sets R1 and R2. The algorithm proceeds in two stages. In the first stage, a matrix M(i,j) is constructed as shown in FIG. 21.

Here E(i,j) and F(i,j) respectively represent the penalty for introducing gaps in sequences R1 and R2, and gm, go and ge are the mismatch, gap opening, and gap extension penalties. The first rows of each of M, E and F are initialized to zero.

In the second stage, the matrix M is traversed in the direction opposite to its construction to find the optimal alignment. Starting at the cell double index (i, j) with the highest score in M, successive moves replace the current double index with either of (i−1, j), (i, j−1) or (i−1, j−1), depending on which of those cells attain the greatest value in M; the moves continue until the value 0 is encountered. Diagonally opposite moves from (i,j) to (i−1, j−1) represent matches or mismatches, and vertical/horizontal moves represent gaps in either of the input strings.

Prior approaches to optimizing Smith-Waterman for the GPU have largely focused on finding the greatest alignment score. Due primarily to the linear storage complexity of the first stage, such approaches can exploit several GPU-related properties related to memory access, achieving very high speeds. CUDASW++3.0, an exemplary implementation of the first stage on the GPU, is capable of a throughput of nearly 120 GCUPS (billion matrix cell updates per second) on 2013 Nvidia cards based on the Kepler architecture.

GPU architecture presents two challenges to the implementation of a two-stage Smith-Waterman. The first is the quadratic storage complexity. If the parallelisation scheme assigns a single alignment to each thread, then at least one matrix of size O(l1/2), where l1 and l2 are the lengths of the input string, has to be stored in the local stack frame. The second challenge, a corollary of the first, is the ratio of the number of memory accesses to the number of mathematical operations—the so-called mem-math ratio. The Smith-Waterman has a very high mem-math ratio: it requires a large number of primitive string manipulations, while its algorithm consists of only the most trivial mathematical operations, none of which are floating-point. The memory pressure and the high mem-math ratio both imply smaller than average GPU speedups, as accesses to global memory on the GPU, where the matrix and other intermediate arrays are stored, are nearly 100 times slower than accesses to thread-based registers and shared memory.

Due to these challenges, the full Smith-Waterman on the GPU, one that includes the second stage, is, by comparison, rarer and less well-explored. Khajeh-Saeed et. al parallelise the computation of entries in the matrix M using a parallel scan algorithm, achieving speedups of nearly 30× for the pairwise alignment of very long strings. Blazewicz et. al use four Boolean matrices, each corresponding to a move direction, for the second stage, a strategy that reduces the quadratic runtime of the second stage to a linear one, and results in speeds, on 2010 Tesla GPUs, of up to 2.5 GCUPS. The fastest and most recent GPU implementation of the full Smith Waterman is the tile-based GSWAB in Liu and Schmidt. In GSWAB, data access patterns are optimized by partitioning the matrices involved into 4×4 tiles. GSWAB achieves average speeds of nearly 50 GCUPs on the Kepler-based GeForce Titan card.

Features of our kernel: Our CUDA kernel for the GPU-based full Smith Waterman is equipped with the following features, all of which are designed to exploit the memory access patterns unique to the GPU while mitigating the effect of the high mem-math ratio.

A single backtracking matrix stored in local memory. Unlike the approach previously described, our approach makes use of a single backtracking matrix M'. Each entry M'(i in M' is a byte that stores the maximum of a particular pair or triplet of scores at (i, j); for instance, the first two bits store the maximum of the match, insertion, and deletion scores, with 00 (respectively 01 and 10) signifying that the match (respectively insertion and deletion) score is the greatest. Similarly, the next pair of bits stores the maximum of the (match+gapOpen, insertion+gapExtension) scores and the pair after that the maximum of the (match+gapOpen, deletion+gapExtension). The final two bits are used to indicate if there is a mismatch at (i, j), j) The single backtracking matrix replaces the triple of matrices M, E, and F in the Smith Waterman recursion equations, reducing, by a factor of three, the amount of storage required on the local stack frame. It also reduces the number of memory accesses, expressed in bytes per mathematical operation, for both storage, during the first stage, and retrieval, during the second stage. Thus, in the first stage, a single byte stored in a thread-local register is packed with the information above before being stored in the matrix. Similarly, in the second stage, a single thread-local byte is received from the matrix and then read to perform the backtrace.

Judicious use of constant memory. GPU-based constant memory is used to store static variables that do not change during the execution of the kernel. Accesses to the same location in constant memory are cached and nearly as fast as register access. However, access to different locations in constant memory is serialized within a set of threads (known as a half-warp). For this reason, only single-valued variables are stored in constant memory; all constant array based variables are instantiated as thread-based registers during kernel launch.

Memory operations expressed as primitive mathematical operations. The substitution function S(Ri[i], R2[7]) can be expressed as a 5×5 matrix S, where each row and column represents a single element from the alphabet A. S is clearly a symmetric matrix in which the diagonal entries are unity and the off-diagonal entries equal to the mismatch penalty. On the other hand, the S(R\[i], R2U]) can also be expressed as a ternary function that returns unity or the mismatch penalty based on whether or not the arguments are equal. Of these, we choose the latter implementation, as it requires significantly less storage, and because all the storage it requires can be register-based and hence local to a thread.

Branch reduction and other miscellany. Execution of threads from a half-warp that take different paths through an if-else statement can be serialized, in a process called branch serialization. To reduce the effects of branch serialization, many if-else statements have been re-expressed as primitive bitwise operations. Further, several critical loops have been unrolled.

Further, our Smith-Waterman kernel also possesses the following implementation features.

Sorting. The sequences in the input sets R1 and R2 are assumed to be of variable length, and input sequences are sorted in increasing order of their length before the kernel is executed.

Streams. A stream is an independent set of instructions, executed in order, on the GPU. Our Smith-Waterman kernel can be instantiated with a variable number of streams; typically, each stream on the CPU corresponds to a thread of execution on the CPU, so that there is no need to share data between CPU threads, and thus no synchronization.

Asynchronicity. Our Smith-Waterman kernel exploits CPU-GPU asynchronicity by the use of pinned memory. Calls to the Smith-Waterman kernel return immediately and reduce thread-wait times to a fraction of what they could otherwise have been.

Comparison with implementation in Liu et. al (Yongchao Liu and Bertil Schmidt. Faster gpu-accelerated smith-waterman algorithm with alignment backtracking for short dna sequences; in Roman Wyrzykowski, Jack Dongarra, Konrad Karczewski, and Jerzy Wazoniewski, editors, Parallel Processing and Applied Mathematics, Lecture Notes in Computer Science, pages 247-257. Springer Berlin Heidelberg, 2014.) Our implementation of the CUDA kernel differs from the one in Liu et. al in the following ways.

MD computation. Our implementation computes the MD string. The MD string is an integral part of an alignment; it specifies if an 'M' on the CIGAR is a match or a mismatch, and also specifies all bases that correspond to a given mismatch and deletion. The computation of the MD string is highly memory-bound, and adds significantly to the time taken by the second stage.

Number of alignments. Given a pair of sets Mi and R2 containing the input sequences, the approach in Liu et. al performs all pairwise alignments |Ri|×|R2|. By contrast, our kernel only accepts input sets with the same cardinality, and performs alignments between the ith element of each set.

Length of input data. The datasets in Liu et. al contain sequences of the same length. By contrast, our implementation contains reads of vastly varying lengths. These reads are sorted in order of length before kernel execution.

Hardware configuration. Our kernel has been optimized for the Nvidia K10 Tesla card. The K10 has 1536 cores operating at a base clock frequency of 745 MHz, a total memory of 3.0 GB, and a total memory bandwidth of 160 Gbps. On the other hand, the implementation in Liu et. al uses the much more recent GTX Titan card. The Titan has 2688 cores with a base clock frequency of 837 MHz and a boost clock frequency of 876 MHz, a total memory of 6.0 GB, and a total memory bandwidth of 288.4 Gbps.

Each of the above points, except the second, results in an overall benefit for the approach in Liu et. al over ours, making a direct comparison infeasible. In addition, regardless of the hardware used, the first and third point would act together to significantly reduce the throughput in GCUPs of our approach over the one in Liu et. al. However, we do note that, modulo the hardware differences, the performance we obtain (see following section) is of the same order as that of Liu et. al.

TABLE 19

Comparison of the performance of the GPUSeq Aligner vs. various publicly available alignment tools.

| Alignment Tool | Throughput in Gbps/pt (higher is better) |
| --- | --- |
| GPUSeq Aligner | 2.5e−3 |
| SOAP3-dp | 2e−3 |
| BWA [5] | 1.3e−4 |
| Bowtie2 [4] | 2.5e−4 |
| CUSHAW2 [11] | 2.5e−4 |

The throughput for all the publicly available tools is computed from Luo et. al, Table 19, entry 2. The throughput for the GPUSeq Aligner includes the time taken to perform mate rescue.

Performance of the Smith-Waterman kernel: The GPU-based DP kernel is capable of a throughput of 7.8 billion DPs/hr, given read/reference pairs with average lengths 100 and 110 respectively, with each varying within a band of 10 bp. This translates to a speed of about 22 GCUPs (billion cell-updates per second), and is thirty-five times faster than the corresponding CPU-based program. The DP kernel scales gracefully with an increase in number of GPUs; thus, the throughput is 14.9 billion DPs/hr on 2 GPUs, for a speed of about 43 GCUPs. The speed also scales as expected with an increase in read length, generating a throughput of 4.1 billion DPs/hr given read/reference pairs with average lengths 150 and 164 respectively.

Note that Liu et. al obtain a speed of about 50 GCUPs on their far more recent GPU, which, for all practical purposes, can be taken to be at least twice as fast as the K10 Tesla, the GPU on which the figures above are obtained.

Performance of the GPUSeq Aligner: The GPUSeq Aligner differs from other publicly-available aligners. It has been explicitly designed for higher-end machines; the machine we use to benchmark the Aligner possesses 16 cores/32 threads@2.7 GhZ, 2 K10 Tesla GPUs, 64 GB of RAM and a 1 TB SSD. This is already divergent, say, from SOAP3, in the benchmarking of which a single quad-core machine with 64 GB RAM is used. To address the differences in benchmarking machines used by the various aligners, we compare various aligners using the number of aligned gigabases per second per CPU thread (Gbps/pt).

Even this metric provides only a guideline, since all CPU cores do not perform in the same way, and all memory is not equally fast.

The performance of the GPUSeq Aligner is comparable to SOAP3-dp; however, since the machine in the latter approach runs at a higher clock-rate, a direct evaluation is difficult. Interestingly, the highest throughput per thread for the GPUSeq Aligner is attained at 10 threads, with a progressive decrease in throughput per thread as the number of threads are increased. However, the decrease in throughput per thread is not so drastic as to decrease overall throughput as the number of threads are increased; thus, running the GPUSeq Aligner with 16 threads is faster than running it with 8 threads, though not twice as fast.

We also run the GPUSeq Aligner on the 1.16 billion 151 bp paired-end NA12878 dataset. Timing for various situations on that dataset with 30 threads is given in Table 20. The results indicate that mate rescue increases accuracy while not being considerably slower, and that the collection of statistics for base quality recalibration takes an additional one hour, while not involving a significant degree of I/O, as is usually the case.

TABLE 20

Aligner timings in various situations.

| Situation | Timing |
| --- | --- |
| Alignment | 1 h 37 minutes |
| Alignment + mate rescue | 1 h 47 minutes |
| Alignment + bqsr stats (Quality Covariate) | 2 h 20 minutes |
| Alignment + bqsr stats (Quality + Cycle + Context Covariate) | 2 h 42 minutes |

Summary of GPUSeq Aligner performance: The GPUSeq Aligner is fast; its speed is comparable to SOAP3 the fastest publicly-available alignment tool, and between 7 and 20 times as fast as other popular alignment tools such as Bowtie2, CUSHAW2, and BWA. The performance of its GPU-based Smith-Waterman implementation is comparable to that of GSWAB the fastest currently available such program, while being able to handle variable length reads. The GPU-based Smith-Waterman also takes advantage of streams and asynchronicity, advanced CUDA features that result in an implementation that is convenient to use on multi-core machines.

More information about GPUSeq is provided below.

We present GPUSeq, a program for high-performance GPU-based DNA sequence analysis. GPUSeq replaces computationally intensive CPU-bound steps in DNA-Seq with heavily optimized counterparts developed for the GPU. The results are (i) A fast DNA alignment tool, capable of aligning 1.16 billion reads from the human genome in 90 minutes; (ii) a fast SNP caller, capable of calling variants on an aligned, sorted version of the aforementioned sample in 45 minutes; and (iii) a fast overall DNA sequence analysis workflow, capable of performing alignment, mate rescue, split read alignment, base quality score recalibration (BQSR), indel realignment, and variant calling on the same sample in under 8 hours. GPUSeq inherits much of its algorithms, as well as its accuracy, from the DNA analysis workflow of Strand NGS1. Note that this workflow of Strand NGS is itself significantly faster than the equivalent GATK pipeline running on a similar architecture.

Introduction: Sequence analysis is computationally intensive. On a contemporary single-core CPU, human whole genome sequence analysis takes anywhere between a few days to a week, a figure that improves to about 24 hours with the simultaneous introduction of parallelism and multi-core CPUs. Further improvements are possible only if relatively novel computing paradigms are embraced. The Graphics Processing Unit, or GPU, is exemplary in this regard. The typical contemporary GPU possesses a very high memory bandwidth, is capable of a throughput nearly two orders of magnitude greater than that of a single CPU core, and is equipped with a C-like programming idiom. All of these attributes make it an ideal platform for fast and parallel sequence analysis.

GPUSeq is the result of a systematic multi-year effort by Strand Life Sciences, to port performance critical steps of DNA sequence analysis to the GPU. In its current form, GPUSeq combines a GPU-based aligner and a GPU-based variant caller with CPU-based split read alignment, base quality recalibration, and indel realignment. Each computational step in GPUSeq corresponds directly to a step in the Strand NGS DNA sequence analysis workflow while benefitting from a significant speedup due to its integration with the GPU.

The input to GPUSeq is a reference sequence and multiple sets of paired- or single-end reads. There are two stages of output. The first stage is sequence alignment, in which each read is aligned to the reference genome. The second stage is variant calling, in which variation at a particular genetic locus is statistically determined using all reads ascribed to that locus. These stages collectively constitute the sequence analysis workflow.

A section below briefly discusses the GPUSeq workflow, and in particular those aspects of it that are GPUrelated. Later sections respectively outline the accuracy and performance of the GPUSeq workflow.

Figure 22:
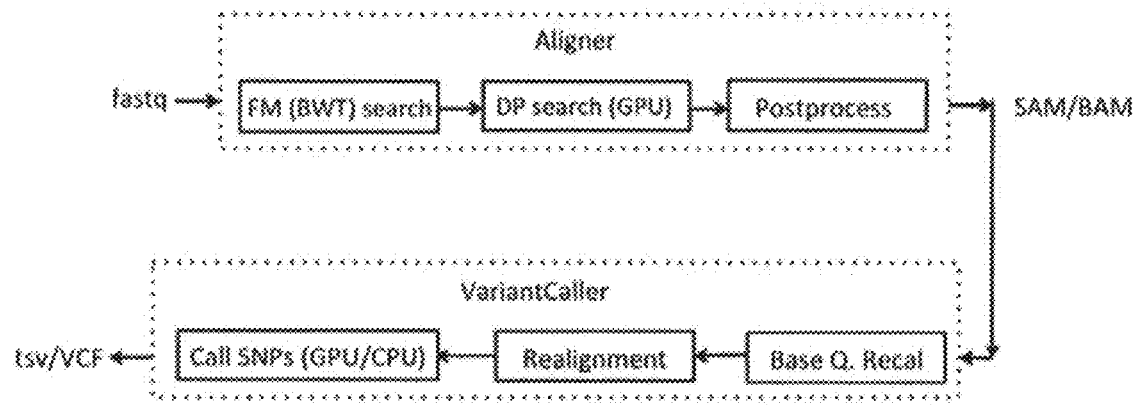
FIG. 22 shows an example of a GPUSeq workflow.

GPUSeq workflow: GPUSeq aligns and calls variants on a set of reads, producing a file in the variant call format (VCF) as output (FIG. 22). FIG. 22 shows the GPUSeq workflow. The base quality recalibration and realignment steps in the variant caller are both optional. The most computationally intensive steps in GPUSeq are executed on the GPU; those that are more memory intensive are, by contrast, executed in parallel on the CPU (Table 21).

The two major stages in GPUSeq are alignment and variant calling; the GPUSeq Aligner maps reads to genomic locations, while the VariantCaller performs base quality recalibration, indel realignment, and variant calling. Memory heavy steps are executed on the CPU, while steps involving more mathematical computations are executed on the GPU, "mCPU" in the final column stands for multi-threaded CPU.

TABLE 21

Computational features of each step in the GPUSeq workflow.

| Step | Features | Platform |
| --- | --- | --- |
| FM search (Aligner) | Memory heavy | mCPU |
| Dynamic programming (DP) stage (Aligner) | Low mem-math ratio | GPU |
| Base quality recalibration (Aligner & VariantCaller) | Memory heavy | mCPU |
| Realignment (VariantCaller) | Memory heavy | mCPU |
| Variant calling (VariantCaller) | Low mem-math ratio for posterior/biases | mCPU + GPU |

Aligner: The Aligner aligns single- or paired-end fastq files to a reference genome in the presence of a Ferragina-Manzini search index (based on the Burrows Wheeler Transform, or BWT). By default, it writes aligned reads to chromosomal buckets, where each bucket contains all reads that map to a chromosomalregion. Optionally, the Aligner can also collect statistics needed for base quality recalibration and perform split-read alignment.

Figure 23:
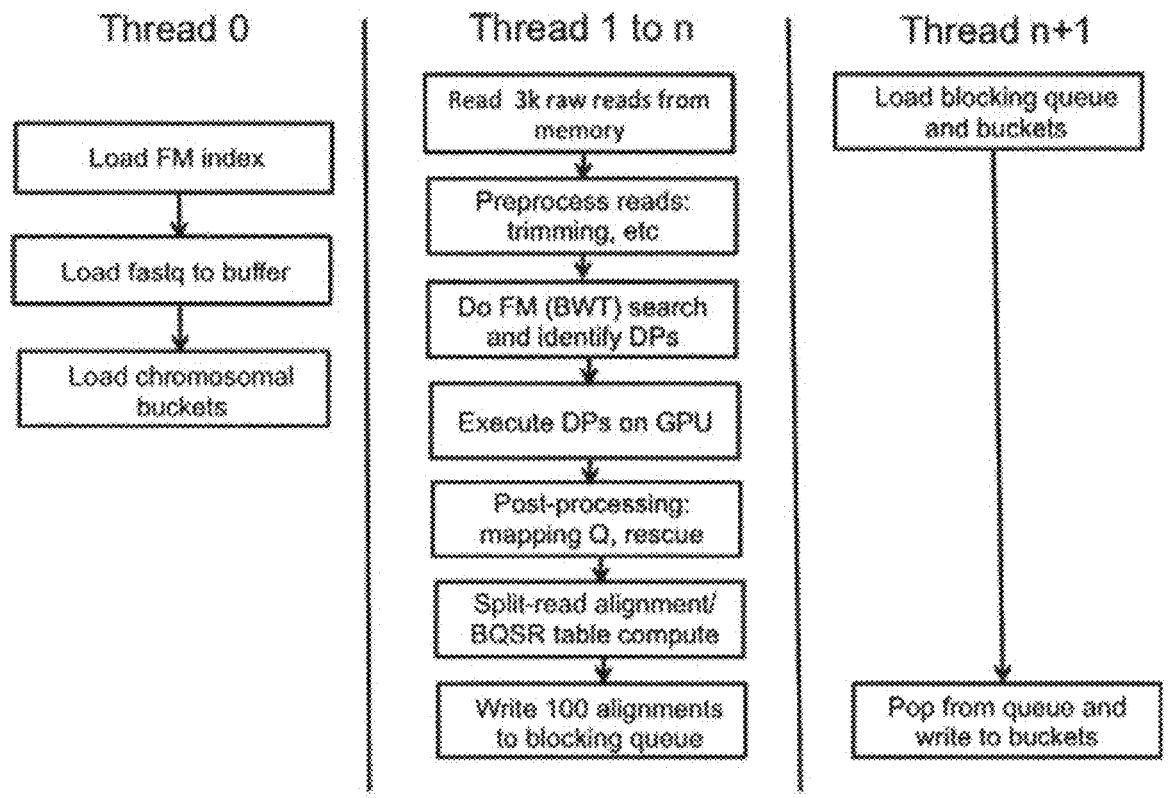
FIG. 23 (shown as FIG. 20, above) shows a schematic representation of load distribution between CPU and GPU.

A detailed workflow of the Aligner is presented in FIG. 23. As with many approaches to sequence alignment, it performs a global Ferragina-Manzini (FM) search followed by a local dynamic programming (DP) search (FIG. 23), resulting in a set of optimal alignments against the reference. The DP stage occurs exclusively on the GPU; each parallel thread on the GPU is responsible for solving a single dynamic programming problem.

In GPUSeq, the global search phase is implemented using multiple CPU threads, with each thread processing a number of reads from the input fastq file (FIG. 23). The search phase generates several (typically between three and nine) DP problems per read, each of which represents a possible alignment location. These are sent to the GPU in batches, where they are solved and returned to the CPU for the postprocessing stage. The postprocessing stage is responsible for identifying the best alignment for a given read or pair of reads and writing that alignment to a file. In paired-end alignment, it can also additionally attempt to align a poorly-aligning or translocated read to within a small distance of its well-aligned mate, based on the expected insert length; this process is called mate rescue, and improves the overall accuracy of alignment, resulting in fewer unaligned reads and fewer translocated read pairs.

Variant Caller: The VariantCaller calls variants on the output of the Aligner. By default, it writes a per-chromosome 'tsv' file. Each line in the tsv file corresponds to a SNP call, and contains values relevant to the call separated by tabs.

The detailed workflow of the VariantCaller is presented in FIG. 24. Variant calling occurs in two broad phases. The first, optional, phase consists of base quality recalibration and indel realignment, each of which can be enabled or disabled by the user. The second phase is variant calling.

In GPUSeq, indel realignment, based on techniques from GATK and Dindel, is implemented using multiple CPU threads, with each thread processing a set of reads in a given chromosomal region (FIG. 24). Once reads in a region are realigned, SNP variants are called on them in two stages. In the first stage, a multithreaded CPU-based pileup accumulates all bases aligning to each location in the region. In the second stage, variants are called at each location using either the GPU or CPU; each thread during the calling phase, whether on the GPU or the CPU, computes posterior Phred scores and biases at a single location. These are computed using a Bayesian method similar to that in Li et. al, taking into account the base qualities, mapping qualities, and coverage at the given location. Variants that pass the score threshold are written to either a tab-separated file (tsv) or a VCF file. For details on the variant calling method, see Gupta et. al.

Accuracy: The outputs of the GPUSeq Aligner and VariantCaller duplicate those of existing alignment and post-alignment tools in Strand NGS. In particular, the Aligner differs from the Strand NGS aligner only with respect to the DP stage, which is GPU-based in the former. A similar observation holds for posterior probability computation in the VariantCaller. Finally, barring the parallelism scheme, the program for indel realignment in the VariantCaller is identical to the one in Strand NGS.

Due to this equivalence, GPUSeq inherits the accuracy of the sequence analysis workflow in StrandNGS.

Performance: Two measures of performance are relevant. The first relates to the speed of each of the steps run on GPU as compared to its corresponding CPU timings. The second relates to the speed of the overall program, including other performance-related bottlenecks. We examine GPUSeq relative to both these metrics in the discussions to follow. See also FIGS. 25A and B for a comparison of GPUSeq with the StrandNGS DNA-Seq workflow. FIGS. 25A and B show Time taken by each step in (A) GPUSeq (FIG. 25A) and (B) Strand NGS DNA-Seq (FIG. 25B) on the NA12878 whole genome sample described above. Note that each of the sort, base quality recalibration and realignment steps in Strand NGS also includes a quality control statistics collection phase that is absent in GPUSeq.

All timing-related information in this section is with respect to a system with the following specifications.

CPU. 16-core/32-thread Intel Xeon@ 2.7 Ghz.

GPU. 1×K10 NVIDIA Tesla, 1536 cores @ 745 Mhz, 2.8 GB, bandwidth 160 Gbps. 2 GPUs on board. A single GPU is supported, but will slow things down by a factor of about 1.5.

Memory. 64 GB RAM @ 1600 MhZ.

Storage. 1 TB SSD with minimum sequential write speed of 550 MB/s.

Further, timings provided below are with respect to an Illumina HiSeq 2500 whole genome paired-end sequencing of the CEPH NA12878 genome, containing 1.16 billion 150 bp reads.

DP-stage GPU performance: The GPU-based DP kernel is capable of a throughput of 7.8 billion DPs/hr with average read length 100 bp and gap size 5 bp, falling to 4.8 billion DPs/hr as the read length increases to 150 bp. This translates to a speed of about 22 GCUPs (billion cell-updates per second) per GPU, for a total of 44GCUPs on both GPUs. This is respectively 35 and 70 times faster than the corresponding CPU program for the same parameters.

SNP-stage GPU performance: The posterior probability SNP kernel can compute SNP scores and PV4 biases for about 2 million genomic locations per second with an average coverage per location of 350. This is ninety-eight times as fast as the corresponding CPU-based program.

Aligner: Overall Performance: The overall performance of the Aligner depends on a number of factors, including, most importantly, the time taken in the FM search stage to generate exact matches and DPs for a given read. With 20 threads, the FM stage in the Aligner takes about 1 hour and 28 minutes to generate nearly 400 million exact matches and 6 billion DPs on the NA12878 dataset. The GPU-based DP stage is run in parallel and takes about an hour to compute these DPs. Finally, 10 postprocessing threads take an additional 10 minutes to generate the final pair of alignment for a given pair of reads as well as to write those alignments to file. The total alignment time is thus about 1 hour 37 minutes.

TABLE 22

Aligner timings in various situations.

| Workflow Options | Timing |
| --- | --- |
| Alignment | 1 hr 37 min |
| Alignment + mate rescue | 1 hr 47 min |
| Alignment + BQSR stats (Quality Covariate) | 2 hrs 20 min |
| Alignment + BQSR stats (Quality + Cycle + Context Covariate) | 2 hrs 42 min |

TABLE 23

VariantCaller timings in various situations.

| Workflow Options | Timing |
| --- | --- |
| Variant calling (indel realignment + SNP calling) | 4 hrs 48 min |
| Variant calling (SNP calling) | 3 hrs 20 min |
| Variant calling (base quality recalibration + indel realignment + SNP calling) | 5 hrs 01 min |

Note that the time required to sort the input alignments is implicit to each of the timings above.

There are optional parts of the Aligner workflow that add to the time above (Table 23).

VariantCaller: Overall Performance: The VariantCaller benefits rather less than the Aligner from GPU-based code. Despite the SNPGPU kernel being nearly a hundred times as fast as its CPU counterpart, SNP pileup, indel realignment, and file parsing bottlenecks contribute to an overall execution time of nearly five hours. Of this, about 50 minutes are spent in the SNP caller and 1 hours and 30 minutes in the realigner; the rest of the time is divided equally between parsing the input alignments and sorting them. See Table 23 for the time taken by the VariantCaller.

Equivalence Rules

As described above, if variants found in the test sample are unknown, they are tested for equivalence with curated variants. If a variant can be predicted to be equivalent to a known variant, then a rule is fired. In the description below, the apparatus or a method of using these apparatuses may be estimated by applying the equivalence rules or principles described in the examples below. In these examples, equivalence is qualitatively parsed, including high equivalence (H), which may include an exact match, medium equivalence (M), low equivalence (L) and non-equivalence (no equivalence).

There may be multiple levels of equivalence. For example, in some variations there are two levels of equivalence: Level 1 is Functional equivalence, and Level 2 is Variant type. Level 1 can include an exact match to a tested variant (100% match). Level 2 can include loss of function (LoF) and gain of function (GoF) variants and may also include exact matches of these types.

LoF variants can include point mutations, which will be called out as a LoF variant based on the following equivalence rules with curated variants. LoF point mutations can include premature stops or ESS variants, damaging non-synonymous variants, small InDels, DelIns variants, or deletions. For premature stops and ESS variants, equivalence can be established through all known LoF variants downstream of the case variant in the following order of importance: 1.) Exact aa match (H); 2) All other Stops downstream, including ESS and frameshift variant causing premature truncation (in increasing order of distance from case variant) (H); and 3) All other NS (Nonsynonymous or missense) known LOF variants downstream (in increasing order of distance from case variant) (H).

For damaging NS variants, equivalence can be established by predictors and conservation. For example, an LoF variant with an exact aa change match (H); a LoF variant with a match with a high confidence variant class (defined as a residue/group of resues/exon with known functional significance) (M); a LoF variant at the same codon with a different aa change/single aa deletion (M); and all regions/subdomains/domains with functional annotation for missense variants (L). For all regions/subdomain/domains with functional annotation for missense variants, equivalence can be shown with the smallest entity having a functional annotation (subdomain, if not domain, etc.).

For small InDels (e.g., up to 60 bp, about 40% of 150 bp reads), there are a few difference scenarios. In case of frame-shift variants, equivalence is established in the same manner as point mutations causing premature stops. The codon at which the frame-shift starts is considered for the equivalence rules. In the case of aa deletions (in-frame deletions), equivalence can be shown by a LoF variant with the exact aa changes or a subset of the changes is compared to the case variant (H); a LoF variant matching with high confidence variant class (defined as an exact change in residue/group of residues/exon with known functional significance) (M); a LoF NS variant at the same codon which is deleted (M); LoF small deletions (not causing frame-shift) overlapping with the case variant (L); all regions/subdomain/domains with functional annotation for missense variants (L). For all regions/subdomain/domains with functional annotation for missense variants, equivalence can be shown with the smallest entity having a functional annotation (subdomain, if not domain, etc.). In the case of aa insertions (in-frame insertions), equivalence can be stablished by LoF variant with exact aa changes (H); LoF insertion at the same location, but with a different sequence (M); for an insertion of length 1 at position n, all curated LoF NS variants at positions (n+1 to n+1+1) (L);); all regions/subdomain/domains with functional annotation for missense variants (L). For all regions/subdomain/domains with functional annotation for missense variants, equivalence can be shown with the smallest entity having a functional annotation (subdomain, if not domain, etc.).

Equivalence can be stablished for DelIns Variants in the following manners. Frameshift or premature stops can be treated the same as point mutations causing premature stops. The codon at which the frameshift starts is used to apply the equivalence rules (H). For in-frame deletion or insertion of amino acids, equivalence can be established by an exact aa match (H). DelIns variants will follow the same equivalence rules as in-frame deletion followed by in-frame insertion rules. In case the equivalence can be made with either the deletion only or the insertion only, or if made with both, giving contradictory results, the variant can be labeled "Functional Significance Ambiguous".

For deletions, equivalence can be established as follows. In the case of an exact match including ESS variants which cause that exon to be skipped (H), equivalence can be shown to all LoF variants (except premature stop and frameshift variants) within the lost exon (M). In the case of an exact match including ESS variants which cause deleted exons to be skipped (H), if the 3' end of the gene is lost, equivalence can be shown to all LoF variants overlapping with the lost exons, otherwise all LoF variants (except premature stop and frameshift variants) within the lost exons (M).

GoF variants can include the non-synonymous (missense) variants, in-frame deletions, in-frame insertions, premature stops and frameshift variants, DelIns variants, Amplifications, and gene fusions.

For non-synonymous (missense) variants, equivalence can be shown if the variant has an exact match with a curated GoF variant (H); if it has an exact match with a curated GoF variant class (explicitly specified exons, domains NOT residues) (M); if it is at the same codon(s) as 2 or more curated GoF non-synonymous variants (M); or if it is at the same codon(s) as 1 or more curated GoF non-synonymous variant.

For In-frame deletions, equivalence can be shown if the variant has an exact match with a curated GoF variant (H);

if it has an exact match with a curated GoF variant class (explicitly specified exons and domains, not residues) (M); if it is a superset of a curated GoF inframe deletion variant (M); or if it is overlapping with a curated GoF inframe deletion or non-synonymous variant (L).

For in-frame insertions, equivalence can be shown by an exact match with a GoF variant (H); an exact match with a curated GoF variant class (explicitly specified exons and domains, not residues) (M); if the insertion occurs at the same location as a curated insertion variant but the inserted sequence is different (L); or for an insertion of length l at position n, all curated GoF non-synonymous variants at positions (n+1 to n+l+1) (L).

For premature stops and frameshift variants, equivalence can be shown by an exact match with a curated GoF truncation variant (H) or if it occurs in the same domain as a curated GoF truncation variant (L). In all other cases, premature stops and frameshifts cannot be considered important for GoF variants and should be discarded.

DelIns variants can include frameshift or premature stops or in-frame deletion or insertion of amino acids. For frameshift and premature stop variants, equivalence can be shown in the same way as premature stops and frameshift variants as just described. The codon at which the frameshift starts is considered for the equivalence rules. In the case of in-frame deletion or insertion of amino acids, equivalence can be shown by an exact amino acid match (H). DelIns variants will follow the same equivalence rules as in-frame deletion followed by in-frame insertion rules. In case the equivalence can be made with both the deletion and insertion and it gives contradictory results, the variant can be labeled "Functional Significance Ambiguous".

For Amplifications, only full gene amplifications are considered.

For gene fusions, equivalence can be established where break points overlap with curated variants.

Fast Implementation Using CPU/GPU Combinations: We have engineered the above steps to run on machines with attached GPU cards. Different stages of the algorithm have different memory/compute needs. We move structured compute intensive tasks to the GPU while retaining memory intensive or unstructured compute tasks to the CPU. Using the appropriate combination and several engineering steps which communicate efficiently between the CPU and the GPU, our core alignment algorithm now aligns at the rate of 2.5 MBs/s/thread using a Kepler K10 GPU card, 5× faster that commonly used algorithms, and at least 20% faster than the fastest known GPU algorithms.

The following key uses and components of the above methods and apparatuses can be noted: (1) R&D process for designing and validating new custom multi-gene panels: Although the process as a whole may not be patentable, we can point to several novel aspects of the workflow that we innovated. (2) Production test delivery process and pipeline, e.g., see herein for an example using Somatic Cancer panels ("Strandadvantage"): described above. (3) Production test delivery process and pipeline for other, including Germline, panels (e.g., Cancer and inherited disease). This may be very similar to the process described in this document. Specific customizations for germline panels compared to somatic panels can be noted. (4) Build, Operate and Transfer (BOT) or Build, Operate and Jointly Own (BOJO) process for SmartLab delivery to hospital systems, cancer care centers or other healthcare organizations: This is described in detail below ("Strand SmartLab"). (5) Biomarkers and companion Dx: The clinical exome panel or the whole exome sequencing approach followed by the pipeline for NGS data analysis and interpretation described herein may help discover novel biomarkers to aide in new drug clinical trials process. Once the Biomarkers are established for a particular drug to stratify patients into groups such as responders, non-responders, responders with adverse side effects, and non-responders with adverse side effects, companion diagnostic panel(s) may then be designed using the process described in "Panel Design" subsection described above.

Part III: Overall Description

The overall method of estimating a patient's response to a plurality of cancer drugs comprises steps to design the panel to be used for testing a patient sample in order to measure the patient-specific marker values, determine equivalence levels with the reference markers and output the estimated drug response using the marker processing apparatus.

Figure 27:
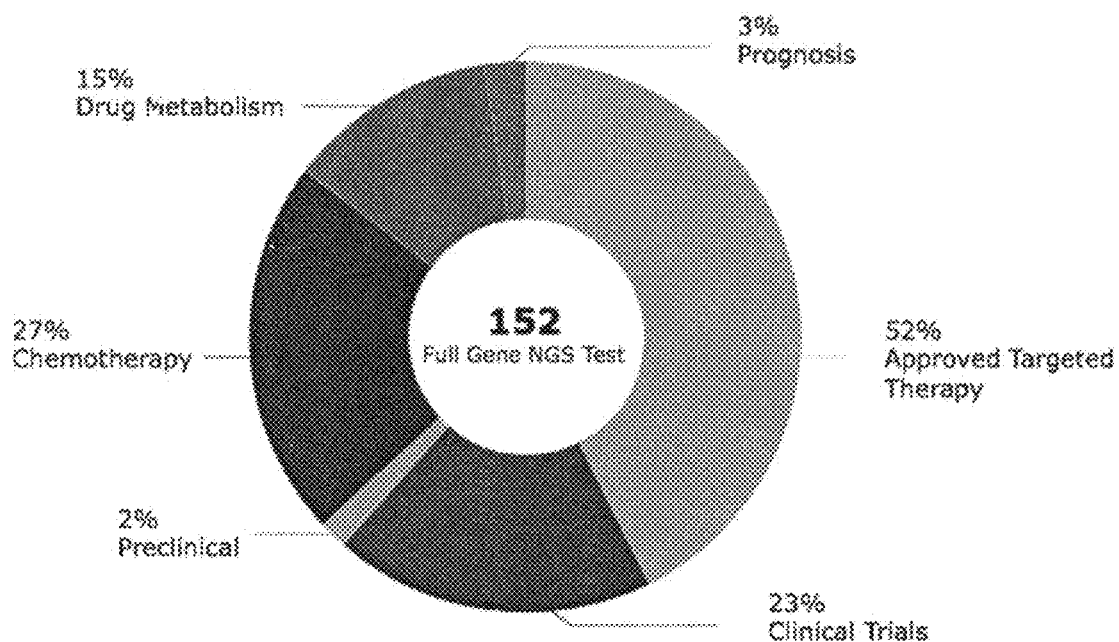
FIG. 27 is a graph illustrating the break-up of the 152 genes on the exemplary NGS panel.

The methods for NGS panel design are faced with an inherent tradeoff between covering a large number of markers that can impact drug response on one hand and managing the cost of running the assay and interpreting the measured patient-specific marker values. The NGS panel may be designed to include regions from the set of genes that modulate the response to chemotherapies and targeted therapies, genes that are commonly targeted in clinical trials on cancer drugs, or genes that modulate the metabolism of some of these drugs, or impact prognosis and disease progression. A literature survey may be used to determine the set of genes from each category. In one exemplary embodiment of the invention, the NGS panel was designed using 152-genes identified thus. A break-up of these genes is as shown in FIG. 27.

Sequencing the entire genic content of these genes would result in a very large amount of sequencing and increase the cost of the test. Hence the choice of regions to sequence from these genes is equally critical. The following techniques may be employed to choose the regions to sequence from these genes: All important reference markers involved in solid tumors need to be covered by the target regions of the panel. In one exemplary embodiment, important somatic reference markers may be derived from public databases such as the COSMIC database. Coding regions of genes annotated in public databases such as Refseq, UCSC and Ensembl may be combined for each gene, and the DNA coordinates for all known transcripts merged to construct a super transcript DNA coordinate for each gene. All known COSMIC mutations (SNV, INDELs up to 35 bp) that overlap with the super transcript coordinates may then be considered as targets. In addition to somatic markers, coding germline markers may be included for the genes involved in drug metabolism. These may be derived from public databases such as ClinVar and HGMD. Targets may be designed to overlap with these specific variants only and need not cover the entire gene.

For genes whose copy number status is important, the design may include target regions spread from across the gene to maximize detection accuracy of whole gene copy number alteration events. To do this, probes may be equally interspaced along the entire length of the gene, covering all exons, wherever possible. If the distance between two adjacent exons is too large, or the number of exons in the gene is less, intronic probes may be introduced to ensure adequate representation.

For genes involved in translocations, the most common breakpoints may be identified from a public database such as COSMIC based on the frequency of occurrence and these breakpoint regions densely covered with probes to enable high-resolution breakpoint detection.

For tumor suppressor genes, a Loss of Function (LOF) may be caused by novel markers. Therefore, all exons of tumor suppressor genes may be considered as targets. Whereas for oncogenes, interpretation is usually limited to the well-characterized gain-of-function (GOF) markers only and therefore only exons containing the known GOF variants may be considered as targets.

To optimize the panel size and number of probes, overlapping and adjacent targets within a certain minimum distance may be merged.

Probe design may be set to balance specificity and coverage and set to 1× tiling.

A few examples of these design techniques are shown below purely for the purposes of illustration.

Figure 28:
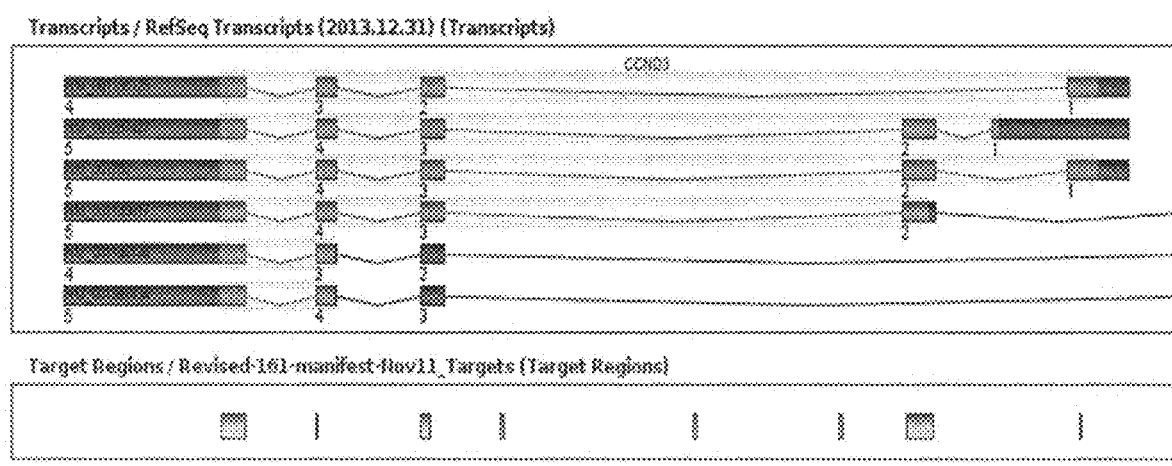
FIG. 28 illustrates intronic regions added to the panel design for better copy number detection.

In one embodiment of the panel design, additional intronic targets were added to ensure accurate copy number analysis of the CCND3 gene as shown in FIG. 28.

Figure 29:
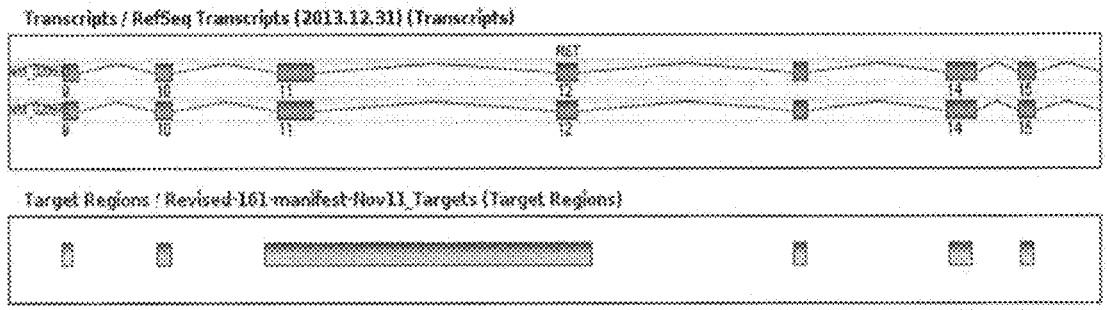
FIG. 29 illustrates an entire intronic region added for sensitive detection of marker breakpoints.

In another exemplary embodiment of the panel design, the entire intron of RET was targeted to ensure sensitive detection of breakpoints falling in this intron, as shown in FIG. 29.

Figure 30:
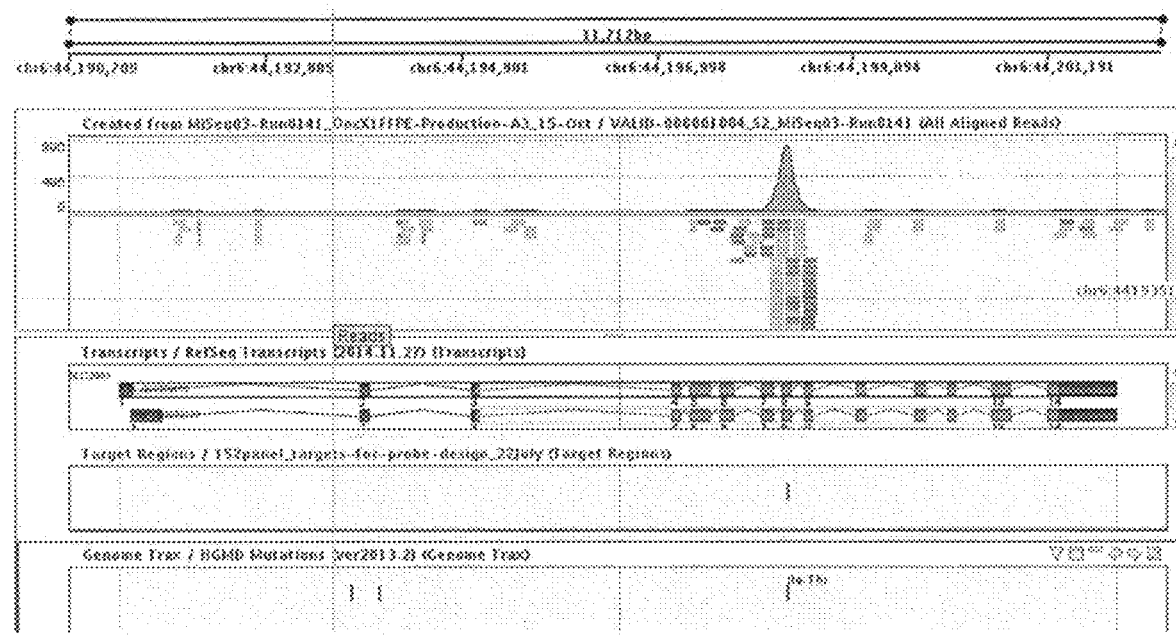
FIG. 30 illustrates target regions overlapping individual metabolism related marker.

In yet another exemplary embodiment of panel design, a single target region was assigned to a gene (SLC29A1 in this case) to cover a marker with known implications to metabolism of certain cancer drugs. As illustrated in FIG. 30, the coverage track at the top shows that mainly reads originating from the target region have been sequenced.

Figure 31:
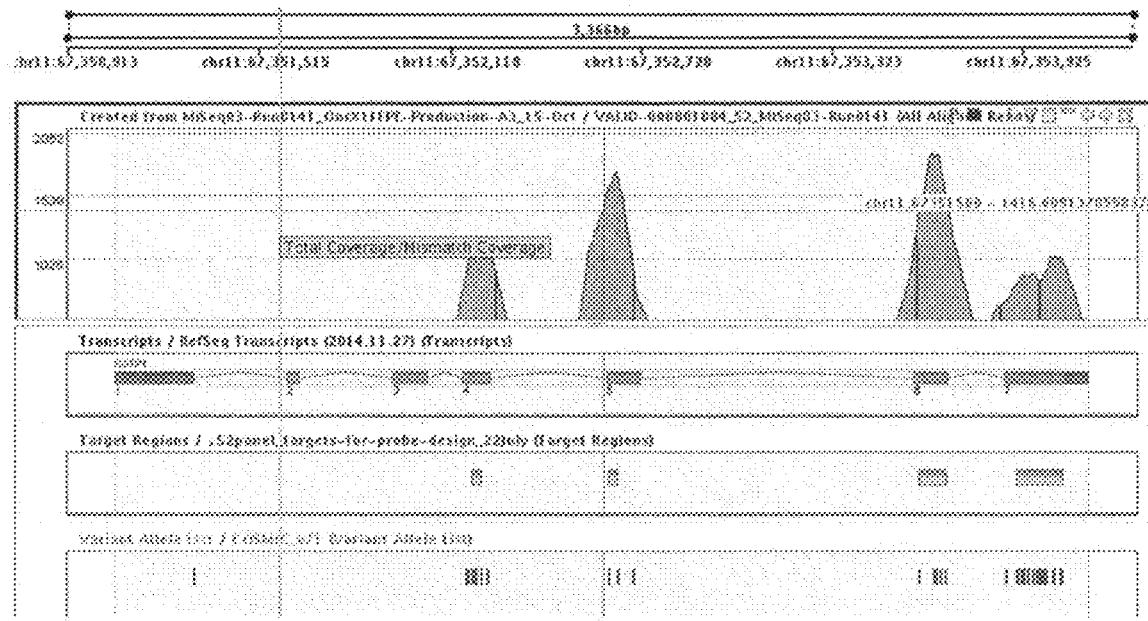
FIG. 31 shows target regions for oncogenes designed to overlap known markers from the COSMIC database.

In another example, FIG. 31 shows how targets were designed for the GSTP1 oncogene. Only exons 4-7 where COSMIC variants have been observed with high frequency were chosen as targets. The coverage track on a illustrative sample shows that the desired goal has been achieved.

The sample testing protocol comprises the steps performed in the laboratory to transform the patient sample to the raw data for the measurement of the patient-specific marker values. The sample drawn from the patient may include in one form fresh tissue extracted from the area of the cancer via a biopsy, and in another form, sample that has been stored in the form of Formalin-fixed, paraffin-embedded (FFPE) tissue. Fresh tissue typically obtained after a surgery provides tumor DNA of very high quality. Fresh tissue needs to be stored in RNAlater from Thermo Fischer, Inc. at room temperature or flash frozen in liquid nitrogen in order to be stored and transported for testing. FFPE tissues are conducive to long term storage at room temperature but suffer from poor quality due to improper fixing conditions and storage. A portion of the sample is utilized for performing the IHC tests as needed for determining the response to the Standard of Care drugs for the specific tissue. Another portion of the sample is utilized in performing NGS tests using the NGS panel described earlier.

One exemplary embodiment of the NGS sample testing protocol is optimized using SureSelect XT2 reagent kits from Agilent Technologies to process samples with greater than 20% tumor content and with at least 200 ng of input DNA. The tumor content is measured using a routine Hematoxylin and eosin stain (H&E stain) in a pathology lab before proceeding with further sample testing. After extraction of the tumor DNA from the patient sample, the amount of tumor DNA is quantified using the Qubit dsDNA HS Assay Kit from Thermo Fischer Scientific, USA.

Figure 32:
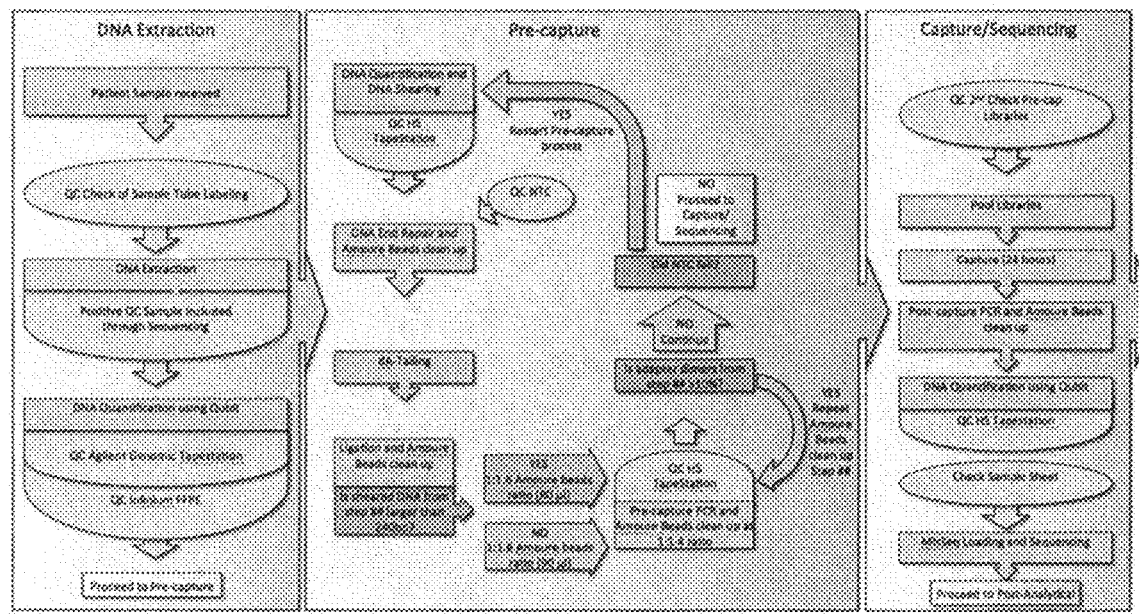
FIG. 32 illustrates a protocol for the NGS panel using SureSelect XT2 reagent kit.

This exemplary embodiment is illustrated in FIG. 32, and the key steps are outlined further below:

1. DNA Extraction:
   a. Sample FFPE DNA is extracted using a standard FFPE DNA extraction kit such as Qiagen All prep FFPE extraction kit in one embodiment, or QiaAMP FFPE DNA extraction kit in another embodiment. Since FFPE DNA is highly fragmented and of inferior quality compared to fresh tissue, it is assessed using a real time PCR assay such as Infinium HD FFPE QC Assay in one embodiment, or KAPA hgDNA Quantification and QC Kit in another exemplary embodiment.
2. Pre-capture:
   a. 200 ng of quantified d.s. DNA is sheared using a Covaris instrument for 260-280 seconds to ensure >70% of the original DNA lies between 150 and 200 bp peak. In other embodiments of the assay, the DNA may be sheared using Bioraptor.
   b. All standard steps in the preparation of sample library are followed as per Agilent SureSelect XT2 guidelines except that no size selection is performed post shearing. Post adaptor ligation, clean-up to remove unbound adaptors is carried out using DNA to Ampure ratio of 1:1.6. 13 cycles of PCR are performed for FFPE DNA to get adequate DNA library from individual samples.
   c. Post PCR, adaptor ligated pre-cap libraries are cleaned up using pre-cap libraries to Ampure beads ratio of 1:1.4. The pre-capture library for each sample is individually assessed using a Tape Station or BioAnalyser instrument from Agilent technologies. If greater than 10% of the total library is made up of 120 bp fragments which could arise from adaptor dimers as well, a mild size selection using 1.4:1 ampure beads to DNA is used to remove these smaller fragments.
3. Capture and Sequencing:
   a. 6 to 8 individual libraries are quantified and pooled in equal concentration to make up a total amount of 1500 ng DNA and hybridized to biotin labelled RNA probes, for 24 hours.
   b. The hybridization protocol is followed as per SS-XT2 standard protocol. Following cleanup, 12 (FFPE) PCR cycles are performed to get the final pooled library.
   c. The final library is cleaned using 1.5:1 ampure beads to DNA.
   d. As previously described, the library is checked on Tape station or Bioanalyzer and if the 120 bp fragment is greater than 10% of the pooled library, it is cleaned up again using Ampure beads.
   e. 12.5 pM library is loaded on a V3 sequencing kit (2×151 PE sequencing) on a MiSeq sequencer from Illumina, Inc. to obtain 9-10 GB total output, ~1200 cluster density and >90% Q30 reads. This allows for ~1-1.2 GB (more than five million reads) sequencing output per sample. In other embodiments of the assay, the sequencing may be performed on a NextSeq or a HiSeq sequencer from Illumina, Inc. to generate 1.5-3 GB data per sample.

As mentioned already, FFPE tissues suffer from poor availability of tumor DNA. Accordingly, another exemplary embodiment of the NGS sample testing protocol is optimized using NEBNext Ultra II from New England Biolabs to process patient samples with even 50 ng of input DNA. In this form, 3-4 samples are pooled into a single capture as opposed to 6-8 samples in the SS-XT2 protocol. Also, sequencing of the pooled and captured libraries are performed using a Miseq, Nextseq or Hiseq such that each samples received 3-6 GB data per sample. The steps of this protocol are outlined below:

1. DNA is extracted using a standard FFPE DNA extraction kits as before.
2. Since FFPE DNA is highly fragmented and of inferior quality compared to fresh tissue, it is assessed using a real time PCR assay as above 3. 50-100 ng of qubit (Life technologies) quantified d.s. DNA is sheared using a Covaris for 350-500 seconds. A mild size selection is performed using DNA to AMpure ration of 1:1.7 to remove the smaller fragments that adversely affect the size of adaptor ligated pre-cap library.
4. All subsequent standard steps in the preparation of library are followed as per NEB NEXT ULTRA-II guidelines except that no size selection is performed post-adaptor ligation. Optimized adaptor concentration for library generation is $6*10^4$ pM (lower than recommended protocol). Adaptor ligation efficiency is enhanced by the use of 3% PEG in ligation reaction for FFPE samples.
5. PCR for 10-11 cycles are performed for fresh tissue/cell line and control FFPE DNA for generating adequate pre-cap libraries. For clinical FFPE DNA 13-14 cycles PCR is performed to get adequate DNA library from individual samples.
6. Post PCR, adaptor ligated pre-cap libraries are cleaned-up using pre-cap libraries to Ampure beads ratio of 1:1.8. The pre-capture library for each sample is individually assessed using a tape station (Agilent technologies). If greater than 10% of the total library is made up of 120 bp fragments which could arise from adaptor dimers then pre-cap libraries to Ampure beads ratio of 1:1.8 is used to remove these smaller fragments. The library is eluted in 30 µl of buffer.
7. 1-5 individual libraries are quantified and pooled in equal concentration to make up a total amount of 1500 ng DNA and hybridized to biotin labelled RNA probes, for 24 hours
8. The hybridization protocol is followed as per SS-XT2 standard protocol. The captured DNA targets from the pooled pre-caps is amplified using 11 cycles of PCR. The pooled final library is cleaned using 1.8:1 ampure beads to DNA*. Optimized elution volume for library: 50 ul post ligation and final.
9. As previously described, the library is checked on Tape station and if the 120 bp fragment is greater than 10% of the pooled library, it is cleaned up again using Ampure beads. Optimized sequencing plexing: pooled capture is 1-4 5 libraries.
10. 13 pM library is loaded on a V3 sequencing kit (2×151 PE sequencing) to obtain 9-10 GB total output, ~1200 cluster density and >90% Q30 reads. This allows for ~3 GB (more than 30 million reads) sequencing output per sample.

The IHC sample testing protocol follows a process of detecting proteins in the patient sample by using standard antibodies designed for each protein. In one exemplary embodiment, this may outsourced to an external registered pathology lab in order to perform the IHC testing.

The quantification of the level of protein expression in each stain, whether it is nuclear, cytoplasmic or membranous, to generate the patient-specific marker value measurement for the IHC markers may consider one or more of stain features such as intensity of the stain and the percentage of reactive tumor cells. The criteria for a positive, negative or equivocal measurement for each IHC marker may be based on literature evidence for the marker and standarization over a set of control samples.

Figure 33:
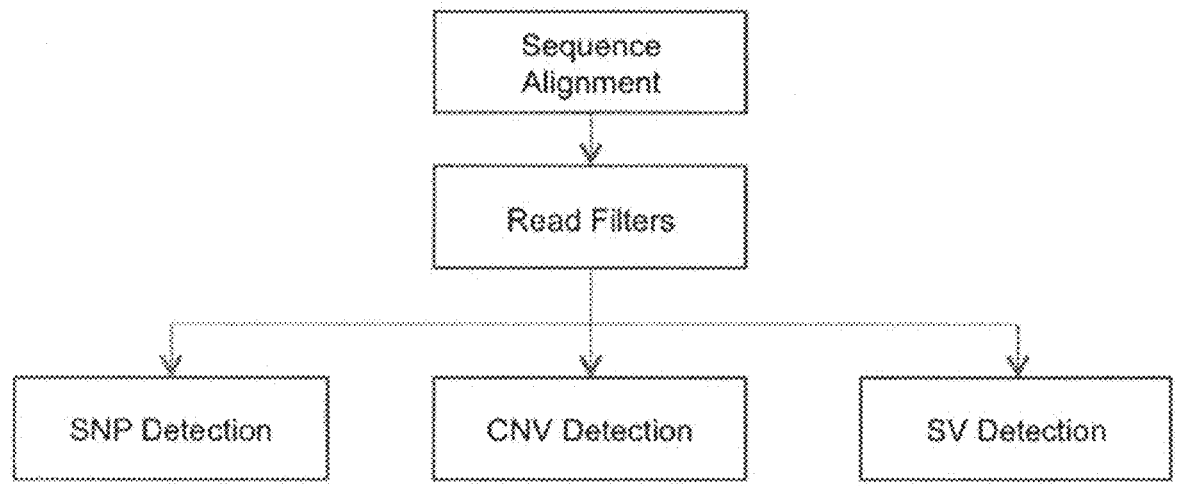
FIG. 33 illustrates steps in the patient-specific marker value generation pipeline.

The raw data generated from the lab for the NGS panel is in the form of sequence reads, 2×151 bp in length in one exemplary embodiment, and are transformed to patient-specific marker values using algorithms executed as part of a patient-specific marker value generation pipeline. The algorithms in the patient-specific marker value generation pipeline may include sequence alignment, Read filters, SNP detection, copy number calling, translocation detection, and Pipeline Quality Checks as shown in FIG. 33. Further, the details of each of the algorithms given therein including the parameters of the individual steps are for the purpose of illustration only.

In one exemplary embodiment, these algorithms are executed by a computer processor. In another embodiment, these algorithms are executed by a computer processor in tandem with a graphics processor resulting in overall speed improvements of up to 10×.

The 'Sequence Alignment' step maps the reads generated by the sequencer to the reference genome.

While doing this alignment, bases with poor quality (<Q10) at the 3' end of the read are clipped, and reads whose length is less than 25 bp (possibly because of the 3' clipping) are ignored. Also, reads are screened against a contaminant database before the alignment.

The reads preprocessed thus are then aligned using a two-step process: i) a fast exact-match lookup step using Burrows Wheeler Transform (BWT) to narrow the potential match locations, and ii) a dynamic programming (DP) step for an accurate final alignment.

In the first step, the short listing of the potential match locations is done based on the length of the maximal exact match (longest subsequence of the read having an exact match) at each of the locations.

In the second step the execution time of the DP can be reduced by doing a banded DP with a band size equal to the length of the longest indel to be detected by the aligner.

The parameters of the alignment procedure can be set such that the identified read matches have at most a specified % of mismatches and a specified % of gaps. In one of the embodiments, these numbers are 5% and 45% respectively. Also, reads that match the genome at more than a specified number of locations are ignored.

If a read pair doesn't get a pair of matches for the two reads such that the matches have the correct orientation and are within 6 standard deviations of the expected insert length from each other, then such read pairs are subjected to a rescue process. In this process, the algorithm takes each match for each of the reads, and scans a window of size (mean insert length+6 standard deviations) around this match, performing a dynamic programming procedure to locate matches within this window for the other read.

Reads that are still unaligned are subjected to a split-read procedure, where the read is split into two parts, each of which is independently aligned to the genome. This procedure helps in aligning reads that span breakpoints caused by large indels, copy number changes or structural variants (SVs). The aligner determines the split based on a read prefix or suffix matching substantially, as discovered in the dynamic programming procedure above. The breakpoints obtained from the alignments of the two segments of the read are refined further by doing a gapped DP between the original read and a padded concatenation of the reference sequences to which each of the two segments aligned. The upstream reference sequence is padded by appending bases, and the downstream reference sequence is padded by prepending bases. The result of this DP is a new alignment without 'noise', i.e., mismatches and other events near the split boundary. The breakpoints discovered in this manner are further used to improve the alignments of other reads near the breakpoint, and also to rescue some unaligned reads. This comprehensive approach allows for high-resolution detection of large indels and SVs.

In one of the embodiments, an additional pre-processing is done that helps in better alignment of reads spanning small near-tandem duplications. The pre-processing step detects if any stretch of the sequence is duplicated within the read, and checks whether the alignment for the read can be improved after the duplicated stretch is removed. In such cases, the duplicated stretch is replaced in the match record as a putative insertion.

Since alignment algorithms map each read independently to the reference genome, it may result in some alignment artefacts. These misalignments can lead to false positive SNP calls. Local realignment of reads is done as a post-processing step in order to correct these artefacts. It essentially corrects alignments of reads containing insertions/deletions close to the end of the read based on alignments of other reads in the region. Local realignment consists of the following steps: i) Identify regions of reads to be realigned, ii) Generate candidate haplotypes in each identified region, iii) Infer most likely haplotypes, and iv) Realign reads to most likely haplotypes. In step (iii) the best non-reference haplotype is selected after evaluating all the candidate haplotypes by scoring them based on gapless alignments of the reads in the region to each of them. In one of the embodiments, the method allows for selecting two non-reference haplotypes instead of always including reference as one of the haplotypes.

Once the alignment is done, reads with average quality less than 20 are removed from further processing. Also, reads in which some of the bases are N are removed. The remaining reads are processed to remove duplicate reads. Reads are considered duplicate if they have the same sequence and same alignment, and their mates have the same start coordinate. Among such multiple reads all except one are removed. The eliminated duplicates typically represent PCR copies and not true independent template molecules needed for variant calling.

The next steps in the patient-specific marker value generation pipeline are directed towards measuring markers such as single nucleotide polymorphisms (SNPs), Insertions and Deletions (InDels), copy number variants (CNVs) and specific structural variants (SVs) such as translocations from the tests performed using the NGS panel.

Figure 34:
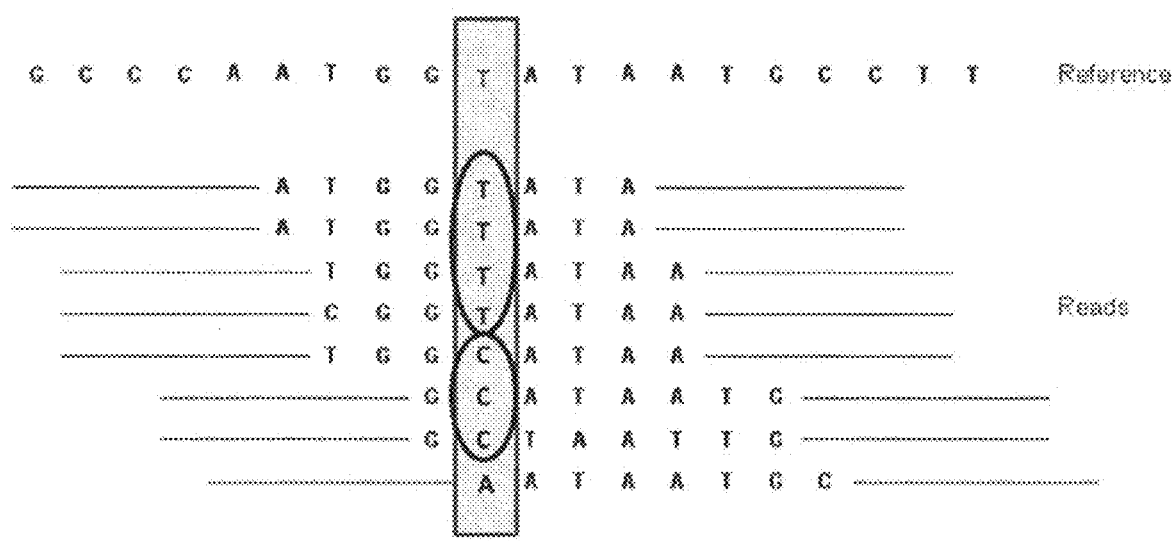
FIG. 34 illustrates a read distribution at a genomic location used by SNP detection algorithm.

SNP detection algorithms compare the nucleotides present on aligned reads against the reference, at each position. Based on the distribution of As, Ts, Gs, and Cs at that position, and the likelihood of error, the algorithm determines if a SNP exists in the patient sample at that location. This is depicted in FIG. 34.

One of the methods used to determine SNP calls is the Bayesian SNP calling algorithm. This algorithm considers the nucleotide or the base taken by each read covering the location, as well as its associated base quality and finds the consensus genotype. The consensus genotype is the one most likely to have caused the observed data and is computed using Bayes principle. This method works well for detecting germline variants but is not capable of calling somatic variants which typically manifest as a low frequency mutation due to normal cell contamination of the tumor sample and/or tumor heterogeneity.

In the present embodiment of the patient-specific marker value generation pipeline, the somatic variants are detected using an adaptation of the standard binomial SNP calling method to take the base qualities into account. The binomial SNP calling method, like the Bayesian approach, considers the base taken by each read covering the location, as well as its associated base quality, denoted collectively by D, to decide whether there is a variant at that location. But the binomial caller does this by computing the probability, P of observing a data D' with the same total number of bases and at least as many variant bases as D has, with the assumption that the location has the reference genotype, and that the variants are due to sequencing error only. Only the variant allele with the highest frequency of occurrence is considered for the computation of the probability P and the other variant alleles are ignored. This probability is then converted into a score as Score=$-10 \log_{10}P$. If this score is greater than 50, then the location is reported as a variant location.

The standard binomial test for calling SNPs requires one overall error rate and cannot use the qualities of all the individual bases. One way to arrive at the overall error rate from the base qualities in D is to compute the error rate corresponding to the lowest base quality from D. But this may make the results very sensitive to any noisy outlier bases with very low quality which may lead to false negatives. In order to avoid this problem, we ignore all the bases with qualities less than a threshold Qt, and run the binomial test with the error rate corresponding to the lowest quality from the remaining bases. To make the test more robust, this process is repeated for multiple values of Qt and a variant is reported if it is called for any of the thresholds Qt. Typically Qt is varied from 20 to 30 and if a variant is called in any of these tests, the method reports the variant and the lowest Q at which the variant is called. In case different variants are called at the same locus in these multiple tests, only the one with the highest score is currently reported. However it is possible to infer tumor heterogeneity from these multiple variants if they happen to have scores above a certain threshold.

For each of the variants, the method reports some additional attributes such as supporting reads (SR) %, strand bias, PV4 biases, presence in dbSNP, overlap with homopolymer regions, etc. The reported variant calls are filtered based on some of these attributes to eliminate potential false positives. The patient-specific marker value generation pipeline described here includes a framework to define filters based on one or more of the additional attributes reported, and include them in the variant calling process. As an example of such filters, one of the embodiments of the pipeline filters out indels called with a supporting read proportion (SR %) less than 10% of the total reads covering a base if they lie in a homopolymer region of length 6 or more bases.

Somatic copy number variants are typically detected using a depth-of-coverage (DOC) approach which computes for each genomic region, the ratio of the number of reads in the tumor to that in the matched normal sample. Since sequencing two biological samples—normal and tumor—for each patient is expensive, the patient-specific marker value generation pipeline described here uses a pre-computed normal profile derived from a collection of normal samples.

The processing involves computing read counts in the tumor sample in every region of the manifest. Read counts are normalized for each region by taking into account the region coverage, total sample read count, region size and panel size. Normalized read counts are further corrected for GC bias and are then compared against the profile created from normal samples. The profile consists of means and standard deviations of the normalized coverages of a set of normal samples for each of the regions in the manifest. The profile is created in an iterative process in which outlier samples are eliminated at each step till there are no more outlier samples. At every step, mean and standard deviation are computed from the remaining samples, and a Z-score for each region is computed for every sample that indicates deviation from the mean as a multiple of the standard deviation. A region is marked as deviant for a given sample, if it exceeds a specified Z-score cut-off. A sample with more than a specified number of deviant regions is considered as an outlier sample and is eliminated for the next iteration.

By using a profile created thus, the copy number for each target region is computed as twice the ratio of the corrected normalized read count of the sample to that of the profile.

Once the copy numbers for the individual target regions are computed, the copy number for the entire gene is computed as the average of the copy numbers accorded to the constituent target regions of the gene, weighted by region size. Thus longer target regions influence the final copy number more than shorter ones. An amplification is called if the final copy number for the gene exceeds a qualifying cut-off value. To restrict the number of false positives, an additional check requires the number of target regions supporting the amplification call to exceed a sufficiency threshold value as well. Deletion calls follow a similar protocol.

In order to help visually evaluate the detected copy number variants at various levels like target regions, genes, etc., the patient-specific marker value generation pipeline includes a visualization of the results which shows the CNV values for each target region across all the chromosomes in a single view. In one embodiment of this visualization, a web browser shows the CNV values in two view modes: a single sample view and a multi-sample view.

Figure 35:
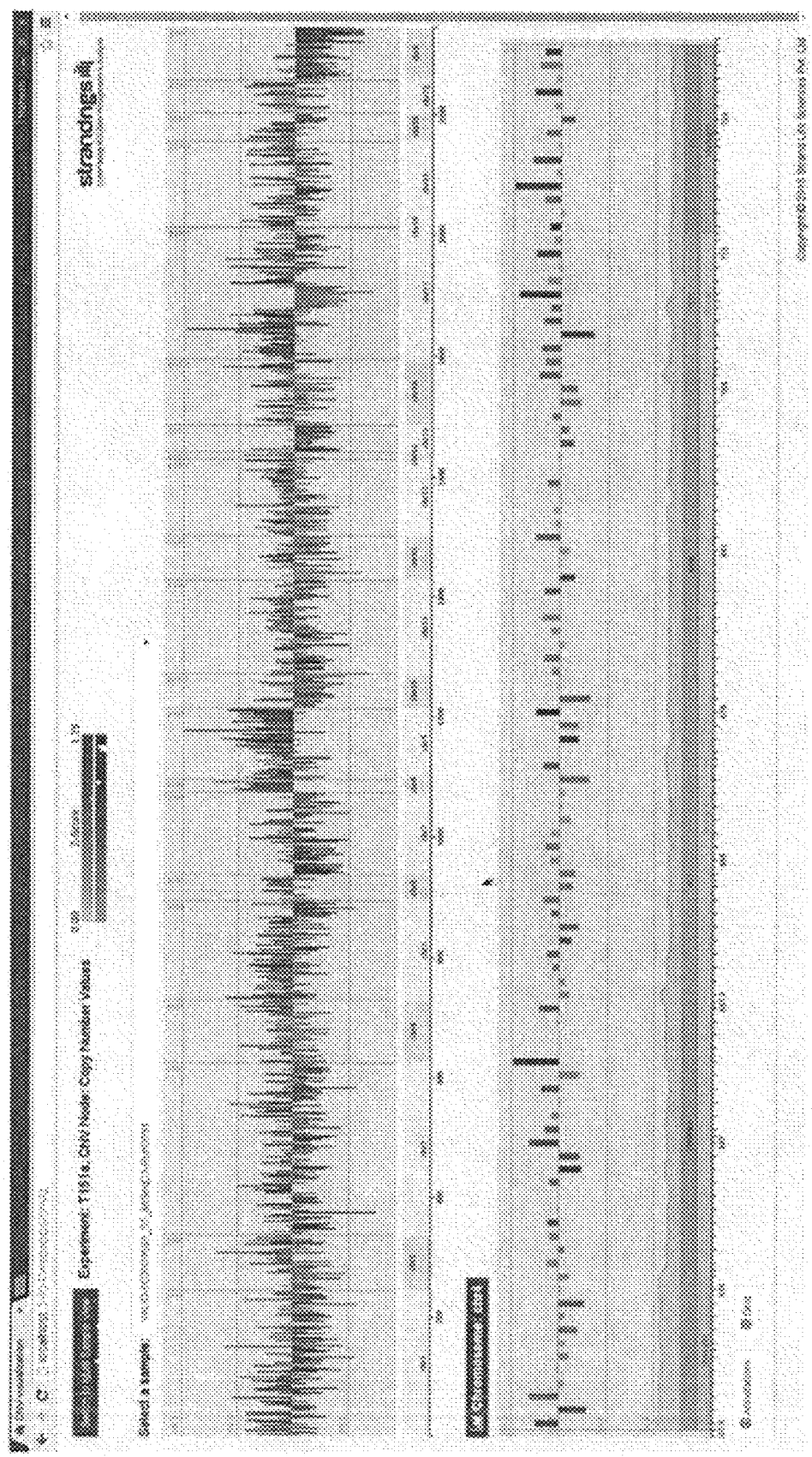
FIG. 35 illustrates copy number visualization focused on the genes of the panel.

The Single Sample View (see the figure below) shows a bar chart with the CNV values for each target region across the chromosomes. The intensity of the bar denotes the Z-score of that region i.e., darker the color, higher is the Z-score. The length of the chromosomes is based on the number of target regions present and not on the actual chromosome size. The bars in each chromosome are colored differently to enable easier identification of the chromosomal boundaries. The chromosomes are also colored by the p and the q arms. The X-axis shows the different target regions, and the Y-axis indicates the corresponding CNV values. Clicking on each chromosome also launches a zoomed-in view of that region right below the main chromosome view. This highlighted view allows the user to visualize the targets per chromosome in great detail along with other annotation information such as GC %, overlapping genes and the band information. The zoomed in view also has tabs that allow users to turn off annotation and data information. Another option is to enable or disable the grids shown in the plot of FIG. 35. A sample chooser at the top allows the user to switch between various samples.

Doing a mouseover on the main view, gives the CNV, Z-score and the chromosome information for the selected target in a tooltip. A mouseover on the zoomed in view gives all this information in a tooltip along with additional information about the target region such as start, end, length, GC %, gene, and band information. Clicking on the tooltip in the zoomed-in view launches this information in a window from where the information can be saved.

The patient-specific marker value generation pipeline described here includes a method for SV detection that detects translocations in the patient sample. The SV detection algorithm helps discover all SVs (including translocations) from aberrant paired-end reads and the split reads generated by the aligner. Split reads are the reads that come from regions that span the breakpoints corresponding to the SVs such as insertions, deletions, translocations, etc. and align in a split manner to non-adjacent parts of the genome.

The basic approach in the SV detection is to first classify the split reads into different types based on the relative position and orientation of the split-segments of the read as shown in FIG. 36.

The split reads are then clustered based on their type and location, and the possible SVs which could have resulted in these clusters are deduced. Detection of SVs using split-aligned reads identifies the breakpoints with 1-bp resolution, provided there is sufficient coverage at the breakpoints.

In the cancer context, the discovery of SVs can be difficult because only a small fraction of cells that were sequenced may harbor the SV. In such cases we can consider a list of well-known translocations and identify reads that support the translocation event. The Elastic Genome Browser™ in Strand NGS can then show a genome browser view which simulates the translocation and aids in visual verification.

In another embodiment, the patient-specific marker value generation pipeline is implemented on a computer system that has graphics processing unit (GPU) in addition to the standard central processing unit (CPU). Due to the very high memory bandwidth and a throughput orders of magnitude greater than that of a single CPU core, the most computationally intensive steps in the pipeline are executed on the GPU whereas those that are more memory intensive are executed in parallel on the CPU. Specifically, the alignment and SNP calling utilize the combination of CPU and GPU for a faster execution whereas CNV detection and SV detection are executed solely on the CPU.

The aligner in the GPU embodiment called 'GPUSeq Aligner' is a multithreaded sequence alignment scheme that works optimally on high-memory machines with multiple cores. Recall that FIG. 23 shows the schematic describing the distribution of the load between the CPU and the GPU. It also shows how the various threads in the CPU coordinate in the overall execution. The compute-intensive part of the alignment process which is the execution of a large number of dynamic programming steps is done on the GPU whereas the other tasks such as reading the raw reads, the BWT search, and the writing of the aligned reads are handled by the CPU.

The detailed SNP detection workflow was presented in FIG. 24, described above. Here the local realignment, and the generation of pileups are executed on the CPU whereas the actual SNP calling related calculations including the computation of PV4 biases at each of the loci are done on the GPU.

Whereas the parallelism in the aligner is read-based, the SNP detection uses a hybrid of various kinds of parallelism. Underlying this hybrid approach is the concept of bucket-wise chromosomal enumeration of reads: each chromosome during the alignment phase is subdivided into a predetermined number of buckets. A chromosomal bucket consists of a number of reads that map to a range of genomic locations.

The parallelism is achieved in the various steps as follows:

Local realignment: Parallelism in local realignment is region-based, and occurs in two phases. In the first phase, regions from the span of buckets in memory are identified. In the second phase, a set of threads operates in parallel on these regions, identifying and realigning reads within them.

SNP calling: SNP calling is parallelised on the basis of coverage. First, the coverages at all locations corresponding the set of buckets in memory are computed. The sum of coverages S provides a rough estimate of the amount of computation involved. Each of the m threads is then assigned a range of contiguous locations such that the sum of coverages in the range equals S/m. Variants are then called by each thread on the assigned range of locations.

Figure 37:
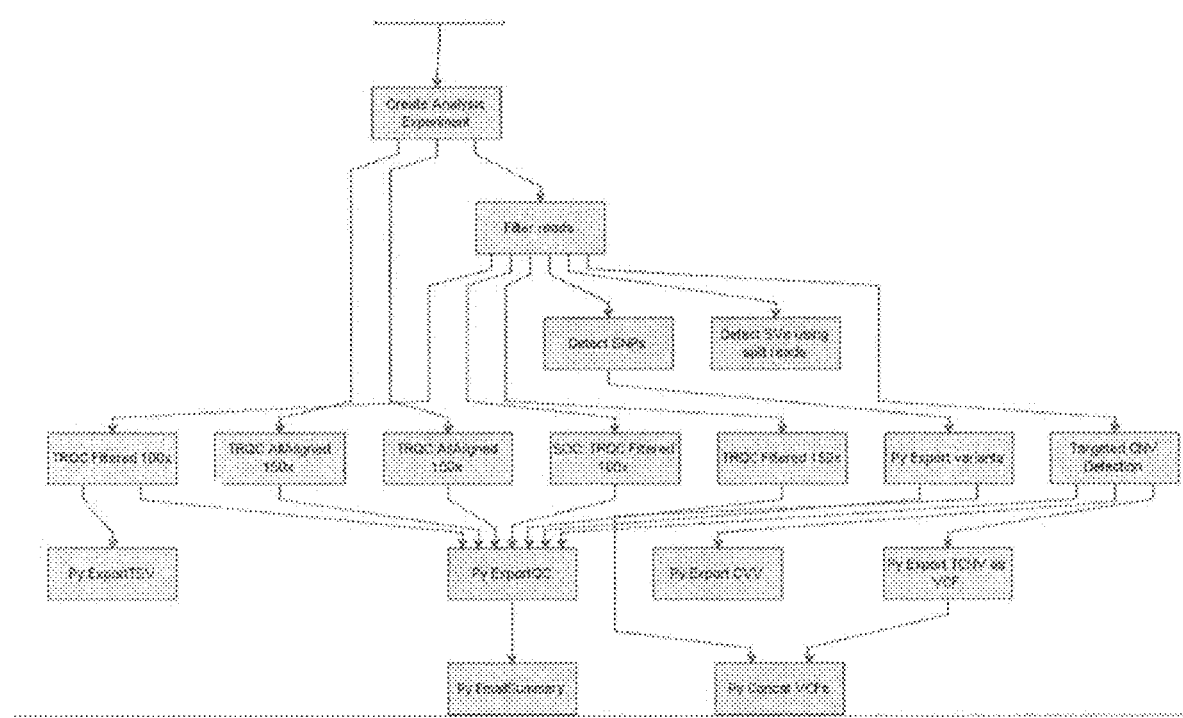
FIG. 37 illustrates post alignment steps, including quality control steps as discussed herein.

The last step in the patient-specific marker value generation pipeline is a QC step in which QC information is compiled from the data and results generated in earlier stages of the pipeline. A portion of the post-alignment section of the pipeline is shown in FIG. 37 for illustrative purposes.

The collected QC information is used for three purposes: trending analysis: to ensure the assay is performing at the desired level and that the variants present in the control sample are being detected appropriately; sample correctness: to ensure that the sample has been handled correctly during the wet-lab processing and that the sample meta-data noted in the test request form matches with the meta-data that can be computed from the data; and sample result qualification: to assess which subset of results generated by the pipeline are reliable and can be used confidently for interpretation.

The 152-gene NGS test is a multiplexed assay designed to sequence a batch of 6 (or 8) samples together. The samples are combined into a single library using a molecule-based-pooling strategy (described elsewhere) that was conceived to ensure parity in the number of reads generated per sample. The number of reads generated per sample in the batch is monitored to ensure that parity amongst the samples is indeed as expected. The median and standard-deviation in the number of reads, the ratio of the best and worst performing samples are some measures that are used as indicators of this parity.

The fraction of bases with quality above 30 (on the Phred scale), the fraction of reads that were aligned successfully to the genome, the fraction of reads that align to the target regions, and the number of duplicates in the data are all compared against established ranges to ensure that the hybridization, PCR, and other steps of the protocol were well-behaved.

The 152-test is a multi-day protocol. Since a batch of samples are processed together extra bioinformatics checks are carried out to ensure that sample mis-labeling and sample contamination (by non-human DNA) or by other samples are detected easily. Some of the QC checks that are designed for these purposes are described below.

Males have one copy each of chromosome X and Y, while females have two copies of chromosome X. Thus, the ratio of the number of reads mapping to the two chromosomes will be quite different for the two sexes. For each panel, the expected ratios are first established by sequencing a large number of samples of either sex.

Then, for each sample the ratio is computed and the pipeline checks if the ratio matches one of the two expected ratios and, if so, whether the computed sex matches the sex associated with the sample. For samples whose ratio does not match either of the two expected ratios, a further analysis is carried out to check if it matches a XXY or XYY genotype or if the cause is cross-sample contamination.

A mutation at a particular loci is detected via NGS data by analyzing all the reads that overlap to the loci. In the case of heterozygous variants approximately half the reads will harbor the variant allele while the remaining reads will have the wild-type allele. The % of reads that harbor the variant allele is called the supporting read % (SR %) of the detected variant. The SR % is expected to be ~50% for heterozygous variants and ~100% for homozygous variants when the total number of reads is sufficiently high. However because of multiple factors such as low coverage, unequal amplification during the wet-lab assay, biases during alignment, presence of pseudogenes (or gene families) the SR % can vary from the expected number.

Figure 38:
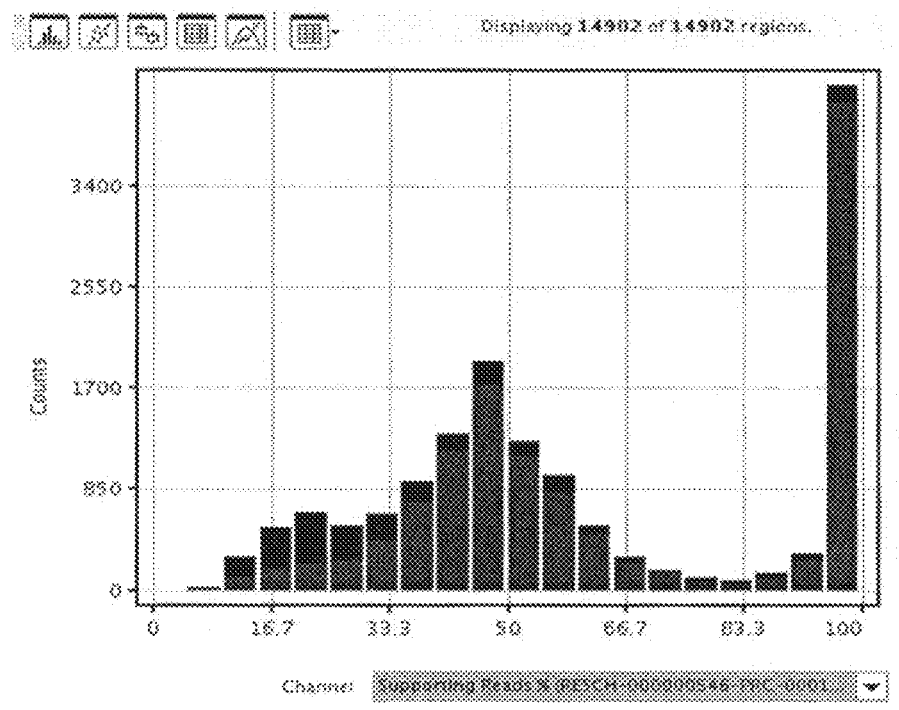
FIG. 38 shows a normal distribution of supporting reads percentage for a sample.

Shown in FIG. 38 is the SR % of all variants detected during a typical run. The variants are colored by their presence in dbSNP—red indicates the variant is present in precisely the detected manner in dbSNP, brown indicates there is some dbSNP variant overlapping this loci, and blue indicates the variant is not present in dbSNP.

Figure 39:
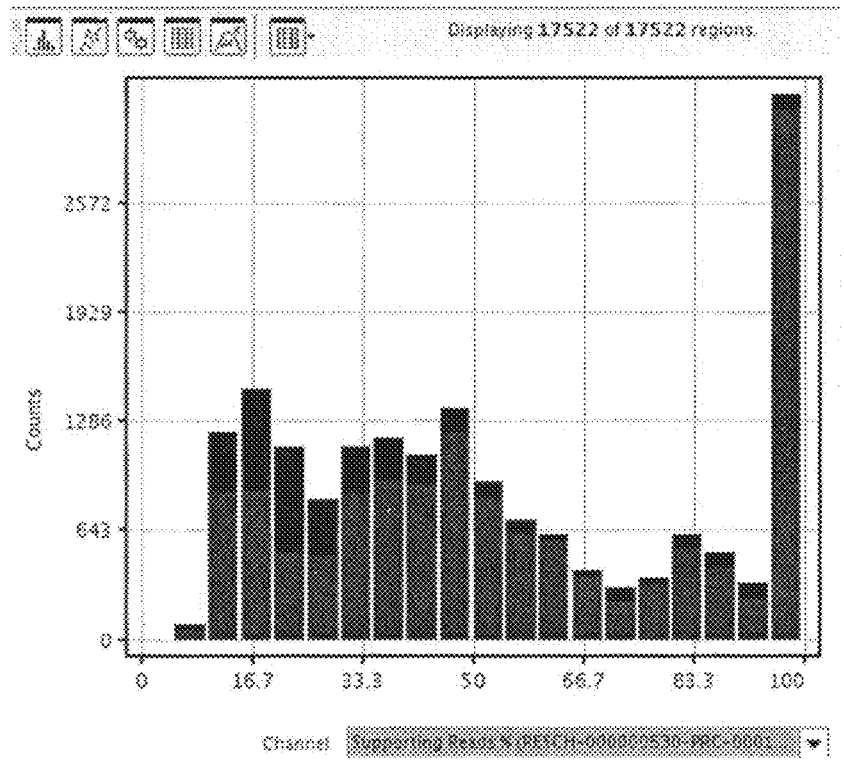
FIG. 39 illustrates a distribution of supporting reads percentage for a contaminated sample.

When the analysis is restricted to single base substitutions present in dbSNP (roughly corresponding the variants colored in FIG. 38), the distribution is quite symmetric and the shape of the distribution can be captured by a vector $S=[s\_0, s\_1, s\_2, \ldots, s\_9]$ where $s\_i$ indicates the fraction of detected dbSNP variants with SR in the range $[i*10, (i+1)*10]$. For instance, In the distribution shown above, $s\_9$, $s\_4$, and $s\_5$ would be the larger elements in the S vector. The mean and standard deviation for the S-vector may be derived after analyzing a sufficient number of samples. See, e.g., FIG. 39.

For the patient sample then, the S vector is computed and compared against the pre-computed mean S-vector. If the two vectors differ substantially at multiple elements of the vector then the most plausible explanation is that the sample has been contaminated with another sample. This QC check is automatically carried out and a sample is flagged if such a deviation is observed. The following picture shows the expected output in a test run to simulate sample contamination.

Another method of detected the cross-sample contamination is to check if the number of detected variants is significantly larger than the number of variants expected per sample.

It is possible that the same sample is mis-labeled and run twice in a batch. To detect these errors, the SNPs detected in each sample are compared against the SNPs detected in all the other samples in the batch. If the similarity between two samples is much higher than expected then the samples are flagged and manually inspected.

Sequencing FFPE samples is complicated because incorrect fixation, age of the sample, amount of cross-linking, low yields can all affect the performance of the assay. Described below are QC metrics that are used to determine how SNP and CNV calls should be interpreted.

The SNP calls are generally made at a cutoff of 2% SR since many variants detected below this threshold are sequencing artifacts. However, in compromised FFPE samples, many C>T false positives can occur at low SR % levels. To assess if this is indeed the case, the software computes two sets of numbers: (a) the total number of variants detected at >2% SR and the % of non-dbSNP variants, the % C>T/G>A variants in this set (b) the total number of variants detected at >5% SR and the % of non-dbSNP variants, the % C>T/G>A variants in this set.

In well-behaved samples the numbers in the two sets are roughly the same since there are very few variants detected in the 2-5 SR % range. But in compromised samples there are a substantial number of artefactual variants in this range and the two sets of numbers are therefore different.

In such samples if the latter set of numbers nonetheless resemble the expected metrics, the sample is flagged to indicate that high frequency mutations are reliable but that variants with SR close to 5% should be treated with extra caution during interpretation. If, however, the latter set of numbers are still higher that the expected metrics, the sample is rejected and not carried forward.

Figure 40:
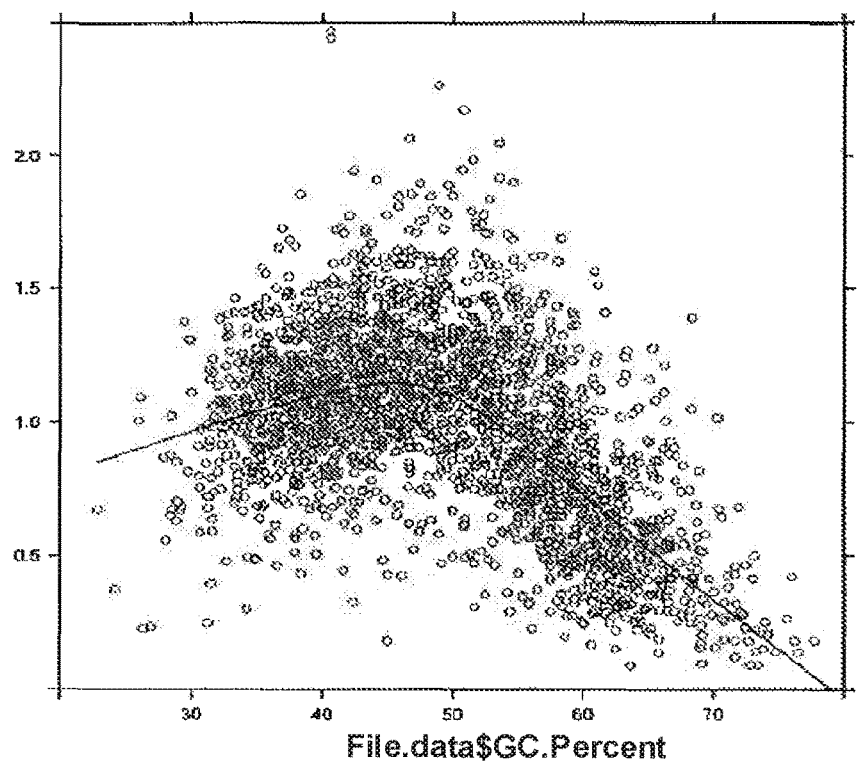
FIG. 40 shows a normal plot of GC vs corrected normalized average coverage.

Copy numbers are called for each target region independently by comparing coverage of a region with the expected coverage. However, it is well-known that during sequencing different GC % regions amplify differently—regions with very high/low GC are expected to get less coverage than regions with moderate GC. GC-correction and normalized coverage are used to mitigate the effect of GC and variation in the length of the target regions. After these corrections, the typical GC vs corrected normalized average coverage plot is calculated. One illustrative plot is shown in FIG. 40.

The shape of the pattern displayed by the majority of well-behaved samples can be captured by a vector.

Figure 41:
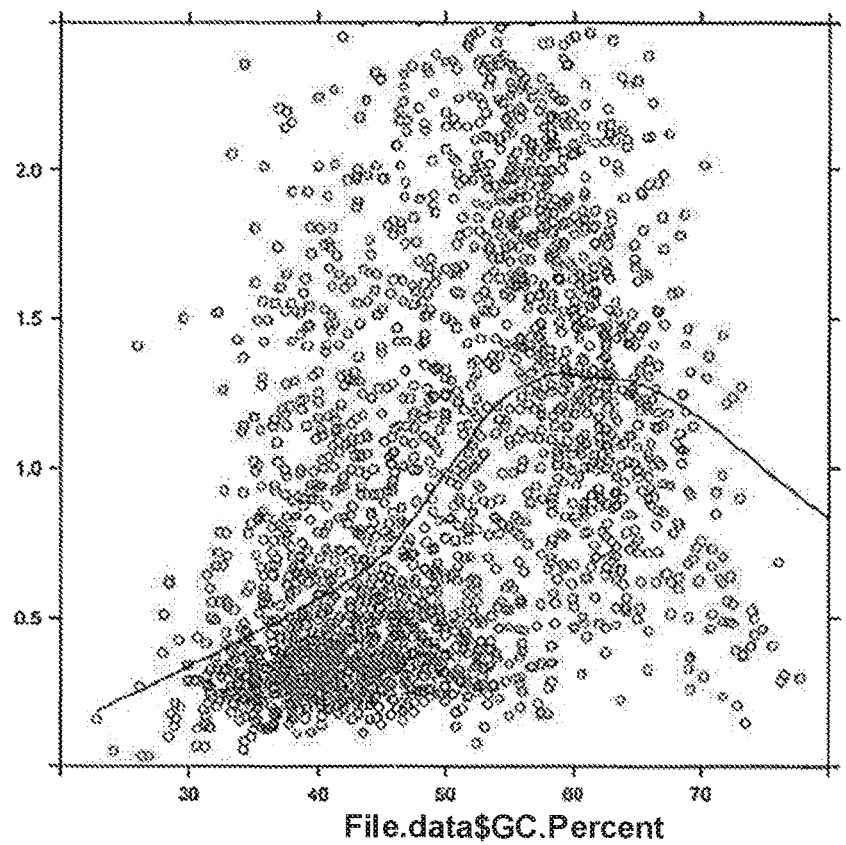
FIG. 41 is a plot of GC vs coverage for a sample with sequencing abnormalities.

However, compromised samples can behave very differently. The image in FIG. 41 shows one example.

When the copy number variants are calculated for such samples, a large number of regions will be falsely detected as copy number variant regions. The % of copy number variant regions and the difference in the shape of the GC vs. coverage plots are indications that the copy number calls may not be reliable. These are flagged by the QC pipeline.

Figure 42:
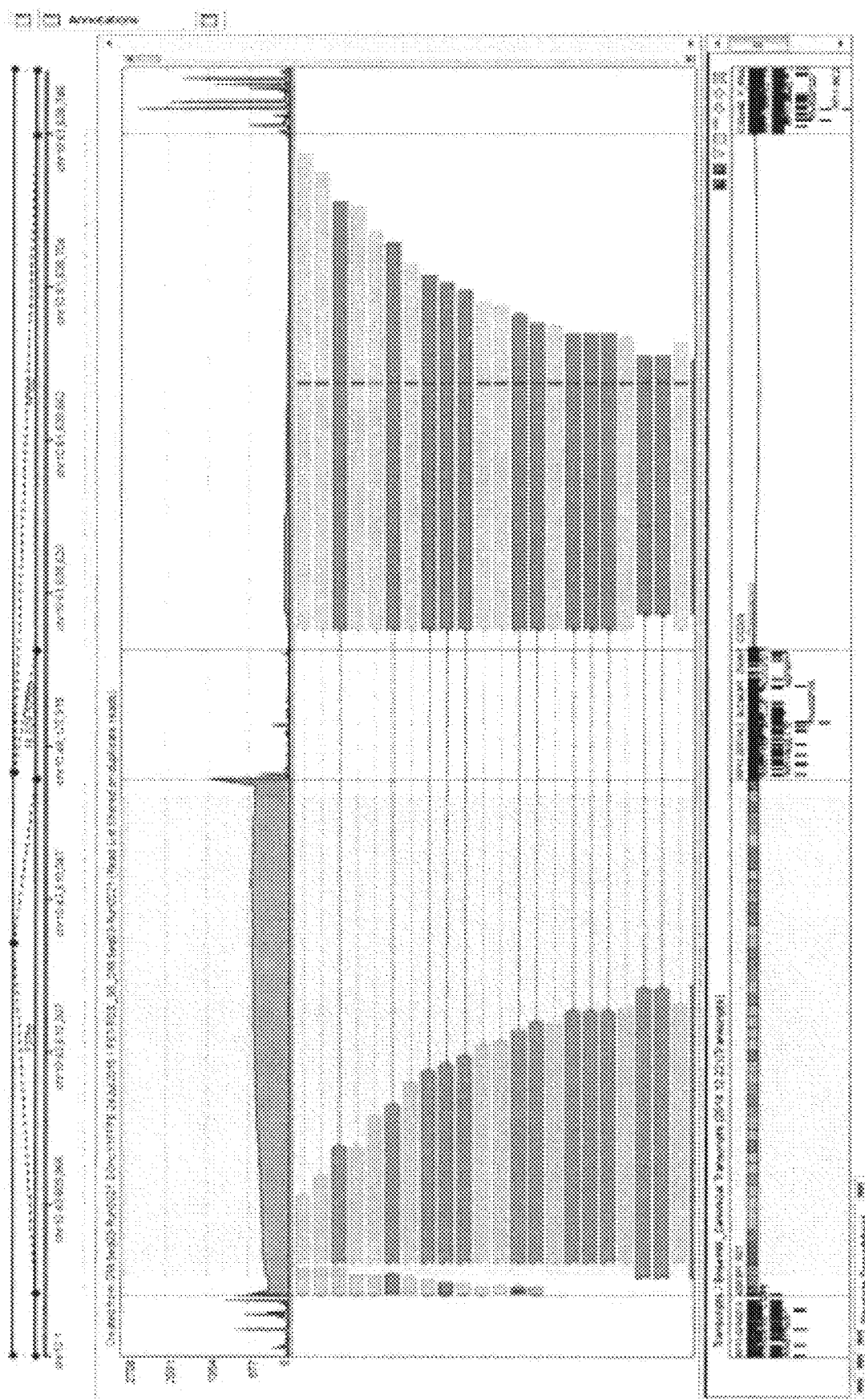
FIG. 42 illustrates an Elastic Genome Browser view of a translocation involving the genes RET and CCDC6.

The SVs detected can be Quality Checked using the Elastic Genome Browser™ which allows displaying different genomic regions at different zoom levels simultaneously. This feature makes it possible to collapse the uninteresting regions and expand the interesting regions in a genome browser track facilitating easy validation of phenomena spanning large/multiple genomic regions such as gene fusions, novel splices, and large structural variations. As an example, FIG. 42 shows the fusion of the genes RET and CCDC6 in one of the samples in the Elastic Genome Browser™. In this view the regions of the two genes around the breakpoints are shown in greater detail whereas the large intermediate region is compressed. From this view one can clearly see that the reads are nicely split between the genes with the breakpoints are well aligned.

The specification of the zoom levels for different regions in the Elastic Genome Browser™ is called the 'Elastic Bookmark'. In one embodiment, the SV detection method outputs the detected SVs along with the corresponding elastic bookmarks. Just double-clicking on any SV in the result list will launch the elastic genome browser view with the pre-computed elastic bookmark. It is also possible to define the bookmarks manually by adding pins at the top of the genome browser to define the different regions and dragging them to appropriate locations to define the zoom levels for these regions.

The output of the patient-specific marker value generation pipeline is the patient-specific marker values that have been QCed for their validity. These are entered into the marker processing apparatus for further processing. In one exemplary embodiment, the patient-specific marker values may be entered into the marker processing apparatus via a web based browser interface that is controlled to allow only authorized personnel access to the apparatus. In another exemplary embodiment, a program may be used to automatically enter the patient-specific marker values into the apparatus via well-defined Application Programming Interfaces (APIs).

Figure 43:
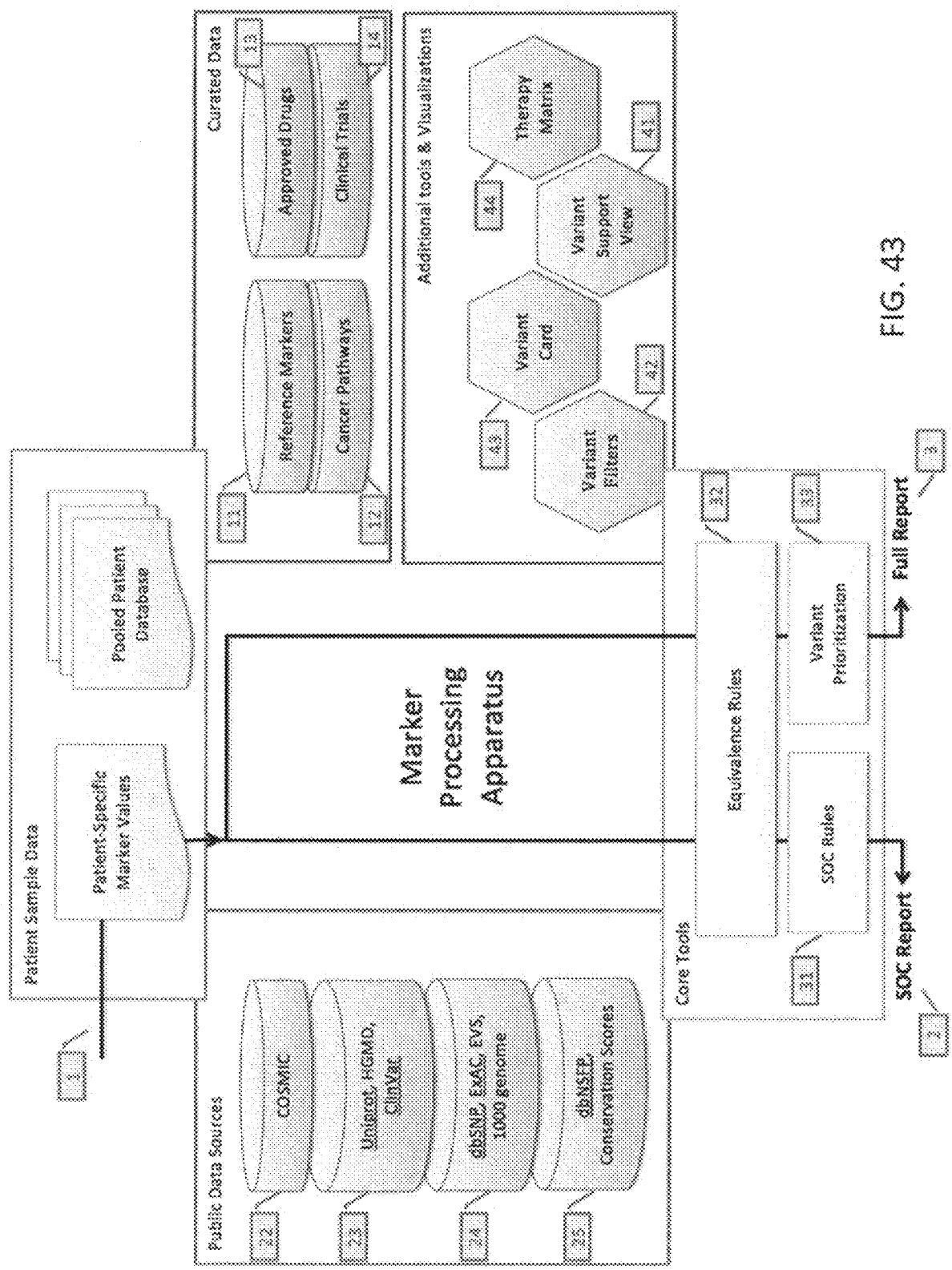
FIG. 43 is a schematic block diagram of the marker processing apparatus.

A block diagram of the marker processing apparatus is shown in FIG. 43. The marker processing apparatus takes in as input the measured patient-specific marker values (#1) and produces as output as estimated drugs response for the standard of care drugs specific to the tissue of the patient sample in the form of a SOC report (#2) and additional therapy suggestions in the form of a Full Report (#3).

The marker processing apparatus comprises a manually curated database of reference markers (#11) annotated with their functional significance. Each reference marker may be annotated using peer reviewed journal literature as having a Loss of Function, a Gain of Function or no Functional impact on the gene that it falls in. The database also contains information about the protein domains that the markers fall in and aggregated summaries for each of the domains.

The NGS panel includes oncogenes, tumor suppressor genes and pleiotropic genes as explained in the panel design. Tumor suppressor genes are more conducive to the equivalence rules explained further below as compared to the oncogenes or the pleiotropic genes. Hence the breadth of curation needed for tumor suppressor genes is relatively lower.

In one exemplary embodiment of the methods for curating the reference markers, the following steps are undertaken:
1. All variants recorded in the COSMIC database for each oncogene may be subjected to extensive search in literature for experimental evidence of their functional impact.
2. The functional impact of a marker in an oncogene depends on its impact on the oncogenic gain of function of the protein. Hence, only markers which have been experimentally validated to enhance the oncogenic function of the protein, or markers that alter well known hotspot codons which harbor more than two experimentally validated markers may be annotated functionally for oncogenes.
3. Well known hotspot codons may be identified based on number of citations, and also based on the number of alterations reported for each codon exceeding two.
4. A cutoff may be set for markers in tumor suppressor genes based on the frequency of the occurrence of the marker in the COSMIC database.
5. Any damaging marker in a functionally relevant domain of a tumor suppressor can affect the protein function. Hence, based on the published evidence on the functional relevance of a domain, as well as, published reports on the functional impact of reported markers in that domain, any damaging variant in such a protein region may be annotated functionally for a tumor suppressor.
6. Markers in pleiotropic genes may be handled similar to markers in oncogenes.

Protein domains may be curated in a multi-stage process, an exemplary embodiment of which may include the following steps. In the first stage:
1. Protein domains may be curated from different public sources to accurately determine boundaries of the domain.
2. For proteins where records on the canonical isoform in well-known public databases correlated with the single most reported isoform in published studies, all data may be recorded based on the single isoform. For proteins where the databases indicated more than one experimentally verified isoform, and published studies indicated existence of different tissue specific isoforms, the data may be recorded with respect to both the isoforms.
3. Studies involving experimental characterization of the protein may alone be considered for curation. The different domains and key residues may be recorded, and annotations made with reference to the canonical protein isoform, as well as the tissue specific isoforms.

In the second stage:
4. Reference markers annotated as either LOF or GOF, based on the published experimental evidence, may be clustered into the domains that they overlap with.

Based on the overall functional impact of variants in a domain, a condensed summary that captures the domain function as well as the impact of the markers in that domain may be recorded.

5. The domain level summaries may be recorded for missense markers differently from markers that cause a frameshift or truncation in the protein.

The condensed summary is used by the marker processing apparatus while reporting the subset of patient-specific tested markers that are used to output estimated drug response.

The marker processing apparatus also comprises a curated database of a number of cancer drugs and their gene targets, cancer pathways and clinical trials. Cancer drugs (#13) and clinical trials (#14) may be derived from a public database such as the NCI database and the gene targets of the drugs may be mapped based on literature curation. These drugs may be organized into drug classes based on commonality of their gene target. The collection of cancer-related pathways (#12) may be derived from public data sources. In addition to their direct targets, each drug/drug class may be mapped to one or more genes on the panel using these pathways. For instance, a LOF marker in a Tumor Suppressor gene upstream of a drug target in the pathway could potentially be targetable by this drug. This collection of drug class-gene pairs is accumulated in the Therapy matrix tool (#44).

The marker processing apparatus also comprises a variety of public databases. Public data sources may comprise a) database of somatic variants reported by community such as COSMIC (#22); b) databases of germline variants (#23) reported and curated by community such as HGMD, ClinVar and parts of UniProt; c) database of germline variants collected from population studies (#24), databases such as dbSNP, ExAC, EVS and 1000 genomes project; and d) databases that provide outcomes of bioinformatics predictions (#25) including functional prediction and conservation of missense variants such as dbNSFP. These databases may be updated on a periodic basis and are used by the various tools described further below.

The marker processing apparatus also comprises the SOC rules (#31), that relate collections of reference markers to the expected response of the SOC drugs for a specific tissue. The SOC rules are manually curated using information from disparate peer reviewed literature.

The list of standard of care drugs for each cancer tissue type is put together from the list of current FDA approved drugs and other drugs recommended in commonly published clinical guidelines for treatment. The list of reference markers that are known to have an impact on the set of standard of care drugs for a tissue are curated from published literature. The available literature evidence may be characterized to assign a strength of evidence to each marker-drug combination taking into account particulars of the studies such as whether it is a clinical or preclinical study as well as the size of the study. For each drug class-gene pair under consideration, literature evidence was curated and categorized as a) evidence from clinical studies in the same tumor type b) evidence from preclinical studies in the same tumor type c) evidence from clinical studies in other tumor types. Evidence in category c) was considered for reporting provided it was available from at least two distinct tumor types and if there was an ongoing clinical trial relevant to the tumor type at hand. Evidence in category b) was considered only in some variations. Only the highest levels of evidence may comprise the SOC rules for the drugs of each cancer tissue type.

The evidence available for each rule is evaluated and summarized in a concise statement, highlighting key clinical studies in support of the recommendation. These SOC rules also take into account different drug responses for marker combinations within a particular gene. For example, when occurring alone, exon19 inframe deletions in EGFR suggest response to EGFR tyrosine kinase inhibitors like erlotinib. However, when EGFR exon 19 inframe deletions co-occur with EGFR p.Thr790Met missense mutation, it suggests poor response to EGFR tyrosine kinase inhibitors. Each of these evidences are curated into separate SOC rules.

Following this procedure, the list of genes/proteins known to impact drug response in an exemplary collection of the tissues is catalogued below for the purposes of illustration only:

Colon—APC, BRAF, EGFR, KRAS, NRAS, PIK3CA, PTEN, MET, SMAD4, UGT1A1, DPYD, TS, TOP1, ERCC1, MSI Breast—BRCA1, BRCA2, CDKN2A, EGFR, ERBB2, PIK3CA, SMAD4, MDR1, TOP2A, TS, ER, PR, HER2, TUBB3, PTEN Lung—EGFR, ERBB2, KRAS, MET, PIK3CA, ALK, RET, ROS, RRM, TLE3, TS, TUBB3, ERCC1, MDR1, PD-L1

Melanoma—BRAF, KIT, NRAS, PTEN, MGMT, PD-L1

Ovarian—AKT1, BRAF, KRAS, MLH1, MSI, PIK3CA, PTEN, TP53

Brain—BRAF, EGFR, MGMT, IDH1, IDH2, PIK3CA, PTEN, CIMP

It should be noted that the list of standard of care drugs for a specific cancer type may change over time as newer drugs are approved by FDA and more drugs are included in commonly published clinical guidelines. The markers associated with the standard of care drugs may also change over time as more clinical or pre-clinical studies are conducted and published.

Each of the SOC rules may be recorded as an expression that characterizes the response of a specific standard of care drug for a specific tissue conditioned on a set of reference markers: response (drug D, tissue T|marker condition C)=R as per literature evidence L, or, the response of a drug D in cancer tissue T given condition C of markers is known to be R as per literature evidence L. The response may record the expected eligibility, efficacy or toxicity of the drug in a tissue given the condition of reference markers. The various levels for the drug response may thus include Enhanced response at one extreme, Poor response at another, and other levels in between such as Limited-Enhanced and Reduced response. Some drugs may be known to be Ineligible under certain marker conditions, while others may be known to be Toxic.

The markers condition refers to the presence or absence of a single marker or a combination of markers from one or more genes. The marker can either be a specific marker (for e.g. V600E in BRAF) or a generic marker based on a functional class (for e.g. any Gain of Function markers), based on a locational class (for e.g. variants at codon 1047) or based on the nature of the marker (for e.g. in-frame insertions). The combination of markers may be specified using standard Boolean operators like AND, OR, NOT with specific or generic exceptions. The Boolean operators may be enhanced, for e.g. a special OR or an SOR operator based on the Boolean OR operator, to handle conditions where the marker is neither present, nor absent but may have not been measured, failed measurement or measured equivocally.

An example marker condition is show below for the purposes of illustration: [{(any GOF except T790M) AND (NOT an exon 20 in-frame insertion) in EGFR} AND {any GOF in KRAS}]

An example of a rule is shown below for the purposes of illustration: Response(Trastuzumab|{SOR(ERBB2 amplifications, ERBB2 IHC+, ERBB2 GOF(except p.Glu321Gly, p.Gly778_Pro780dup)) AND SOR(PIK3CA amplifications, PIK3CA GOF(except p.Ala1066Val, p.Arg38His, p.Glu453Lys, p.Arg975Ser, p.Pro124Leu))}=Limited-Enhanced based on the following literature evidence—Trastuzumab therapy is approved for HER2 overexpressing breast cancer. Clinical evidence from studies with breast cancer patients has reported that the subset of patients with HER2-positive tumors (overexpressed, amplified, or with activating mutations) benefited from trastuzumab therapy. Clinical studies with HER2-positive breast cancer patients have also reported that the combination of trastuzumab with chemotherapeutic agents such as paclitaxel, was significantly superior to chemotherapy alone in terms of overall response rate, overall survival, and time to disease progression. Clinical evidence has suggested a limited response to anti-HER2 drugs in the presence of an activated PI3K pathway due to PIK3CA alterations. A clinical study with breast cancer patients which found a benefit from trastuzumab therapy in the HER2-positive subpopulation, however, also observed that activating mutations in PI3KCA was significantly associated with a reduced time-to-progression and overall survival.

Upon entering the patient specific marker values into the marker processing apparatus, the marker processing apparatus may be used to determine an equivalence level for the subset of patient specific marker values relative to the reference SOC marker values based on a set of equivalence rules. For each patient specific marker measured with a specific value, the marker processing apparatus may evaluate its equivalence with any of the reference SOC marker values from within the same gene with an equivalence level of high, medium or low confidence.

Figure 44:
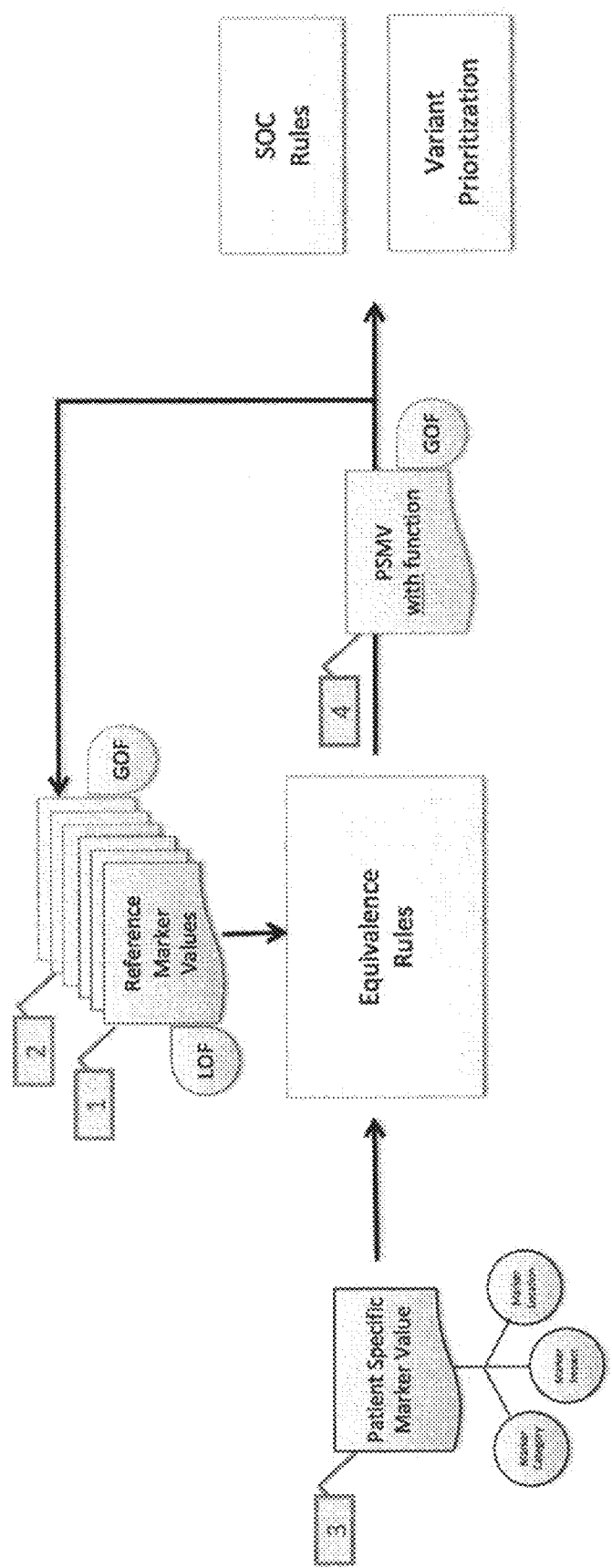
FIG. 44 illustrates equivalence rules depicting a patient specific marker value being annotated with GOF.

The equivalence rules are depicted in FIG. 44.

The equivalence rules start by classifying the patient specific marker values (#3) into categories based on gene structural and functional properties and the predicted impact of the marker on these properties. Gene structural and functional properties may include the character sequence of the gene and its corresponding protein, regions annotated within these sequences as functionally important, and the overall function of the gene (oncogene, tumor suppressor, pleiotropic or unknown). The impact of the marker on these sequences is predicted and the marker impact is accordingly determined as nonsense, frameshift, non-synonymous, in-frame indels etc.

Then the patient specific marker is evaluated for equivalence with each marker in the library of reference markers within the same gene, taking into account the marker's category (if it is a point mutation, or an InDel, etc.), the marker's impact, and the marker's position within the gene. Similar or worse effects of the patient-specific marker as compared to the reference marker are considered for equivalence. Along with an equivalence level, a confidence level of high, medium or low is also predicted. In case the patient-specific marker is the same as a reference marker, such markers are also assigned a high confidence of equivalence.

The equivalence rules may further be used to annotate the functional significance of the patient specific markers based on the functionally annotated database of reference markers that have either a GOF (#2) or LOF (#1) functional significance. In one exemplary embodiment, the marker processing apparatus comprises a database of about 3000 functionally annotated reference markers. The equivalence rules allow many more patient specific markers beyond these curated reference markers to be assigned a functional significance, thus reducing the time required for establishing their functional significance through a manual literature survey. Finally, the newly annotated patient-specific marker value may be curated and added to the library of reference markers.

In one exemplary embodiment of an equivalence rule, a patient specific marker that indicates a premature truncation in a Tumor Suppressor gene is equivalent to a reference marker with high confidence if it is an exact match or if the reference marker is a premature stop, or a frameshift variant or an Essential Splice Site (ESS) variant resulting in a premature stop downstream of the patient specific marker, and is annotated with a LOF functional significance if such a reference marker is found. On the other hand, a patient specific marker that indicates a non-synonymous change in an Oncogene is equivalent to a reference marker with low confidence if it occurs at the same codon as the reference marker which is annotated as a GOF, but with a single different non-synonymous change.

The marker processing apparatus then processes the patient specific marker value via the SOC rules or the variant prioritization tool depending on whether it needs to create the SOC report or the full report, as depicted in the schematic block diagram in FIG. 19.

The marker processing apparatus executes the appropriate SOC rules for each of the standard of care drugs in order to estimate the drug response. When multiple SOC rules are fired for the same drug, it is likely that the outcome predicted by each of the rules for the drug is concordant. However, it may also so happen that the SOC rules may predict contradicting outcomes for the drug. In such cases, the net effect may be obtained by weighing the distinct markers differently, based on their level of evidence and taking the effect with the highest quality evidence. Independent discordant effects on a drug, one indicating Enhanced response and the other indicating Poor response, may be combined into an intermediate category, called for example Limited-Enhanced response. If the discordant effects are related because the involved markers are from a well-known cancer pathway, then their effects may be combined taking the pathway into account. For example, an EGFR amplification concurrent with a PIK3CA LOF variant were combined to indicate enhanced response for EGFR inhibitors provided they were coupled with an mTOR inhibitor, e.g., Everolimus.

In another aspect of this invention, the response of a cancer patient with a specific type of cancer to a plurality of cancer drugs not specific to the cancer type of the patient, referred to as off-label drugs, and to a plurality of clinical trials for the specific type of cancer is determined using the marker processing apparatus with the object of determining additional therapies that may be applicable to the patient.

In this aspect of the innovation, the marker processing apparatus categorizes and prioritizes the patient-specific marker values after the evaluation of the equivalence rules. The markers that were annotated as LOF or GOF are categorized thus and prioritized the highest. Markers without even a low confidence LOF or GOF label are further categorized as follows. Such markers, if present in the COSMIC database are categorized as such and prioritized next. Of the remaining markers, markers with low population allele frequencies, and either conserved and predicted to be damaging to gene function by sufficiently many in-silico predictors (PolyPhen, SIFT, etc.), or those that induced premature gene truncation, are labeled as Damaging and prioritized next. All the rest of the markers are categorized as Like Benign and prioritized the last.

The prioritized markers are now available to a manual interpreter to determine any additional off-label drugs that may be applicable to the patient, any clinical trials that the patient may enroll in and any prognosis predictions for the patient based on the patient-specific marker values. The marker processing apparatus provides a collection of tools to enable this process.

Figure 45:
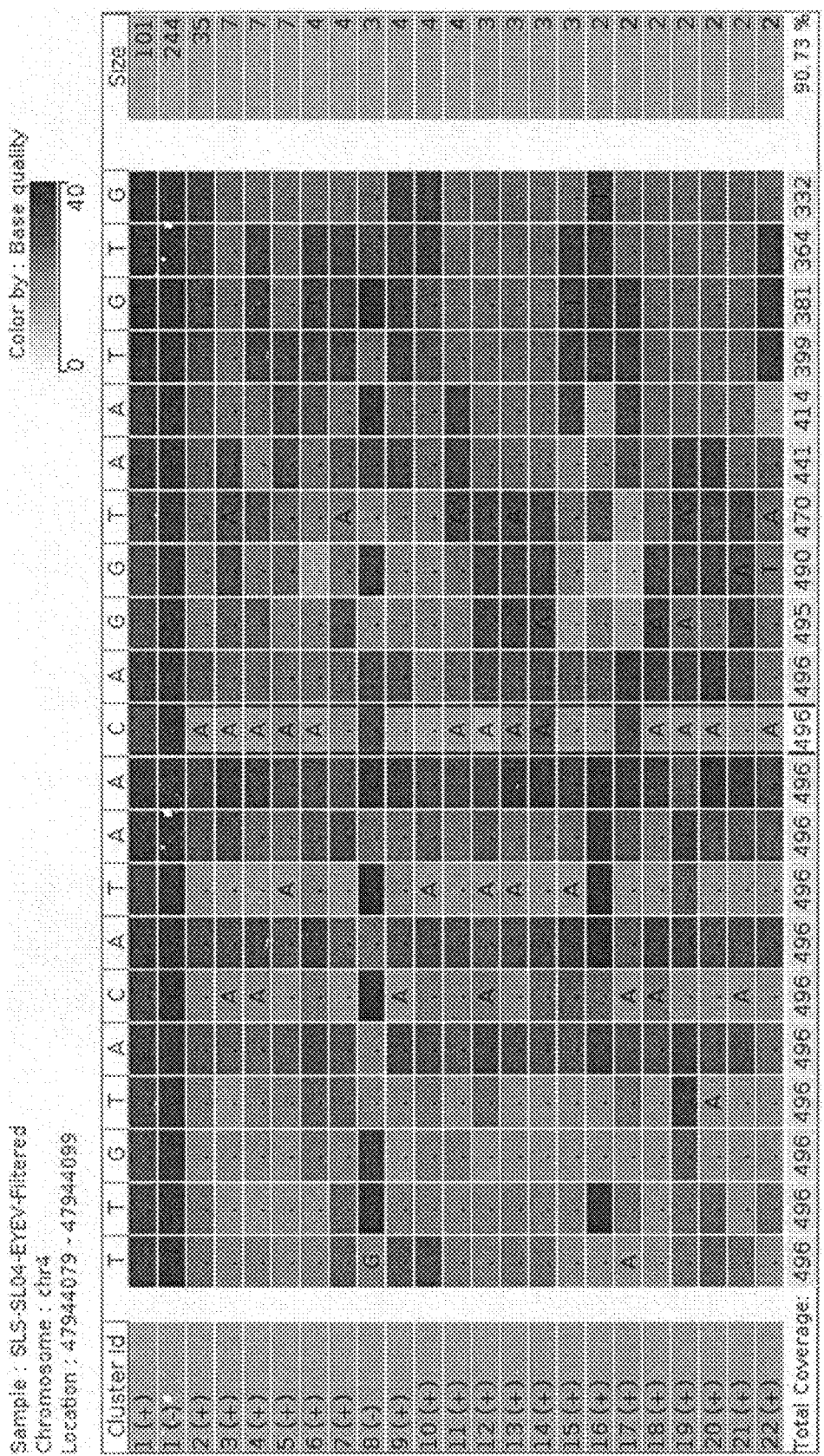
FIG. 45 illustrates one example of a Variant Support View.

The Genome Browser may not be the most efficient way to visualize the SNP's, especially when it involves insertions, since the genome browser always shows the reads aligned to the ungapped reference genome. In addition, in areas of high coverage it is difficult to see all the supporting reads for a variation. The Variant Support View allows the display of SNPs and small InDels in a manner that is independent of the reference genome and groups identical reads together. FIG. 45 depicts a sample variant in the variant support view.

The view shows the variants in the reads in a region surrounding the specified location on the genome. By default a region of 10 bp width on each side is considered, but smaller or larger widths for the surrounding regions can be chosen. The top row of the view shows the bases in the reference sequence below which are shown clusters of reads with identical bases in the region of interest. The reference sequence is expanded, if required, to accommodate any insertions in the reads in that region. The insertions are indicated by '-' in the reference sequence whereas '-' in the cluster sequences indicate deletions. A '.' in the cluster sequence means either all the reads in that cluster contain the reference allele at that base, or there are no reads passing through that base. Clipped portions of the reads are dropped for the purpose of the computation of the clusters. Spliced portions are indicated by '*'. The number of reads in each cluster is shown to the right of the sequence. In addition, it is possible to split each cluster of the reads into sub-clusters corresponding to the positive and the negative strands.

The view also provides an option to color the bases in each of the clusters by base quality, mapping quality, or positional bias. Each base in a cluster is given a color corresponding to the average of the selected parameter over all the reads of that cluster passing through that base. The positional bias of a base in a read is computed as its distance from the 3' end of the read. This value will be equal to zero for the base at the 3' end. As typically the base quality degrades towards the 3' end, the positional bias can be used as an alternative measure of confidence in cases where the base qualities are not very reliable.

The view with its sortable columns and cluster sizes is especially helpful in verifying heterozygous SNPs and SNPs that fall in high coverage regions. Large clusters with multiple variant positions can be used to detect haplotype blocks.

Figure 46:
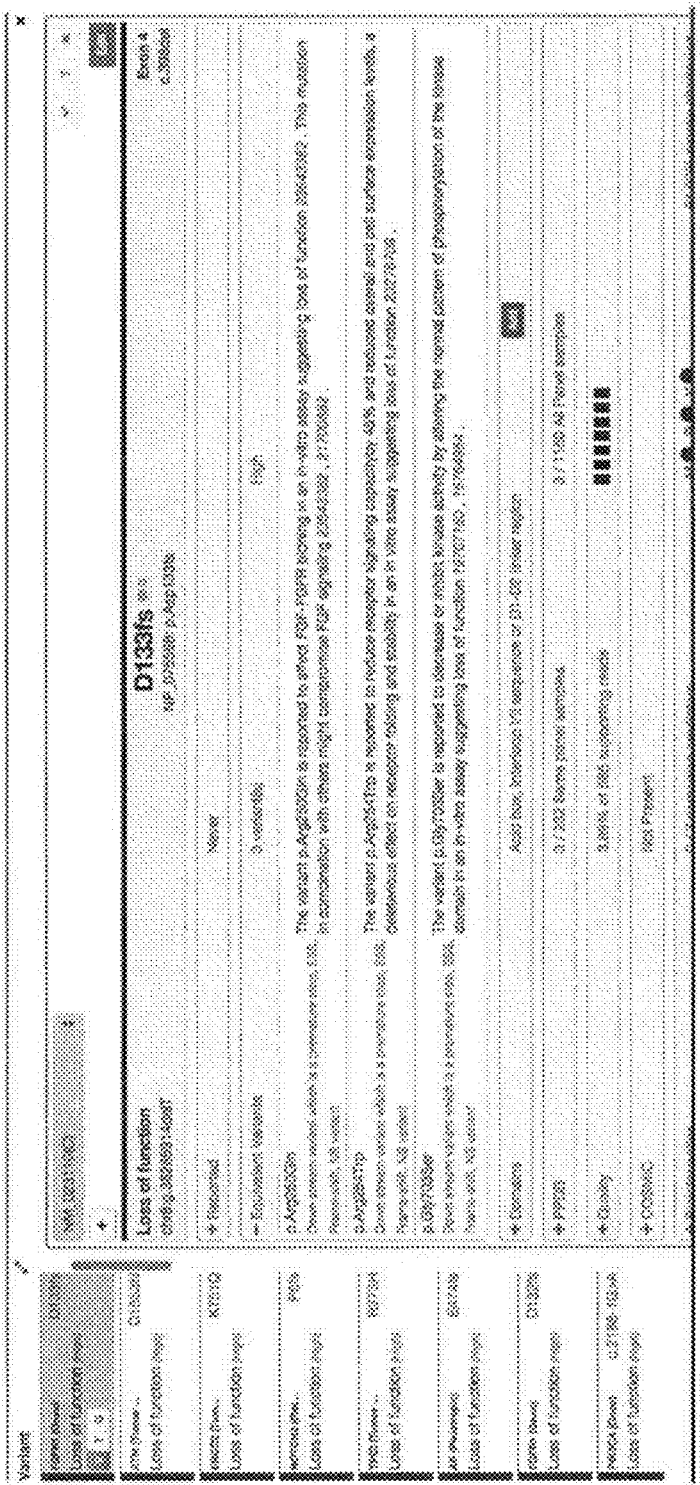
FIG. 46 shows one example of a Variant Card that succinctly depicts all relevant information about the variants.

The variant card is yet another tool in the marker processing apparatus that brings together information about the variant from various sources, including public databases, outputs of bioinformatics algorithms, older cases from within the system, etc. FIG. 46 shows an example variant card, the variant in this case equivalent to three other variants.

The marker processing apparatus also provides other (standard) tools to be able to quickly shortlist the variants that are likely to be harmful and targetable. The Variant filtering tool is one such that provides the ability to quickly narrow down the variants to the ones of interest.

Once variants and thereby genes have been shortlisted, the next step is to identify the drugs that can be used to target these genes—either directly or via some gene upstream or downstream. To this end, the Marker processing apparatus provides the Therapy Matrix tool. The therapy matrix readily lays out the possible list of off-label drugs and clinical trials that can be reported upon.

Figure 47:
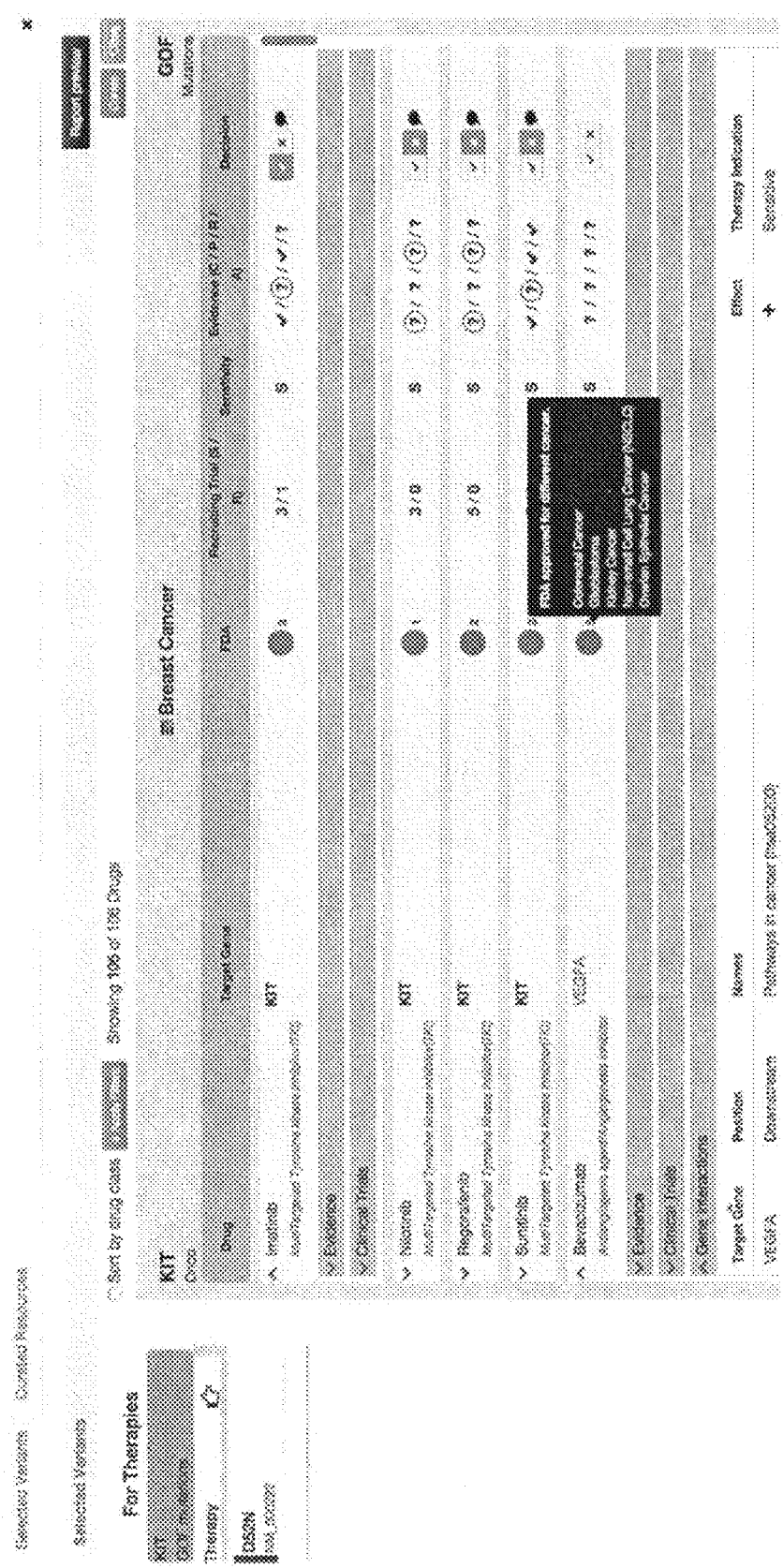
FIG. 47 shows a therapy matrix that provides a shortlist of off-label drugs and clinical trials that may be applicable to the patient sample.

Shown in FIG. 47 is an example where a GOF variant was found in KIT, and Imatinib can be used to directly target the gene directly, or Bevacizumab can be used to target VEGFA that is downstream of KIT. The therapy matrix helps the interpreter go over the set of candidate drugs and identify additional drugs that might work for the patient or trials that the patient can enroll in.

The marker processing apparatus also enables automatic creation of the SOC report, and semi-automated creation of the full report for the patient sample.

Part II: SmartLab

The methods and systems described herein may be referred to as "SmartLab". SmartLab is an example of a unique, cost effective, and turnkey solution that may help hospitals and cancer centers provide their patients with faster diagnoses and more effective treatment options by offering in-house, NGS-based, genetic and genomic testing services for cancer and inherited diseases. SmartLab also helps hospitals distinguish themselves in their communities, gain patients, and create new profit centers for their organizations.

Each SmartLab may be tailored meet the customer's needs from consulting, design, infrastructure and equipment to gene panels, data analysis solutions, staffing, training and CAP/CLIA certification.

SmartLab may be hospitals, cancer care centers, and healthcare systems to capture the rapidly growing market for NGS-based diagnostics. Based on current analysis of economics of genetic and genomic testing, groups that have, or anticipate, sample volumes exceeding 2,000 per year for genetic and genomic tests will benefit from the SmartLab solution described herein.

The SmartLab may provide organizations with all the necessary components to offer in-house, NGS-based genetic and genomic tests in high-impact disease areas. This can include full CAP/CLIA laboratory build out and certification. It is a stress-tested solution from one of the largest healthcare markets in the world.

SmartLab may help hospitals and clinicians more effectively diagnose, treat, and monitor patients who have, or who are at risk of developing, cancer, cardiovascular disease, eye disease, or rare inherited diseases, thereby improving patient outcomes. SmartLab may help hospitals reduce risk and cost by making it easier and faster for clinicians to identify in advance which treatments are likely to be effective and safe for their patients. SmartLab may enhance the brand value of partner organizations, helps them differentiate themselves from their regional competitors, empowers their participation in personalized medicine clinical research programs, and provides them with a new profit center.

SmartLab Components: Core Platform, Infrastructure, Services, and Expertise

The SmartLab Core Platform may include a lab blueprint and a menu of genetic and genomic tests in high impact disease areas.

For example, a Lab Blueprint may include a Blue print for implementation of Clinical Genomics and Molecular Diagnostics tests in a CAP/CLIA/ISO15189 compliant manner.

SmartLab customizable sample tracking and automation workflow software (Elixir) may also be included, as described above. This may include a laboratory information management system (LIMS) with seamless sample and order tracking and role notifications; this may be customized to integrate with existing LIMS systems.

Figure 26:
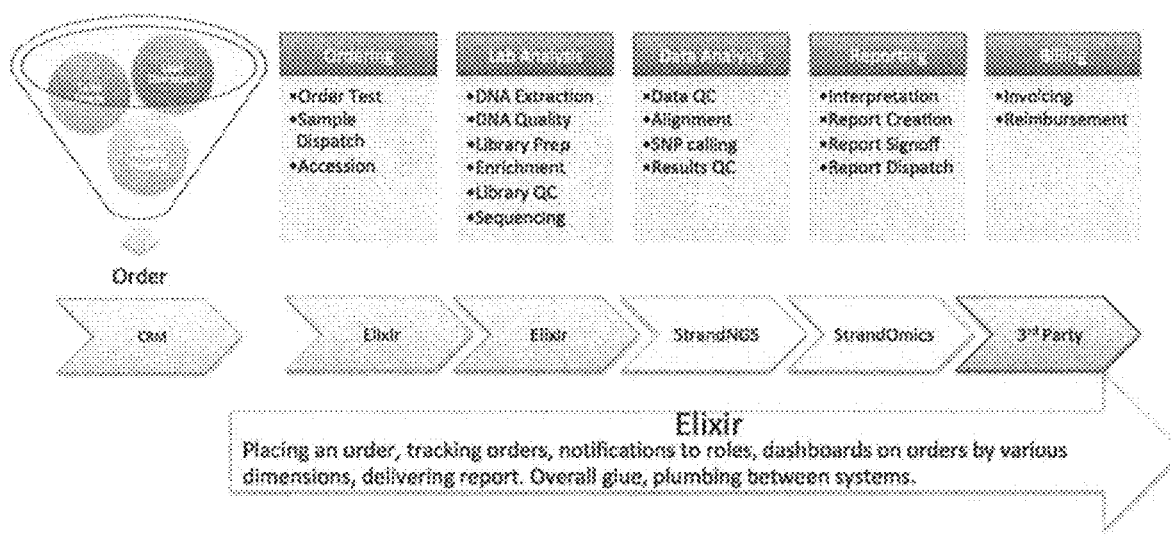
FIG. 26 is an example of a workflow for a "SmartLab" as described herein.

FIG. 26 shows one example of a SmartLab integration with EMRs via APIs.

The methods and apparatuses described herein may also allow genetic and genomic test menus. For example, design, validation, and implementation of multi-gene panel tests for cancer and inherited diseases may be configured. Organizations using SmartLab (e.g., Smartlab partners) may have access to custom-designed and off-the-shelf multi-gene panel tests, and customized panels may also be designed and used. For example, a list of disease-specific gene panel tests includes: Somatic Cancer Panel: 151-genes for solid tumor mutation profiling; Germline Cancer Panels: 92-gene comprehensive germline cancer panel and 3-gene breast/ovarian panel; Multi-gene HemeOnc Panel for cancer mutations; Pharmacogenomics Panel(s): qPCR array panel for cardiovascular drugs, anti-depressants, anti-virals, pain meds, etc. Uses FDA biomarkers for pharmacogenomics; Clinical Exome Panel: 4800 genes for the diagnosis of rare inherited diseases Cardiovascular Panel: 206 genes for the diagnosis of inherited cardiovascular diseases; Eye Panel: 182 genes for the diagnosis of inherited eye diseases; Tests for Minimal Residual Disease (MRD) using Circulating Tumor DNA Biomarkers. These tests use digital PCR and NGS technologies to help monitor efficacy of cancer therapies.

A test menu may be designed and optimized. For example, including an order of priority, and launch timing, e.g., through a SmartLab joint managing committee.

Alternatively partnership models may be used:
Model 1: Build, Operate and Transfer (BOT)

In this model, the hospital or healthcare organization is the sole investor and owner of the SmartLab and retains the subsequent revenues and profits. The SmartLab may be delivered in a BOT model over a period of 1.5-2 years. Consulting services may be provided on a fee for service basis. Software and genetic and genomic tests are licensed.
Model 2: Build, Operate and Jointly Own (BOJO)

In this model, the hospital or healthcare organization may jointly invest with the SmartLab provider to cover the capital expenditures involved in building and operationalization of the SmartLab. The ownership interest may be proportional to the capital invested by each party. SmartLab may be jointly managed by a committee represented by members of both parties.
SmartLab Infrastructure: Equipment and Software A systematic and objective evaluation of an organization's current infrastructure and equipment and goals may be performed and used to identify any gaps and enable a cost effective solution for building a SmartLab. For example: Sequencers: NGS, Sanger; IT infrastructure including computational hardware, Storage and Cloud services; databases, laboratory instruments, and supporting automation systems; and/or qPCR, microarray and other laboratory instruments.
Software for NGS Data Analysis, Interpretation and Reporting StrandNGS: software that supports multiple workflows for NGS data analysis including read alignment, variant calling, RNA-seq, small RNA-seq, DNA-seq and ChIP-seq experiments may be provided. Compatible with all major sequencers and operating platforms. Helps clinical researchers rapidly find and analyze variants of interest.

StrandOmics: Genomic interpretation and reporting platform built for interpreters by interpreters to analyze germline and somatic Laboratory Developed Tests and provide clinicians with information that assists in diagnosis and treatment decisions. The software follows ACMG and NCCN guidelines in prioritizing relevant genes based on their pathogenicity. In addition to integrating public databases such as ClinVar, COSMIC and HGMD, StrandOmics is powered by a manually curated database of variant-phenotype associations from the literature along with supporting evidence.

Elixir: Software platform that connects data and workflows across all the software systems including Strand-NGS, StrandOmics, LIMS, billing, sample tracking and automation. Elixir provides your teams with visibility from order to billing, making it easy to track each order's progress, find relevant information fast and identify and resolve any bottlenecks.

Alchemy: The interpretation of variants is done using a large collection of heterogeneous bioinformatics resources. However, data sources can be contradictory, may even be erroneous, and are frequently updated. Most data sources are external but Strand's curation team is a source of variants and domains as well. The sources are used to create a wide variety of biological objects such as genes, transcripts, proteins, domains, variants, pathways, diseases, tissues, phenotypes, drug/therapies, clinical trials etc. Frequently multiple data sources are used for creation of a single object—genes are created using NCBI Gene, Ensembl and Uniprot resources. Ensuring that the data used for interpretation is "correct" at all times is a challenging task which the Alchemy framework addresses.
Smartlab Services The SmartLab services may include full regulatory support for obtaining CLIA, CAP, and ISO15189 certifications for the SmartLab: metrics & data analytics for LEAN Six Sigma processes, Continuous Quality Improvement (CQI) and Total Quality Management (TQM); Genomic data interpretation and genetic counseling services. Cancer panel data interpretation includes information on available targeted therapies and clinical trials; consultations, for example, SmartLab staff and clinicians may be provided to assist with any aspects of the SmartLab workflows; billing and reimbursement services may also be provided; research and development of custom integrated molecular diagnostics tests may be provided; health outcomes research may be provided to show economic value of clinical genomics and molecular diagnostics testing in hospitals (cost avoidance and cost savings); customized continuing medical education programs may be provided; design, planning and development of translational research ecosystems may also be provided.

The cost of sequencing is typically going down and becoming commoditized. The key cost differentiator for genetic & genomic testing services is now interpretation. A dedicated team of scientists may efficiently and effectively curate genes included in particular gene panels (e.g., adding approximately new variant-references, etc.).

The combination of an automated informatics pipeline onsite, powered by expert manual curation may provide a particularly effective combination.

Laboratory Information Management Systems (LIMS), clinical genomics equipment, liquid handling automation, and developing bioinformatics pipelines may be used to form the SmartLab software ecosystem described heroin. This may be scalable and replicable and may be deployed at partnering sites to accelerate the establishment and standardization of clinical genomics and molecular diagnostics work-flows within most enterprise IT infrastructures, or in combination with the Cloud. The SmartLab IT infrastructure may be HIPAA compliant.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of estimating a patient's response to a plurality of cancer drugs or therapies using a marker processing apparatus, the method comprising:

entering a plurality of patient-specific marker values into the marker processing apparatus, wherein the plurality of patient-specific maker values were identified by testing a patient sample for a plurality of markers to identify the patient-specific marker values;

using the marker processing apparatus to determine an equivalence level for at least some of the patient-specific marker values relative to reference marker values in a library of reference marker values by applying set of equivalence rules, followed by setting the equivalence level, wherein the equivalence level includes: high equivalence, medium equivalence, low equivalence or no equivalence;

using the marker processing apparatus to determine patient-specific marker values that are likely benign from those having no equivalence to a reference marker value by applying structural rules to the patient specific marker values having no equivalence to the reference marker value to identify a structural defect in a marker referenced by the patient specific marker value;

using the marker processing apparatus to automatically prioritize patient-specific marker values having equivalence to the reference marker, wherein the equivalence is high equivalence, medium equivalence or low equivalence;

identifying drugs or therapies related to markers corresponding to patient-specific marker values having equivalence to a reference marker value; and outputting an estimated response to the identified drug or therapy based on the determined equivalence level patient-specific marker values.

2. The method of claim 1, wherein using the marker processing apparatus to determine an equivalence level comprises comparing the at least some of the patient-specific marker values to the reference marker values in the library and applying equivalence rules to determine the equivalence levels.

3. The method of claim 1, further comprising associating patient-specific marker values that are equivalent to a reference marker value with high equivalence or low equivalence with a marker characteristic from the reference marker value.

4. The method of claim 1, further comprising associating patient-specific marker values that are equivalent to a reference marker value with high equivalence or low equivalence with a marker characteristic from the reference marker value and comprising one of: gain of function or loss of function.

5. The method of claim 1, further comprising associating patient-specific marker values that are equivalent to a reference marker value with high equivalence or low equivalence with a drug or therapy effect that is already associated with the reference marker value.

6. The method of claim 1, further comprising, after using the marker processing apparatus to determine an equivalence level for at least some of the patient-specific marker values relative to reference marker values in a library of reference marker values, using the marker processing apparatus to find a match from a Catalogue of Somatic Mutations In Cancer (COSMIC) database of variants for patient-specific marker values having no equivalence to a reference marker value, and associating the patient-specific marker values having no equivalence to a reference marker value but with a match to the COSMIC database to the matched COSMIC variant.

7. The method of claim 6, further comprising, after using the marker processing apparatus to determine an equivalence level for at least some of the patient-specific marker values relative to reference marker value in a library of reference marker values and after using the marker processing apparatus to find matches from the COSMIC database of variants, using the marker processing apparatus apply a structural rule to patient-specific marker values having no equivalence to a reference marker value and no match to the COSMIC database of variants, to identify a structural defect in a marker referenced by the patient specific marker value.

8. The method of claim 1, further comprising, after using the marker processing apparatus to determine an equivalence level for at least some of the patient-specific marker values relative to reference marker values in a library of reference marker values, using the marker processing apparatus apply a structural rule to patient-specific marker values having no equivalence to a reference marker value to identify a structural defect in a marker referenced by the patient specific marker value;

wherein the structural defect comprises one of: low minimum allele frequency, protein shortening, and modification of highly conserved region.

9. The method of claim 1, wherein using the marker processing apparatus to determine patient-specific marker values that are likely benign from those having no equivalence to a reference marker value comprises identifying patient-specific marker values as likely benign where the patient-specific marker values have no equivalence to a reference marker value, and do not have a match with a Catalogue Of Somatic Mutations In Cancer (COSMIC) database of variants, and for which a set of structural rules does not indicate a structural defect; and using the marker processing apparatus to automatically prioritize patient specific marker values comprises prioritizing based on prioritizing patient-specific marker values having equivalence to a reference marker value before patient-specific marker values that have a match from a Catalogue Of Somatic Mutations In Cancer (COSMIC) database of variants, and before patient-specific markers having a structural defect.

10. The method of claim 1, wherein identifying drugs or therapies related to markers corresponding to patient specific marker values having equivalence to the reference marker values comprises identifying drugs or therapies when a marker corresponding to one of the patient-specific marker values is a gene, and identifying a drug or therapy associated with that gene or a gene downstream of the gene.

11. The method of claim 1, wherein identifying drugs or therapies comprises identifying drugs or therapies related to markers corresponding to the patient-specific marker values that match to the COSMIC database or have a structural defect in the marker.

12. The method of claim 1, further comprising performing a pathway analysis to identify targetable genes based on markers corresponding to patient-specific marker values having equivalence to the reference marker values.

13. The method of claim 1, wherein the marker processing apparatus determines first plurality of cancer drugs or second plurality of drugs or both based on the equivalence level of the at least some of the patient specific marker values; and wherein the first plurality or second plurality of drugs from amongst a set of approved drugs, off-label drugs, approved drugs for the cancer type of patient and recommended drugs for early stage treatment of the cancer type of the patient, wherein the cancer type selected from group comprising breast cancer, non-small cell lung cancer, colon cancer, melanoma, ovarian cancer and brain cancer.

14. The method of claim 1, wherein the library comprises an indicator of a functional significance of the reference marker values and an association of the reference marker values to a response of one or more cancer drugs of the selected first plurality of cancer drugs; and wherein using the library of reference marker values in the marker processing apparatus to estimate a response for each of the selected first plurality of cancer drug or second plurality of drug or both based on the equivalence values of patient specific reference values that are equivalent to reference marker values which refer to a drug from the first plurality of cancer drugs or second plurality of cancer drugs or both.

15. The method of claim 14, wherein using the library of reference marker values in the marker processing apparatus to estimate a response comprises using the library of reference marker values to estimate a single response for each of the selected first plurality of cancer drugs or second plurality of cancer drugs or both, by resolving conflicts in estimated responses based on the patient-specific reference values that are equivalent to reference marker values which refer to the same drug from the first plurality of cancer drugs;

wherein the estimated response for each of the first plurality of drugs or second plurality of drugs or both, comprises one of standard response, favourable response, poor response or an intermediate response.

16. The method of claim 1, wherein outputting from the marker processing apparatus comprises outputting the report within 4 hours or less.

17. The method of claim 1, wherein the plurality of markers comprises markers for genomic events including nucleotide variants (SNVs), insertions and deletions (In-Dels), copy number variants (CNVs), structural variants (SVs) including translocations, micro satellite instability (MSI) and protein expression levels.

18. The method of claim 1, wherein testing the patient sample comprises testing a sample from fresh tissue or from formalin-fixed paraffin-embedded (FFPE) blocks using: Next Generation Sequencing (NGS), Immunohistochemistry (IHC), Polymerase Chain Reaction (PCR) and fluorescent in-situ hybridizations (FISH) to determine the plurality of marker values.

19. The method of claim 1, wherein testing the patient sample for a plurality of markers to determine a plurality of patient-specific marker values comprises using an automated patient-specific marker value generation pipeline; and wherein in the patient-specific marker value generation pipeline comprises: aligning, SNP detection, copy number calling, translocation detection, and Quality Checks (QC), using a Central Processing Unit (CPU) and a Graphical Processing Unit (GPU) to augment the execution on the CPU.

20. The method of claim 1, wherein the marker processing apparatus is modified based on the equivalence level of the patient-specific marker values; and wherein modifying the marker processing apparatus comprises enriching the library of reference marker values by patient-specific marker values found equivalent to reference marker values.

* * * * *